(12) United States Patent
Serrano-Wu et al.

(10) Patent No.: US 11,963,960 B2
(45) Date of Patent: Apr. 23, 2024

(54) COMPOUNDS FOR TREATING OR INHIBITING RECURRENCE OF ACUTE MYELOID LEUKEMIA

(71) Applicant: Flash Therapeutics, LLC, Boxford, MA (US)

(72) Inventors: Michael Serrano-Wu, Belmont, MA (US); Zhixiong Ye, New York, NY (US); Kejia Ding, Shanghai (CN)

(73) Assignee: Flash Therapeutics, LLC, Boxford, MA (US)

( * ) Notice: Subject to any disclaimer, the term of this patent is extended or adjusted under 35 U.S.C. 154(b) by 139 days.

(21) Appl. No.: 17/201,827

(22) Filed: Mar. 15, 2021

(65) Prior Publication Data

US 2021/0299128 A1 Sep. 30, 2021

(30) Foreign Application Priority Data

Mar. 16, 2020 (WO) ................. PCT/CN2020/079464

(51) Int. Cl.
| | | |
|---|---|---|
| A61K 31/519 | (2006.01) | |
| A61K 31/4985 | (2006.01) | |
| A61K 31/53 | (2006.01) | |
| A61K 31/541 | (2006.01) | |
| A61K 31/635 | (2006.01) | |
| A61K 31/675 | (2006.01) | |
| A61P 35/02 | (2006.01) | |
| C07D 487/04 | (2006.01) | |
| C07D 487/10 | (2006.01) | |
| C07D 519/00 | (2006.01) | |
| C07F 9/6584 | (2006.01) | |

(52) U.S. Cl.
CPC ........ *A61K 31/519* (2013.01); *A61K 31/4985* (2013.01); *A61K 31/53* (2013.01); *A61K 31/541* (2013.01); *A61K 31/635* (2013.01); *A61K 31/675* (2013.01); *C07D 487/04* (2013.01); *C07D 519/00* (2013.01); *C07F 9/6584* (2013.01); *C07B 2200/05* (2013.01)

(58) Field of Classification Search
CPC .. A61K 31/519; A61K 31/4985; A61K 31/53; A61K 31/541; A61K 31/635; A61K 31/675; C07D 487/04; C07D 519/00; C07D 487/10; C07F 9/6584; C07B 2200/05; A61P 35/02
See application file for complete search history.

(56) References Cited

U.S. PATENT DOCUMENTS

| | | | |
|---|---|---|---|
| 2003/0153752 A1 | 8/2003 | Hirst et al. | |
| 2015/0210698 A1* | 7/2015 | Ishikawa | A61K 31/4985 |
| | | | 514/249 |
| 2016/0200730 A1* | 7/2016 | He | A61P 9/00 |
| | | | 514/262.1 |
| 2021/0299128 A1 | 9/2021 | Serrano-Wu et al. | |

FOREIGN PATENT DOCUMENTS

| | | |
|---|---|---|
| CA | 3021550 A1 | 11/2016 |
| CN | 1520298 A | 8/2004 |
| CN | 105481862 A | 4/2016 |
| WO | WO-1998/041525 A1 | 9/1998 |
| WO | WO-01/19829 A2 | 3/2001 |
| WO | WO-2002/076986 A1 | 10/2002 |
| WO | WO-2002/080926 A1 | 10/2002 |
| WO | WO-2005/074603 A2 | 8/2005 |
| WO | WO-2008/121742 A2 | 10/2008 |
| WO | WO-2014/017659 A1 | 1/2014 |
| WO | WO-2014/063061 A1 | 4/2014 |
| WO | WO-2018/052120 A1 | 3/2018 |
| WO | WO-2020/239103 A1 | 12/2020 |
| WO | WO-2020/263935 A1 | 12/2020 |
| WO | WO-2021/071922 A1 | 4/2021 |
| WO | WO-2021/184154 A1 | 9/2021 |
| WO | WO-2021/188417 A1 | 9/2021 |

OTHER PUBLICATIONS

International Search Report and Written Opinion for International Application No. PCT/CN2017/079464 dated Dec. 16, 2020.
Bertoli et al., "Dexamethasone in hyperleukocytic acute myeloid leukemia," Haematologica, 103(6): 988-998 (2018).
International Search Report and Written Opinion for International Application No. PCT/US2021/022322 dated Jul. 1, 2021.
Koda et al., "Identification of pyrrolo [2,3-d] pyrimidines as potent HCK and FLT3-ITD dual inhibitors," Bioorg Med Chem Lett, 27(22): 4994-4998 (2017).
Saito et al., "A Pyrrolo-Pyrimidine Derivative Targets Human Primary AML Stem Cells in Vivo," Sci Transl Med, 5(181): 181ra52 (2013).
Song et al., "Synergistic cytotoxicity of sorafenib with busulfan and nucleoside analogs in human FLT3-ITD-positive acute myeloid leukemia cells," Biol Blood Marrow Transplant, 20(11): 1687-1695 (2014).
Wu et al., "Discovery of a highly potent FLT3 kinase inhibitor for FLT3-ITD-positive AML," Leukemia, 30(10): 2112-2116 (2016).
Yuki et al., "Activity cliff for 7-substituted pyrrolo-pyrimidine inhibitors of HCK explained in terms of predicted basicity of the amine nitrogen," Bioorg Med Chem Lett, 25(16): 4259-4264 (2017).

* cited by examiner

Primary Examiner — Joseph R Kosack
Assistant Examiner — Sagar Patel
(74) Attorney, Agent, or Firm — Foley Hoag LLP; David P. Halstead; Lawrence P. Tardibono

(57) ABSTRACT

This invention relates to compounds for treating acute myeloid leukemia or inhibiting recurrence of acute myeloid leukemia and for inhibiting growth of and/or killing leukemic stem cells.

19 Claims, No Drawings

COMPOUNDS FOR TREATING OR INHIBITING RECURRENCE OF ACUTE MYELOID LEUKEMIA

This application claims the benefit of International Patent Application No. PCT/CN20/79464, filed Mar. 16, 2020, which is hereby incorporated by reference in its entirety.

BACKGROUND

Acute myeloid leukemia (hereafter also referred to as "AML") is a hematological malignancy with a poor prognosis that often occurs in adults, and the 5-year survival rate thereof is predicted to be 20%. In some cases, it is possible to temporarily reduce the number of AML cells to a level below the detection limit through AML treatment. This condition is referred to as "complete remission." However, AML often recurs despite achieving complete remission, and for many patients, recurrent AML results in death. Accordingly, there is an urgent need to develop more durable treatments for AML.

While conventional chemotherapeutic agents would realize temporary remission of AML, its recurrence has been an issue of concern. In particular, a very low survival rate in cases of recurrence has been a serious issue of concern. New approaches for treating AML and other hematologic cancers are needed.

SUMMARY OF THE INVENTION

The present invention provides compounds that inhibit the growth of leukemic stem cells and/or treat acute myeloid leukemia, or inhibit recurrence of acute myeloid leukemia.

In some embodiments, the present disclosure relates to compounds of Formula (I):

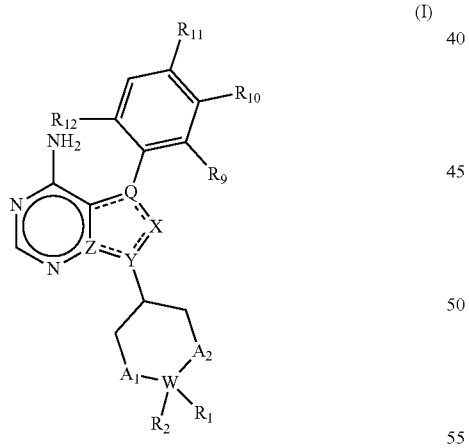

wherein
each Q, Y and Z is independently selected from N and C, and X is N or C—$R^a$;
provided that at least one of Q, X, Y and Z is N, and each dashed bond is independently a single or double bond such that the bicycle they form is a heteroaryl;
$R_1$ is selected from alkyl, alkenyl, alkynyl, amino, acylamino, cycloalkyl, cycloalkylalkyl, heterocyclyl, heterocyclylalkyl, aryl, arylalkyl, heteroaryl, and heteroaralkyl;

either
a) W is N, $R_2$ is absent, and $A_1$ and $A_2$ are each $CH_2$;
b) W is C, $R_2$ is selected from H, halo, CN, alkyl, alkoxy, hydroxy, acyloxy, and amino, and $A_1$ and $A_2$ are each independently selected from $CH_2$ and O; or
c) W is C, and $R_1$ and $R_2$ are taken together to form a =$CH_2$-amido, cycloalkyl, and heterocyclyl, and $A_1$ and $A_2$ are each independently selected from $CH_2$ and O;

$R^a$ is selected from H, halo, CN and alkyl;
$R_9$ is selected from H, halo, alkyl, alkoxy, hydroxy, acyloxy, and amino;
$R_{10}$ is H or alkoxy;
$R_{11}$ is aryloxy, heteroaryloxy, arylalkyl, alkoxycarbonyl, ureido or —C(O)-aryl; and
$R_{12}$ is selected from H, halo, CN, alkyl, alkoxy, hydroxy, and acyloxy;
provided that the compound of Formula (I) is not

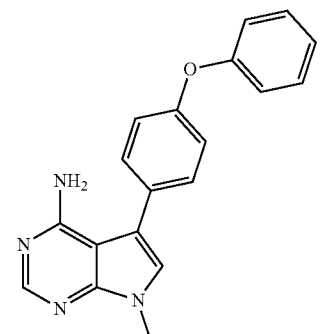

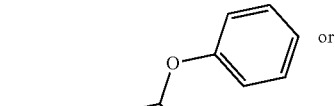

or

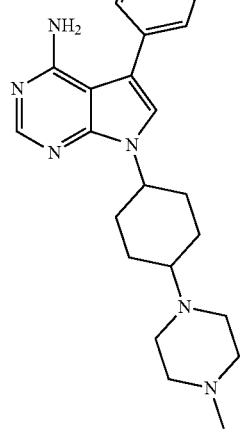

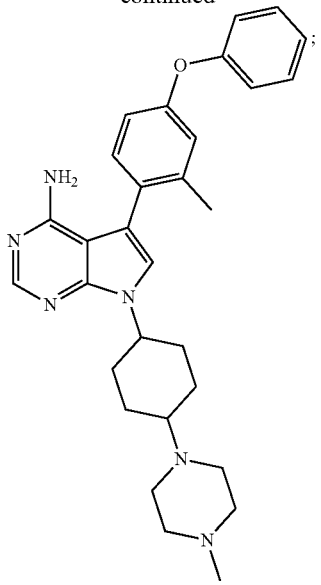

and if W is C, $R_2$, $R_9$ and $R_{12}$ are each hydrogen, and $R_{11}$ is unsubstituted phenyloxy, then $R_1$ is not —NHCH$_2$OH, —NHCH$_2$COOH, —NHCH$_2$CONH$_2$, —NHCH$_2$CH$_2$NH$_2$, —NH(CH$_2$)$_2$N(Me)$_2$, —NHCH$_2$-pyridinyl, —NHCO-pyridyl, —C(O)OEt, —NH-tetrahydropyran, —NH(CH$_2$)$_3$imidazolyl, —NHCH$_2$pyrrolidinyl, —NHpyrrolidinonyl,

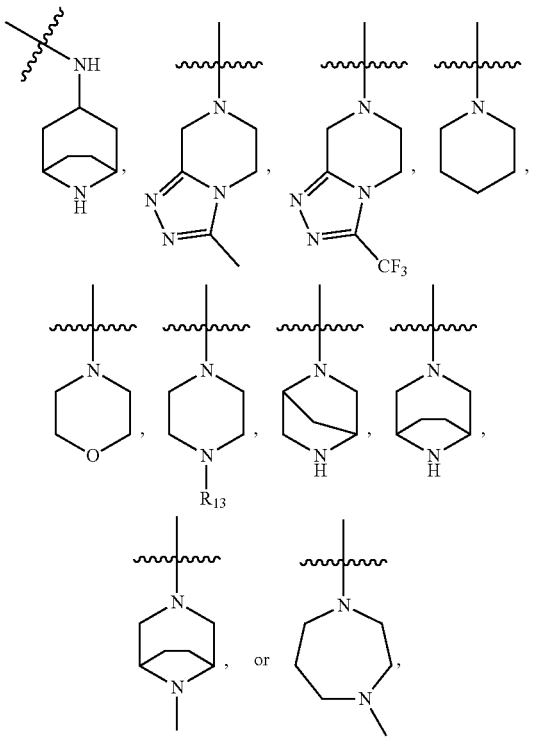

wherein $R_{13}$ is selected from H, ethyl, isopropyl, t-butyl, —CH$_2$OCH$_3$, —CH$_2$CH$_2$OH and —CH$_2$CH$_2$OCH$_3$; and if W is N, $R_9$ and $R_{12}$ are each hydrogen, and $R_{11}$ is unsubstituted phenyloxy, then $R_1$ is not piperidinyl.

The present disclosure further relates to methods of co-inhibiting HCK and BCL-2 in cells, comprising contacting the cells with a compound disclosed herein and a BCL-2 inhibitor.

The present disclosure further relates to methods of killing cells having an FLT3-ITD mutation, comprising contacting the cells with a compound disclosed herein and a BCL-2 inhibitor.

The present disclosure further relates to methods of treating acute myeloid leukemia, comprising conjointly administering to a subject a compound disclosed herein and a BCL-2 inhibitor.

DETAILED DESCRIPTION

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —$CN$ and the like. Exemplary substituted alkyls are described below. Cycloalkyls can be further substituted with alkyls, alkenyls, alkoxys, alkylthios, aminoalkyls, carbonyl-substituted alkyls, —$CF_3$, —$CN$, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

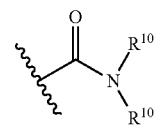

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

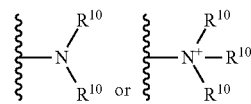

wherein each $R^{10}$ independently represents a hydrogen or a hydrocarbyl group, or two $R^{10}$ are taken together with the N atom to which they are attached complete a heterocycle having from 4 to 8 atoms in the ring structure. The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably, the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

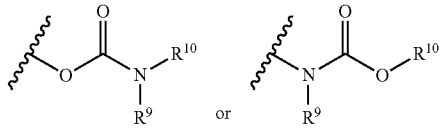

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

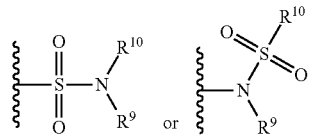

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

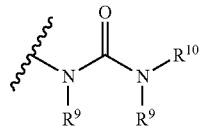

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the subject of one or more of the disclosed compositions. If it is administered prior to clinical manifestation of the unwanted condition (e.g., disease or other unwanted state of the subject) then the treatment is prophylactic (i.e., it protects the subject against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of Formula (I)). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of Formula (I) in a formulation represented above can be replaced with the corresponding suitable prodrug, e.g., wherein a hydroxyl in the parent compound is presented as an ester or a carbonate or carboxylic acid.

An "effective amount", as used herein, refers to an amount that is sufficient to achieve a desired biological effect. A "therapeutically effective amount", as used herein refers to an amount that is sufficient to achieve a desired therapeutic effect. For example, a therapeutically effective amount can refer to an amount that is sufficient to improve at least one sign or symptom of cancer.

A "response" to a method of treatment can include a decrease in or amelioration of negative symptoms, a decrease in the progression of a disease or symptoms thereof, an increase in beneficial symptoms or clinical outcomes, a lessening of side effects, stabilization of disease, partial or complete remedy of disease, among others.

Overview

In certain embodiments, provided herein is a compound of formula (I):

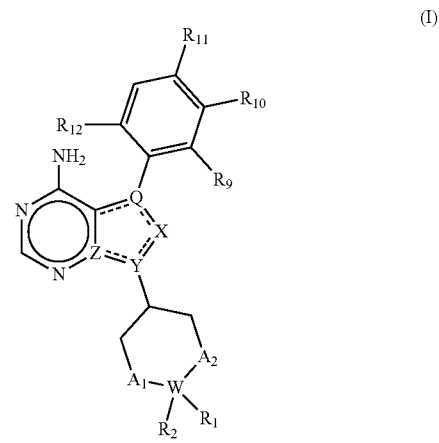

wherein each Q, Y and Z are independently selected from N and C, and X is N or C—$R^a$;

provided that at least one of Q, X, Y and Z is N, and each dashed bond is independently a single or double bond such that the bicycle they form is a heteroaryl;

$R_1$ is selected from alkyl, alkenyl, alkynyl, amino, acylamino, cycloalkyl, cycloalkylalkyl, heterocyclyl, heterocyclylalkyl, aryl, arylalkyl, heteroaryl, and heteroaralkyl;

either a) W is N, $R_2$ is absent, and $A_1$ and $A_2$ are each $CH_2$;

b) W is C, $R_2$ is selected from H, halo, CN, alkyl, alkoxy, hydroxy, acyloxy, and amino, and $A_1$ and $A_2$ are each independently selected from $CH_2$ and O; or c) W is C, and $R_1$ and $R_2$ are taken together to form a =$CH_2$-amido, cycloalkyl, and heterocyclyl, and $A_1$ and $A_2$ are each independently selected from $CH_2$ and O;

$R^a$ is selected from H, halo, CN and alkyl;

$R_9$ is selected from H, halo, alkyl, alkoxy, hydroxy, acyloxy, and amino;

$R_{10}$ is H or alkoxy;

$R_{11}$ is aryloxy, heteroaryloxy, arylalkyl, alkoxycarbonyl, ureido or —C(O)-aryl; and $R_{12}$ is selected from H, halo, CN, alkyl, alkoxy, hydroxy, and acyloxy;

provided that the compound of Formula (I) is not

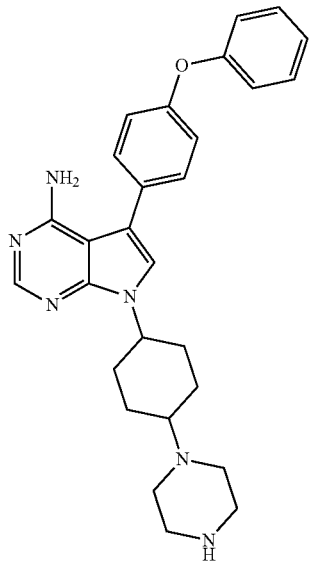

or

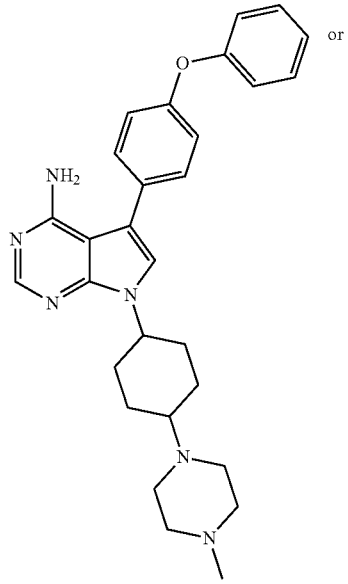

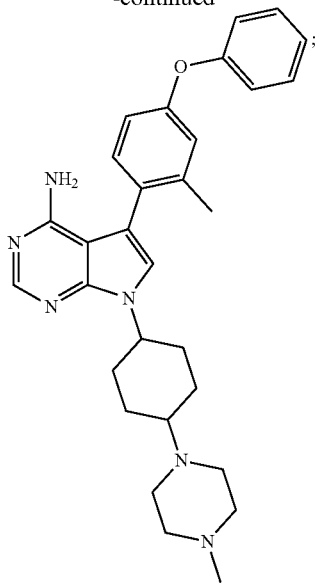

and if W is C, $R_2$, $R_9$ and $R_{12}$ are each hydrogen, and $R_{11}$ is unsubstituted phenyloxy, then $R_1$ is not —NHCH$_2$OH, —NHCH$_2$COOH, —NHCH$_2$CONH$_2$, —NHCH$_2$CH$_2$NH$_2$, —NH(CH$_2$)$_2$N(Me)$_2$, —NHCH$_2$-pyridinyl, —NHCO-pyridyl, —C(O)OEt, —NH-tetrahydropyran, —NHCH$_2$pyrrolidinyl, —NH(CH$_2$)$_3$imidazolyl, —NHpyrrolidinonyl,

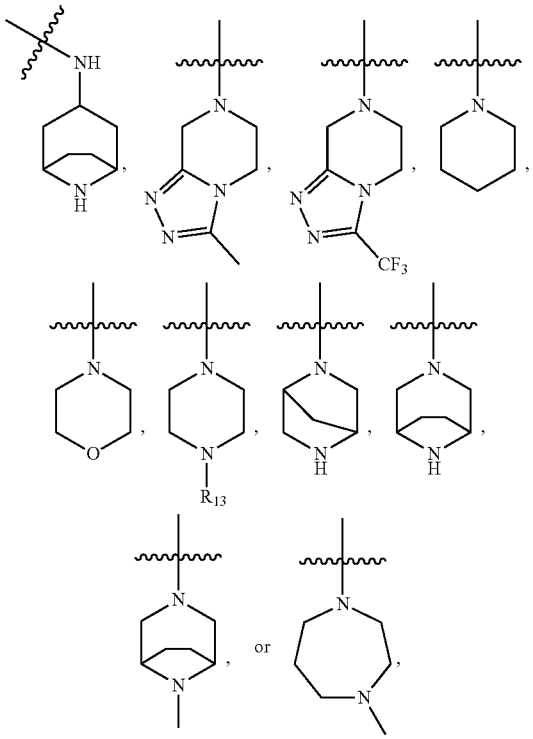

wherein $R_{13}$ is selected from H, ethyl, isopropyl, t-butyl, —CH$_2$OCH$_3$, —CH$_2$CH$_2$OH and —CH$_2$CH$_2$OCH$_3$; and if W is N, R₉ and R₁₂ are each hydrogen, and R₁₁ is unsubstituted phenyloxy, then R₁ is not piperidinyl.

In certain embodiments, the compound has the structure:

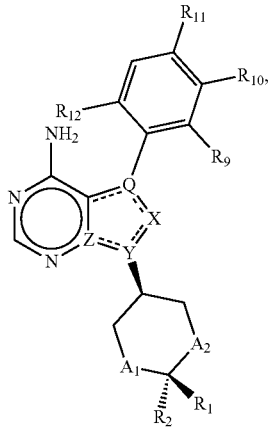

wherein $R_2$ is H.

In other embodiments, the compound has the structure:

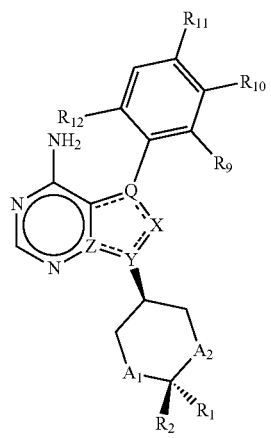

wherein $R_2$ is H.

In other embodiments, the compound has the structure:

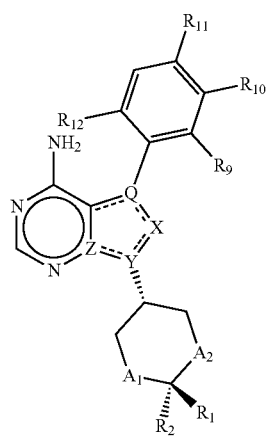

wherein $R_2$ is H.

In other embodiments, the compound has the structure:

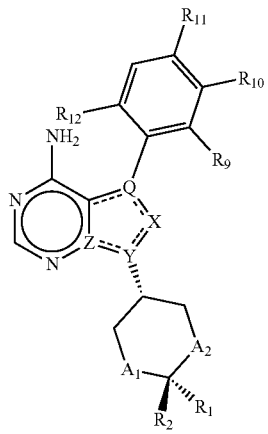

wherein $R_2$ is H.

In some embodiments, at least two of Q, X, Y, and Z are N. In some such embodiments, at least three of Q, X, Y, or Z are N. In some such embodiments, all of Q, X, Y, and Z are N.

In some embodiments, at least Q is N.

In some embodiments, at least X is N. In some such embodiments, at least X and Z are N.

In some embodiments, at least Y is N. In some such embodiments, at least X and Y are N.

In some embodiments, at least Z is N.

In some embodiments, $R_1$ is

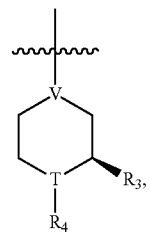

V is N or CH; T is N or CH; $R_3$ is alkyl; and $R_4$ is H or alkyl.

In some embodiments, $R_1$ is

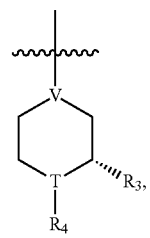

V is N or CH; T is N or CH; $R_3$ is alkyl; and $R_4$ is H or alkyl.

In some embodiments, Q is C, X is C—R$^a$, R$^a$ is H, Y is N and Z is C; Q is C, X is C—R$^a$R$^a$ is halo, Y is N and Z is C; Q is C, X is N, Y is C and Z is N; Q is C, X is N, Y is N and Z is C; Q is N, X is C—R$^a$, R$^a$ is H, Y is C and Z is C; Q is C, X is C—R$^a$, R$^a$ is H, Y is C and Z is N; or Q is C, X is C—R$^a$, R$^a$ is H, Y is N and Z is C.

In some embodiments, Q is C, X is N, Y is C and Z is N; Q is C, X is C—$R^a$, $R^a$ is H, Y is N and Z is C; or Q is C, X is N, Y is N and Z is C.

In some embodiments, $A_1$ and $A_2$ are both $CH_2$. In other embodiments, $A_1$ and $A_2$ are both O.

In some embodiments, W is N and $R_2$ is absent. In other embodiments, W is C.

In some embodiments, $R_2$ is selected from H, hydroxy and amino.

In some embodiments, $R_1$ is selected from alkyl, amino, cycloalkyl, heterocyclyl, heterocyclylalkyl, and heteroaryl. In certain preferred embodiments, $R_1$ is a 6-membered heterocyclyl, preferably comprising 2 nitrogen ring atoms. In particularly preferred embodiments, $R_1$ is a 1,4-piperazinyl ring.

In certain such embodiments, $R_1$ is selected from

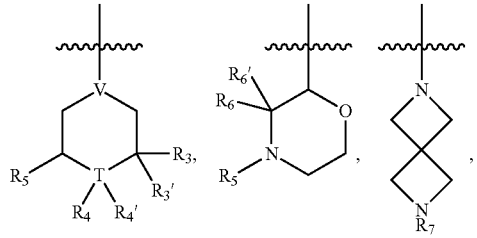

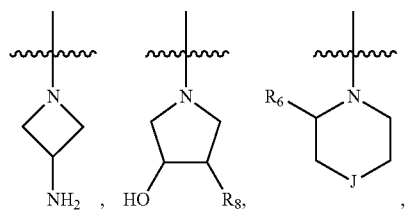

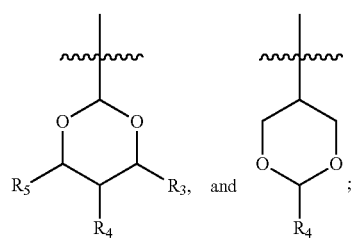

wherein V is N or CH; either T is N and $R_4'$ is absent, or T is C; J is selected from sulfonyl, C(H)sulfonamido, and >P(=O)-alkyl; $R_3$ is selected from H, halo, CN, alkyl, alkoxy, hydroxy, acyloxy, amino, amido, cycloalkyl, heterocyclyl, carboxy, and alkoxycarbonyl; $R_3'$ is H or alkyl, or $R_3$ and $R_3'$ taken together with the carbon atom to which they are attached form a cycloalkyl; $R_4$ is selected from H, halo, CN, alkyl, alkoxy, acyloxy, amino, and amido; $R_4'$ is H or alkyl; $R_5$ is H or alkyl; $R_6$ and $R_6'$ are each H; $R_6$ and $R_6'$ together with the carbon atom to which they are attached form an oxo; $R_7$ is H or alkyl; and $R^8$ is H, hydroxy, acyloxy, or amino.

In some such embodiments, $R^1$ is

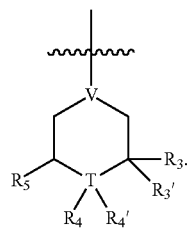

In some such embodiments, V is N. In other such embodiments, V is CH.

In some such embodiments, T is N. In other such embodiments, T is C.

In certain embodiments, W is C, $R_2$ is H, V is CH, and T is N. In other embodiments, W is C, $R_2$ is H, V is N and T is C. In still other embodiments, W is C, $R_2$ is H, V is N, and T is N. In still further other embodiments, W is N, $R_2$ is absent, V is CH, and T is N.

In some embodiments, $R_3$ is selected from H, alkyl, amino, cycloalkyl, heterocyclyl, carboxy, and alkoxycarbonyl. In certain such embodiments, $R_3$ is H. In other such embodiments, $R_3$ is alkyl. In some such embodiments, $R_3$ is methyl.

In some embodiments, each $R_4$ is independently selected from H, alkyl, amino, and amido. In certain such embodiments, $R_4$ is H. In other such embodiments, $R_4$ is alkyl. In some such embodiments, $R_4$ is methyl.

In some embodiments, $R_5$ is H.

In certain embodiments, $R_9$ is selected from halo, alkyl, alkoxy, hydroxy, acyloxy, and amino, preferably alkyl or halo, most preferably halo. In certain most preferred embodiments, $R_9$ is F.

In some embodiments, $R_{12}$ is H or halo.

In some embodiments, $R_{11}$ is selected from amido,

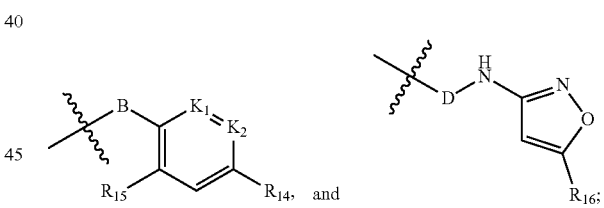

wherein B is selected from —O—, $CH_2$, CHOH, NH, $N(C_{1-6}alkyl)$ and carbonyl; $K_1$ and $K_2$ are independently selected from N and $CR_{13}$; D is selected from —$CH_2$—C(O)—, —NH—C(O)—, $N(C_{1-6}alkyl)$-C(O), and —$CH_2S(O)_2$—; $R_{13}$ is selected from H, halo, CN, alkyl, alkoxy, hydroxy, acyloxy, alkoxycarbonyl, amino, amido, and alkoxycarbonyl; $R_{14}$ is selected from H, halo, CN, alkyl, alkoxy, hydroxy, acyloxy, alkoxycarbonyl, amino, amido, and alkoxycarbonyl; $R_{15}$ is selected from H, halo, CN, alkyl, alkoxy, hydroxy, acyloxy, alkoxycarbonyl, amino, amido, and alkoxycarbonyl; and $R_{16}$ is selected from H, halo, CN, alkyl, alkoxy, hydroxy, acyloxy, amino, amido, and alkoxycarbonyl.

In some embodiments, B is —O—.

In some embodiments, $K_1$ is $CR_{13}$. In some such embodiments, $R_{13}$ is selected from H, halo, CN, and alkyl. In certain such embodiments, $R_{13}$ is H or F.

In some embodiments, $R_{14}$ is H or alkyl.

In some embodiments, $R_{15}$ is H or halo.

In some embodiments, D is —NHC(O)—.
In some embodiments, $R_{16}$ is H or alkyl.
In some embodiments, $R_{11}$ is

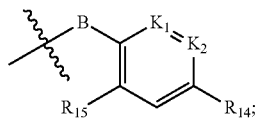

wherein B is O; $K_1$ and $K_2$ are each CH; $R_{14}$ is H; and $R_{15}$ is H. In other embodiments, $R_{11}$ is

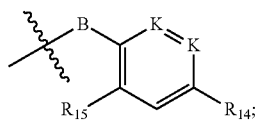

wherein $K_1$ and $K_2$ are each N; and $R_{14}$ and $R_{15}$ are each H. In still other embodiments, $R_{11}$ is

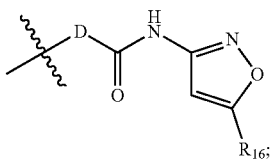

wherein D is NH; and $R_{16}$ is alkyl.

In certain preferred embodiments, the compound of formula (I) is selected from

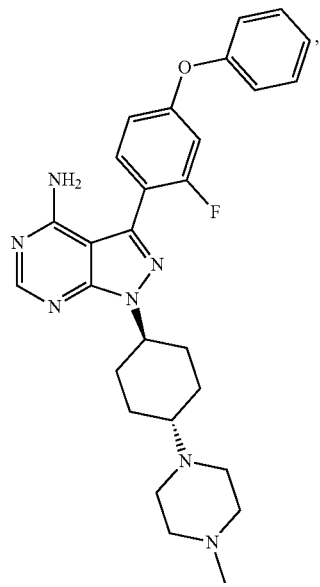

(1)

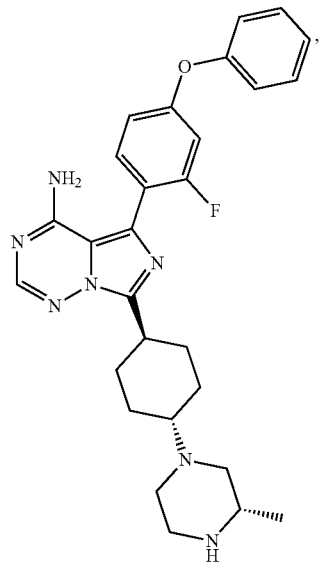

(2)

(3)

(4)
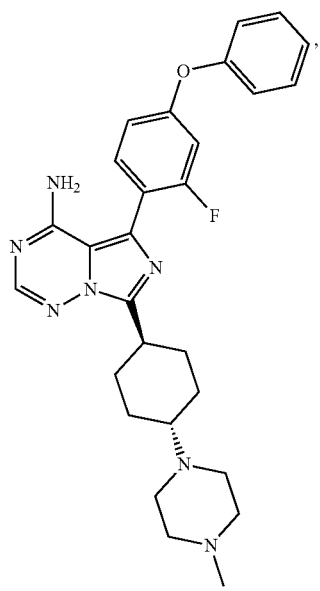
(7)
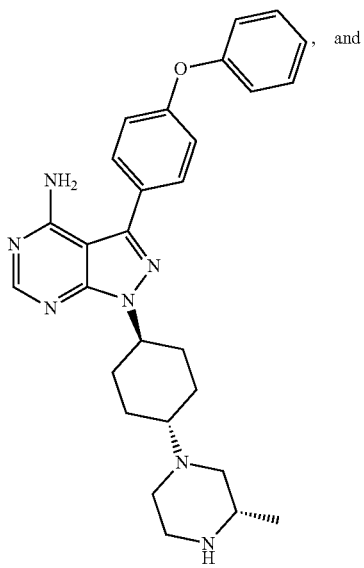
, and
(6)
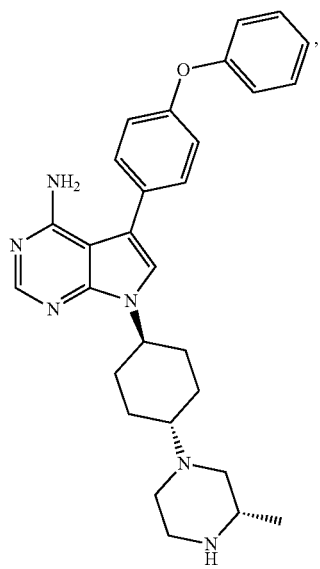
(8)
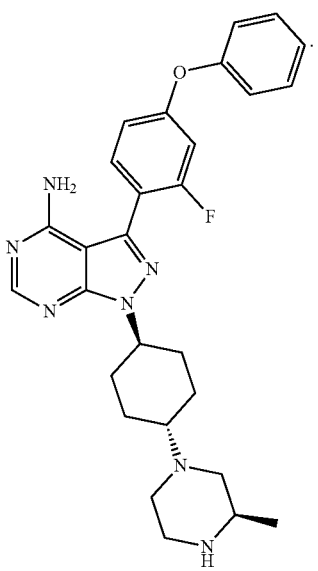
In some such preferred embodiments, the compound of formula (I) is selected from (1)
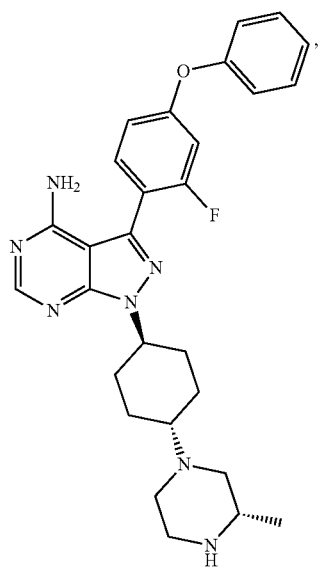
(2)
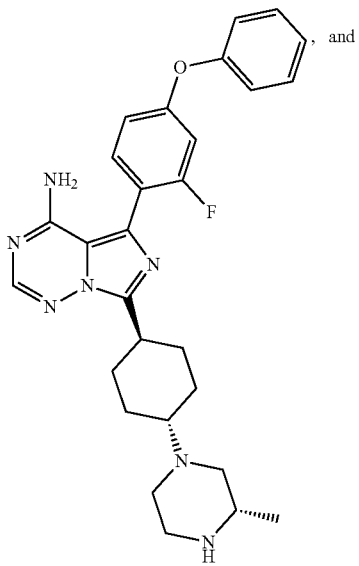
(3)
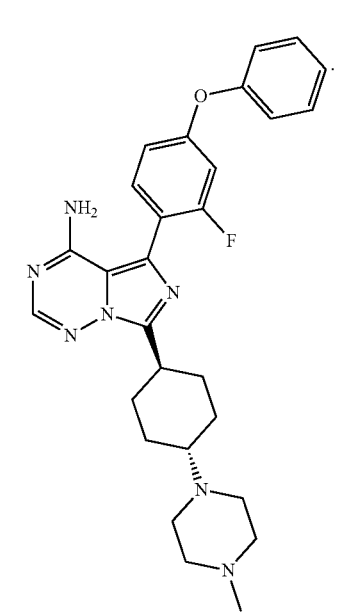
, and
(4)

For example, the compound of formula (I) may be

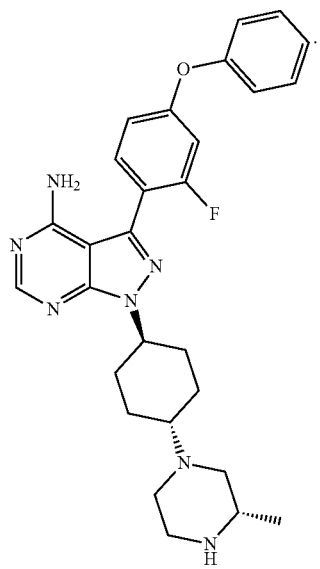
(1)

Alternatively, the compound of formula (I) may be

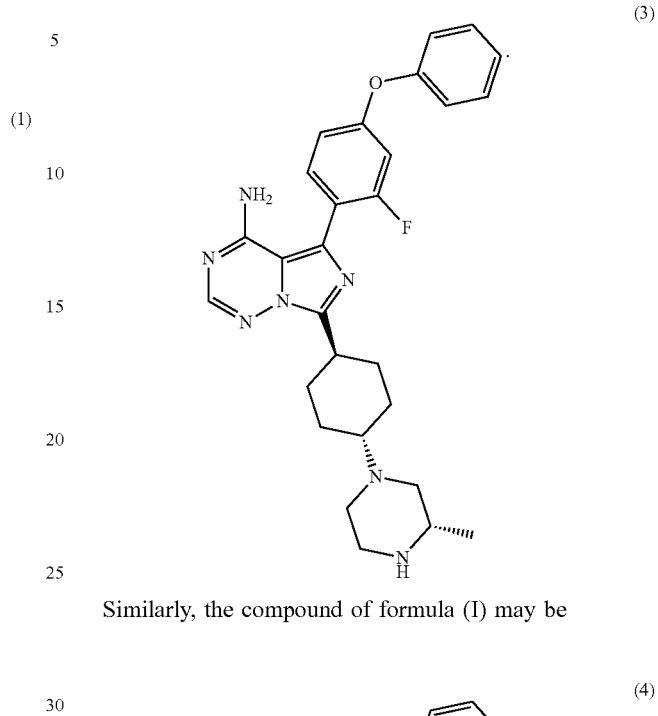

(3)

Similarly, the compound of formula (I) may be (4)

Alternatively, the compound of formula (I) may be

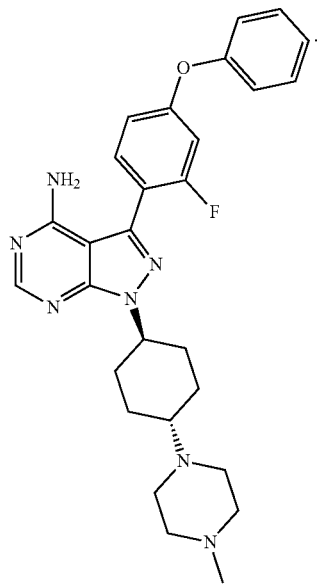
(2)

In certain embodiments, provided herein is a method of co-inhibiting HCK and BCL-2 in a cell, comprising contacting the cell with a compound of formula (I) and a BCL-2 inhibitor. In certain preferred embodiments, the compound is a HCK inhibitor. In some such embodiments, the HCK inhibitor is a dual HCK/FLT3-ITD inhibitor. In certain embodiments, the method further comprises contacting the cell with an FLT3-ITD inhibitor.

In certain embodiments, provided herein is a method of killing a cell having an FLT3-ITD mutation, comprising contacting the cell with a compound of formula (I) and a BCL-2 inhibitor. In certain preferred embodiments, the compound is a HCK inhibitor. In some such embodiments, the HCK inhibitor is a dual HCK/FLT3-ITD inhibitor. In certain embodiments, the method further comprises contacting the cell with an FLT3-ITD inhibitor.

In certain embodiments, provided herein is a method of treating acute myeloid leukemia, comprising conjointly administering to a subject a compound of formula (I) and a BCL-2 inhibitor. In some such embodiments, the subject has FLT3-ITD+ acute myeloid leukemia. In certain such embodiments, the subject has malignant hematopoiesis and/or non-malignant multilineage hematopoiesis characterized by cells having one or more mutations in a gene selected from DNMT3A, IDH2, IDH1, NPM1, TET2, CEBPA, ASXL1, EZH2, SETBP1, SMC3, KIT, NRAS, and WT1. In some such embodiments, the compound of formula (I) is a HCK inhibitor. In certain such embodiments, the method further comprises conjointly administering a FLT3-ITD inhibitor. In other such embodiments, the HCK inhibitor is a dual HCK/FLT3-ITD inhibitor.

In certain embodiments, the HCK inhibitor, the FLT3-ITD inhibitor, and the BCL-2 inhibitor are administered simultaneously or sequentially in separate unit dosage forms. In other embodiments, the method comprises administering a single unit dosage form comprising an HCK inhibitor, a BCL-2 inhibitor, and a pharmaceutically acceptable carrier, adjuvant, or vehicle. In some such embodiments, the single unit dosage form further comprises an FLT3-ITD inhibitor, or wherein the HCK inhibitor is a dual HCK/FLT3-ITD inhibitor.

In certain embodiments, the FLT3-ITD inhibitor is selected from AC220, sorafenib, PKC412, CEP-701, UNC2025, MLN518, KW-2449 and AMG-925, sunitinib, SU5614, AC2206, crenolanib, and PLX3397. In some such embodiments, the BCL-2 inhibitor is selected from AT-101, TW-37, TM-1206, gossypolic acid, gossypolonic acid, apogossypol, apogossypolone, A385358, ABT-737, ABT-263, ABT-199, WEHI-539, BXI-61, BXI-72, obatoclax, JY-1-106, and SAHB peptides. In some such embodiments, the BCL-2 inhibitor is selected from gossypol, obatoclax, ABT-737, ABT-199, and ABT-263. In some such embodiments, the BCL-2 inhibitor is ABT-199. In some such embodiments, the HCK inhibitor is (1) and the BCL-2 inhibitor is ABT-199. In other such embodiments, the HCK inhibitor is (2) and the BCL-2 inhibitor is ABT-199. In still other such embodiments, the HCK inhibitor is (3) and the BCL-2 inhibitor is ABT-199. In yet other such embodiments, the HCK inhibitor is (4) and the BCL-2 inhibitor is ABT-199. In still other such embodiments, the FLT3-ITD inhibitor is AC220 and the BCL-2 inhibitor is ABT-199. In other embodiments, the FLT3-ITD inhibitor is SU5614 and the BCL-2 inhibitor is ABT-737. In some such embodiments, the HCK inhibitor, and/or FLT3-ITD inhibitor, and/or the BCL-2 inhibitor is each present as a pharmaceutically acceptable salt. In some such embodiments, the HCK inhibitor, and/or FLT3-ITD inhibitor, and/or the BCL-2 inhibitor is each present in a pharmaceutically acceptable composition.

Compositions and Salts

In some embodiments, disclosed compounds can be in the form of a pharmaceutically acceptable composition. Disclosed herein are pharmaceutical compositions comprising a FLT3-ITD inhibitor, and/or HCK inhibitor, and/or a BCL-2 inhibitor as described herein and a pharmaceutically acceptable carrier.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Other pharmaceutically acceptable carriers, adjuvants or vehicles include water, saline and dimethylsulfoxide, as well as other hydrophobic or hydrophilic solvents.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions.

Methods of preparing these formulations or compositions include the step of bringing into association a compound described herein with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

Provided herein are pharmaceutically acceptable salts which refer to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of the compound with a suitable base or acid, respectively. Pharmaceutically acceptable salts derived from appropriate bases include alkali metal, alkaline earth metal, ammonium and $N^+$ ($C_{1-4}$alkyl)$_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compound in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredient in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

In certain preferred embodiments, the compound of the invention is conjointly administered with a steroidal anti-inflammatory drug, such as prednisolone, dexamethasone, prednisone, methylprednisolone, beclomethasone, betamethasone, fluticasone, or hydrocortisone. In certain preferred embodiments, the compound of the invention is conjointly administered with dexamethasone. Without wishing to be bound to any particular theory, it is believed that the steroidal anti-inflammatory drug produces a synergistic effect when used in combination with a compound of the invention, as described in U.S. Patent Application Publication No. 2018/0078567, which is hereby fully incorporated herein by reference. The dosage forms of the compound of the invention and of the steroidal anti-inflammatory drug can be appropriately modified by those skilled in the art. In certain preferred embodiments, a compound of the invention is conjointly administered with a cell-cycle inhibitor. Cell-cycle inhibitors suitable for use with compounds of the invention include those known in the art, including, but not limited to, those described in Mills et al., "Recent Advances of Cell-Cycle Inhibitor Therapies for Pediatric Cancer," Cancer Research (2017) doi: 10.158/0008-5472.CAN-17-2066. Exemplary cell-cycle inhibitors suitable for use with compounds of the invention include, but are not limited to palbociclib, ribociclib, abemaciclib, flavopiridol, AT9283, Alisertib, and MK-1775. Dosage forms of a compound of the invention and of a cell-cycle inhibitor can be suitably prepared by those skilled in the art.

In certain preferred embodiments, a compound of the invention is conjointly administered with one or more other anti-apoptosis agents, such as Mcl-1 inhibitors and inhibitor of apoptosis proteins (IAP) antagonists. Suitable Mcl-1 inhibitors include, but are not limited to, those described in Chen et al., "Mcl-1 Inhibitors: A Patent Review," Expert Opinion on Therapeutic Patents (2016) doi: 10.1080/13543776.2017.1249848, which is hereby incorporated by reference herein in its entirety. Such compounds include, but not limited to,
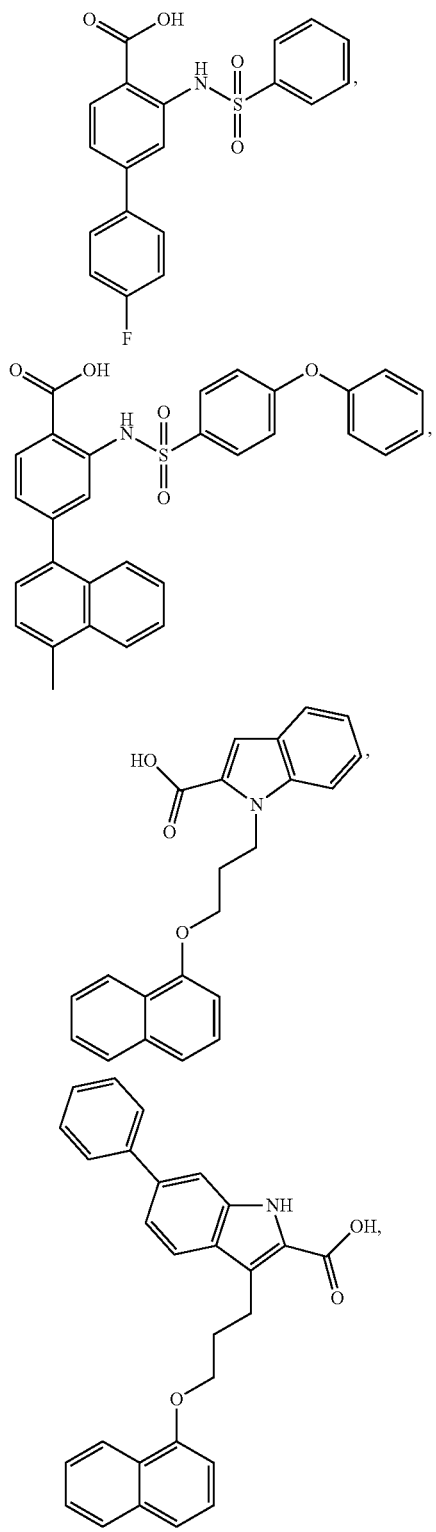
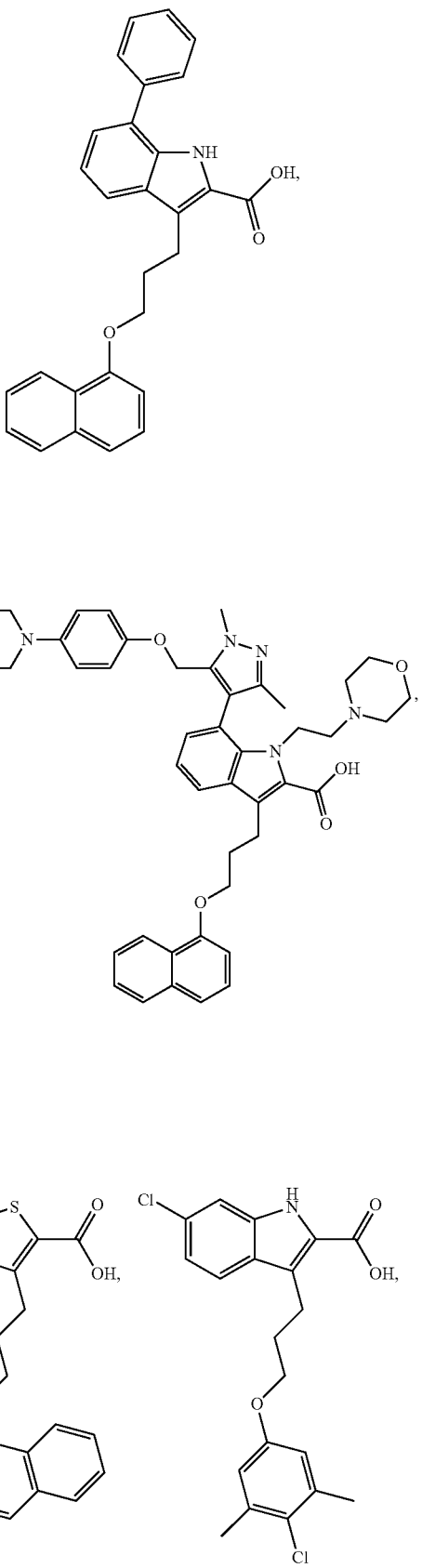

37
-continued
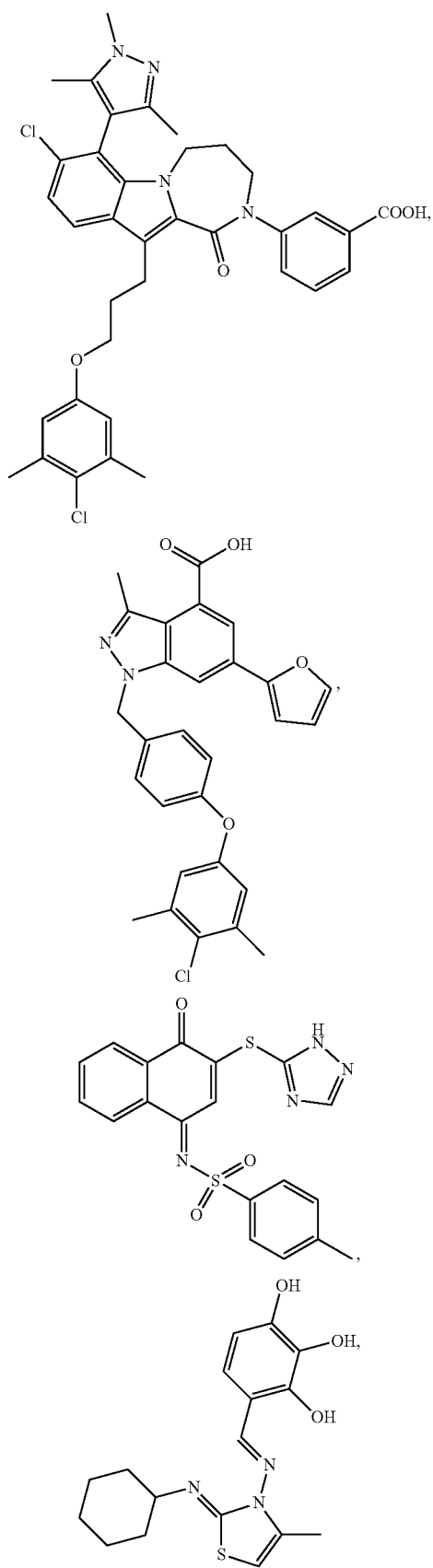
38
-continued
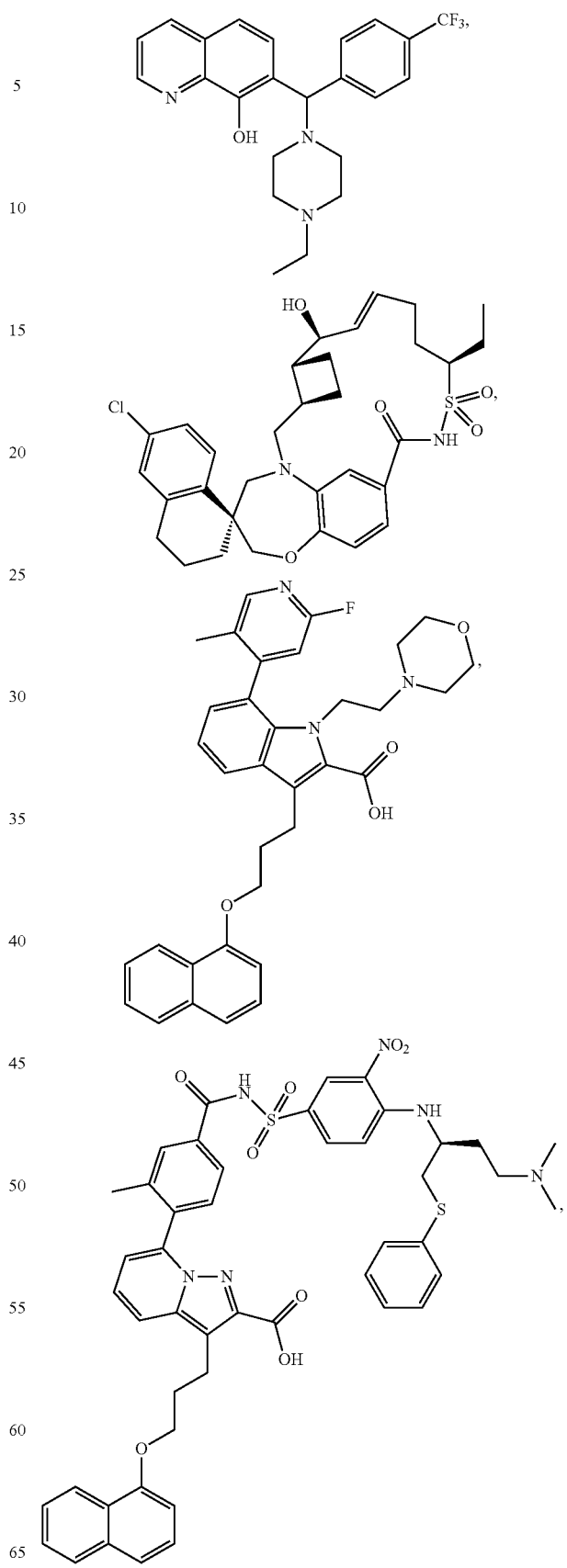

39
-continued
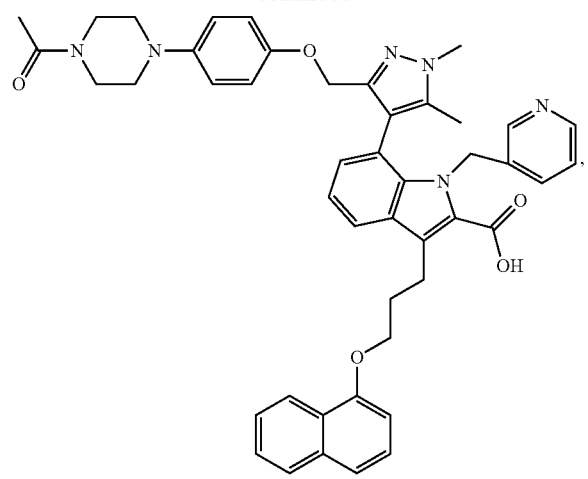
40
-continued
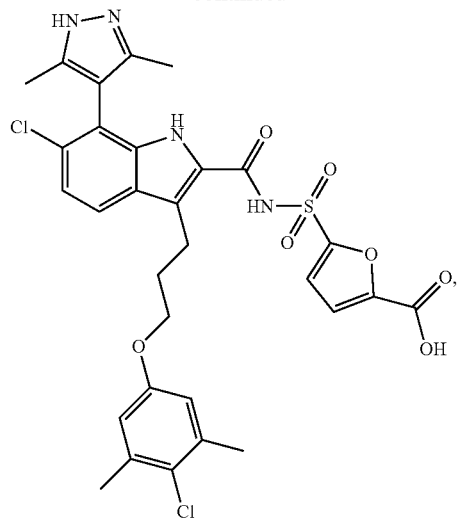
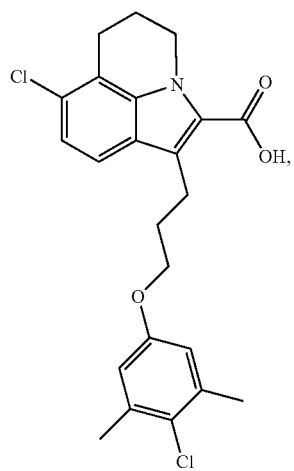
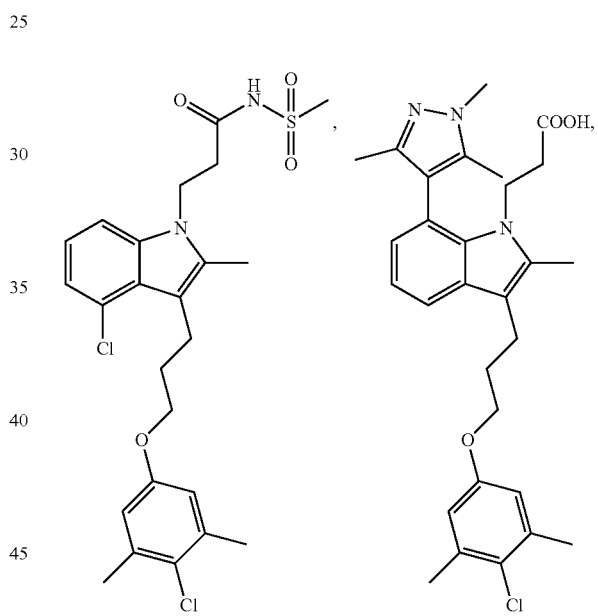
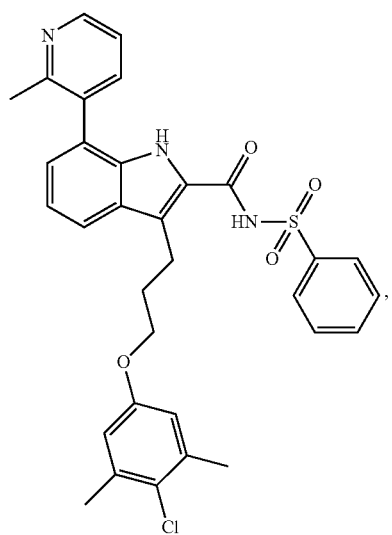

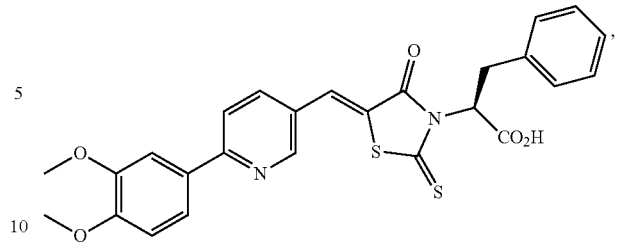
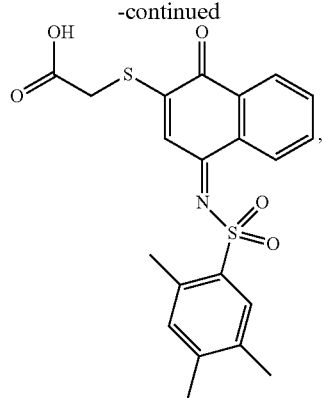
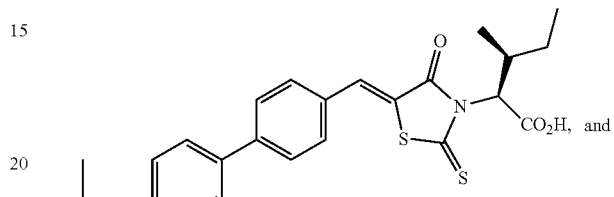
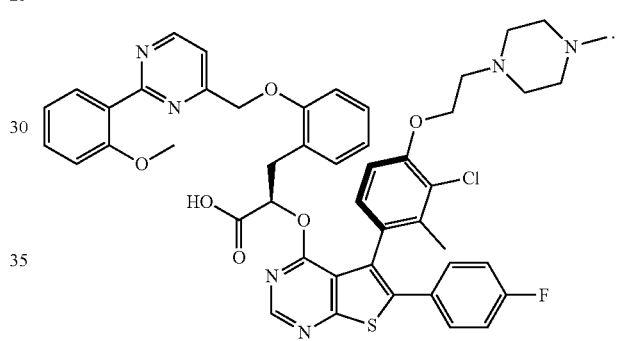
Suitable IAP antagonists include, but are not limited to, those described in Hird et al., "Small Molecule Inhibitor of Apoptosis Proteins Antagonists: a Patent Review," Expert Opinion on Therapeutic Patents (2015) doi: 10.1517/13543776.2015.1041922, which is hereby incorporated by reference herein in its entirety. Such compounds include, but are not limited to,
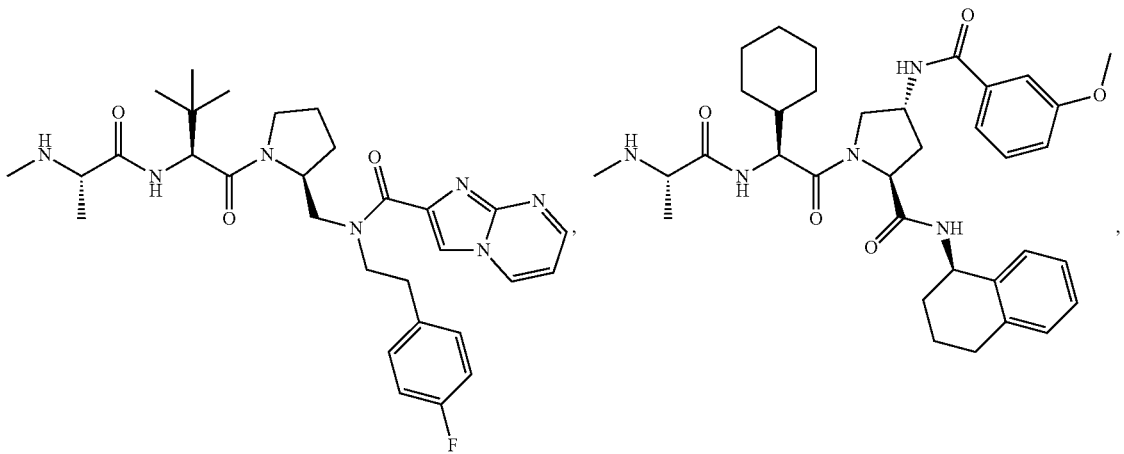

-continued
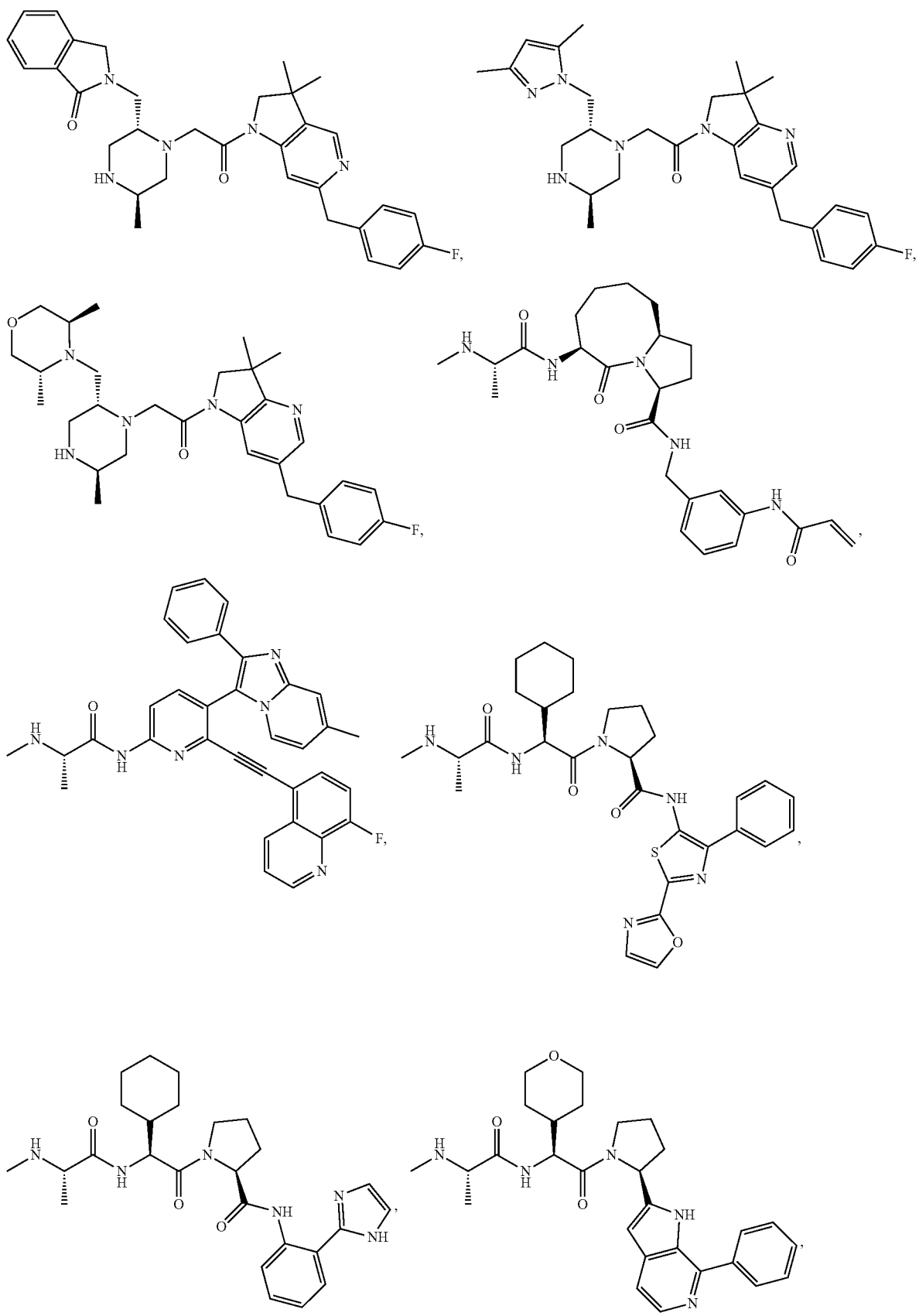

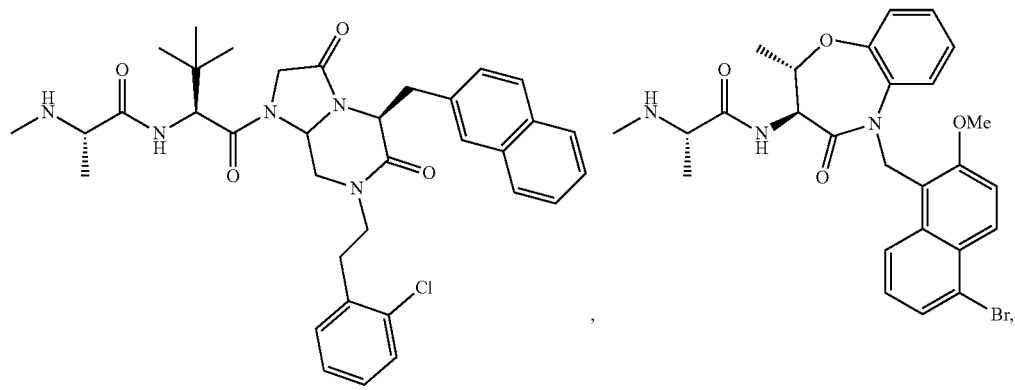
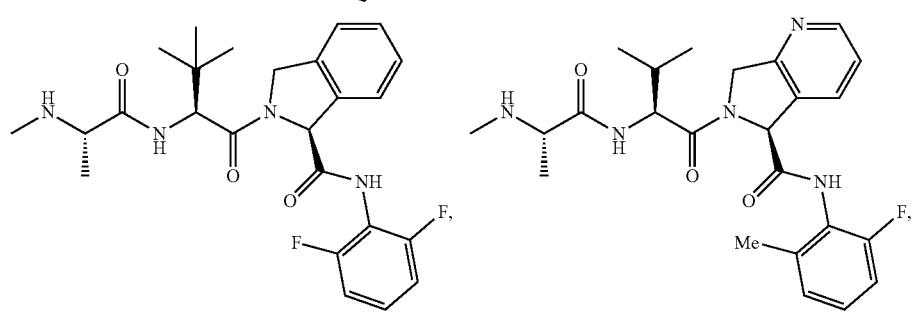
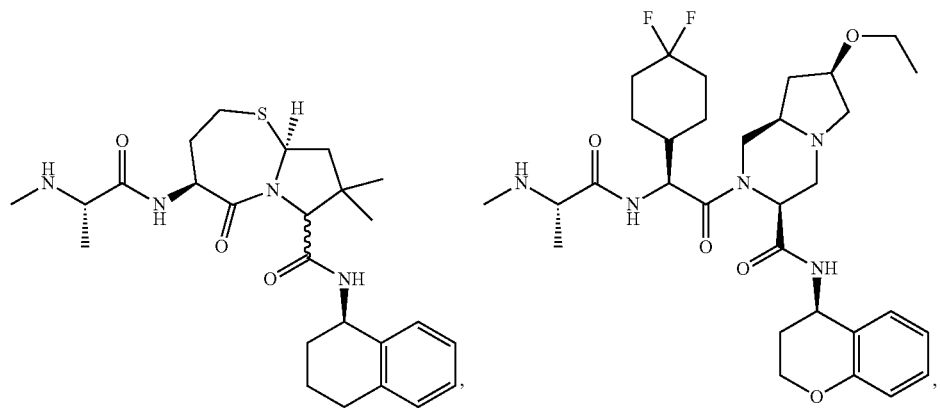
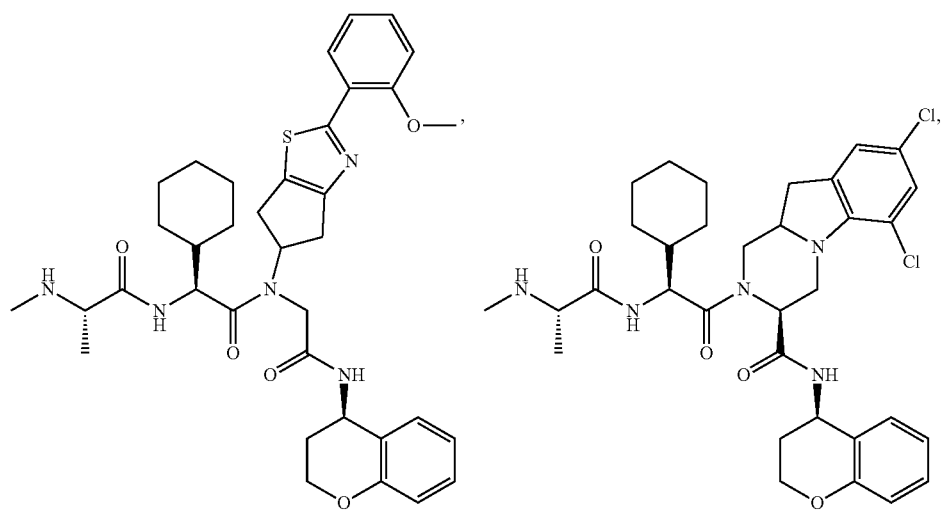

-continued
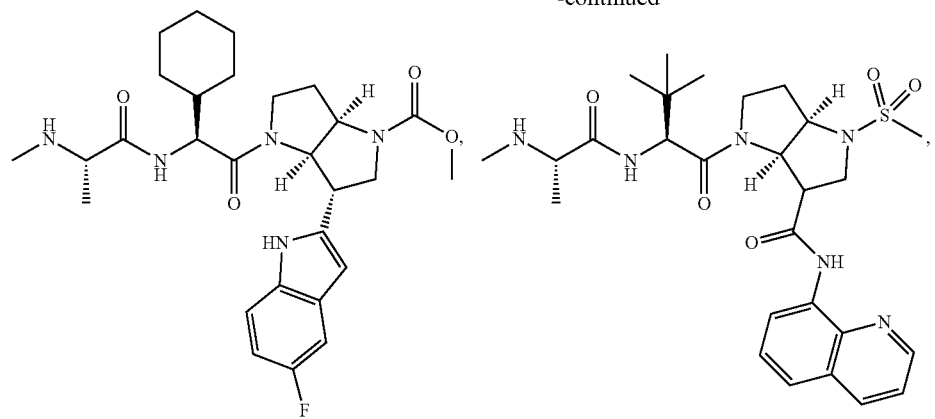
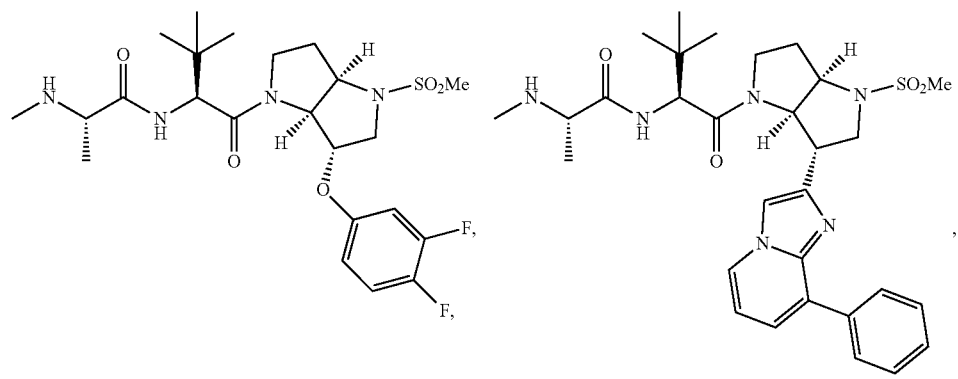
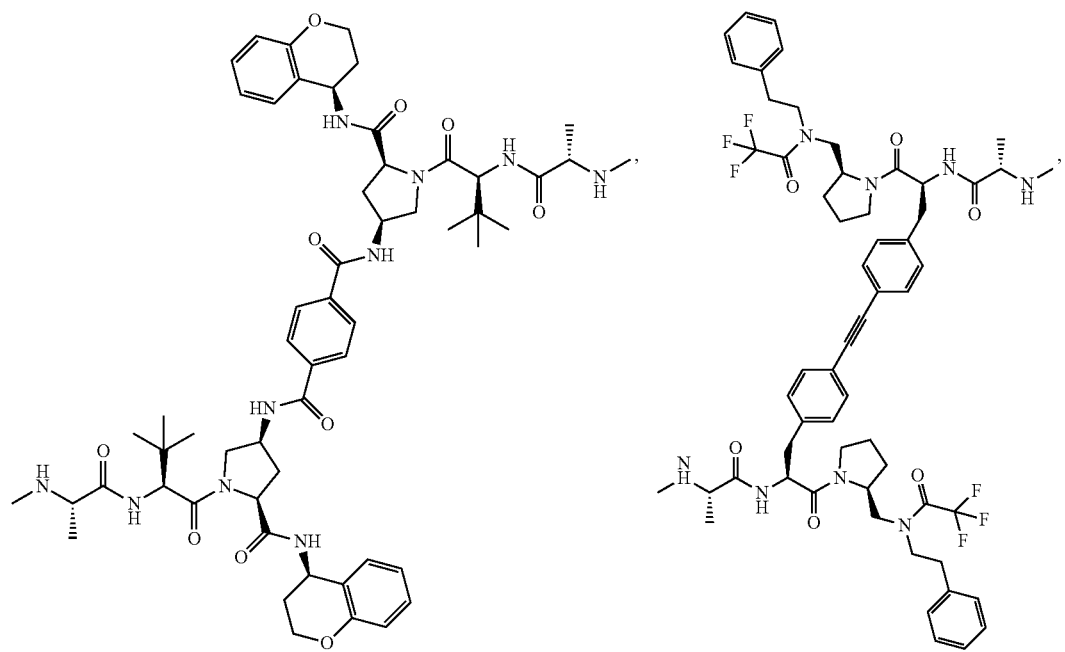

-continued
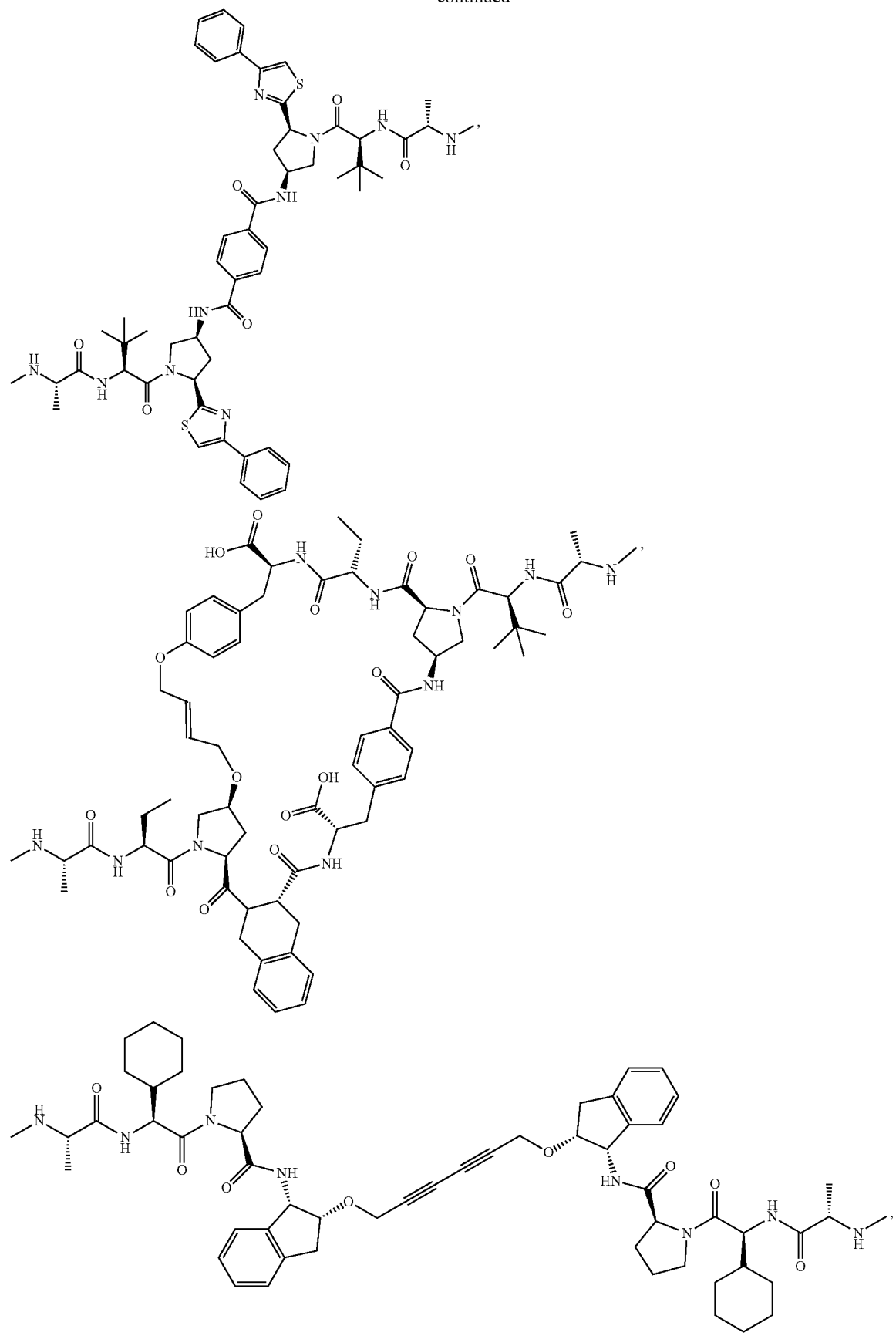

-continued
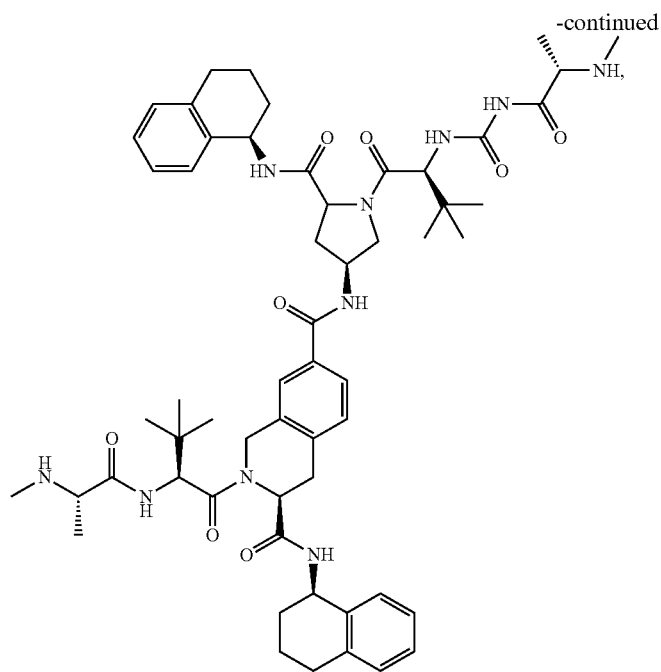
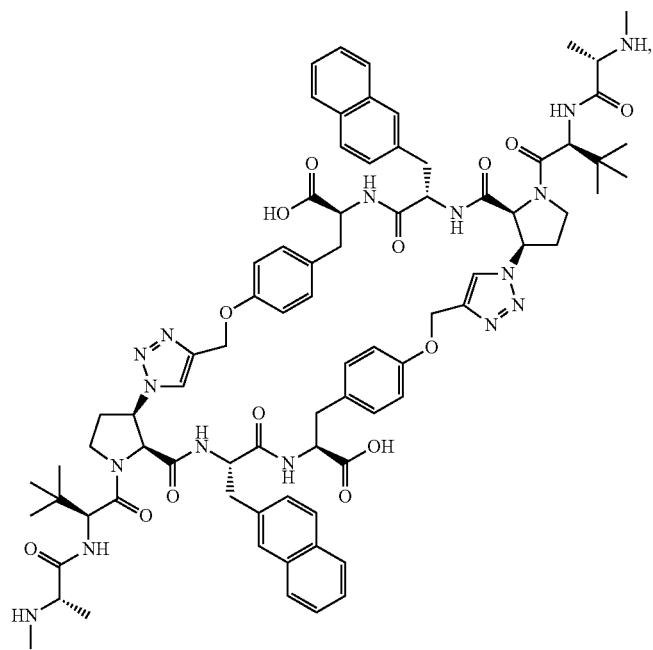

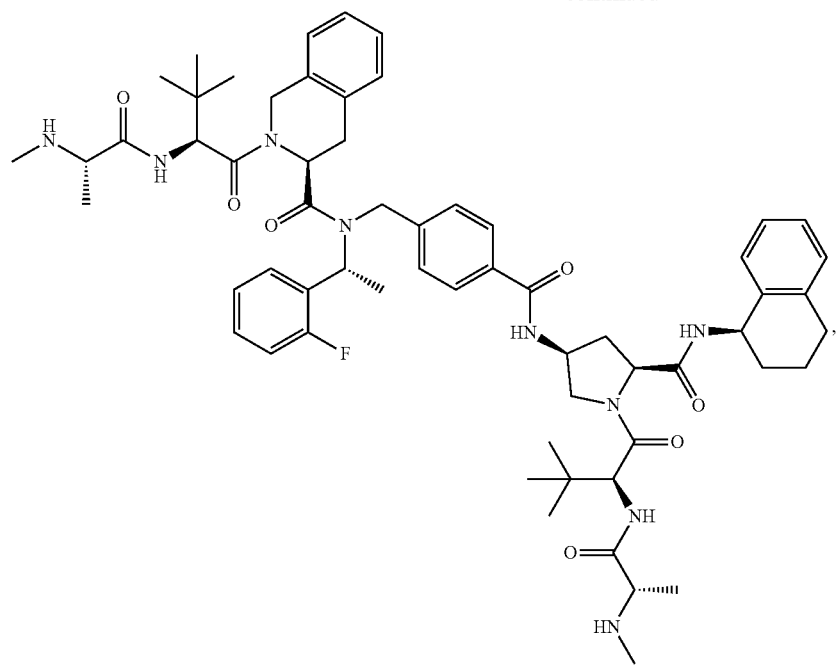
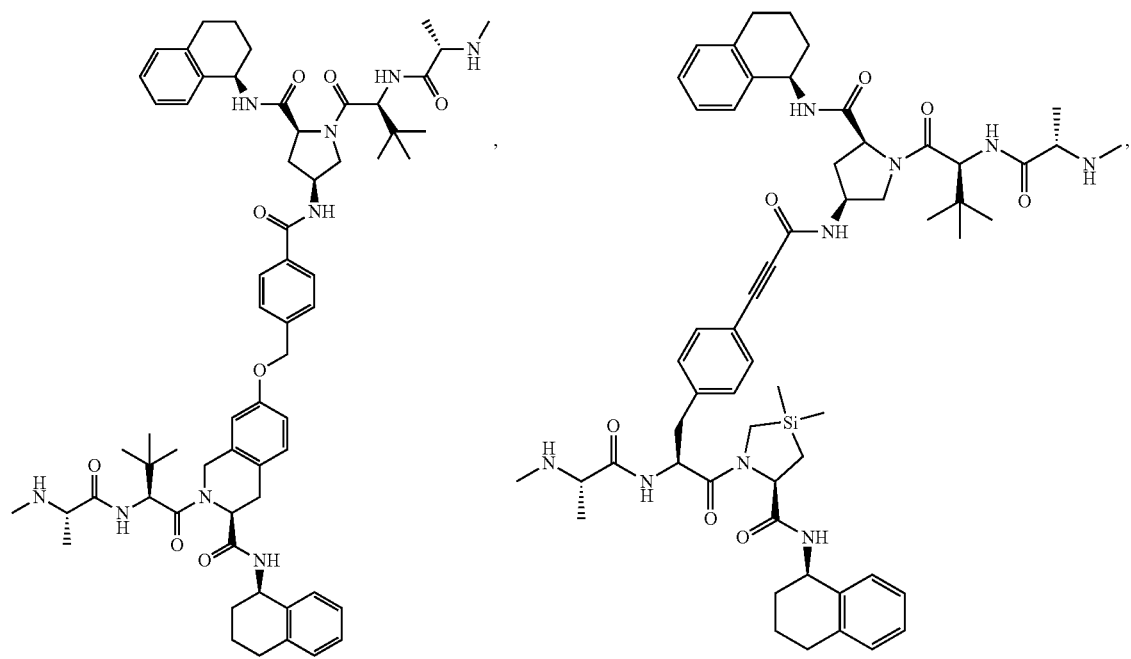

-continued
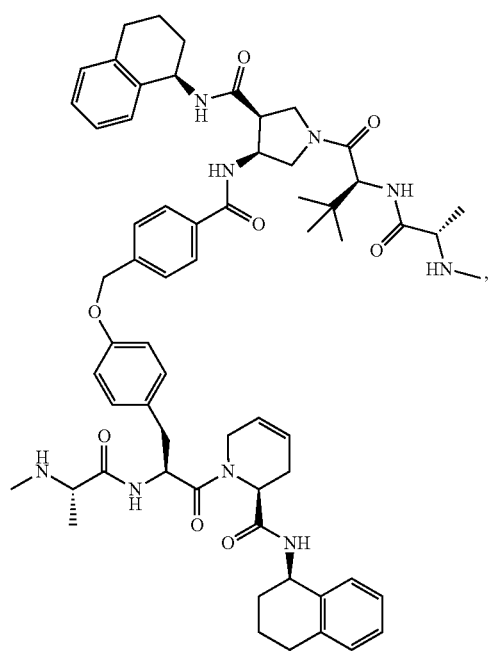
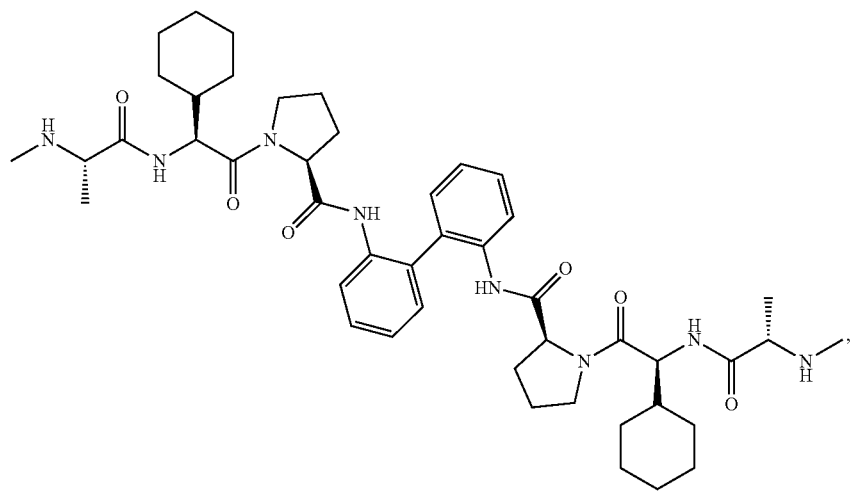

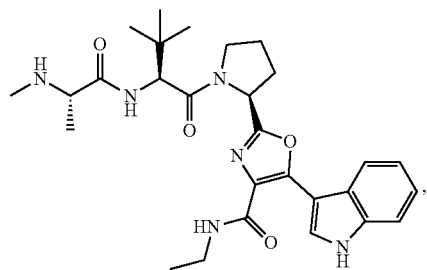
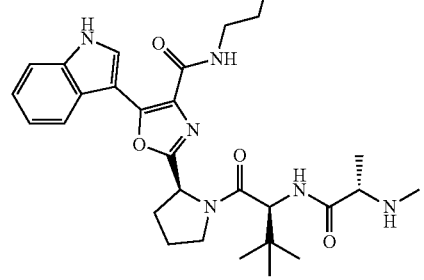
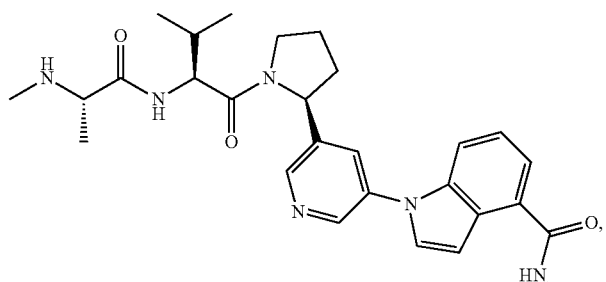
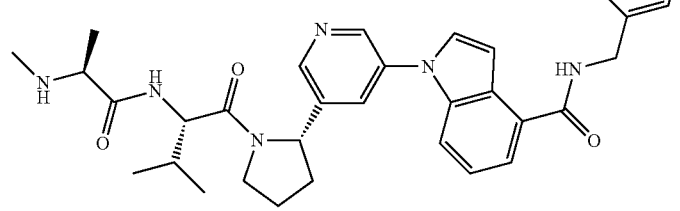

-continued
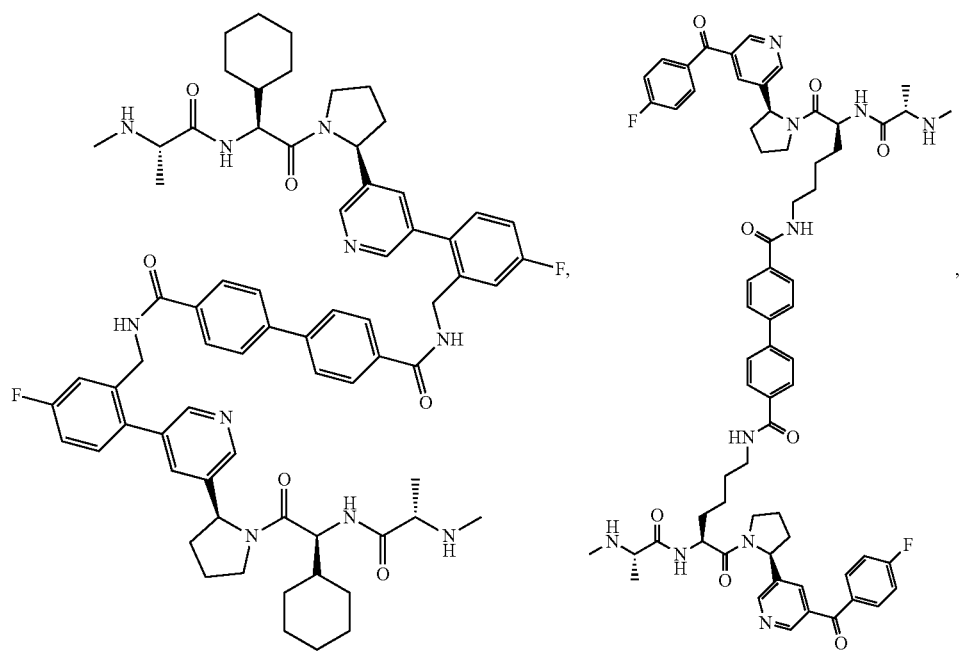
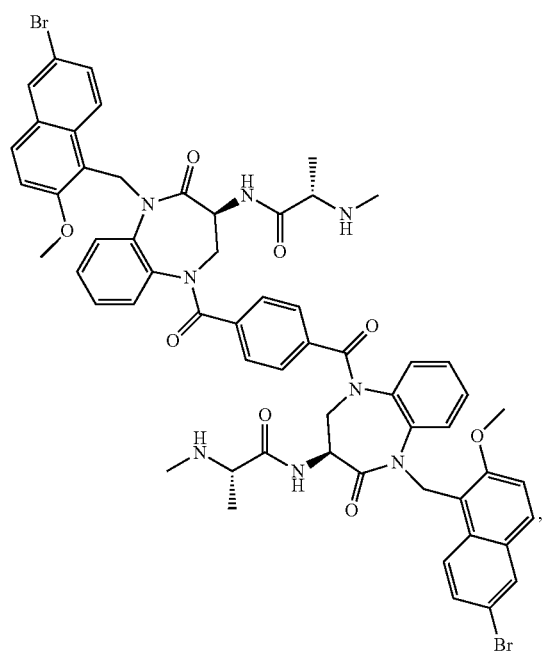

-continued
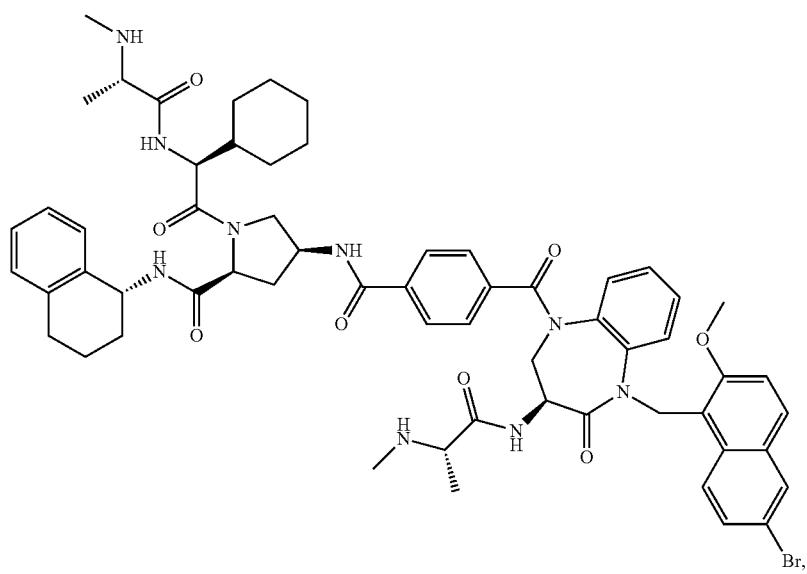
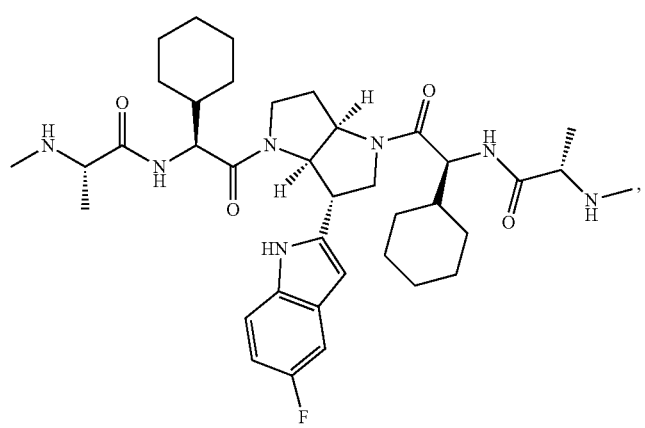
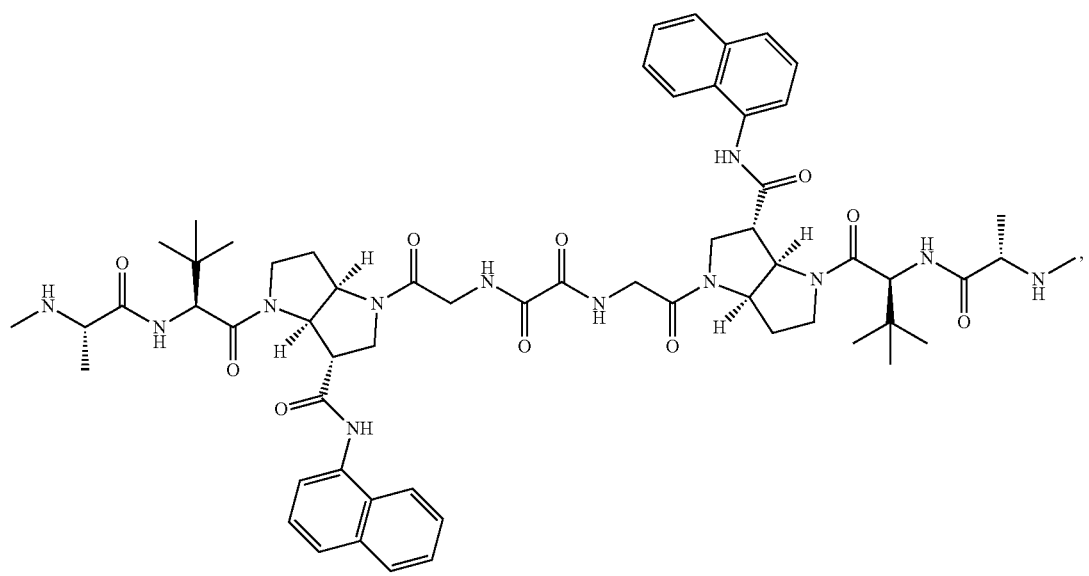

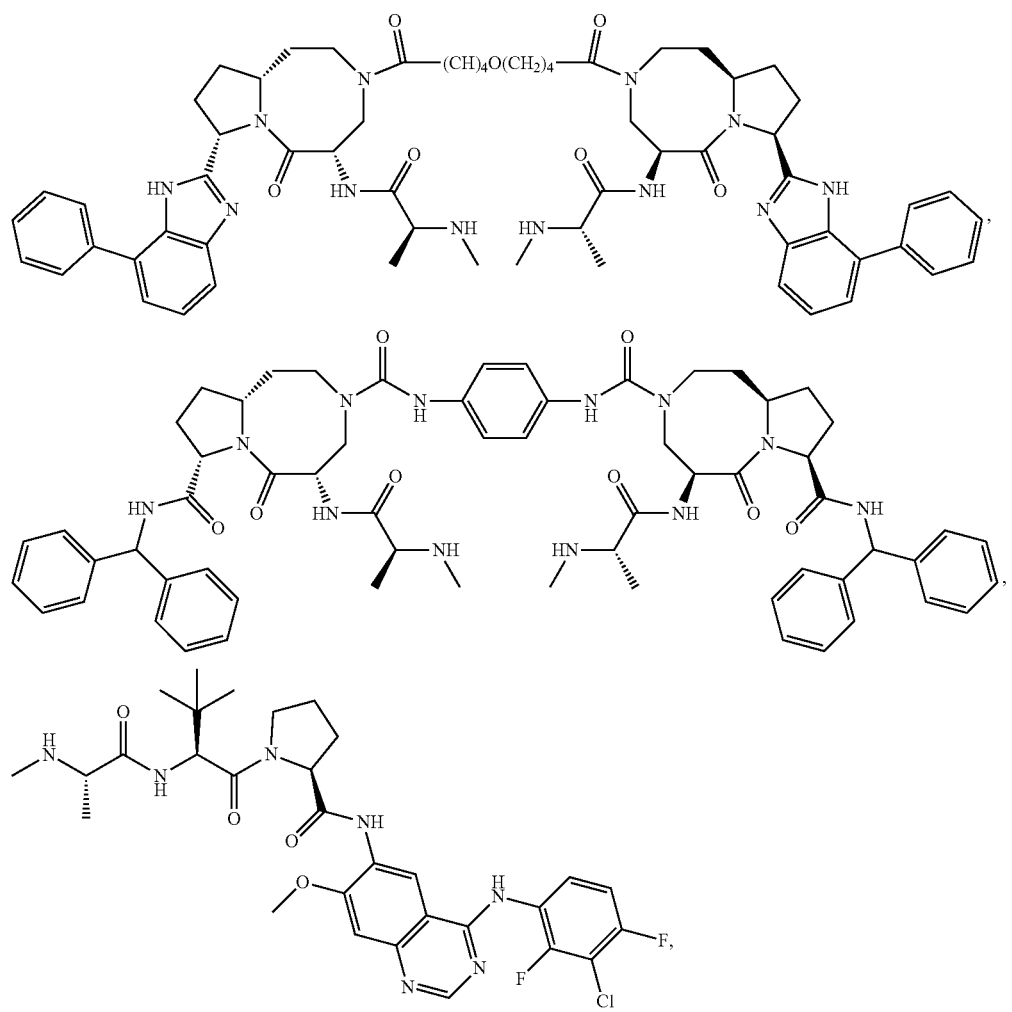
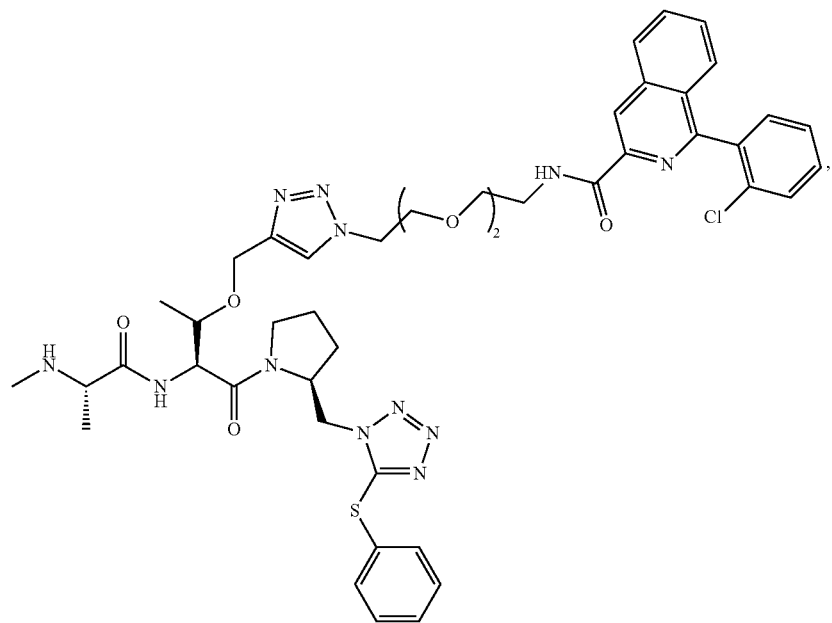

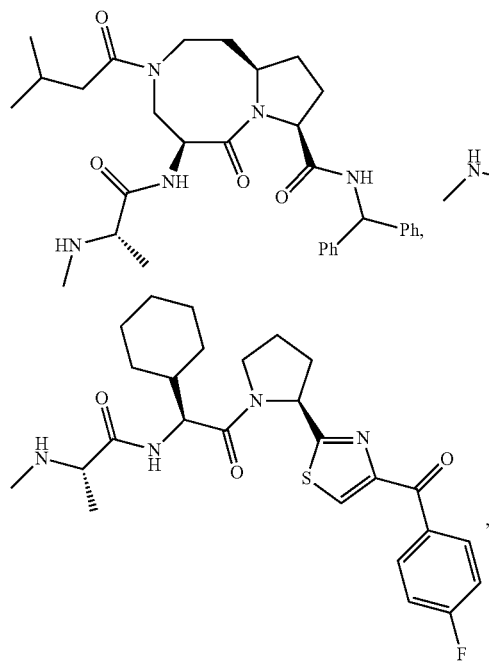
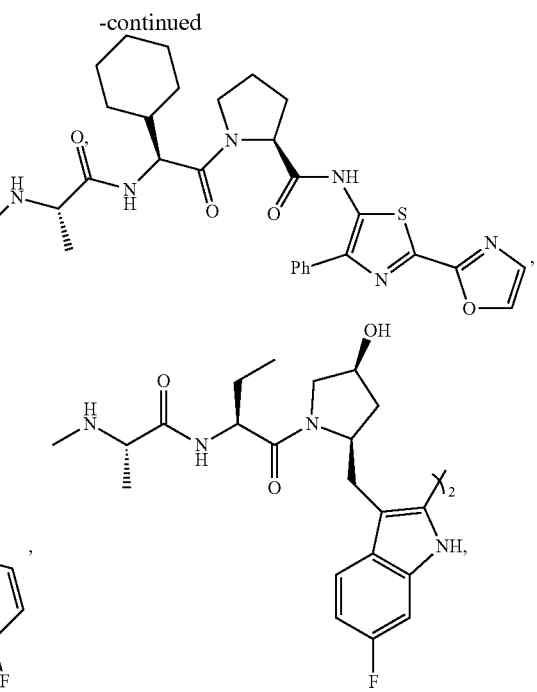

AT-406/Debio 1143, GDC-0917/CUDC-427, LCL161, and TL-32711.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

A compound represented by formula (I), a salt thereof, or a prodrug thereof may inhibit the growth of leukemic stem cells or kill leukemic stem cells. Thus, such compound, a salt thereof, or a prodrug thereof can be used in a pharmaceutical composition for treating acute myeloid leukemia or for inhibiting recurrence of acute myeloid leukemia.

Leukemic stem cells refer to cells that meet at least one of the following requirements:
1: they are cells capable of selectively and exclusively developing leukemia in vivo;
2: they are cells capable of generating a leukemic non-stem cell fraction that cannot spontaneously develop leukemia;
3: they are cells capable of engraftment in vivo; and/or
4: they are cells capable of self-reproduction.

In certain embodiments, leukemic stem cells show characteristics of $CD34^+CD38^-$ cells as surface antigens. In this description, leukemic stem cells obtained from a patient with acute myeloid leukemia are also referred to as "human AML $CD34^+CD38^-$ cells."

When a cell is capable of self-reproduction, such cell is capable of dividing into two cells; that is, a stem cell and a more differentiated precursor cell. The concept of leukemic stem cells has already been established and is commonly accepted in the art (D. Bonnet, J. E. Dick, Nat. Med., 3, 730 (1997); T. Lapidot et al., Nature, 367, 645 (1994)).

In this description, all types of leukemic stem cells are within the scope of "leukemic stem cells." The term "leukemic stem cells" preferably refers to stem cells in which the HCK gene expression level is high, and it more preferably refers to stem cells of acute myeloid leukemia cells.

The target leukemic stem cells in the present invention are generally derived from mammals. Examples of mammals include: laboratory animals, such as mice, rats, hamsters, guinea pigs, and other rodents, and rabbits; domestic animals, such as swine, cattle, goats, horses, sheep, and minks; companion animals, such as dogs and cats; and primates, such as humans, monkeys, cynomolgus monkeys, rhesus monkeys, marmosets, orangutans, and chimpanzees. The target leukemic stem cells in the present invention are preferably derived from primates, such as humans, or rodents, such as mice.

The pharmaceutical composition for killing leukemic stem cells and the pharmaceutical composition for treatment or inhibition of recurrence of acute myeloid leukemia according to the present invention (hereafter, "the pharmaceutical composition(s) of the present invention") have effects of killing leukemic stem cells. The effects of killing leukemic stem cells can be confirmed as the effects of inhibiting the growth of leukemic stem cells throughout the entire cell population.

Since leukemic stem cells are considered to cause recurrent leukemia, recurrence of leukemia can be inhibited and/or prevented with the use of the pharmaceutical composition of the present invention. Specifically, the pharmaceutical compositions of the present invention are also useful for suppressing leukemia (preferably as an agent for inhibiting recurrence of leukemia). Recurrence of leukemia is a condition in which leukemic cells grow again after a patient has achieved partial or complete remission of leukemic symptoms through treatment and leukemic symptoms reappear or worsen. Through administration of pharmaceutical compositions of the present invention to a mammal at a risk of developing (or experiencing recurrence of) leukemia, development (or recurrence) of leukemia can be inhibited and/or prevented.

Acute myeloid leukemia can be brought into complete remission with the use of known chemotherapeutic agents for cancer, such as alkylating agents (e.g., cyclophosphamide and ifosfamide), antimetabolites (e.g., cytarabine, 5-fluorouracil, and methotrexate), antitumor antibiotics (e.g., adriamycin and mitomycin), plant-derived anticancer agents (e.g., vinblastine, vincristine, vindesine, and Taxol), cisplatin, carboplatin, or etoposide. However, AML often recurs after complete remission has been achieved, and for many patients, recurrent AML results in death.

Through administration of pharmaceutical compositions of the present invention to a patient in remission of acute myeloid leukemia, recurrence of acute myeloid leukemia can be prevented.

A compound represented by formula (I) inhibits HCK and/or FLT3, and may retain inhibitor activity in cells that have FLT3/ITD mutations. Accordingly, pharmaceutical compositions containing a compound of the present invention, a salt thereof, or a prodrug thereof may be useful to kill leukemic stem cells. Pharmaceutical compositions containing a compound of the present invention, a salt thereof, or a prodrug thereof may also killing leukemic stem cells with FLT3/ITD mutations. Accordingly, such pharmaceutical compositions may treat acute myeloid leukemia, including acute myeloid leukemia caused by leukemic stem cells having one or more FLT3/ITD mutations.

Pharmaceutical compositions of the present invention can further contain an agent exerting inhibitory effects on FLT3, in addition to a compound represented by formula (I), a salt thereof, or a prodrug thereof, e.g., to bolster efficacy against leukemic stem cells, including leukemic stem cells with Flt3/ITD mutations.

Examples of agents having inhibitory effects on FLT3 used in the present invention include, but are not limited to, Crenolanib, Lestautirinib (CEP-701/KT5555), PKC412 (CGP41251), Tandutinib (MLN518/CT53518), Sunitinib (SU11248), Sorafenib (BA43-9006), Linifanib (ABT-869), Dovitinib (CHIR-258/TKI-258), KW-2449, Quizartinib (AC220), Dovitinib Dilactic acid, Cabozanitib (XL-184), R406, TG101209, Amuvatinib, and ENMD-2076.

ITD mutations in FLT3 can be detected and evaluated by detecting differences from normal types at the site of mutation by PCR, electrophoresis, sequencing, detection with antibodies (e.g., Western blotting or ELISA), or other means, according to need. It can be evaluated that pharmacological efficacy is enhanced in individuals in which ITD mutations in FLT3 are detected in leukemic stem cells compared with individuals in which normal FLT3 is detected in leukemic stem cells. When pharmacological efficacy is evaluated as being enhanced, the pharmaceutical composition of the present invention is administered to the individual. Thus, treatment, inhibition, and/or prevention of recurrence of acute myeloid leukemia can be achieved.

Administration

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally. In certain preferred embodiments, the disclosed methods include orally or parenterally administering any two of, or all three of, a FLT3-ITD inhibitor, an HCK inhibitor, and a BCL-2 inhibitor.

The term "parenteral," as used herein, includes subcutaneous, intravenous, intramuscular, intraocular, intravitreal, intra-articular, intra-synovial, intrasternal, intrathecal, intrahepatic, intraperitoneal, intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A compound disclosed herein can also be in micro-encapsulated form.

The amount of a compound of the present invention that may be combined with the carrier materials to produce a composition in a single dosage form will vary depending upon the subject being treated and the particular mode of administration. In certain embodiments, provided compositions should be formulated so that a dosage of between about 0.01 to about 100 mg/kg body weight/day of the compound can be administered to a subject receiving these compositions. In other embodiments, the dosage is from about 0.5 to about 100 mg/kg of body weight, or between about 1 mg and about 1000 mg/dose, about every 4 to 120 hours, or according to the requirements of the particular drug. Typically, the pharmaceutical compositions of this invention will be administered from about 1 to about 6 times per day.

In some embodiments, the compound is formulated for oral administration at a dosage of approximately 5 mg/kg to approximately 10 mg/kg, preferably at a dosage of approximately 7.5 mg/kg.

It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated.

The amount of a compound of the present invention in the composition will also depend upon the particular compound in the composition.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

EXAMPLES

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions with art-recognized alternatives and using no more than routine experimentation, are within the scope of the present application.

The following examples are put forth so as to provide those of ordinary skill in the art with a complete disclosure and description of how to make and use the methods of the invention, and are not intended to limit the scope of what the inventor(s) regard(s) as the invention.

Unless noted otherwise, the starting materials for the experiments described herein were obtained from commercial sources or known procedures and were used without further modification.

General Methods
Compounds
General Methods

All solvents and reagents were obtained from commercial sources and used without further purification unless indicated otherwise. NMR spectra were obtained on a Bruker Neo 400M spectrometer operating at 400 MHz. Chemical shifts are reported in parts per million (δ) from the tetramethysilane resonance in the indicated solvent. LC-Mass spectra were taken with Agilent 1260-6125B single quadrupole mass spectrometer using a Welch Biomate column (C18, 2.7 um, 4.6*50 mm) eluting with a mixture of solvents A (ACN with 0.05% FA) and B (Water with 0.05% FA) using a gradient elusion. Detection was by DAD (254 nm and 210 nm). Ionization was by ESI. The spectra were analyzed using Chemstation software. Analytical HPLC was performed on the Waters ARC system either under acid-containing condition on a YMC Pack Pro column (C18 S-3 um, 12 nm, 150*2.0 mm) eluting with a mixture of solvents A (ACN with 0.05% FA) and B (Water with 0.05% FA); or under base-containing condition on a Agilent Poroshell HPH C18 column (2.7 um, 2.1*150 mm), eluting with a mixture of solvents C (Water with 0.1% $NH_4OH$) and D (ACN with 0.1% $NH_4OH$) using a gradient elution. The detection was by DAD (254 nm and 210 nm). Preparative HPLC was performed on Waters AutoP system that is coupled with single quadrupole mass spectrometer using a Welch C18 column (5 um, 25*150 mm), eluting with a mixture of solvents A and B. Flash chromatography was carried out on Biotage Isolera Prime system using Welch WelFlash flash columns (40-63 um) eluting with a mixture of solvents as indicated in the experimental procedures.

4-(4-Amino-5-(4-phenoxyphenyl)-7H-pyrrolo[2,3-d]pyrimidin-7-yl) cyclohexanone

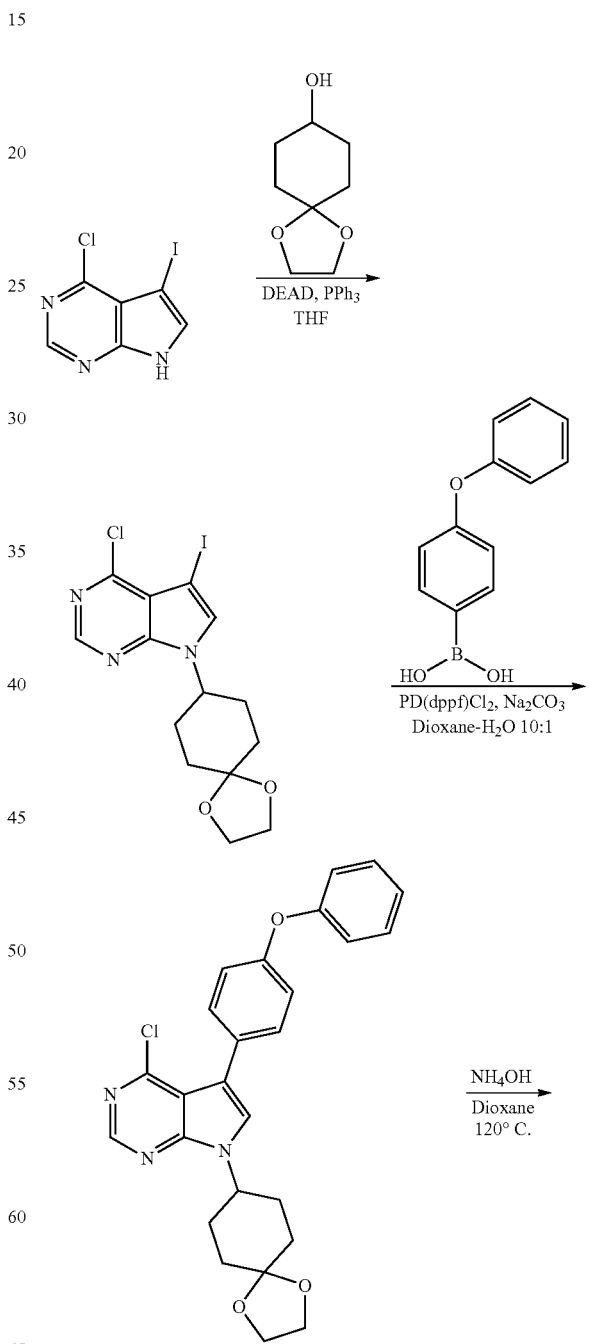

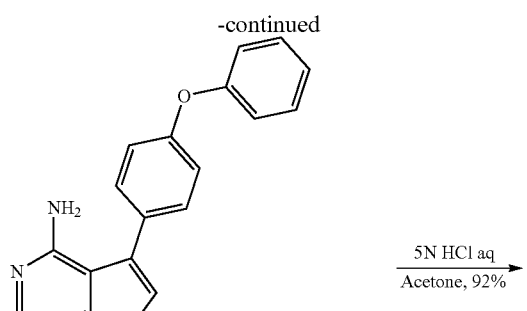

4-Chloro-5-iodo-7-(1,4-dioxaspiro[4.5]decan-8-yl)-7H-pyrrolo[2,3-d]pyrimidine DEAD (170 mL, 1.07 mol) was added dropwise to a stirred mixture of Ph$_3$P (285.1 g, 1.07 mol) and THF (3.12 L) under ice bath cooling. After the reaction mixture was warmed up to room temperature. A solution of 4-dichloro-5-iodo-7H-pyrrolo[2,3-d]pyrimidine (100 g, 0.36 mol) and 1,4-dioxaspiro[4.5]decan-8-ol (170 g, 1.07 mol) in THF (1.2 L) was added dropwise over a period of 60 minutes. The reaction was stirred at room temperature for 3 hours. TLC (EA:PE=1:4) showed complete consumption of the starting material. The solvent was evaporated in vacuo. EA (1.78 L) was added to the residue and the solid was collected by filtration. The solid was washed with EA (300 mL) and dried under reduced pressure to give the title compound as a white solid (139.8 g, 92.7% yield). LCMS: Calculated Exact Mass=419.0, Found [M+H]$^+$ (ESI)=420.0; $^1$H NMR (DMSO-d$_6$) δ ppm: 8.64 (s, 1H), 8.12 (s, 1H), 4.70-4.80 (m, 1H), 3.88-3.95 (m, 4H), 2.08-2.17 (m, 2H), 1.88-1.96 (m, 2H), 1.70-1.84 (m, 4H).

4-Dichloro-5-(4-phenoxyphenyl)-7-(1,4-dioxaspiro[4.5]decan-8-yl)-7H-pyrrolo[2,3-d]pyrimidine A reaction mixture of 4-dichloro-5-iodo-7-(1,4-dioxaspiro[4.5]decan-8-yl)-7H-pyrrolo [2,3-d]pyrimidine (60 g, 143 mmol), (4-phenoxyphenyl) boronic acid (60 g, 286 mmol), Pd(dppf)Cl$_2$ (10 g, 14.3 mmol) and Na$_2$CO$_3$ (45 g, 429 mmol) in (2.5 L) of dioxane-H$_2$O (10:1) was heated to 80° C. and stirred for 3 hours. TLC (PE:EA=4:1) showed complete consumption of the starting material. The solvent was evaporated in vacuo. The residue was extracted with DCM (500 mL×2). The combined organic layer was washed with water, dried over Na$_2$SO$_4$ and concentrated in vacuo. The crude was purified by flash column chromatography (EA:PE=1:4) to give the title compound as a brown solid (42.0 g, 66% yield). LCMS: Calculated Exact Mass=461.1, Found [M+H]$^+$ (ESI)=462.2; $^1$H NMR (DMSO-d$_6$) δ ppm: 8.66 (s, 1H), 7.95 (s, 1H), 7.54-7.56 (m, 2H), 7.41-7.45 (m, 2H), 7.03-7.21 (m, 5H), 4.78-4.87 (m, 1H), 3.89-3.96 (m, 4H), 2.12-2.26 (m, 2H), 1.94-2.02 (m, 2H), 1.74-1.88 (m, 4H).

5-(4-Phenoxyphenyl)-7-(1,4-dioxaspiro[4.5]decan-8-yl)-7H-pyrrolo[2,3-d]pyrimidin-4-amine A reaction mixture of 4-dichloro-5-(4-phenoxyphenyl)-7-(1,4-dioxaspiro[4.5]decan-8-yl)-7H-pyrrolo[2,3-d]pyrimidine (20.3 g, 43.9 mmol), NH$_4$OH (200 mL) and dioxane (200 mL) was stirred at 120° C. in a high pressure reactor for 48 hours. The solid was filtered and dried to obtain the title compound as a white solid (10 g, 51.5% yield). LCMS: Calculated Exact Mass=442.2, Found [M+H]$^+$ (ESI)=443.2.

4-(4-Amino-5-(4-phenoxyphenyl)-7H-pyrrolo[2,3-d]pyrimidin-7-yl)cyclohexanone A reaction mixture of 5-(4-phenoxyphenyl)-7-(1,4-dioxaspiro[4.5]decan-8-yl)-7H-pyrrolo[2,3-d]pyrimidin-4-amine (10 g, 22.6 mmol), HCl (6 N, 160 mL), acetone (160 mL) and THF (36 mL) was stirred at 40° C. for 2 hours. Under ice bath cooling, NaOH (1M, 980 mL) was added to the mixture until pH 8. The solid was collected by filtration, and dried under reduced pressure to give the title compound as a white solid (7.6 g, 84.4% yield). LCMS: Calculated Exact Mass=398.2, Found [M+H]$^+$ (ESI)=399.2; $^1$H NMR (DMSO-d$_6$) δ ppm: 8.17 (s, 1H), 7.40-7.47 (m, 5H), 7.08-7.17 (m, 5H), 6.12 (br.s., 2H), 5.18 (s, 1H), 2.73-2.78 (m, 2H), 2.28-2.40 (m, 4H), 2.15-2.25 (m, 2H).

5-Iodo-7-(1,4-dioxaspiro[4.5]decan-8-yl)-7H-pyrrolo[2,3-d]pyrimidin-4-amine

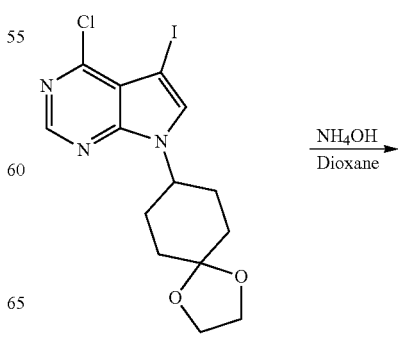

73

-continued

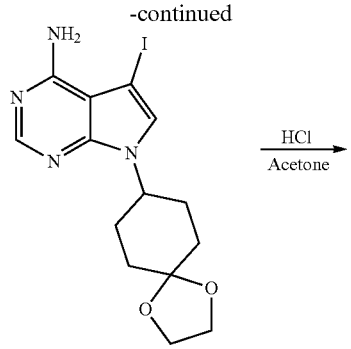

5-Iodo-7-(1,4-dioxaspiro[4.5]decan-8-yl)-7H-pyrrolo[2,3-d]pyrimidin-4-amine

A mixture of 4-chloro-5-iodo-7-(1,4-dioxaspiro[4.5]decan-8-yl)-7H-pyrrolo [2,3-d]pyrimidine (13 g, 31 mmol), NH$_4$OH (200 mL) and dioxane (200 mL) was stirred for 48 hours at 120° C. in a high pressure autoclave. TLC (MeOH:DCM=1:20) showed complete consumption of the starting material. The title compound, a white solid, was collected by filtration, followed by dried under reduced pressure (11.6 g, 93% yield). LCMS: Calculated Exact Mass=400.0, Found [M+H]$^+$ (ESI+)=401.0.

5-Iodo-7-(1,4-dioxaspiro[4.5]decan-8-yl)-7H-pyrrolo[2,3-d]pyrimidin-4-amine

A mixture of 5-iodo-7-(1,4-dioxaspiro[4.5]decan-8-yl)-7H-pyrrolo[2,3-d]pyrimidin-4-amine (11.6 g, 29 mmol), 6M HCl (160 mL), acetone (160 mL) and THF (38 mL) was stirred for 2 hours at 40° C. TLC (EA:PE=1:3) showed complete consumption of the starting material. NaOH solution (980 mL, 1 mol/L) was added to the mixture until pH 8.0 (under ice cooling). The title compound, a white solid, was collected by filtration followed by drying under the reduced pressure (7.6 g, 73% yield). LCMS: Calculated Exact Mass=356.0, Found [M+H]$^+$ (ESI)=357.0; $^1$H NMR (DMSO-d$_6$) δ ppm: 8.12 (s, 1H), 7.60 (s, 1H), 6.65 (br.s., 2H), 5.10 (s, 1H), 2.68-2.74 (m, 2H), 2.23-2.30 (m, 4H), 2.09-2.14 (m, 2H).

74

4-(4-Amino-5-(2-fluoro-4-phenoxyphenyl)-7H-pyrrolo[2,3-d]pyrimidin-7-yl)cyclohexanone

4-(4-Amino-5-(2-fluoro-4-phenoxyphenyl)-7H-pyrrolo[2,3-d]pyrimidin-7-yl)cyclohexanone The solution of 4-(4-amino-5-iodo-7H-pyrrolo[2,3-d]pyrimidin-7-yl) cyclohexanone (300 mg, 0.84 mmol), 2-(2-fluoro-4-phenoxyphenyl)-4,4,5,5-tetramethyl-1,3,2-dioxaborolane (344.0 mg, 1.10 mmol), [1,1'-Bis(diphenylphosphino)ferrocene]dichloropalladium(II) (123.3 mg, 0.17 mmol) and Sodium carbonate (178.6 mg, 1.65 mmol) in dioxane-water (11 mL, 10:1) was stirred at 90° C. under nitrogen for 12 hours. After cooling to room temperature, the mixture was filtered with celite and concentrated to purify by flash chromatography (DCM:MeOH=20:1) to obtain brown oil (400 mg, 114.6% yield, ~80% purity). LCMS: Calculated Exact Mass=416.2; Found [M+H]+ (ESI)=417.0.

4-(4-Amino-3-iodo-1H-pyrazolo[3,4-d]pyrimidin-1-yl) cyclohexanone

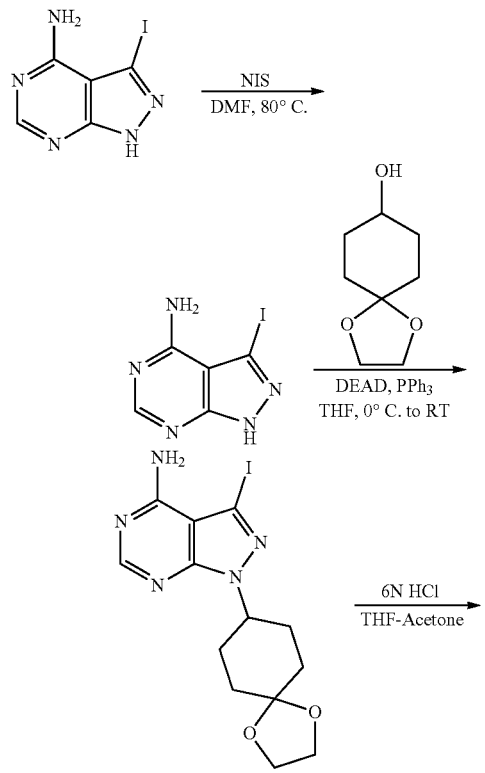

3-Iodo-1H-pyrazolo[3,4-d]pyrimidin-4-amine

NIS (1.99 kg, 8.88 mol) was added in three portions to a mixture of 3-iodo-1H-pyrazolo [3,4-d]pyrimidin-4-amine (1.0 kg, 7.4 mol) in DMF (6 L). The reaction was stirred at 80° C. overnight. The reaction was cooled to room temperature and precipitated. The solid was filtrated and was washed by EtOAc (12 L). The solid was filtrated and dried in vacuo to give the product as the white solid (1.58 kg). LCMS: Calculated Exact Mass=260.9; Found [M+H]$^+$ (ESI)=262.2; $^1$H NMR (DMSO-d$_6$) δ ppm: 8.18 (s, 1H).

3-Iodo-1-(1,4-dioxaspiro[4.5]decan-8-yl)-1H-pyrazolo[3,4-d]pyrimidin-4-amine To an ice bath cooled suspension of 3-iodo-1H-pyrazolo[3,4-d]pyrimidin-4-amine (400 g, 1.53 mol) in THF (5.5 L) was added 1,4-dioxaspiro[4.5]decan-8-ol (480 g, 3.06 mol), PPh$_3$ (600 g, 2.3 mol), followed by dropwise addition of DEAD (400 g, 3 mol) over a period of 4 hours. The reaction was stirred at room temperature for 1 hour and was monitored by LCMS until complete conversion of the starting material. The reaction mixture was concentrated. The crude was washed by THF (400 mL), and then by EtOAc (4 L) to give the product (380 g, 62% yield). LCMS: Calculated Exact Mass=401.0; Found [M+H]$^+$ (ESI)=401.9; $^1$H NMR (400 MHz, DMSO-d$_6$) δ ppm: 8.19 (s, 1H) 4.64-4.79 (m, 1H) 3.85-3.96 (m, 4H) 2.09-2.23 (m, 2H) 1.66-1.90 (m, 6H).

4-(4-Amino-3-iodo-1H-pyrazolo[3,4-d]pyrimidin-1-yl)cyclohexanone

To a suspension of 3-iodo-1-(1,4-dioxaspiro[4.5]decan-8-yl)-1H-pyrazolo[3,4-d] pyrimidin-4-amine (660 g, 1.64 mol) in THF (1.2 L) and acetone (6 L) was added 6N HCl (6 L, 36 mol). The reaction was heated at 60° C. for 1 hour. It was neutralized with 7.5 N NaOH aq. After filtration, the solid product was collected (350 g) and used without further purification. LCMS: Calculated Exact Mass=357.0; Found [M+H]$^+$ (ESI)=357.8; $^1$H NMR (400 MHz, DMSO-d$_6$) δ ppm: 8.23 (s, 1H) 5.10-5.23 (m, 1H) 2.61-2.76 (m, 2H) 2.25-2.40 (m, 5H) 2.14-2.23 (m, 2H).

4-(4-Amino-3-(2-fluoro-4-phenoxyphenyl)-1H-pyrazolo[3,4-d]pyrimidin-1-yl)cyclohexan-1-one

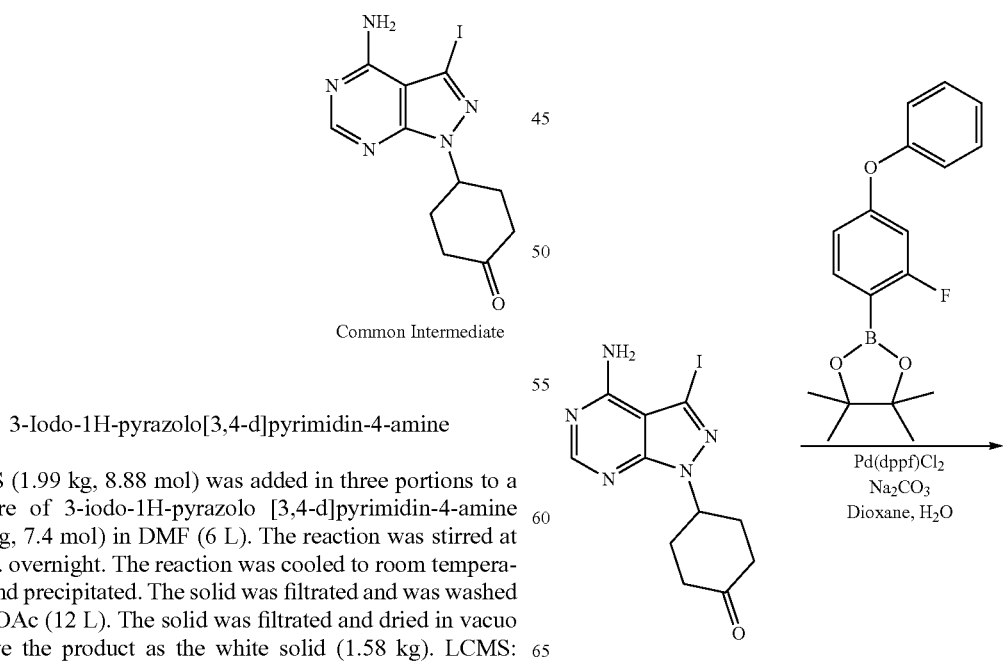

Common Intermediate

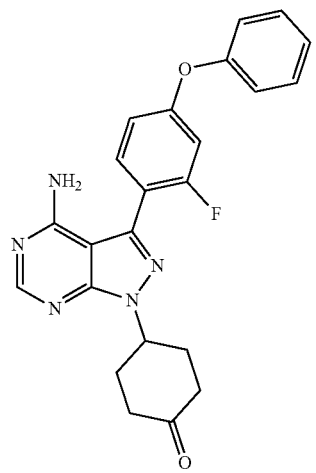

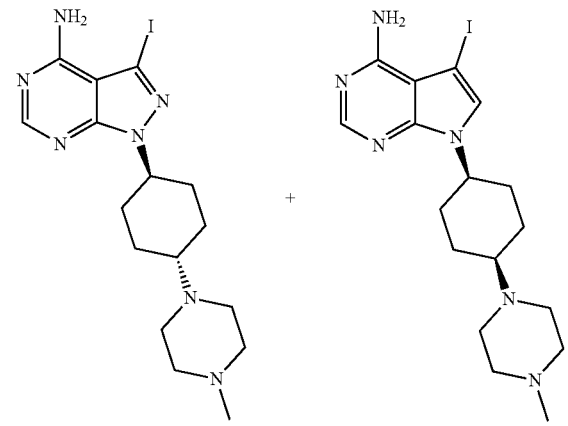

4-(4-Amino-3-(2-fluoro-4-phenoxyphenyl)-1H-pyrazolo[3,4-d]pyrimidin-1-yl)cyclohexan-1-one To a 50 mL round-bottom flask was added 4-(4-amino-3-iodo-1H-pyrazolo[3,4-d] pyrimidin-1-yl) cyclohexanone (3 g, 8.4 mmol), 2-(2-fluoro-4-phenoxyphenyl)-4,4,5,5-tetramethyl-1,3,2-dioxaborolane (3.16 g, 10.08 mmol), Pd(dppf)Cl$_2$ (614 mg, 0.84 mmol), Na$_2$CO$_3$ (3.6 g, 33.5 mmol), 30 mL dioxane-water (9-1, 20 mL). The reaction was stirred at 85° C. under N$_2$ atmosphere overnight. The reaction was cooled to the room temperature, filtrated and concentrated. The crude was purified by flash column chromatography (MeOH in DCM, 0-5%) to obtain the product as a red solid (2.5 g, 71.3% yield) that was used without further purification. LC-MS: Calculated Exact Mass: 417.16; Found [M+H]$^+$ (ESI)=418.15.

5-Iodo-7-((cis)-4-(4-methylpiperazin-1-yl)cyclohexyl)-7H-pyrrolo[2,3-d]pyrimidin-4-amine and

5-Iodo-7-((trans)-4-(4-methylpiperazin-1-yl)cyclohexyl)-7H-pyrrolo[2,3-d]pyrimidin-4-amine A mixture of 5-iodo-7-(1,4-dioxaspiro[4.5]decan-8-yl)-7H-pyrrolo[2,3-d]pyrimidin-4-amine (6.3 g, 17.7 mmol), 1-methylpiperazine (11.71 g, 106.2 mmol), AcOH (0.63 mL, 10.62 mmol) sieves in (50 mL) DCM was stirred for 16 hours at room temperature. NaCNBH$_3$ (2.21 g, 35.4 mmol) was added to the mixture. Then the mixture was stirred at 50° C. for 4 hours. TLC (MeOH:DCM=1:15) showed complete consumption of the starting material. The solvent was evaporated in vacuo. The residue was extracted by DCM (250 mL×2). The combined organic layer was washed with water, dried over anhydrous Na$_2$SO$_4$ and concentrated in vacuo. The residue was purified by flash column chromatography (DCM:MeOH=10:1) to give 5-iodo-7-((trans)-4-(4-methylpiperazin-1-yl) cyclohexyl)-7H-pyrrolo[2,3-d]pyrimidin-4-amine (4.3 g, 55.3% yield) along with the cis isomer. Analytical data for trans isomer: LCMS: Calculated Exact Mass=440.1, Found [M+H]$^+$ (ESI)=441.1; $^1$H NMR (DMSO-d$_6$) δ ppm: 8.08 (s, 1H), 7.53 (s, 1H), 6.58 (br.s., 2H), 4.47 (s, 1H), 2.35 (br.s., 4H), 2.16 (s, 3H), 1.81-1.90 (m, 6H), 1.38-1.44 (m, 2H).

5-Iodo-7-((cis)-4-(4-methylpiperazin-1-yl)cyclohexyl)-7H-pyrazolo[2,3-d]pyrimidin-4-amine and

5-Iodo-7-((trans)-4-(4-methylpiperazin-1-yl)cyclohexyl)-7H-pyrazolo[2,3-d]pyrimidin-4-amine

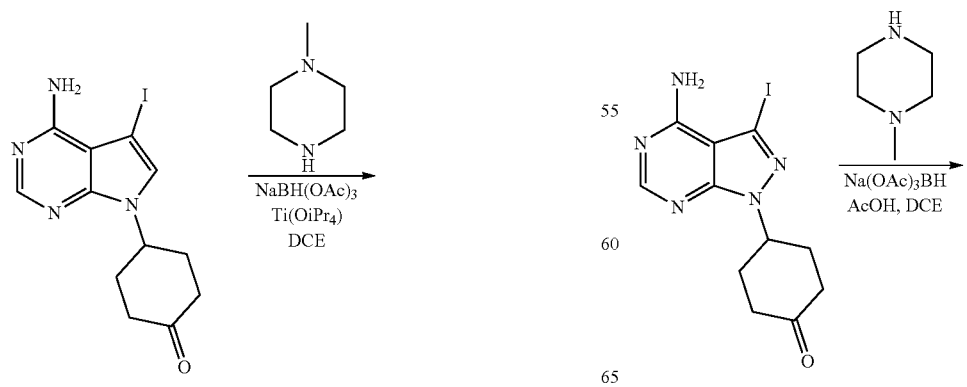

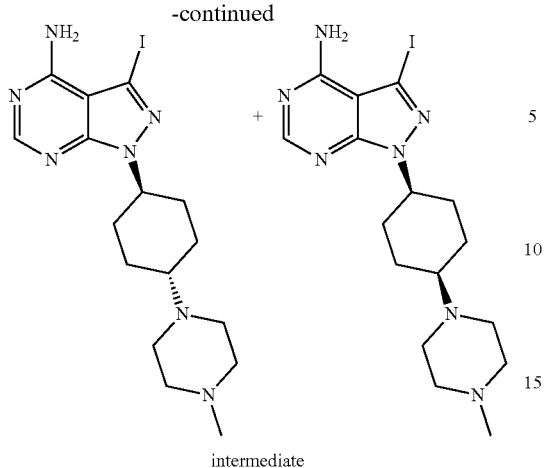

intermediate

5-Iodo-7-((cis)-4-(4-methylpiperazin-1-yl)cyclohexyl)-7H-pyrazolo[2,3-d]pyrimidin-4-amine The solution of 4-(4-amino-3-iodo-1H-pyrazolo[3,4-d]pyrimidin-1-yl) cyclohexanone (700 mg, 1.96 mmol), 1-methylpiperazine (0.65 mL, 11.76 mmol), acetic acid (0.1 mL, 1.96 mmol) and molecular sieves (2.0 g) in 1,2-Dichloroethane (40 mL) was stirred at room temperature for 1 hours. Then, Sodium triacetoxyborohydride (1.2 g, 11.76 mmol) was added and continued to stir for 16 hours at room temperature. Water (150 mL) and dichloromethane (150 mL) were added to the reaction mixture, a saturated aqueous solution of Sodium bicarbonate (120 mL) was further added thereto, and the mixture was partitioned. The organic layer was washed with brine (120 mL) and dried over Sodium sulfate and concentrated to purify by flash chromatography (DCM:MeOH=10:1) to obtain 5-iodo-7-((trans)-4-(4-methylpiperazin-1-yl)cyclohexyl)-7H-pyrrolo[2,3-d]pyrimidin-4-amine as white solid (530 mg, 61.6% yield) along with the corresponding cis isomer. Analytical data for the trans isomer: LCMS: Calculated Exact Mass=440.1; Found [M+H]$^+$ (ESI)=442.1.

(S)-tert-butyl-4-((trans)-4-(4-amino-5-iodo-7H-pyrrolo[2,3-d]pyrimidin-7-yl)cyclohexyl)-2-methylpiperazine-1-carboxylate and

(S)-tert-butyl-4-((cis)-4-(4-amino-5-iodo-7H-pyrrolo[2,3-d]pyrimidin-7-yl)cyclohexyl)-2-methylpiperazine-1-carboxylate

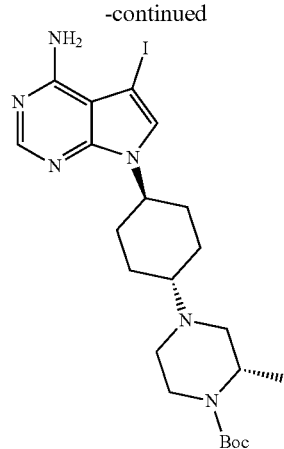

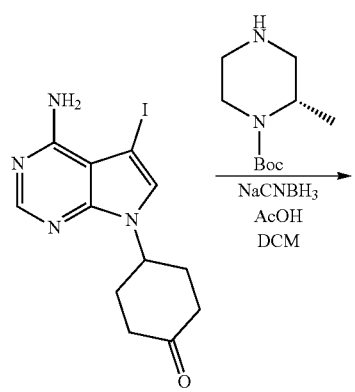

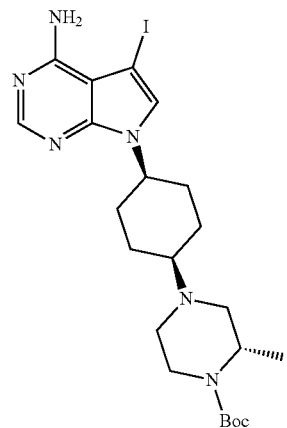

The solution of compound 4-(4-amino-5-iodo-7H-pyrrolo[2,3-d]pyrimidin-7-yl) cyclohexanone (1 g, 2.8 mmol), (S)-tert-butyl 2-methylpiperazine-1-carboxylate (3.36 g, 16.8 mmol) and AcOH (0.1 mL) in DCM (70 mL) was added NaBH$_3$CN (1 g, 16.8 mmol) at room temperature under N$_2$ atmosphere. Then the reaction was stirred at 40° C. for 16 hours. The reaction was extracted by DCM (150 mL) and water. The combined organic layer was washed with aqueous NH$_4$Cl (150 mL), dried over anhydrous Na$_2$SO$_4$ and concentrated in vacuo. The residue was purified by flash column chromatography (DCM:MeOH=20:1) to give a mixture of the two title compounds (2 g) that was used without further purification. LCMS: Calculated Exact Mass=540.17, Found [M+H]$^+$ (ESI)=541.1.

81

5-Iodo-7-((trans)-4-((S)-3-methylpiperazin-1-yl)cyclohexyl)-7H-pyrrolo[2,3-d]pyrimidin-4-amine

82

(S)-tert-butyl-4-((trans)-4-(4-amino-3-iodo-1H-pyrazolo[3,4-d]pyrimidin-1-yl)cyclohexyl)-2-methylpiperazine-1-carboxylate and (S)-tert-butyl-4-((cis)-4-(4-amino-3-iodo-1H-pyrazolo[3,4-d]pyrimidin-1-yl)cyclohexyl)-2-methylpiperazine-1-carboxylate

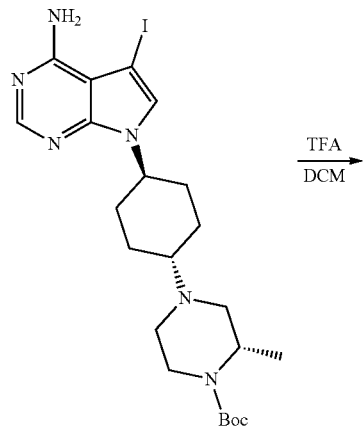

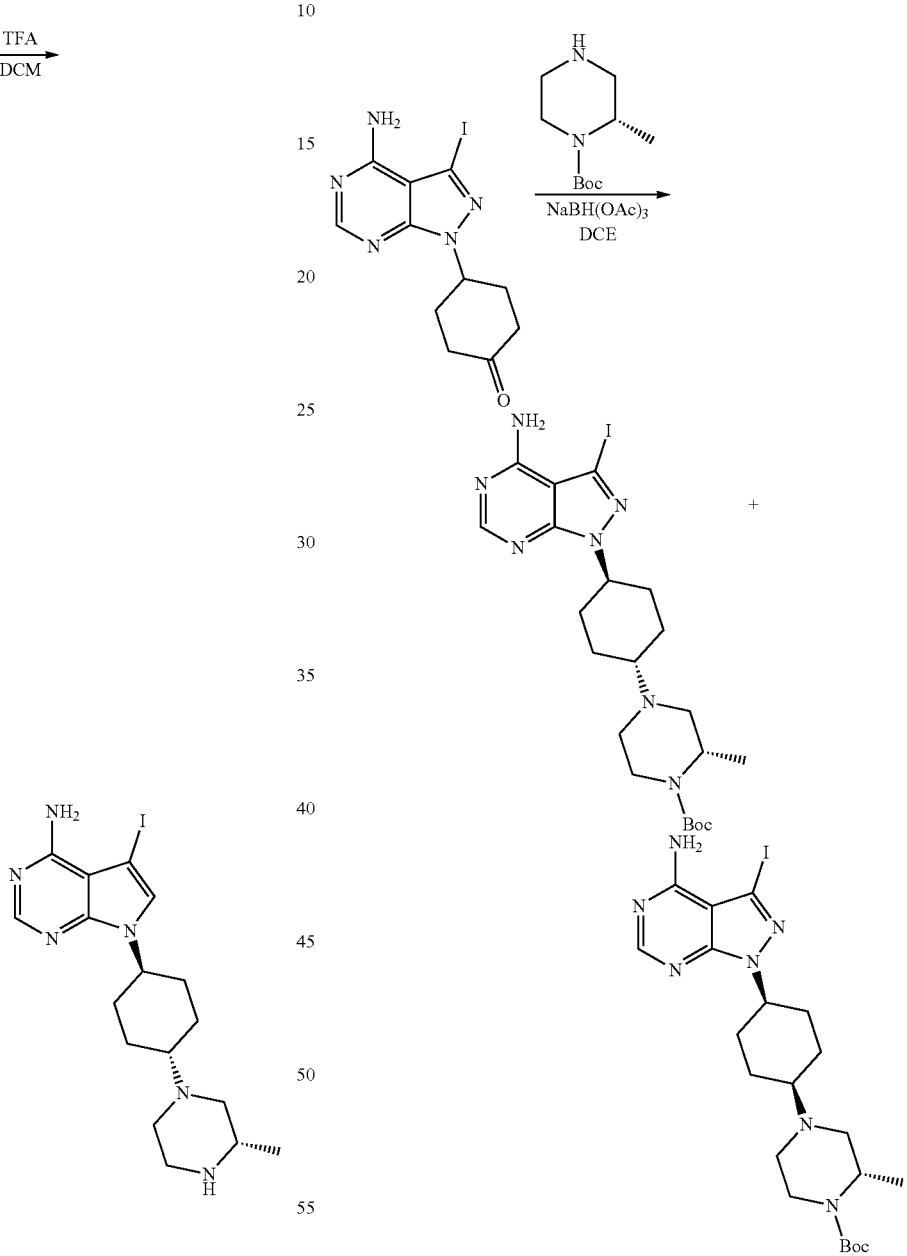

To a solution of (S)-tert-butyl 4-((trans)-4-(4-amino-5-iodo-7H-pyrrolo[2,3-d]pyrimidin-7-yl) cyclohexyl)-2-methylpiperazine-1-carboxylate (1.0 g, 1.85 mmol) in DCM (20 mL) was added TFA (10 mL) dropwise. The reaction mixture was stirred at room temperature for 0.5 hours. The mixture was evaporated and purified with flash column chromatography (MeOH in DCM, 1 to 10% gradient) the title compound as a pale white solid (690 mg, 85% yield).

To a mixture of 4-(4-amino-3-iodo-1H-pyrazolo[3,4-d]pyrimidin-1-yl)cyclohexanone (2.5 g, 7 mmol) and tert-butyl (S)-2-methylpiperazine-1-carboxylate (4.2 g, 21 mmol) in DCE (50 mL) was stirred at 55° C. under $N_2$ atmosphere for 90 min. After it was cooled to room temperature, $NaBH(OAc)_3$ (2076 mg, 9.8 mmol) was added portion-wise, the mixture was stirred at 55° C. under $N_2$ atmosphere for 90 min, then cooled to room temperature and stirred at room temperature overnight. The reaction was monitored via TLC and LCMS until complete consumption of starting material. It was then filtrated and concentrated to give a crude product. The crude was purified by flash column chromatography (0-30% MeOH in DCM) to obtain the title compound as a yellow solid (1.4 g, 36% yield). LCMS: Calculated Exact Mass=541.17; Found [M+H]⁺ (ESI)= 541.82.

5-Iodo-7-((trans)-2-(1-methylpiperidin-4-yl)-1,3-dioxan-5-yl)-7H-pyrrolo[2,3-d]pyrimidin-4-amine and 5-Iodo-7-((cis)-2-(1-methylpiperidin-4-yl)-1,3-dioxan-5-yl)-7H-pyrrolo[2,3-d]pyrimidin-4-amine

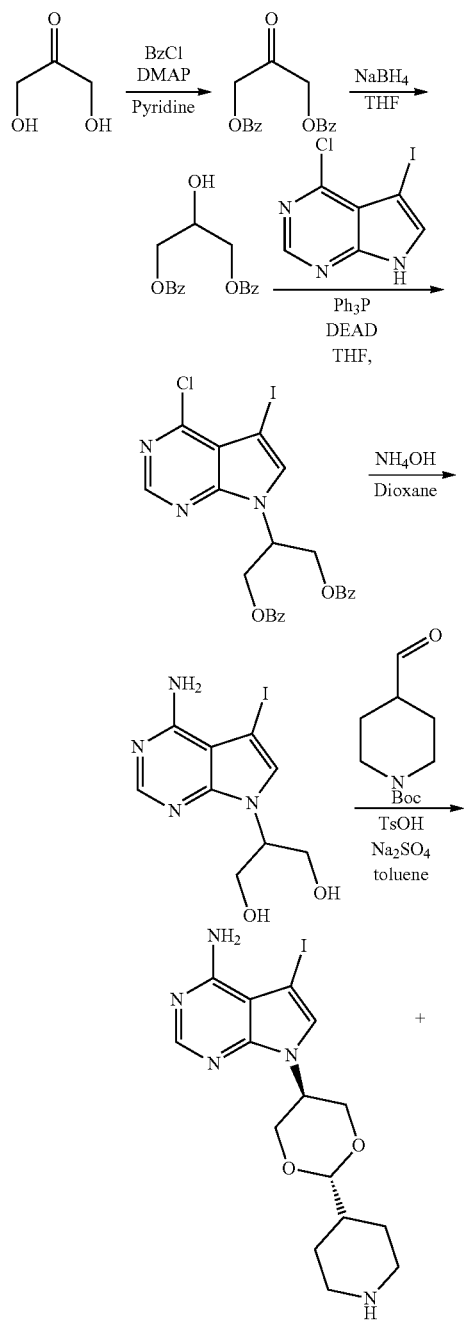

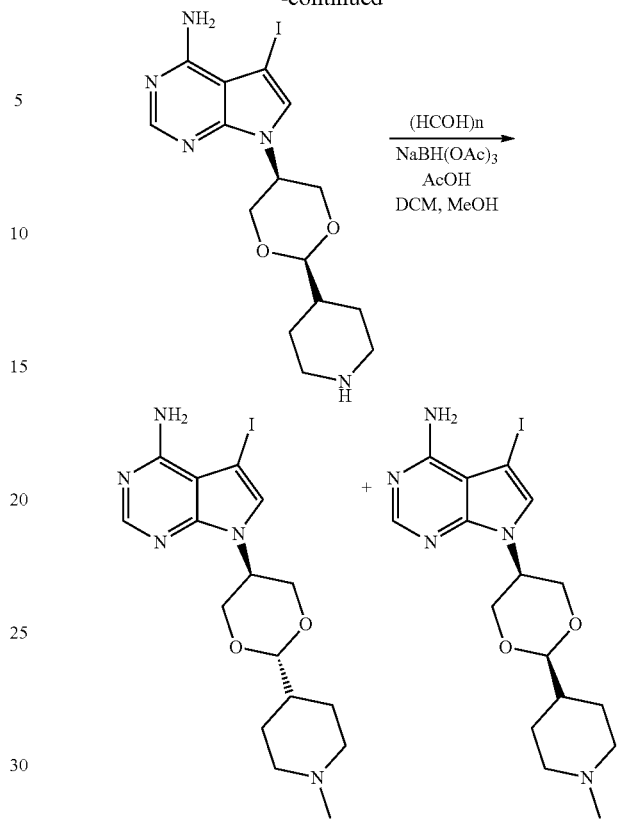

Common Intermediate

2-Oxopropane-1,3-diyl dibenzoate

To an ice bath cooled stirred solution of 1,3-dihydroxy-propan-2-one (30 g, 333 mmol), DMAP (2.1 g, 16.65 mmol) in pyridine (133 mL) was added Benzoyl chloride (85 mL, 732 mmol) dropwise followed by pyridine (120 mL). After addition, the mixture was warmed to room temperature and stirred overnight. The mixture was poured into HCl (6M, 580 mL) at 0° C. The mixture was filtered, washed with water (150 mL×2). The residue was suspended in MeOH (400 mL), filtered to afford the title compound as a white solid (64.6 g, 65% yield)

2-Hydroxypropane-1,3-diyl dibenzoate

To an ice bath-cooled stirred solution of 2-oxopropane-1,3-diyl dibenzoate (15 g, 50 mmol) in THF (150 mL) was added NaBH₄ (2.3 g, 60 mmol) by portions. After addition, the mixture was stirred at 0° C. for 30 minutes. The reaction was quenched by NH₄Cl solution and evaporated. The residue was diluted with EA (200 mL), washed with water (80 mL) and brine (80 mL), dried and concentrated in vacuo and purified with flash column chromatography (EA in PE, 0 to 20% gradient) to afford the title compound as colorless oil (9.02 g, 60% yield).

2-(4-Chloro-5-iodo-7H-pyrrolo[2,3-d]pyrimidin-7-yl)propane-1,3-diyl dibenzoate

To an ice bath-cooled solution of PPh₃ (15.5 g, 59.04 mmol) in THF (100 mL) was added DEAD (10.3 g, 59.04 mmol). The mixture was stirred at room temperature. To the mixture was added a solution of 2-hydroxypropane-1,3-diyl dibenzoate (7.7 g, 25.6 mmol), 4-chloro-5-iodo-7H-pyrrolo [2,3-d]pyrimidine (5.5 g, 19.68 mmol) in THF (60 mL). The reaction was stirred at room temperature for 2 hours. The mixture was evaporated. The residue was diluted with EA (30 mL), filtered and the filtrate was concentrated in vacuo and purified with flash column chromatography (EA in PE, 0 to 40% gradient) to afford the desired product as a white solid (7.1 g, 64% yield). LC-MS: Calculated Exact Mass: 561.0 Found: [M+H]$^+$ (ESI)=561.9; $^1$H NMR (400 MHz, CHLOROFORM-d) δ ppm: 8.61 (s, 1H), 7.90 (m, 4H), 7.52-7.66 (m, 3H), 7.37-7.48 (m, 4H), 5.66 (m, 1H), 4.77-4.99 (m, 4H).

2-(4-Amino-5-iodo-7H-pyrrolo[2,3-d]pyrimidin-7-yl)propane-1,3-diol

A solution of 2-(4-chloro-5-iodo-7H-pyrrolo[2,3-d]pyrimidin-7-yl)propane-1,3-diyl dibenzoate (4.0 g, 7.12 mmol) in dioxane (50 mL) and a concentrated aqueous ammonia solution (50 mL) was heated in a pressure ressel at 120° C. for 18 hours. The mixture was cooled to room temperature and the solvent was distilled off in vacuo to afford a yellow solid. The yellow solid was suspended in water (15 mL), filtered and washed with water (5 mL) to afford a white solid. The white solid was suspended in MeOH (15 mL), filtered and washed with MeOH (5 mL) to afford a white solid (2.0 g, 80% yield). LC-MS: Calculated Exact Mass: 334.0 Found: [M+H]+(ESI)=334.5.

5-Iodo-7-((trans)-2-(piperidin-4-yl)-1,3-dioxan-5-yl)-7H-pyrrolo[2,3-d]pyrimidin-4-amine and 5-Iodo-7-((cis)-2-(piperidin-4-yl)-1,3-dioxan-5-yl)-7H-pyrrolo[2,3-d]pyrimidin-4-amine A solution of 2-(4-amino-5-iodo-7H-pyrrolo[2,3-d]pyrimidin-7-yl)propane-1,3-diol (1.9 g, 5.69 mmol), tert-butyl 4-formylpiperidine-1-carboxylate (15.8 g, 73.93 mmol), TsOH—H$_2$O (14.1 g, 73.93 mmol) and Na$_2$SO$_4$ (40.4 g, 284.34 mmol) in toluene (250 mL) was stirred at 110° C. for 18 hours. After cooling to room temperature, Na$_2$CO$_3$ solution was added and stirred for 15 minutes. The mixture was concentrated. The solid was suspended in DCM/MeOH (v/v=1:10, 400 mL), filtrated, evaporated and purified by flash column chromatography (MeOH in DCM, 0 to 10% gradient) to afford a yellow solid (880 mg, 36% yield). LC-MS: Calculated Exact Mass: 429.1 Found: [M+H]$^+$ (ESI)=429.6.

5-Iodo-7-((trans)-2-(1-methylpiperidin-4-yl)-1,3-dioxan-5-yl)-7H-pyrrolo[2,3-d]pyrimidin-4-amine And 5-Iodo-7-((cis)-2-(1-methylpiperidin-4-yl)-1,3-dioxan-5-yl)-7H-pyrrolo[2,3-d]pyrimidin-4-amine A solution of 5-iodo-7-((2r,5r)-2-(piperidin-4-yl)-1,3-dioxan-5-yl)-7H-pyrrolo [2,3-d]pyrimidin-4-amine (880 mg, 2.05 mmol), formaldehyde (369 mg, 12.3 mmol), and acetic acid (0.5 mL) in DCM/MeOH (v/v=1:2, 45 mL) was stirred at room temperature for 1 hour. NaBH(OAc)$_3$ (3.9 g, 18.45 mmol) was added to the mixture. After stirred at room temperature for 16 hours, water (100 mL) and DCM (400 mL) were added to the mixture followed by a saturated solution of NaHCO$_3$ (200 mL). The organic layer was washed with brine (80 mL), dried over Na$_2$SO$_4$, evaporated and purified with flash column chromatography (MeOH in DCM, 0 to 10% gradient) to afford a mixture of the title compounds as a yellow solid (460 mg, 51% yield). LC-MS: Calculated Exact Mass: 443.1 Found: [M+H]$^+$ (ESI)=443.6; $^1$H NMR (400 MHz, CHLOROFORM-d) δ ppm: 8.22 (s, 1H), 7.79 (s, 1H), 5.70 (br. s., 2H), 4.72-4.81 (m, 1H), 4.51 (m, 1H), 4.15-4.27 (m, 4H), 3.11 (d, J=10.4 Hz, 2H), 2.40-2.52 (m, 4H), 2.10-2.25 (m, 2H), 1.86-1.96 (m, 2H), 1.55-1.81 (m, 2H).

Example 1

7-((trans)-4-(4-methylpiperazin-1-yl)cyclohexyl)-5-(4-phenoxyphenyl)-7H-pyrrolo[2,3-d]pyrimidin-4-amine and Example 2

7-((cis)-4-(4-methylpiperazin-1-yl)cyclohexyl)-5-(4-phenoxyphenyl)-7H-pyrrolo[2,3-d]pyrimidin-4-amine

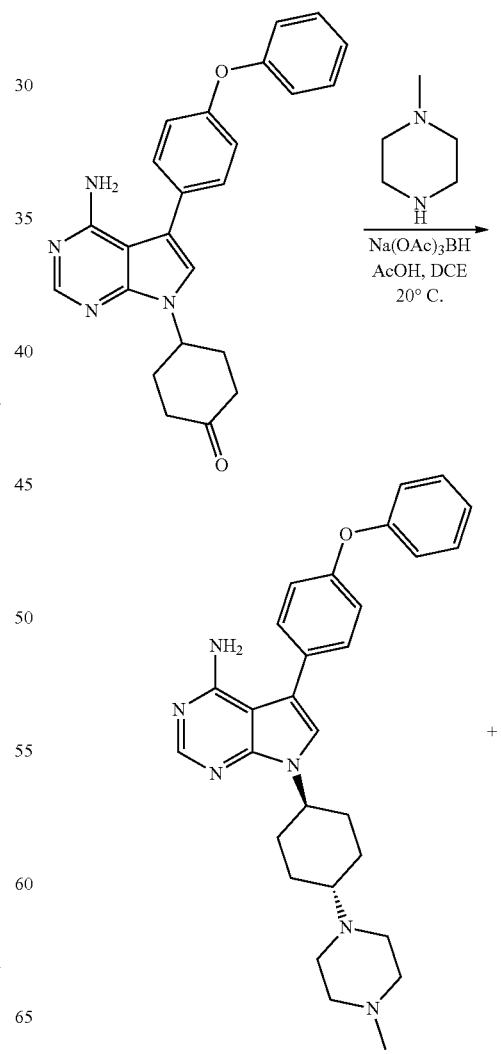

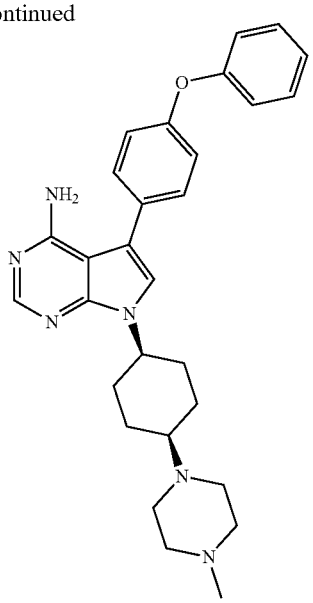

The solution of 4-(4-amino-5-(4-phenoxyphenyl)-7H-pyrrolo[2,3-d]pyrimidin-7-yl)cyclohexanone (500 mg, 1.25 mmol), 1-methylpiperazine (0.4 mL, 3.76 mmol), acetic acid (0.2 mL, 1.88 mmol) and molecular sieves (1.0 g) in 1,2-Dichloroethane (20 mL) was stirred at room temperature for 5 hours. Then, Sodium triacetoxyborohydride (398 mg, 1.88 mmol) was added and continued to stir for 16 hours at room temperature. Water (100 mL) and dichloromethane (100 mL) were added to the reaction mixture, a saturated aqueous solution of Sodium bicarbonate (100 mL) was further added thereto, and the mixture was partitioned. The organic layer was washed with brine (60 mL) and dried over Sodium sulfate and concentrated to purify by flash chromatography (DCM:MeOH=10:1) to obtain 7-((trans)-4-(4-methylpiperazin-1-yl)cyclohexyl)-5-(4-phenoxyphenyl)-7H-pyrrolo[2,3-d] pyrimidin-4-amine as yellow solid (100 mg, 16.5% yield) LCMS: Calculated Exact Mass=482.3; Found [M+H]$^+$ (ESI)=483.3; $^1$H NMR (400 MHz, CHLOROFORM-d) δ ppm: 8.34 (s, 1H), 7.36-7.48 (m, 4H), 7.15-7.20 (m, 1H), 7.07-7.13 (m, 4H), 7.02 (s, 1H), 5.18 (br. s., 2H), 4.70 (tt, J=12.1, 3.8 Hz, 1H), 2.76 (br. s., 4H), 2.63 (br. s., 2H), 2.49-2.60 (m, 2H), 2.36-2.45 (m, 3H), 2.21-2.33 (m, 2H), 2.13 (d, J=12.6 Hz, 2H), 1.76-1.92 (m, 2H), 1.57-1.69 (m, 2H).

Data for 7-(((cis)-4-(4-methylpiperazin-1-yl)cyclohexyl)-5-(4-phenoxyphenyl)-7H-pyrrolo[2,3-d]pyrimidin-4-amine (80 mg, 13.2%) LCMS: Calculated Exact Mass=482.3; Found [M+H]$^+$ (ESI)=483.3; $^1$H NMR (400 MHz, CHLOROFORM-d) δ ppm: 8.29-8.40 (m, 1H), 7.45-7.54 (m, 2H), 7.36-7.45 (m, 2H), 7.17 (t, J=7.4 Hz, 1H), 7.07-7.15 (m, 5H), 5.13 (s, 2H), 4.80-4.90 (m, 1H), 2.58-2.73 (m, 7H), 2.30-2.41 (m, 4H), 2.16-2.28 (m, 5H), 1.86 (dd, J=8.6, 3.8 Hz, 2H), 1.68 (t, J=13.7 Hz, 2H).

Using similar procedures, the following compounds may be obtained:

| Structure | Name | LCMS and NMR |
|---|---|---|
|  | EXAMPLE 3<br>7-((trans)-4-(4-(trideuteriomethyl)piperazin-1-yl)cyclohexyl)-5-(4-phenoxyphenyl)-7H-pyrrolo[2,3-d]pyrimidin-4-amine | LCMS: Calculated Exact Mass = 485.3; Found [M + H]$^+$ (ESI) = 486.3; $^1$H NMR (400 MHz, CHLOROFORM-d) δ ppm: 8.32 (s, 1H), 7.34-7.50 (m, 4H), 7.15 (t, J = 7.3 Hz, 1H), 7.08 (dd, J = 8.1, 5.6 Hz, 4H), 6.98 (s, 1H), 5.13 (br. s., 2H), 4.68 (t, J = 11.9 Hz, 1H), 2.91 (br. s., 7H), 2.62 (br. s., 1H), 2.19-2.29 (m, 2H), 2.15 (d, J = 11.3 Hz, 2H), 1.99-2.07 (m, 1H), 1.79-1.93 (m, 2H), 1.63 (q, J = 11.3 Hz, 2H). |

| Structure | Name | LCMS and NMR |
|---|---|---|
| 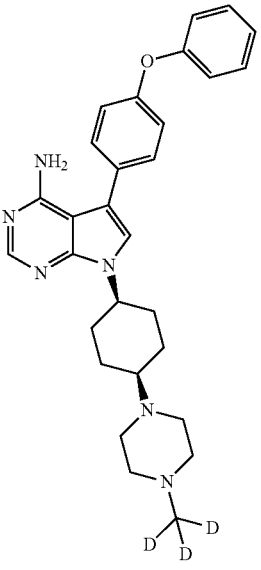 [SMILES: [2H]C([2H])([2H])N1CCN([C@H]2CC[C@@H](n3cc(-c4ccc(Oc5ccccc5)cc4)c4c(N)ncnc43)CC2)CC1] | EXAMPLE 4<br>7-((cis)-4-(4-(trideuteriomethyl)piperazin-1-yl)cyclohexyl)-5-(4-phenoxyphenyl)-7H-pyrrolo[2,3-d]pyrimidin-4-amine | LCMS: Calculated Exact Mass = 485.3; Found [M + H]⁺ (ESI) = 486.3; ¹H NMR (400 MHz, CHLOROFORM-d) δ ppm: 10.88 (br. s., 1H), 8.17 (s, 1H), 7.47 (s, 1H), 7.34-7.44 (m, 4H), 7.15-7.21 (m, 1H), 7.04-7.14 (m, 4H), 5.85 (br. s., 1H), 4.96 (br. s., 1H), 3.52-4.05 (m, 8H), 3.33 (br. s., 1H), 2.28-2.52 (m, 4H), 1.94-2.16 (m, 4H). |
| 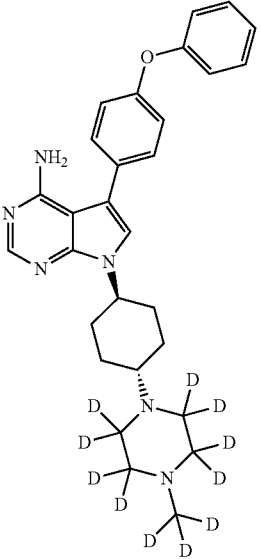 [SMILES: [2H]C([2H])([2H])N1C([2H])([2H])C([2H])([2H])N([C@H]2CC[C@H](n3cc(-c4ccc(Oc5ccccc5)cc4)c4c(N)ncnc43)CC2)C([2H])([2H])C1([2H])[2H]] | EXAMPLE 5<br>7-((trans)-4-(4-d3-methyl-d8-piperazin-1-yl)cyclohexyl)-5-(4-phenoxyphenyl)-7H-pyrrolo[2,3-d]pyrimidin-4-amine | LCMS: Calculated Exact Mass = 493.4; Found [M + H]⁺ (ESI) = 494.4; ¹H NMR (400 MHz, DMSO-d₆) δ ppm: 8.14 (s, 1H), 7.30-7.54 (m, 5H), 6.97-7.24 (m, 5H), 5.98 (br. s., 1H), 4.57 (br. s., 1H), 3.18 (br. s., 1H), 1.89-2.17 (m, 6H), 1.57 (br. s., 2H). |

| Structure | Name | LCMS and NMR |
|---|---|---|
| 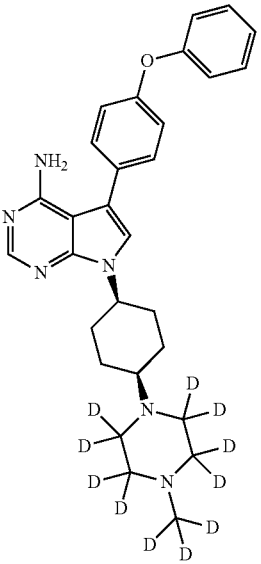 [SMILES: [2H]C([2H])([2H])N1C([2H])([2H])C([2H])([2H])N([C@H]2CC[C@@H](n3cc(-c4ccc(Oc5ccccc5)cc4)c4c(N)ncnc43)CC2)C([2H])([2H])C1([2H])[2H]] | EXAMPLE 6<br>7-((cis)-4-(4-d3-methyl-d8-piperazin-1-yl)cyclohexyl)-5-(4-phenoxyphenyl)-7H-pyrrolo[2,3-d]pyrimidin-4-amine | LCMS: Calculated Exact Mass = 493.4; Found [M + H]+ (ESI) = 494.4; $^1$H NMR (400 MHz, DMSO-d6) δ ppm: 7.48 (d, J = 7.8 Hz, 3H), 7.40 (d, J = 7.8 Hz, 2H), 6.96-7.22 (m, 5H), 5.93 (br. s., 2H), 4.71 (br. s., 1H), 2.03-2.20 (m, 4H), 1.59-1.75 (m, 4H). |
| 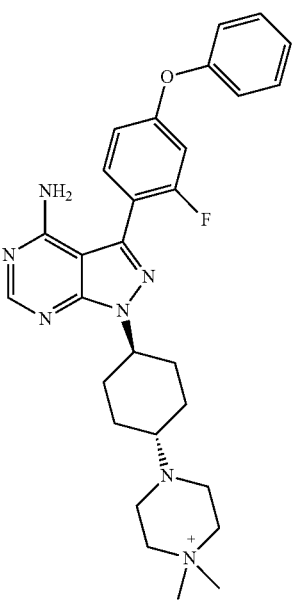 | EXAMPLE 7<br>4-((trans)-4-(4-amino-3-(2-fluoro-4-phenoxyphenyl)-1H-pyrazolo[3,4-d]pyrimidin-1-yl)cyclohexyl)-1,1-dimethylpiperazin-1-ium | LCMS: Calculated Exact Mass = 516.3; Found [M + H]$^+$ (ESI) = 517.1; $^1$H NMR (400 MHz, DMSO-d$_6$) δ ppm: 8.32 (s, 1H) 7.44-7.56 (m, 3H) 7.24 (t, J = 7.38 Hz, 1H) 7.15-7.21 (m, 2H) 6.99-7.06 (m, 1H) 6.95 (d, J = 8.88 Hz, 1H) 4.73 (br. s.,1H) 3.49-3.61 (m, 3H)3.17 (s, 6H) 2.06 (br. s., 6H) 1.60 (br. s., 2H). |

| Structure | Name | LCMS and NMR |
|---|---|---|
| 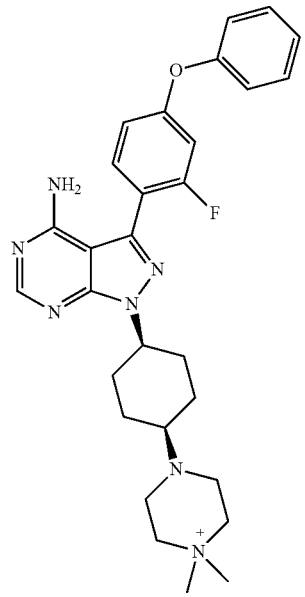 | EXAMPLE 8 4-((cis)-4-(4-amino-3-(2-fluoro-4-phenoxyphenyl)-1H-pyrazolo[3,4-d]pyrimidin-1-yl)cyclohexyl)-1,1-dimethylpiperazin-1-ium | $^1$H NMR (400 MHz, DMSO-d$_6$) δ 8.32 (br. s., 1H), 7.40-7.61 (m, 3H), 7.25 (t, J = 7.4 Hz, 1H), 7.18 (d, J = 7.6 Hz, 2H), 7.04 (dd, J = 11.2, 2.3 Hz, 1H), 6.95 (dd, J = 8.5, 2.3 Hz, 1H), 4.87 (br. s., 1H), 3.50 (br. s., 5H), 3.14 (br. s., 6H), 2.33 (br. s., 1H), 2.25 (br. s., 2H), 2.05 (br. s., 2H), 1.80 (br. s., 4H). |
| 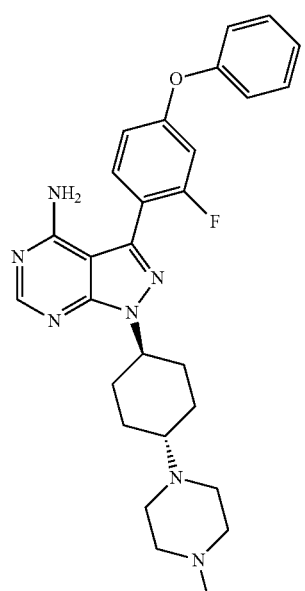 | EXAMPLE 9 1-((trans)-4-(4-ethylpiperazin-1-yl)cyclohexyl)-3-(2-fluoro-4-phenoxyphenyl)-1H-pyrazolo[3,4-d]pyrimidin-4-amine | LCMS: Calculated Exact Mass = 515.28; Found [M + H]$^+$ (ESI) = 516.29; $^1$H NMR (DMSO-d6) δ 8.27 (s, 1H), 7.45-7.54 (m, 3H), 7.24 (t, 7.41 Hz, 1H), 7.18 (d, 7.6 Hz, 2H), 7.03 (dd, J = 11.2, 2.3 Hz, 1H), 6.95 (dd, J = 8.5, 2.3 Hz, 1H), 4.74(s, 1H), 3.14(m, 6H), 2.09 (m, 7H), 1.59-1.72 (m, 5H), 0.97 (t, 7.5 Hz, 3H). |

| Structure | Name | LCMS and NMR |
|---|---|---|
| 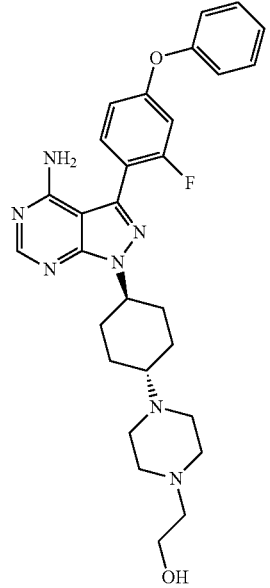 [SMILES: Nc1ncnc2c1c(-c1ccc(Oc3ccccc3)cc1F)nn2[C@H]1CC[C@H](N2CCN(CCO)CC2)CC1] | EXAMPLE 10<br>2-(4-((trans)-4-(4-amino-3-(2-fluoro-4-phenoxyphenyl)-1H-pyrazolo[3,4-d]pyrimidin-1-yl)cyclohexyl)piperazin-1-yl)ethanol | LCMS: Calculated Exact Mass = 531.3; Found [M + H]$^+$ (ESI) = 532.1; $^1$H NMR (400 MHz, DMSO-d$_6$) δ ppm: 8.31 (s, 1H) 7.56 (t, J = 8.51 Hz, 1H) 7.43-7.51 (m, 2H) 7.22-7.29 (m, 1H) 7.16-7.22 (m, 2H) 7.04 (dd, J = 11.26, 2.38 Hz, 1H) 6.96 (dd, J = 8.51, 2.25 Hz, 1H) 4.92 (br. s., 1H) 3.72 (t, J = 5.13 Hz, 2H) 3.57 (br. s., 2H) 3.17 (br. s., 3H) 2.33 (br. s., 2H) 1.98-2.11 (m, 2H) 1.88 (br. s., 4H). |
| 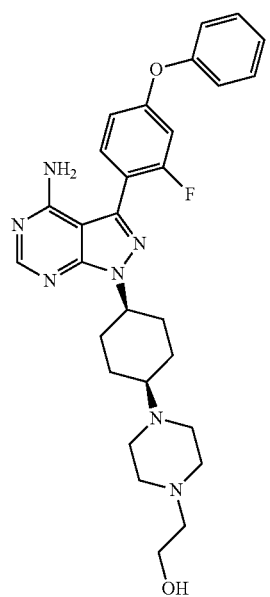 [SMILES: Nc1ncnc2c1c(-c1ccc(Oc3ccccc3)cc1F)nn2[C@H]1CC[C@@H](N2CCN(CCO)CC2)CC1] | EXAMPLE 11<br>2-(4-((cis)-4-(4-amino-3-(2-fluoro-4-phenoxyphenyl)-1H-pyrazolo[3,4-d]pyrimidin-1-yl)cyclohexyl)piperazin-1-yl)ethanol | LCMS: Calculated Exact Mass = 531.3; Found [M + H]$^+$ (ESI) = 532.1; $^1$H NMR (400 MHz, DMSO-d$_6$) δ ppm: 8.25-8.31 (m, 1H) 7.44-7.56 (m, 3H) 7.21-7.27 (m, 1H) 7.19 (dd, J = 8.57, 1.06 Hz, 2H) 7.03 (dd, J = 11.19, 2.44 Hz, 1H) 6.95 (dd, J = 8.50, 2.25 Hz, 1H) 4.75 (br. s., 1H) 3.72 (t, J = 4.88 Hz, 2H) 3.58 (br. s., 2H) 3.51 (br. s., 1H) 3.15 (br. s., 4H) 2.10 (d, J = 7.00 Hz, 6H) 1.69 (br. s., 2H). |

| Structure | Name | LCMS and NMR |
|---|---|---|
| 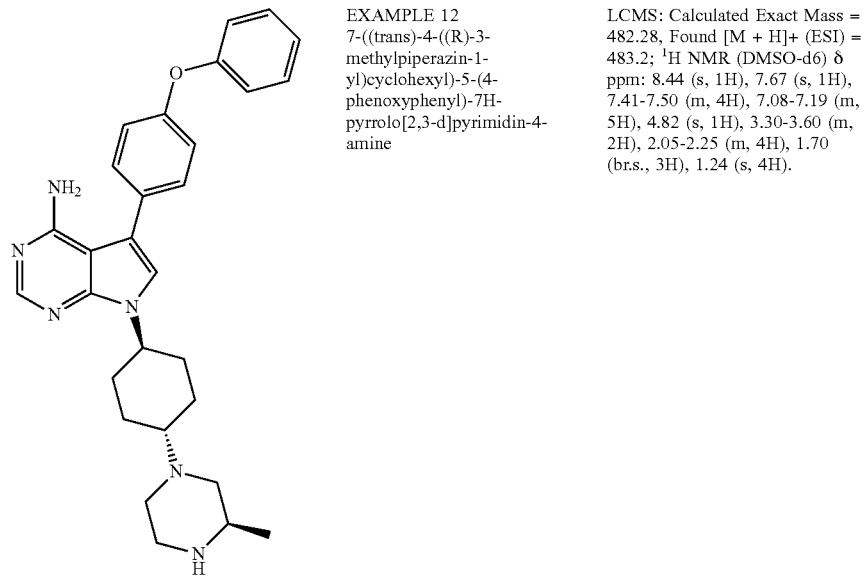 | EXAMPLE 12<br>7-((trans)-4-((R)-3-methylpiperazin-1-yl)cyclohexyl)-5-(4-phenoxyphenyl)-7H-pyrrolo[2,3-d]pyrimidin-4-amine | LCMS: Calculated Exact Mass = 482.28, Found [M + H]+ (ESI) = 483.2; $^1$H NMR (DMSO-d6) δ ppm: 8.44 (s, 1H), 7.67 (s, 1H), 7.41-7.50 (m, 4H), 7.08-7.19 (m, 5H), 4.82 (s, 1H), 3.30-3.60 (m, 2H), 2.05-2.25 (m, 4H), 1.70 (br.s., 3H), 1.24 (s, 4H). |
| 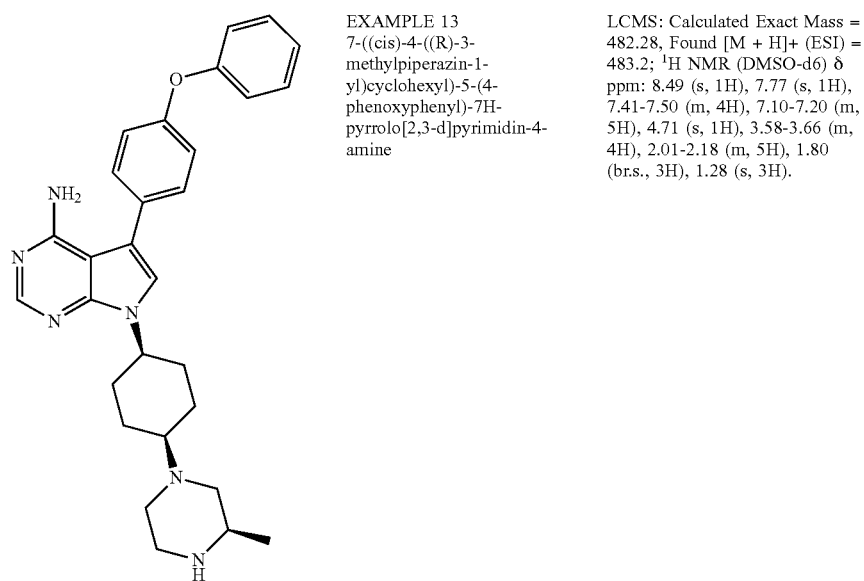 | EXAMPLE 13<br>7-((cis)-4-((R)-3-methylpiperazin-1-yl)cyclohexyl)-5-(4-phenoxyphenyl)-7H-pyrrolo[2,3-d]pyrimidin-4-amine | LCMS: Calculated Exact Mass = 482.28, Found [M + H]+ (ESI) = 483.2; $^1$H NMR (DMSO-d6) δ ppm: 8.49 (s, 1H), 7.77 (s, 1H), 7.41-7.50 (m, 4H), 7.10-7.20 (m, 5H), 4.71 (s, 1H), 3.58-3.66 (m, 4H), 2.01-2.18 (m, 5H), 1.80 (br.s., 3H), 1.28 (s, 3H). |

| Structure | Name | LCMS and NMR |
|---|---|---|
| 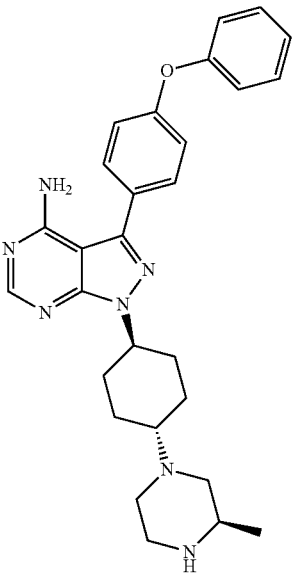 | EXAMPLE 14<br>1-((trans)-4-((R)-3-methylpiperazin-1-yl)cyclohexyl)-3-(4-phenoxyphenyl)-1H-pyrazolo[3,4-d]pyrimidin-4-amine | LC-MS: Calculated Exact Mass:477; Found [M+H]⁺ (ESI) = 478; $^1$H NMR (400 MHz, DMSO) δ 9.30 (d, J = 107.8 Hz, 2H), 8.36 (s, 1H), 7.70-7.61 (m, 2H), 7.49-7.41 (m, 2H), 7.20 (dd, J = 11.7, 4.2 Hz, 1H), 7.15 (ddd, J = 9.4, 7.6, 1.3 Hz, 4H), 4.83-4.72 (m, 1H), 3.42-2.91 (m, 8H), 2.27-2.03 (m, 6H), 1.79 (s, 2H), 1.29 (d, J = 6.5 Hz, 3H). |
| 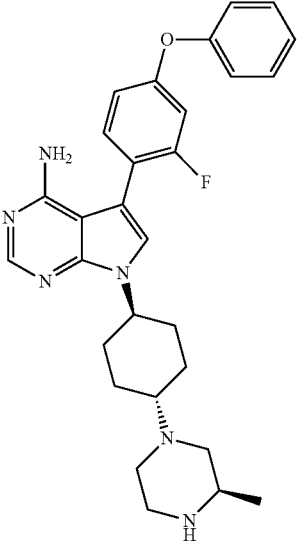 [SMILES: C[C@@H]1CN([C@H]2CC[C@H](n3cc(-c4ccc(Oc5ccccc5)cc4F)c4c(N)ncnc43)CC2)CCN1] | EXAMPLE 15<br>5-(2-fluoro-4-phenoxyphenyl)-7-((trans)-4-((R)-3-methylpiperazin-1-yl)cyclohexyl)-7H-pyrrolo[2,3-d]pyrimidin-4-amine | LCMS: Calculated Exact Mass = 500.3; Found [M + H]⁺ (ESI) = 501.1; $^1$H NMR (400 MHz, DMSO-d$_6$) δ ppm: 8.38 (s, 1H) 7.70 (s, 1H) 7.39-7.52 (m, 4H) 7.23 (t, J = 7.38 Hz, 1H) 7.16 (d, J = 7.75 Hz, 2H) 7.03 (dd, J = 11.26, 2.38 Hz, 1H) 6.93 (dd, J = 8.44, 2.19 Hz, 1H) 4.61-4.68 (m, 1H) 3.79 (m, 1H) 3.42-3.49 (m, 3H) 3.10-3.16 (m, 2H) 2.09 (s, 3H) 1.90-2.07 (m, 2H) 1.68 (br. s., 2H) 1.24 (d, J = 6.13 Hz, 4H). |

| Structure | Name | LCMS and NMR |
|---|---|---|
| 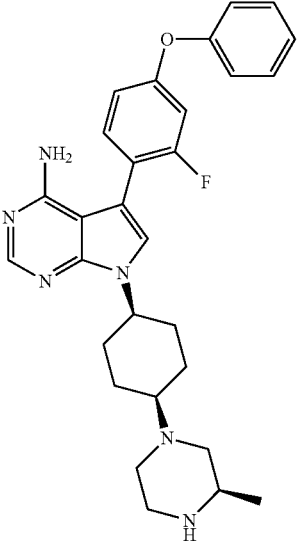 [SMILES: C[C@@H]1CN([C@H]2CC[C@@H](n3cc(-c4ccc(Oc5ccccc5)cc4F)c4c(N)ncnc43)CC2)CCN1] | EXAMPLE 16<br>5-(2-fluoro-4-phenoxyphenyl)-7-((cis)-4-((R)-3-methylpiperazin-1-yl)cyclohexyl)-7H-pyrrolo[2,3-d]pyrimidin-4-amine | LCMS: Calculated Exact Mass = 500.3; Found [M + H]+ (ESI) = 501.1; $^1$H NMR (400 MHz, DMSO-d$_6$) δ 8.43 (br. s., 1H), 7.67 (s, 1H), 7.39-7.51 (m, 3H), 7.23 (t, J = 7.4 Hz, 1H), 7.15 (dd, J = 8.6, 0.9 Hz, 2H), 7.04 (dd, J = 11.1, 2.3 Hz, 1H), 6.93 (dd, J = 8.5, 2.4 Hz, 1H), 4.82 (br. s., 1H), 3.41 (br. s., 2H), 2.04-2.17 (m, 7H), 1.76 (br. s., 4H), 1.23 (d, J = 6.1 Hz, 3H). |
| 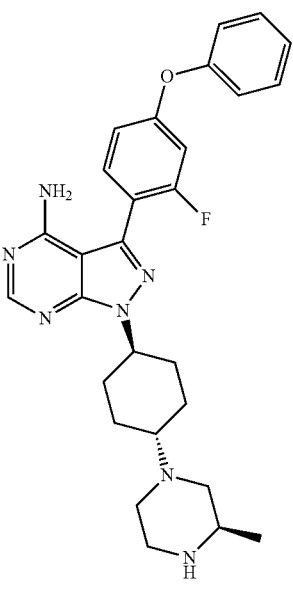 [SMILES: C[C@@H]1CN([C@H]2CC[C@H](n3nc(-c4ccc(Oc5ccccc5)cc4F)c4c(N)ncnc43)CC2)CCN1] | EXAMPLE 17<br>3-(2-fluoro-4-phenoxyphenyl)-1-((trans)-4-((R)-3-methylpiperazin-1-yl)cyclohexyl)-1H-pyrazolo[3,4-d]pyrimidin-4-amine | LC-MS: Calculated Exact Mass: 501.61; Found [M + H]+ (ESI) = 501.91; $^1$H NMR (400 MHz, DMSO-d$_6$) δ ppm: 9.23 (br. s., 1H), 8.38 (s, 1H), 7.43-7.58 (m, 3H), 7.25 (t, J = 7.4 Hz, 1H), 7.19 (dd, J = 8.6, 0.9 Hz, 2H), 7.04 (dd, J = 11.3, 2.3 Hz, 1H), 6.96 (dd, J = 8.5, 2.1 Hz, 1H), 4.78 (d, J = 5.8 Hz, 1H), 3.50-3.60 (m, 5H), 3.24 (br. s., 2H), 3.01 (br. s., 1H), 2.09-2.23 (m, 5H), 2.02-2.09 (m, 1H), 1.72-1.85 (m, 2H), 1.28 (d, J = 6.4 Hz, 3H). |

-continued

| Structure | Name | LCMS and NMR |
|---|---|---|
| 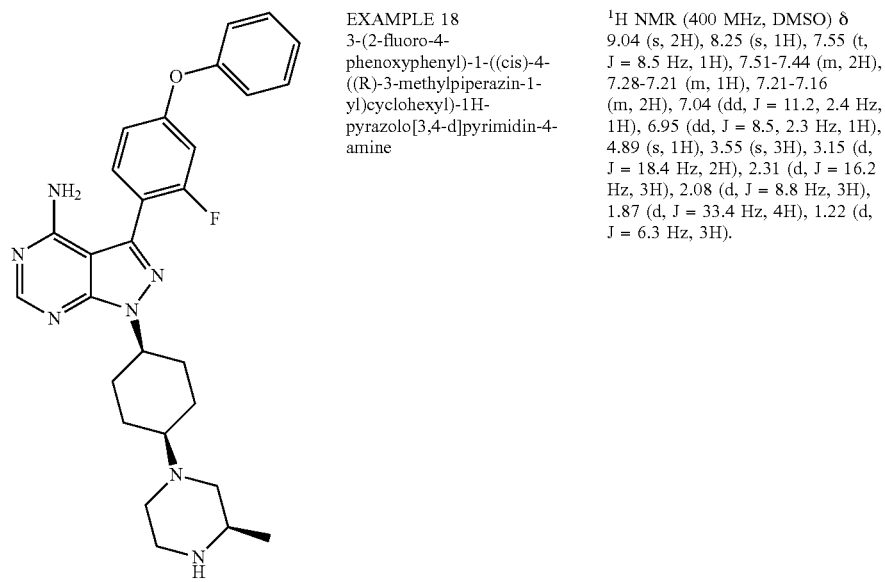 | EXAMPLE 18 3-(2-fluoro-4-phenoxyphenyl)-1-((cis)-4-((R)-3-methylpiperazin-1-yl)cyclohexyl)-1H-pyrazolo[3,4-d]pyrimidin-4-amine | $^1$H NMR (400 MHz, DMSO) δ 9.04 (s, 2H), 8.25 (s, 1H), 7.55 (t, J = 8.5 Hz, 1H), 7.51-7.44 (m, 2H), 7.28-7.21 (m, 1H), 7.21-7.16 (m, 2H), 7.04 (dd, J = 11.2, 2.4 Hz, 1H), 6.95 (dd, J = 8.5, 2.3 Hz, 1H), 4.89 (s, 1H), 3.55 (s, 3H), 3.15 (d, J = 18.4 Hz, 2H), 2.31 (d, J = 16.2 Hz, 3H), 2.08 (d, J = 8.8 Hz, 3H), 1.87 (d, J = 33.4 Hz, 4H), 1.22 (d, J = 6.3 Hz, 3H). |
| 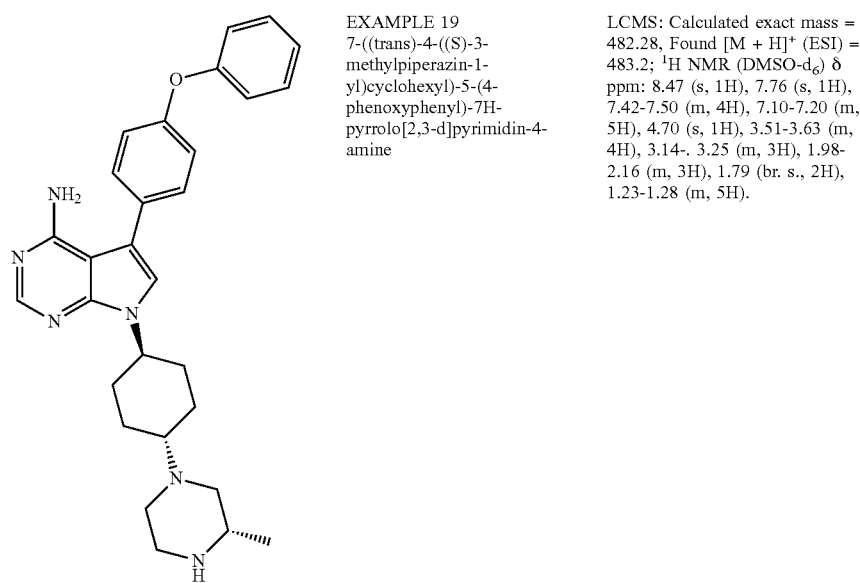 | EXAMPLE 19 7-((trans)-4-((S)-3-methylpiperazin-1-yl)cyclohexyl)-5-(4-phenoxyphenyl)-7H-pyrrolo[2,3-d]pyrimidin-4-amine | LCMS: Calculated exact mass = 482.28, Found [M + H]$^+$ (ESI) = 483.2; $^1$H NMR (DMSO-d$_6$) δ ppm: 8.47 (s, 1H), 7.76 (s, 1H), 7.42-7.50 (m, 4H), 7.10-7.20 (m, 5H), 4.70 (s, 1H), 3.51-3.63 (m, 4H), 3.14-. 3.25 (m, 3H), 1.98-2.16 (m, 3H), 1.79 (br. s., 2H), 1.23-1.28 (m, 5H). |

-continued

| Structure | Name | LCMS and NMR |
|---|---|---|
| | EXAMPLE 20<br>7-((cis)-4-((S)-3-methyl piperazin-1-yl)cyclohexyl)-5-(4-phenoxyphenyl)-7H-pyrrolo [2,3-d]pyrimidin-4-amine | LCMS: Calculated Exact Mass = 482.28; Found [M + H]$^+$ (ESI) = 482.79; $^1$H NMR (DMSO-d6) δ ppm: 8.14 (s, 1H), 7.49 (d, J = 8.5 Hz, 2H), 7.38-7.44 (m, 2H), 7.28 (s, 1H), 7.16 (t, J = 7.3 Hz, 1H), 7.06-7.12 (m, 4H), 6.12 (br. s., 1H), 4.62-4.73 (m, 1H), 2.80-2.92 (m, 3H), 2.68-2.77 (m, 2H), 2.02-2.14 (m, 5H), 1.65-1.79 (m, 3H), 1.54 (t, J = 13.0 Hz, 2H), 1.43 (t, J = 10.2 Hz, 1H), 0.94 (d, J = 6.1 Hz, 3H). |
| | Example 21<br>1-((trans)-4-((S)-3-methylpiperazin-1-yl)cyclohexyl)-3-(4-phenoxyphenyl)-1H-pyrazolo[3,4-d] pyrimidin-4-amine | LC-MS:Calculated Exact Mass: 483.27; Found: [M + H]$^+$ (ESI) = 484.3<br>$^1$H NMR (400 MHz, DMSO-d$_6$) δ ppm: 8.24 (s, 1H), 7.62-7.69 (m, 2H), 7.41-7.49 (m, 2H), 7.11-7.23 (m, 5H), 4.60-4.70 (m, 1H), 2.87 (d, J = 11.8 Hz, 1H), 2.64-2.77 (m, 4H), 2.38 (br. s., 1H), 2.16-2.24 (m, 1H), 1.96-2.07 (m, 4H), 1.85-1.96 (m, 3H), 1.49 (dd, J = 12.2, 4.2 Hz, 2H), 0.97 (d, J = 6.2 Hz, 3H) |

-continued

| Structure | Name | LCMS and NMR |
|---|---|---|
| 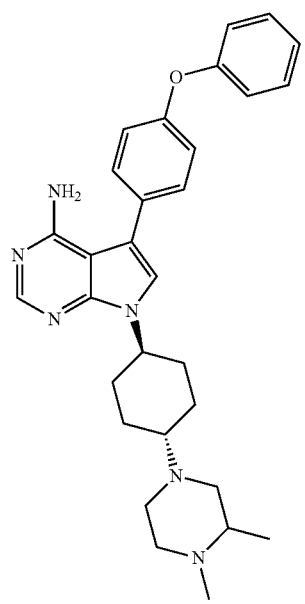 [SMILES: CC1CN([C@H]2CC[C@H](n3cc(-c4ccc(Oc5ccccc5)cc4)c4c(N)ncnc43)CC2)CCN1C] | EXAMPLE 22<br>7-((trans)-4-(3,4-dimethylpiperazin-1-yl)cyclohexyl)-5-(4-phenoxyphenyl)-7H-pyrrolo[2,3-d]pyrimidin-4-amine | LCMS: Calculated Exact Mass = 496.3, Found [M + H]$^+$ (ESI) = 497.3; $^1$H NMR (DMSO-d6) δ ppm: 8.14 (s, 1H), 7.32-7.47 (m, 6H), 7.07-7.17 (m, 6H), 7.10-7.20 (m, 5H), 6.14 (br.s., 1H), 4.57 (br.s., 1H), 2.810-2.99 (br.s., 4H), 2.60-2.80 (m, 5H), 1.91-2.03 (m, 8H), 1.47-1.60 (m, 2H). |
| 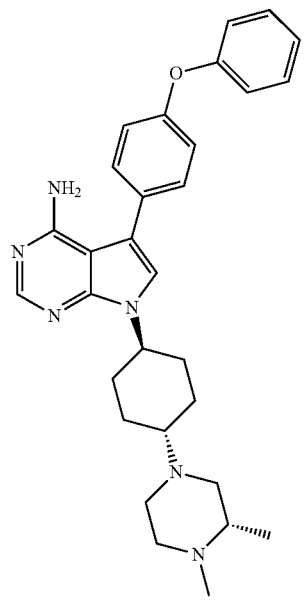 [SMILES: C[C@H]1CN([C@H]2CC[C@H](n3cc(-c4ccc(Oc5ccccc5)cc4)c4c(N)ncnc43)CC2)CCN1C] | EXAMPLE 23<br>7-((trans)-4-((S)-3,4-dimethylpiperazin-1-yl)cyclohexyl)-5-(4-phenoxyphenyl)-7H-pyrrolo[2,3-d]pyrimidin-4-amine | LCMS: Calculated Exact Mass = 496.3; Found [M + H]$^+$ (ESI) = 496.83; $^1$H NMR (DMSO-d$_6$) δ ppm: 8.13 (s, 1H), 7.38-7.49 (m, 5H), 7.13-7.19 (m, 1H), 7.05-7.13 (m, 4H), 6.11 (br. s., 1H), 4.55 (s, 2H), 2.73 (br. s., 3H), 2.33 (br. s., 2H), 2.16 (br. s., 4H), 1.85-2.03 (m, 8H), 1.45 (d, J = 12.2 Hz, 2H), 0.93-1.00 (m, 3H). |

| Structure | Name | LCMS and NMR |
|---|---|---|
| 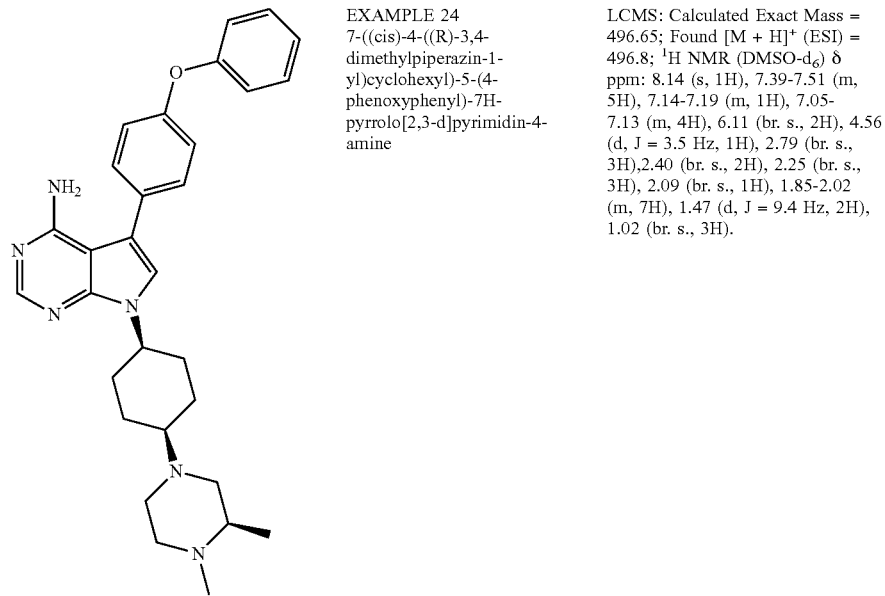 | EXAMPLE 24<br>7-((cis)-4-((R)-3,4-dimethylpiperazin-1-yl)cyclohexyl)-5-(4-phenoxyphenyl)-7H-pyrrolo[2,3-d]pyrimidin-4-amine | LCMS: Calculated Exact Mass = 496.65; Found [M + H]$^+$ (ESI) = 496.8; $^1$H NMR (DMSO-d$_6$) δ ppm: 8.14 (s, 1H), 7.39-7.51 (m, 5H), 7.14-7.19 (m, 1H), 7.05-7.13 (m, 4H), 6.11 (br. s., 2H), 4.56 (d, J = 3.5 Hz, 1H), 2.79 (br. s., 3H), 2.40 (br. s., 2H), 2.25 (br. s., 3H), 2.09 (br. s., 1H), 1.85-2.02 (m, 7H), 1.47 (d, J = 9.4 Hz, 2H), 1.02 (br. s., 3H). |
| 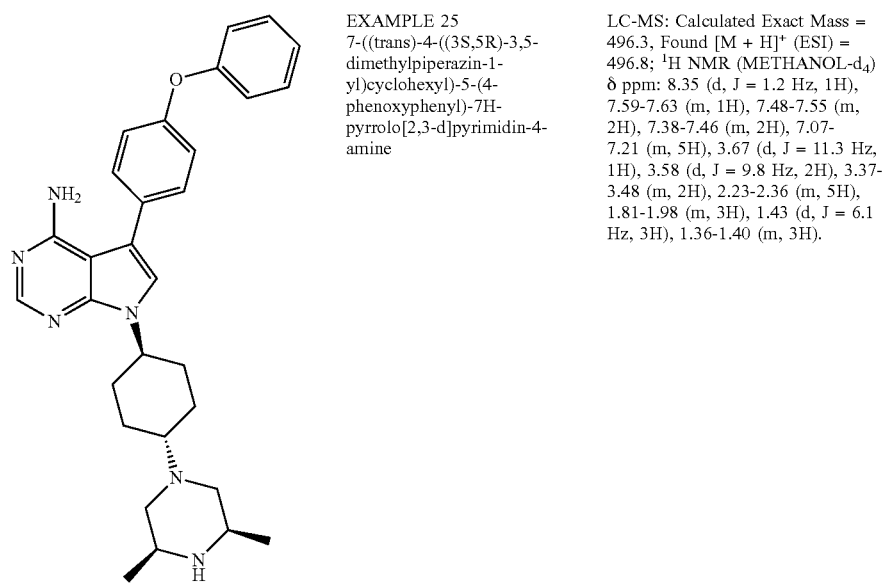 | EXAMPLE 25<br>7-((trans)-4-((3S,5R)-3,5-dimethylpiperazin-1-yl)cyclohexyl)-5-(4-phenoxyphenyl)-7H-pyrrolo[2,3-d]pyrimidin-4-amine | LC-MS: Calculated Exact Mass = 496.3, Found [M + H]$^+$ (ESI) = 496.8; $^1$H NMR (METHANOL-d$_4$) δ ppm: 8.35 (d, J = 1.2 Hz, 1H), 7.59-7.63 (m, 1H), 7.48-7.55 (m, 2H), 7.38-7.46 (m, 2H), 7.07-7.21 (m, 5H), 3.67 (d, J = 11.3 Hz, 1H), 3.58 (d, J = 9.8 Hz, 2H), 3.37-3.48 (m, 2H), 2.23-2.36 (m, 5H), 1.81-1.98 (m, 3H), 1.43 (d, J = 6.1 Hz, 3H), 1.36-1.40 (m, 3H). |

| Structure | Name | LCMS and NMR |
|---|---|---|
| 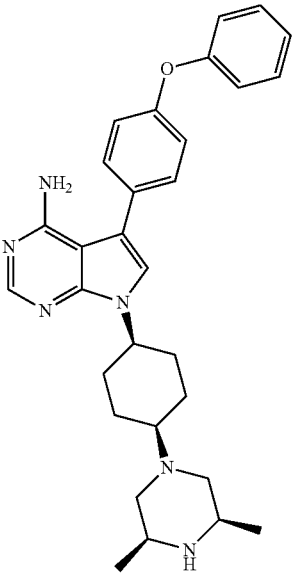 [SMILES: C[C@@H]1CN([C@H]2CC[C@@H](n3cc(-c4ccc(Oc5ccccc5)cc4)c4c(N)ncnc43)CC2)C[C@H](C)N1] | EXAMPLE 26<br>7-((cis)-4-((3S,5R)-3,5-dimethylpiperazin-1-yl)cyclohexyl)-5-(4-phenoxyphenyl)-7H-pyrrolo[2,3-d]pyrimidin-4-amine | LC-MS: Calculated Exact Mass = 496.3, Found [M + H]$^+$ (ESI) = 496.8; $^1$H NMR (METHANOL-$d_4$) δ ppm: 8.23 (s, 1H), 7.49 (s, 1H), 7.37-7.42 (m, 2H), 7.30 (t, J = 7.9 Hz, 2H), 6.96-7.10 (m, 5H), 3.39 (d, J = 8.2 Hz, 2H), 3.32 (d, J = 11.3 Hz, 2H), 2.90 (br. s., 1H), 2.57 (t, J = 12.1 Hz, 2H), 2.10 (d, J = 3.4 Hz, 4H), 1.92-2.06 (m, 2H), 1.65 (d, J = 8.5 Hz, 2H), 1.24-1.29 (m, 6H). |
| 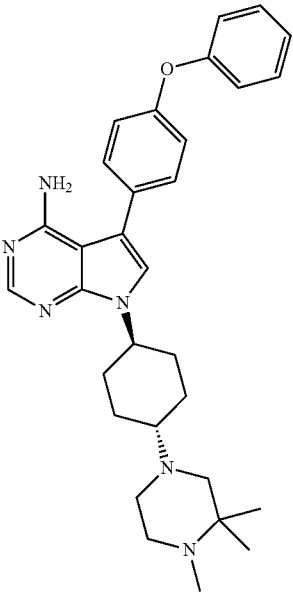 [SMILES: CN1CCN([C@H]2CC[C@H](n3cc(-c4ccc(Oc5ccccc5)cc4)c4c(N)ncnc43)CC2)CC1(C)C] | EXAMPLE 27<br>5-(4-phenoxyphenyl)-7-((trans)-4-(3,3,4-trimethylpiperazin-1-yl)cyclohexyl)-7H-pyrrolo[2,3-d] pyrimidin-4-amine | LC-MS: Calculated Exact Mass = 510.3, Found [M + H]$^+$ (ESI) = 511.1; $^1$H NMR (CHLOROFORM-d) δ: 8.21 (s, 1H), 7.41 (t, J = 7.9 Hz, 2H), 7.35 (d, J = 8.5 Hz, 2H), 7.20 (s, 1H), 7.09 (d, J = 8.0 Hz, 3H), 7.11 (d, J = 8.2 Hz, 2H), 2.81 (s, 3H), 2.33 (d, J = 11.4 Hz, 3H), 2.28 (t, J = 7.6 Hz, 2H), 1.99-2.04 (m, 5H), 1.59-1.64 (m, 6H), 1.26 (br. s., 3H), 1.25 (br. s., 3H). |

-continued

| Structure | Name | LCMS and NMR |
|---|---|---|
| 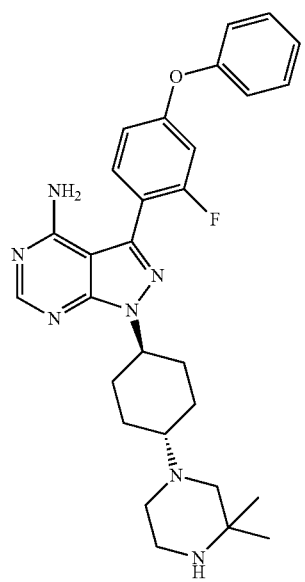 [SMILES: CC1(C)CN([C@H]2CC[C@H](n3nc(-c4ccc(Oc5ccccc5)cc4F)c4c(N)ncnc43)CC2)CCN1] | EXAMPLE 28 1-((trans)-4-(3,3-dimethylpiperazin-1-yl)cyclohexyl)-3-(2-fluoro-4-phenoxyphenyl)-1H-pyrazolo[3,4-d]pyrimidin-4-amine | LCMS: Calculated Exact Mass = 515.28; Found [M + H]$^+$ (ESI) = 516.25; $^1$H NMR (DMSO-d$_6$) δ ppm: 8.87 (br. s., 1H), 8.33 (s, 1H), 7.43-7.59 (m, 3H), 7.16-7.30 (m, 3H), 7.03 (dd, J = 11.3, 2.3 Hz, 1H), 6.95 (dd, J = 8.5, 2.3 Hz, 1H), 4.71 (br. s., 1H), 3.24 (br. s., 2H), 2.89 (br. s., 3H), 2.67 (br. s., 2H), 1.90-2.20 (m, 6H), 1.62 (br. s., 2H), 1.36 (br. s., 6H). |
| 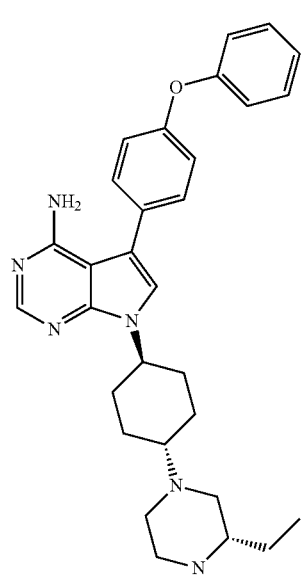 | EXAMPLE 29 7-((trans)-4-((S)-3-ethylpiperazin-1-yl)cyclohexyl)-5-(4-phenoxyphenyl)-7H-pyrrolo[2,3-d]pyrimidin-4-amine | LC-MS: Calculated Exact Mass: 496.3; Found [M + H]$^+$ (ESI) = 497.1; $^1$H NMR (400 MHz, DMSO) δ 9.28 (s, 2H), 8.48 (s, 1H), 7.77 (s, 1H), 7.52-7.47 (m, 2H), 7.47-7.41 (m, 2H), 7.19 (t, J = 7.4 Hz, 1H), 7.17-7.08 (m, 4H), 4.72 (t, J = 11.7 Hz, 1H), 3.62 (d, J = 12.5 Hz, 5H), 3.39 (s, 2H), 3.28 (s, 4H), 3.03 (s, 1H), 2.22-1.94 (m, 7H), 1.82 (s, 3H), 1.74-1.58 (m, 3H), 0.99 (t, J = 7.5 Hz, 3H). |

| Structure | Name | LCMS and NMR |
|---|---|---|
| 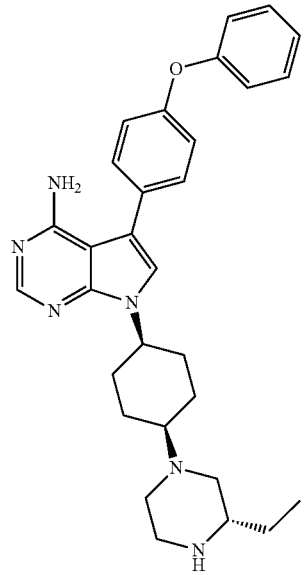 [SMILES: CC[C@H]1CN([C@H]2CC[C@@H](n3cc(-c4ccc(Oc5ccccc5)cc4)c4c(N)ncnc43)CC2)CCN1] | EXAMPLE 30<br>7-((cis)-4-((S)-3-ethylpiperazin-1-yl)cyclohexyl)-5-(4-phenoxyphenyl)-7H-pyrrolo[2,3-d]pyrimidin-4-amine | LC-MS: Calculated Exact Mass: 496.3; Found [M + H]$^+$ (ESI) = 497.1; $^1$H NMR (400 MHz, DMSO) δ 9.11 (s, 2H), 8.47 (s, 1H), 7.67 (s, 1H), 7.50 (d, J = 8.6 Hz, 2H), 7.47-7.39 (m, 2H), 7.19 (t, J = 7.4 Hz, 1H), 7.16-7.07 (m, 4H), 4.85 (s, 1H), 3.40 (d, J = 54.1 Hz, 7H), 2.28-1.96 (m, 6H), 1.83 (s, 4H), 1.63 (dd, J = 14.5, 7.3 Hz, 2H), 0.98 (t, J = 7.5 Hz, 3H). |
| 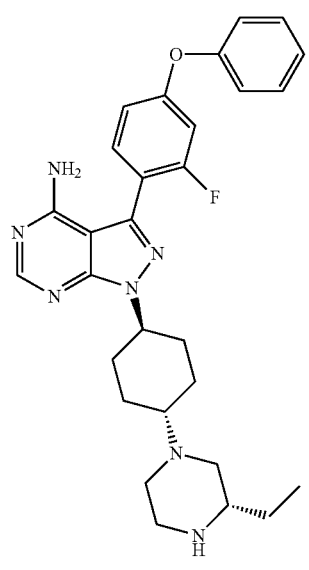 [SMILES: CC[C@H]1CN([C@H]2CC[C@H](n3nc(-c4ccc(Oc5ccccc5)cc4F)c4c(N)ncnc43)CC2)CCN1] | EXAMPLE 31<br>1-((trans)-4-((S)-3-ethylpiperazin-1-yl)cyclohexyl)-3-(2-fluoro-4-phenoxyphenyl)-1H-pyrazolo[3,4-d]pyrimidin-4-amine | LCMS: Calculated Exact Mass = 515.28; Found [M + H]$^+$ (ESI) = 516.27; $^1$H NMR (DMSO-d6) δ ppm: 8.29 (s, 1H), 7.56 (t, 8.5 Hz, 1H), 7.48 (m, 2H), 7.25 (t, 7.4 Hz, 1H), 7.17-7.20 (m, 2H), 7.03 (dd, J = 11.2, 2.3 Hz, 1H), 6.95 (dd, J = 8.5, 2.3 Hz, 1H), 4.94 (s, 1H), 3.17(m, 6H), 2.09 (m, 7H), 2.33 (m, 3H), 2.09 (m, 3H), 1.89 (m, 4H), 1.56-1.65 (m, 2H), 0.94 (t, 7.5 Hz, 3H) |

| Structure | Name | LCMS and NMR |
|---|---|---|
| 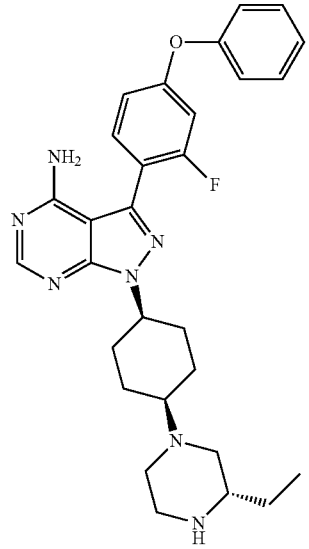 [SMILES: CC[C@H]1CN([C@H]2CC[C@@H](n3nc(-c4ccc(Oc5ccccc5)cc4F)c4c(N)ncnc43)CC2)CCN1] | EXAMPLE 32<br>1-((cis)-4-((S)-3-ethylpiperazin-1-yl)cyclohexyl)-3-(2-fluoro-4-phenoxyphenyl)-1H-pyrazolo[3,4-d]pyrimidin-4-amine | LCMS: Calculated Exact Mass = 515.28; Found [M + H]$^+$ (ESI) = 516.26; $^1$H NMR (DMSO-d$_6$) δ ppm: 8.27 (s, 1H), 7.45-7.54 (m, 3H), 7.24 (t, 7.41 Hz, 1H), 7.18 (d, 7.6 Hz, 2H), 7.03 (dd, J = 11.2, 2.3 Hz, 1H), 6.95 (dd, J = 8.5, 2.3 Hz, 1H), 4.74(s, 1H), 3.14(m, 6H), 2.09 (m, 7H), 1.59-1.72 (m, 5H), 0.97 (t, 7.5 Hz, 3H) |
| 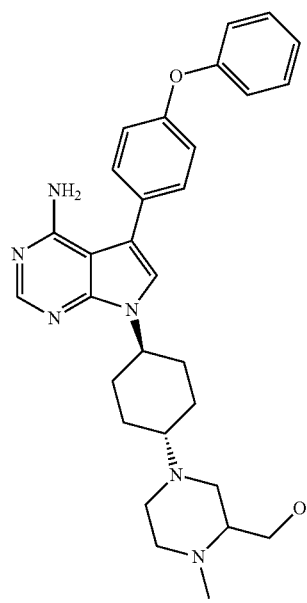 | EXAMPLE 33<br>(4-((trans)-4-(4-amino-5-(4-phenoxyphenyl)-7H-pyrrolo[2,3-d]pyrimidin-7-yl)cyclohexyl)-1-methylpiperazin-2-yl)methanol | LCMS: Calculated Exact Mass = 512.3; Found [M + H]+ (ESI) = 513.2; $^1$H NMR (400 MHz, DMSO-d$_6$) δ ppm: 8.14 (s, 1H), 7.33-7.51 (m, 5H), 7.03-7.21 (m, 5H), 6.11 (br. s., 2H), 4.71 (d, J = 7.3 Hz, 1H), 4.46-4.65 (m, 1H), 3.54-3.67 (m, 1H), 3.10-3.21 (m, 1H), 2.82-2.97 (m, 3H), 2.15-2.44 (m, 5H), 2.09-2.13 (m, 2H), 1.85-2.03 (m, 6H), 1.32-1.61 (m, 2H). |

| Structure | Name | LCMS and NMR |
|---|---|---|
| 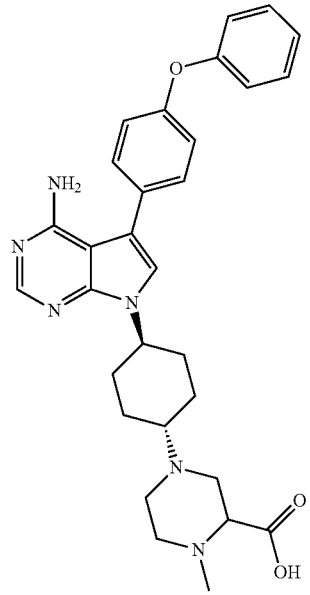 | EXAMPLE 34 4-((trans)-4-(4-amino-5-(4-phenoxyphenyl)-7H-pyrrolo[2,3-d]pyrimidin-7-yl)cyclohexyl)-1-methylpiperazine-2-carboxylic acid | LCMS: Calculated Exact Mass = 526.3; Found [M + H]+ (ESI) = 527.2; $^1$H NMR (400 MHz, DMSO-$d_6$) δ ppm: 8.13 (s, 1H), 7.38-7.52 (m, 5H), 7.09 (dd, J = 8.4, 3.8 Hz, 5H), 4.72 (br. s., 1H), 4.11 (br. s., 1H), 1.93-2.01 (m, 4H), 1.45-1.63 (m, 14H). |
| 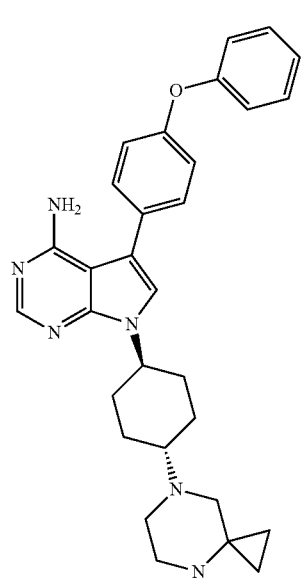 | EXAMPLE 35 7-((trans)-4-(4,7-diazaspiro[2.5]octan-7-yl)cyclohexyl)-5-(4-phenoxyphenyl)-7H-pyrrolo[2,3-d]pyrimidin-4-amine | LCMS: Calculated Exact Mass = 494.3; Found [M + H]$^+$ (ESI) = 495.0; $^1$H NMR (400 MHz, DMSO-$d_6$) δ ppm: 8.46 (s, 1H), 7.74 (s, 1H), 7.38-7.54 (m, 4H), 7.02-7.25 (m, 5H), 4.63-4.78 (m, 1H), 3.27-3.75 (m, 8H), 2.16-2.29 (m, 2H), 1.95-2.15 (m, 4H), 1.75 (d, J = 10.9 Hz, 2H), 1.14 (S, 2H), 0.99 (S, 2H). |

| Structure | Name | LCMS and NMR |
|---|---|---|
| 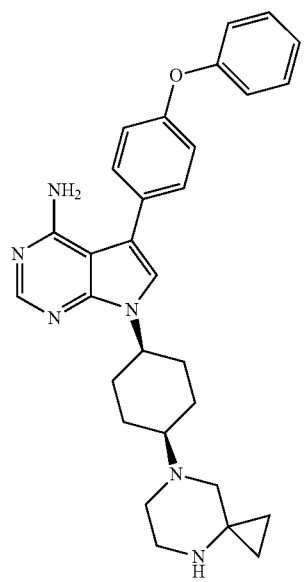 [SMILES: Nc1ncnc2c1c(-c1ccc(Oc3ccccc3)cc1)cn2[C@H]1CC[C@@H](N2CCNC3(CC3)C2)CC1] | EXAMPLE 36<br>7-((cis)-4-(4,7-diazaspiro[2.5]octan-7-yl)cyclohexyl)-5-(4-phenoxyphenyl)-7H-pyrrolo[2,3-d]pyrimidin-4-amine | LCMS: Calculated Exact Mass = 494.3; Found [M + H]+ (ESI) = 495.0; $^1$H NMR (400 MHz, DMSO) δ 8.44 (s, 1H), 7.64 (s, 1H), 7.50 (d, J = 8.5 Hz, 2H), 7.43 (t, J = 7.8 Hz, 2H), 7.18 (t, J = 7.1 Hz, 1H), 7.12 (dd, J = 11.1, 8.8 Hz, 4H), 4.80 (s, 1H), 3.71 (s, 6H), 2.22 (s, 2H), 2.04 (s, 2H), 1.79 (s, 4H), 0.97 (d, J = 45.7 Hz, 4H) |
| 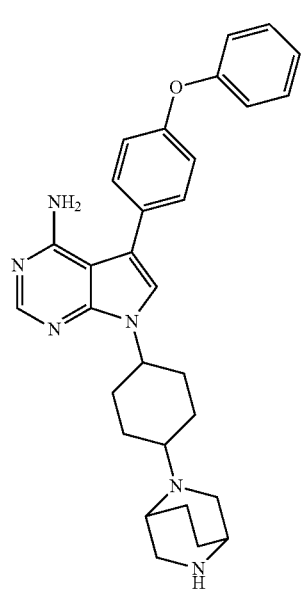 [SMILES: Nc1ncnc2c1c(-c1ccc(Oc3ccccc3)cc1)cn2C1CCC(N2CC3CCC2CN3)CC1] | EXAMPLE 37<br>7-(4-(2,5-diazabicyclo[2.2.2]octan-2-yl)cyclohexyl)-5-(4-phenoxyphenyl)-7H-pyrrolo[2,3-d]pyrimidin-4-amine | LCMS: Calculated Exact Mass = 494.3; Found [M + H]+ (ESI) = 494.9; $^1$H NMR (400 MHz, DMSO-d$_6$) δ ppm: 9.52 (br. s., 1H) 8.50 (s, 1H) 7.64 (s, 1H) 7.49 (d, J = 8.55 Hz, 2H) 7.37-7.46 (m, 2H) 7.18 (t, J = 7.32 Hz, 1H) 7.11 (t, J = 9.31 Hz, 4H) 4.89-4.93 (m, 1H) 4.00-4.05 (m, 1H) 3.81-3.89 (m, 2H) 3.61-3.66 (m, 2H) 3.50-3.56 (m, 2H) 2.20-2.26 (m., 3H) 2.01-2.06 (m, 8H) |

-continued

| Structure | Name | LCMS and NMR |
|---|---|---|
| 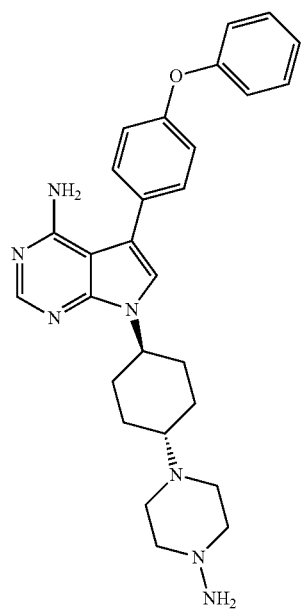 [SMILES: Nc1ncnc2c1c(-c1ccc(Oc3ccccc3)cc1)cn2[C@H]1CC[C@H](N2CCN(N)CC2)CC1] | EXAMPLE 38 7-((trans)-4-(4-aminopiperazin-1-yl)cyclohexyl)-5-(4-phenoxyphenyl)-7H-pyrrolo[2,3-d]pyrimidin-4-amine | LCMS: Calculated Exact Mass = 483.3; Found [M + H]$^+$ (ESI) = 484.3; $^1$H NMR (400 MHz, DMSO-$d_6$) δ ppm: 10.31 (s, 1H) 9.76 (s, 2H) 8.48 (s, 1H) 7.76 (s, 1H) 7.49 (d, J = 8.24 Hz, 2H) 7.44 (t, J = 7.93 Hz, 2H) 7.18 (t, J = 7.32 Hz, 1H) 7.07-7.16 (m, 4H) 4.62-4.75 (m, 1H) 3.64 (d, J = 10.68 Hz, 2H) 3.39 (d, J = 10.07 Hz, 2H) 3.19-3.35 (m, 3H) 3.01 (d, J = 10.99 Hz, 2H) 2.23 (d, J = 10.38 Hz, 2H) 2.08-2.17 (m, 2H) 1.96-2.08 (m, 2H) 1.66-1.84 (m, 2H) |
| 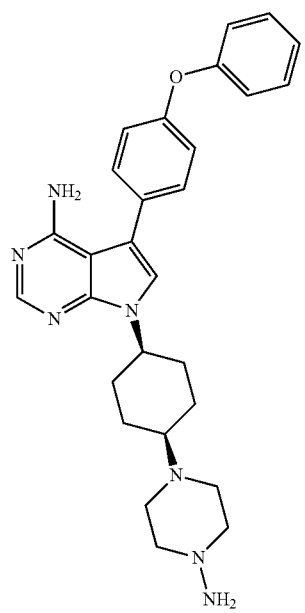 [SMILES: Nc1ncnc2c1c(-c1ccc(Oc3ccccc3)cc1)cn2[C@H]1CC[C@@H](N2CCN(N)CC2)CC1] | EXAMPLE 39 7-((cis)-4-(4-aminopiperazin-1-yl)cyclohexyl)-5-(4-phenoxyphenyl)-7H-pyrrolo[2,3-d]pyrimidin-4-amine | LCMS: Calculated Exact Mass = 483.3; Found [M + H]$^+$ (ESI) = 484.3; $^1$H NMR (400 MHz, DMSO-$d_6$) δ ppm: 9.71 (s, 3H), 8.46 (s, 1H), 8.46 (s, 1H), 7.64 (s, 1H), 7.50 (d, J = 8.6 Hz, 2H), 7.43 (t, J = 7.9 Hz, 2H), 7.18 (t, J = 7.4 Hz, 1H), 7.12 (dd, J = 13.2, 8.2 Hz, 4H), 4.88 (s, 1H), 3.65-3.74 (m, 8H), 3.29-3.34 (m, 4H), 3.19-3.21 (m, 3H), 3.00-3.02 (m, 2H), 2.31 (d, J = 7.0 Hz, 2H), 2.02 (t, J = 23.6 Hz, 6H). |

| Structure | Name | LCMS and NMR |
|---|---|---|
| 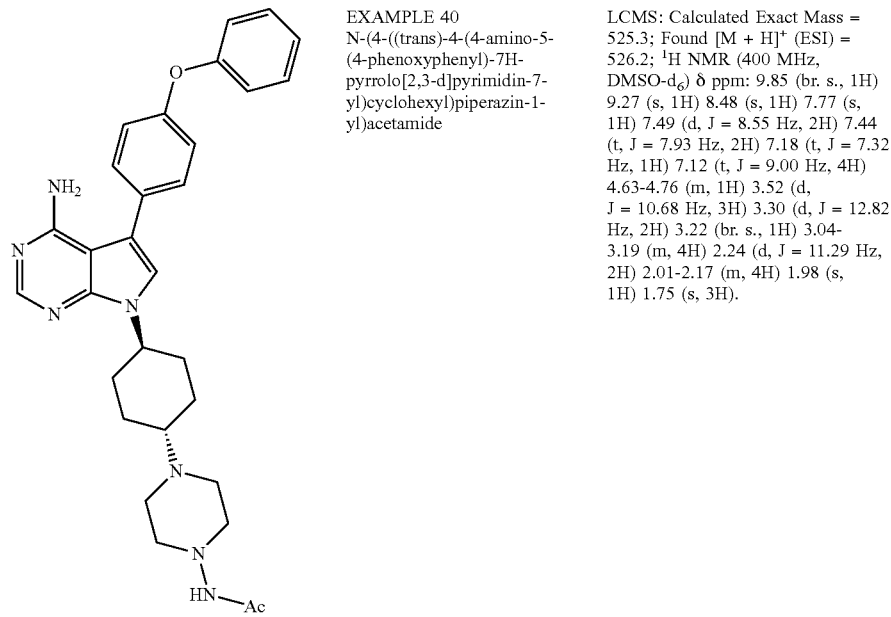 | EXAMPLE 40<br>N-(4-((trans)-4-(4-amino-5-(4-phenoxyphenyl)-7H-pyrrolo[2,3-d]pyrimidin-7-yl)cyclohexyl)piperazin-1-yl)acetamide | LCMS: Calculated Exact Mass = 525.3; Found [M + H]$^+$ (ESI) = 526.2; $^1$H NMR (400 MHz, DMSO-d$_6$) δ ppm: 9.85 (br. s., 1H) 9.27 (s, 1H) 8.48 (s, 1H) 7.77 (s, 1H) 7.49 (d, J = 8.55 Hz, 2H) 7.44 (t, J = 7.93 Hz, 2H) 7.18 (t, J = 7.32 Hz, 1H) 7.12 (t, J = 9.00 Hz, 4H) 4.63-4.76 (m, 1H) 3.52 (d, J = 10.68 Hz, 3H) 3.30 (d, J = 12.82 Hz, 2H) 3.22 (br. s., 1H) 3.04-3.19 (m, 4H) 2.24 (d, J = 11.29 Hz, 2H) 2.01-2.17 (m, 4H) 1.98 (s, 1H) 1.75 (s, 3H). |
| 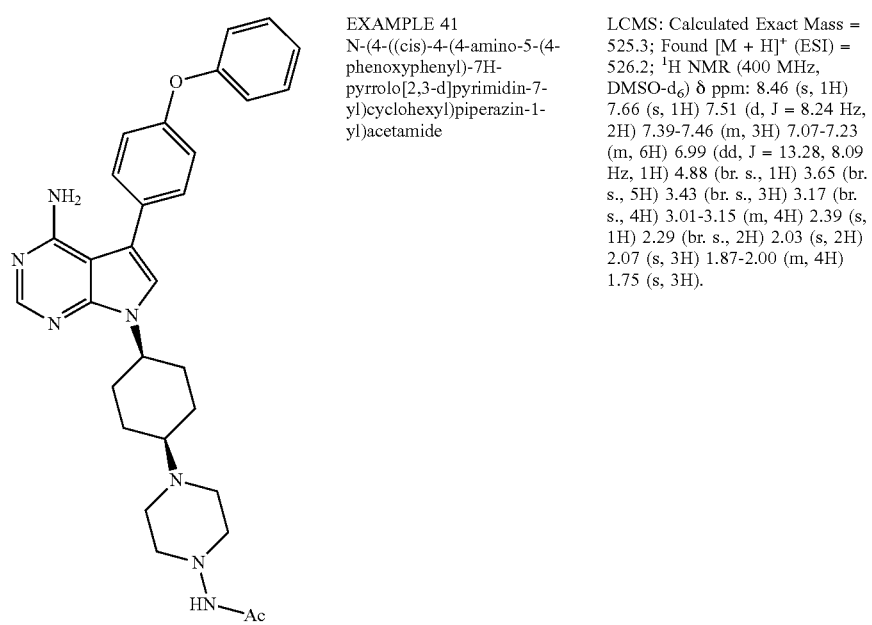 | EXAMPLE 41<br>N-(4-((cis)-4-(4-amino-5-(4-phenoxyphenyl)-7H-pyrrolo[2,3-d]pyrimidin-7-yl)cyclohexyl)piperazin-1-yl)acetamide | LCMS: Calculated Exact Mass = 525.3; Found [M + H]$^+$ (ESI) = 526.2; $^1$H NMR (400 MHz, DMSO-d$_6$) δ ppm: 8.46 (s, 1H) 7.66 (s, 1H) 7.51 (d, J = 8.24 Hz, 2H) 7.39-7.46 (m, 3H) 7.07-7.23 (m, 6H) 6.99 (dd, J = 13.28, 8.09 Hz, 1H) 4.88 (br. s., 1H) 3.65 (br. s., 5H) 3.43 (br. s., 3H) 3.17 (br. s., 4H) 3.01-3.15 (m, 4H) 2.39 (s, 1H) 2.29 (br. s., 2H) 2.03 (s, 2H) 2.07 (s, 3H) 1.87-2.00 (m, 4H) 1.75 (s, 3H). |

| Structure | Name | LCMS and NMR |
|---|---|---|
| 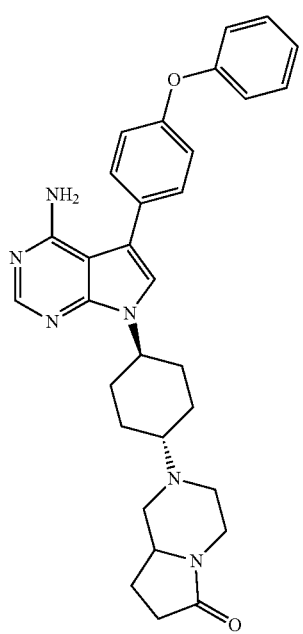 [SMILES: Nc1ncnc2c1c(-c1ccc(Oc3ccccc3)cc1)cn2[C@H]1CC[C@H](N2CCN3C(=O)CCC3C2)CC1] | EXAMPLE 42<br>2-((trans)-4-(4-amino-5-(4-phenoxyphenyl)-7H-pyrrolo[2,3-d]pyrimidin-7-yl)cyclohexyl)hexahydropyrrolo[1,2-a]pyrazin-6(2H)-one | LCMS: Calculated Exact Mass = 522.27; Found [M + H]$^+$ (ESI) = 523.07; $^1$H NMR (DMSO-d$_6$) δ ppm: 8.14 (s, 1H), 7.39-7.49 (m, 5H), 7.17 (t, J = 7.4 Hz, 1H), 7.06-7.14 (m, 4H), 4.56 (br. s., 1H), 3.76-3.82 (m, 1H), 3.71 (dd, J = 12.5, 2.8 Hz, 1H), 3.52 (d, J = 7.0 Hz, 1H), 3.40 (d, J = 7.3 Hz, 1H), 3.00 (dd, J = 11.6, 3.5 Hz, 2H), 2.80-2.89 (m, 2H), 2.60-2.79 (m, 2H), 2.22-2.24 (m,1H), 2.18-2.21 (m, 1H), 2.14-2.17 (m, 1H), 2.11-2.14 (m, 1H), 2.07-2.11 (m, 1H), 1.98 (br. s., 1H), 1.91-1.95 (m, 2H), 1.88 (br. s., 1H), 1.49-1.56 (m, 2H). |
| 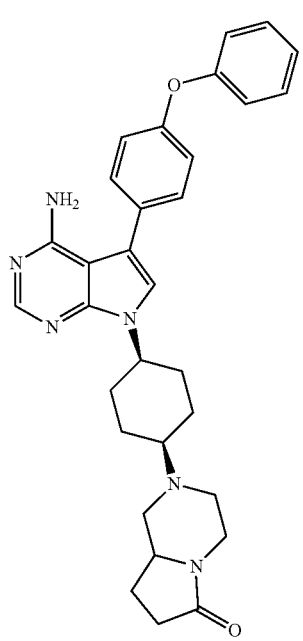 [SMILES: Nc1ncnc2c1c(-c1ccc(Oc3ccccc3)cc1)cn2[C@H]1CC[C@@H](N2CCN3C(=O)CCC3C2)CC1] | EXAMPLE 43<br>2-((cis)-4-(4-amino-5-(4-phenoxyphenyl)-7H-pyrrolo[2,3-d]pyrimidin-7-yl)cyclohexyl)hexahydropyrrolo[1,2-a]pyrazin-6(2H)-one | LCMS: Calculated Exact Mass = 522.64; Found [M + H]$^+$ (ESI) = 523.07; $^1$H NMR (DMSO-d$_6$) δ ppm: 9.81 (br. s., 1H), 8.48 (s, 1H), 7.69 (s, 1H), 7.51 (d, J = 8.6 Hz, 2H), 7.41-7.47 (m, 2H), 7.08-7.22 (m, 5H), 4.90 (br. s., 1H), 4.05(d, J = 12.4 Hz, 1H), 3.91 (br. s., 1H), 3.80 (d, J = 10.5 Hz, 1H), 3.67 (d, J = 11.6 Hz, 1H), 3.41 (br. s., 1H), 3.13 (d, J = 12.9 Hz, 1H), 2.94 (br. s., 1H), 2.85(br. s., 1H), 2.25-2.41 (m, 4H), 2.18-2.25 (m, 1H), 1.92-2.13 (m, 6H), 1.57-1.69 (m, 1H). |

| Structure | Name | LCMS and NMR |
|---|---|---|
| 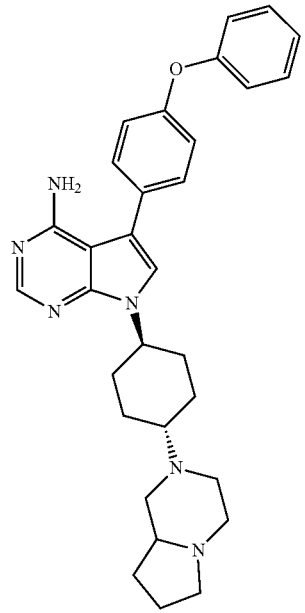 [SMILES: Nc1ncnc2c1c(-c1ccc(Oc3ccccc3)cc1)cn2[C@H]1CC[C@H](N2CCN3CCCC3C2)CC1] | EXAMPLE 44<br>7-((trans)-4-(hexahydropyrrolo[1,2-a]pyrazin-2(1H)-yl)cyclohexyl)-5-(4-phenoxyphenyl)-7H-pyrrolo[2,3-d]pyrimidin-4-amine | LCMS: Calculated Exact Mass = 508.3, Found [M + H]$^+$ (ESI) = 509.3;<br>$^1$HNMR (400 MHz, DMSO-d6) δ ppm: 8.51 (s, 1H), 7.79 (s, 1H), 7.35-7.57 (m, 5H), 7.05-7.26 (m, 6H), 4.66-4.77 (m, 1H), 3.72 (br. s., 3H), 3.57 (br. s., 4H), 2.94-3.24 (m, 2H), 2.19 (br. s., 3H), 1.93-2.16 (m, 7H), 1.79 (d, J = 11.6 Hz, 3H). |
| 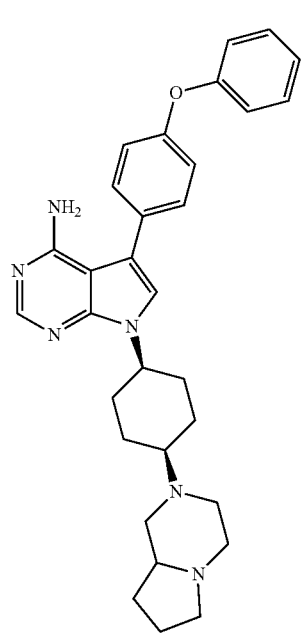 [SMILES: Nc1ncnc2c1c(-c1ccc(Oc3ccccc3)cc1)cn2[C@H]1CC[C@@H](N2CCN3CCCC3C2)CC1] | EXAMPLE 45<br>7-((cis)-4-(hexahydropyrrolo[1,2-a]pyrazin-2(1H)-yl)cyclohexyl)-5-(4-phenoxyphenyl)-7H-pyrrolo[2,3-d]pyrimidin-4-amine | LCMS: Calculated Exact Mass = 508.3, Found [M + H]$^+$ (ESI) = 509.3;<br>$^1$HNMR (400 MHz, DMSO-d6) δ ppm: 8.49 (s, 1H), 7.67 (s, 1H), 7.36-7.56 (m, 4H), 7.04-7.22 (m, 5H), 4.84 (br. s., 1H), 4.16 (br. s., 5H), 3.47 (br. s., 4H), 2.23 (d, J = 11.8 Hz, 2H), 2.12 (br. s., 3H), 2.01 (br. s., 3H), 1.81 (br. s., 5H). |

| Structure | Name | LCMS and NMR |
|---|---|---|
| 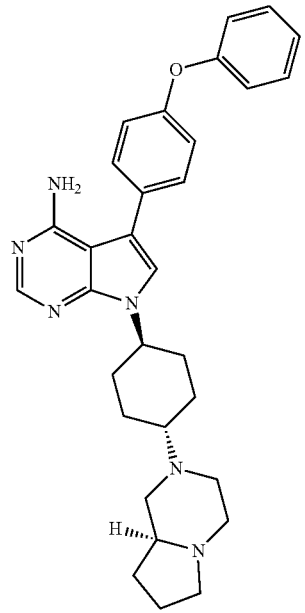 [SMILES: Nc1ncnc2c1c(-c1ccc(Oc3ccccc3)cc1)cn2[C@H]1CC[C@H](N2CCN3CCC[C@H]3C2)CC1] | EXAMPLE 46 7-((trans)-4-((S)-hexahydropyrrolo[1,2-a]pyrazin-2(1H)-yl)cyclohexyl)-5-(4-phenoxyphenyl)-7H-pyrrolo[2,3-d]pyrimidin-4-amine | LCMS: Calculated Exact Mass = 508.3; Found [M + H]$^+$ (ESI) = 509.3; $^1$H NMR (400 MHz, DMSO-d$_6$) δ ppm: 10.41 (br. s., 1H) 8.14 (s, 1H) 7.36-7.56 (m, 6H) 7.16 (t, J = 7.48 Hz, 1H) 7.05-7.13 (m, 5H) 6.10-6.14 (m, 2H) 4.50-4.59 (m., 1H) 3.17 (m, 2H) 1.78-2.08 (m, 11H) 1.54 (m, 3H). |
| 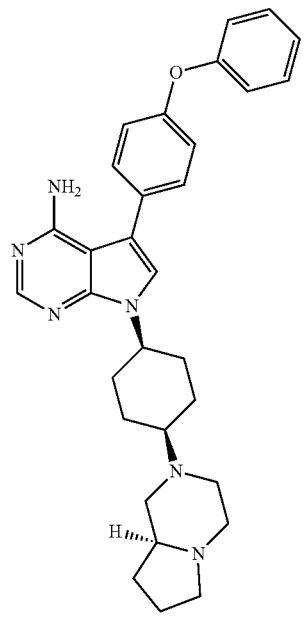 [SMILES: Nc1ncnc2c1c(-c1ccc(Oc3ccccc3)cc1)cn2[C@H]1CC[C@@H](N2CCN3CCC[C@H]3C2)CC1] | EXAMPLE 47 7-((cis)-4-((S)-hexahydropyrrolo[1,2-a]pyrazin-2(1H)-yl)cyclohexyl)-5-(4-phenoxyphenyl)-7H-pyrrolo[2,3-d]pyrimidin-4-amine | $^1$H NMR (400 MHz, DMSO-d$_6$) δ 8.51 (s, 1H), 7.66 (s, 1H), 7.39-7.52 (m, 4H), 7.07-7.22 (m, 5H), 4.87 (br. s., 1H), 3.51 (br. s., 2H), 2.18-2.27 (m, 2H), 2.14 (br. s.,2H), 2.02 (br. s., 2H), 1.89 (br. s., 3H). |

| Structure | Name | LCMS and NMR |
|---|---|---|
| | EXAMPLE 48<br>7-((trans)-4-((R)-hexahydropyrrolo[1,2-a]pyrazin-2(1H)-yl)cyclohexyl)-5-(4-phenoxyphenyl)-7H-pyrrolo[2,3-d]pyrimidin-4-amine | LCMS: Calculated Exact Mass = 508.3; Found [M + H]$^+$ (ESI) = 509.3; $^1$H NMR (400 MHz, DMSO-d$_6$) δ ppm: 8.46 (s, 1H) 7.77 (s, 1H) 7.49 (d, J = 8.54 Hz, 2H) 7.44 (t, J = 7.78 Hz, 2H) 7.18 (t, J = 7.48 Hz, 1H) 7.11 (d, J = 8.85 Hz, 2H) 7.13 (d, J = 8.54 Hz, 2H) 4.66-4.69 (m, 1H) 3.58-3.62 (m, 2H) 3.45-3.49 (m, 3H) 3.10-3.14 (m, 4H) 1.92-2.21 (m, 10H) 1.71-1.74 (m, 3H). |
| | EXAMPLE 49<br>7-((cis)-4-((R)-hexahydropyrrolo[1,2-a]pyrazin-2(1H)-yl)cyclohexyl)-5-(4-phenoxyphenyl)-7H-pyrrolo[2,3-d]pyrimidin-4-amine | LCMS: Calculated Exact Mass = 508.3; Found [M + H]$^+$ (ESI) = 509.3; $^1$H NMR (400 MHz, DMSO-d$_6$) δ ppm: 8.15 (s, 1H) 7.47 (d, J = 8.24 Hz, 2H) 7.42 (t, J = 7.93 Hz, 2H) 7.16 (t, J = 7.48 Hz, 1H) 7.03-7.13 (m, 4H) 4.65-4.71(m, 1H) 3.70-3.75 (m, 1H) 3.50-3.56 (m, 1H) 3.22-3.26 (m, 2H) 3.17 (d, J = 4.88 Hz, 1H) 3.02-3.08 (m, 2H) 2.70-2.73 (m, 1H) 2.65 (d, J = 16.78 Hz, 1H) 2.03-2.07 (m, 6H) 1.95-1.99 (m, 2H) 1.89-1.91 (m, 1H) 1.68-1.70 (m, 2H) 1.60-1.62 (m, 2H). |

-continued

| Structure | Name | LCMS and NMR |
|---|---|---|
| | EXAMPLE 50<br>7-((trans)-4-(4-amino-4-methylpiperidin-1-yl)cyclohexyl)-5-(4-phenoxyphenyl)-7H-pyrrolo[2,3-d]pyrimidin-4-amine | LC-MS: Calculated Exact Mass = 496.3, Found [M + H]$^+$ (ESI) = 497.08; $^1$H NMR (DMSO-d$_6$) δ ppm: 8.35 (s, 1H), 8.24 (br. s., 2H), 7.54-7.63 (m, 1H), 7.39-7.54 (m, 3H), 7.07-7.21 (m, 4H), 3.30 (br. s., 4H), 3.16 (br. s., 2H), 2.33 (br. s., 2H), 2.09 (br. s., 1H), 1.90-2.05 (m, 7H), 1.29-1.42 (m, 3H), 1.23 (br. s., 2H). |
| | EXAMPLE 51<br>7-((cis)-4-(4-amino-4-methylpiperidin-1-yl)cyclohexyl)-5-(4-phenoxyphenyl)-7H pyrrolo[2,3-d]pyrimidin-4-amine | LC-MS: Calculated Exact Mass = 496.3, Found [M + H]$^+$ (ESI) = 497.08; $^1$H NMR (DMSO-d$_6$) δ ppm: 9.78 (br. s., 1H), 8.37 (br. s., 2H), 8.29 (br. s., 1H), 7.65 (br. s., 1H), 7.38-7.52 (m, 3H), 7.06-7.22 (m, 4H), 3.52 (br. s., 1H), 3.45 (br. s., 1H), 3.34 (br. s., 2H), 3.17 (d, J = 10.7 Hz, 2H), 2.14-2.31 (m, 2H), 1.87-2.14 (m, 7H), 1.76 (d, J = 10.7 Hz, 1H), 1.41 (s, 2H), 1.33 (br. s., 1H), 1.23 (br. s., 2H). |

| Structure | Name | LCMS and NMR |
|---|---|---|
| 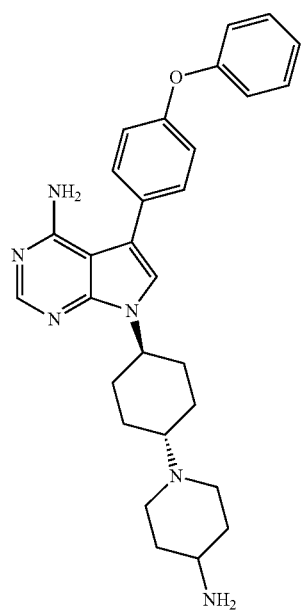 | EXAMPLE 52<br>7-((trans)-4-(4-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]$^+$ (ESI) = 483.3; $^1$H NMR (DMSO-d$_6$) δ ppm: 8.13 (s, 1H), 7.37-7.48 (m, 5H), 7.12-7.20 (m, 1H), 7.09 (dd, J = 8.2, 3.4 Hz, 4H), 6.09 (br. s., 1H), 4.54 (t, J = 11.3 Hz, 1H), 2.81(d, J = 11.3 Hz, 2H), 2.63 (t, J = 10.5 Hz, 1H), 2.43 (t, J = 11.6 Hz, 1H), 2.22 (t, J = 10.8 Hz, 2H), 1.93-2.05 (m, 3H), 1.88 (t, J = 10.5 Hz, 4H), 1.74 (d, J = 10.1 Hz, 2H), 1.43-1.55 (m, 2H), 1.26-1.34 (m, 2H). |
| 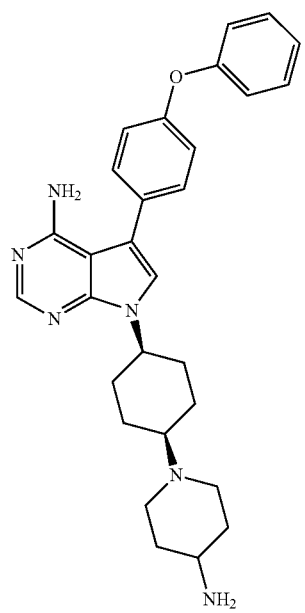 | EXAMPLE 53<br>7-((cis)-4-(4-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]$^+$ (ESI) = 483.3; $^1$H NMR (DMSO-d$_6$) δ: 9.48 (br. s., 1H), 8.43 (s, 1H), 8.16 (br. s., 2H), 7.63 (s, 1H), 7.51 (d, J = 8.2 Hz, 2H), 7.43 (t, J = 7.9 Hz, 2H), 7.17-7.21 (m, 1H),7.08-7.16 (m, 4H), 4.88 (br. s., 1H), 3.68 (d, J = 11.6 Hz, 2H), 3.49 (d, J = 17.7 Hz, 1H), 3.36 (br. s., 1H), 3.30 (br. s., 1H), 3.07 (d, J = 9.5 Hz, 2H), 2.33 (br.s., 2H), 2.12 (d, J = 12.8 Hz, 2H), 1.99 (br. s., 5H), 1.74-1.90 (m, 2H). |

| Structure | Name | LCMS and NMR |
|---|---|---|
| 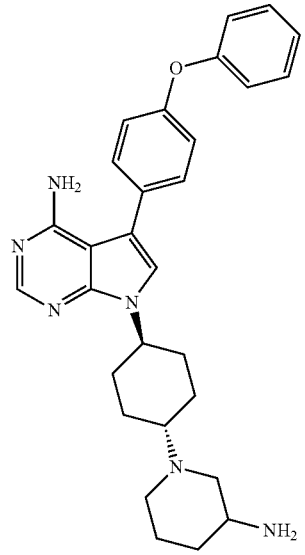 | EXAMPLE 54
7-((trans)-4-(3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]+ (ESI) = 483.3; $^1$H NMR (DMSO-$d_6$) δ ppm: 8.45 (s, 1H), 8.36 (br. s., 2H), 7.72 (s, 1H), 7.38-7.53 (m, 4H), 7.06-7.24 (m, 4H), 4.74 (br. s., 1H), 3.61 (br. s., 2H), 3.49 (br. s., 2H), 3.40 (br. s., 2H), 2.98 (br. s., 1H), 1.93-2.23 (m, 7H), 1.81 (br. s., 3H), 1.53 (d, J = 11.0 Hz, 1H). |
| 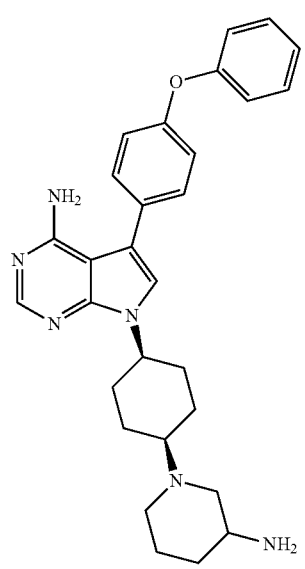 [SMILES: Nc1ncnc2c1c(-c1ccc(Oc3ccccc3)cc1)cn2[C@H]1CC[C@@H](N2CCCC(N)C2)CC1] | EXAMPLE 55
7-((cis)-4-(3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]+ (ESI) = 483.3; $^1$H NMR (DMSO-$d_6$) δ ppm: 8.43 (s, 1H), 8.31 (br. s., 2H), 7.63 (br. s., 1H), 7.49 (d, J = 8.2 Hz, 2H), 7.43 (t, J = 7.8 Hz, 2H), 7.18 (t, J = 7.3 Hz, 1H), 7.11 (t, J = 8.7 Hz, 4H), 4.89 (br. s., 1H), 3.67 (br. s., 9H), 2.87 (br. s., 2H), 2.33 (br. s., 2H), 1.90-2.13 (m, 7H), 1.50 (d, J = 12.5 Hz, 1H). |

| Structure | Name | LCMS and NMR |
|---|---|---|
| | EXAMPLE 56<br>7-((trans)-4-((S)-3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]$^+$ (ESI) = 483.3; $^1$H NMR (DMSO-d$_6$) δ 10.41 (br. s., 1H), 8.43 (s, 1H), 8.32 (br. s., 2H), 7.70 (s, 1H), 7.48 (d, J = 8.5 Hz, 2H), 7.43 (t, J = 7.8 Hz, 2H), 7.18 (t, J = 7.3 Hz,1H), 7.08-7.15 (m, 4H), 4.73 (br. s., 1H), 3.59 (br. s., 1H), 3.34-3.55 (m, 3H), 2.97 (br. s., 1H), 2.00-2.25 (m, 7H), 1.78-1.93 (m, 2H), 1.75 (br. s., 1H), 1.52 (d, J = 13.1 Hz, 1H). |
| | EXAMPLE 57<br>7-((cis)-4-((S)-3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]$^+$ (ESI) = 483.3; $^1$H NMR (DMSO-d$_6$) δ 8.13 (s, 1H), 7.48 (d, J = 8.5 Hz, 2H), 7.37-7.45 (m, 2H), 7.31 (s, 1H), 7.14-7.19 (m, 1H), 7.04-7.13 (m, 4H), 6.10 (br. s., 1H),4.62-4.73 (m, 1H), 2.81 (d, J = 8.9 Hz, 1H), 2.73 (d, J = 3.7 Hz, 1H), 2.67 (br. s., 1H), 2.09-2.20 (m, 3H), 2.05 (d, J = 14.6 Hz, 2H), 1.97 (br. s., 1H), 1.76(br. s., 1H), 1.65-1.73 (m, 4H), 1.46-1.60 (m, 3H), 0.99-1.09 (m, 1H). |

| Structure | Name | LCMS and NMR |
|---|---|---|
| 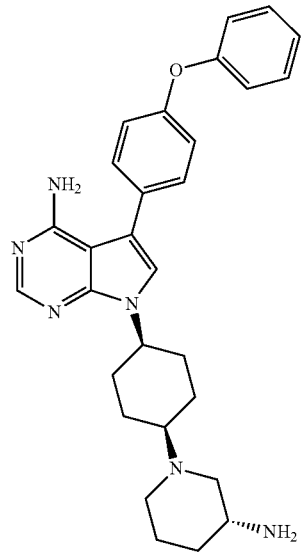 [SMILES: Nc1ncnc2c1c(-c1ccc(Oc3ccccc3)cc1)cn2[C@H]1CC[C@@H](N2CCC[C@@H](N)C2)CC1] | EXAMPLE 58<br>7-((cis)-4-((R)-3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]+ (ESI) = 483.3; $^1$H NMR (DMSO-d$_6$) δ 8.14 (s, 1H), 7.48 (d, J = 8.5 Hz, 2H), 7.36-7.45 (m, 3H), 7.16 (t, J = 7.3 Hz, 1H), 7.10 (t, J = 9.0 Hz, 4H), 6.11 (br. s., 2H), 4.69 (t, J = 11.0 Hz, 1H), 3.09 (br. s., 1H), 2.69 (br. s., 1H), 2.25 (br. s., 2H), 2.18 (br. s., 1H), 2.09-2.18 (m, 2H), 2.05 (d, J = 15.9 Hz, 2H), 1.65-1.76 (m, 4H), 1.51-1.61 (m, 3H), 1.35 (br. s., 1H). |
| 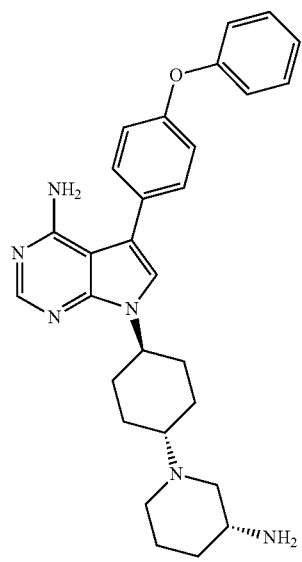 [SMILES: Nc1ncnc2c1c(-c1ccc(Oc3ccccc3)cc1)cn2[C@H]1CC[C@H](N2CCC[C@@H](N)C2)CC1] | EXAMPLE 59<br>7-((trans)-4-((R)-3-aminopiperidin-1-yl)cyclohexyl)-5-(4-phenoxyphenyl)-7H-pyrrolo[2,3-d]pyrimidin-4-amine | LCMS: Calculated Exact Mass = 482.3; Found [M + H]+ (ESI) = 483.3;; $^1$H NMR (DMSO-d$_6$) δ 8.13 (s, 1H), 7.39-7.48 (m, 5H), 7.16 (t, J = 7.3 Hz, 1H), 7.09 (dd, J = 7.9, 5.2 Hz, 4H), 6.11 (br. s., 2H), 4.55 (t, J = 11.4 Hz, 1H),3.04 (br. s., 1H), 2.83 (d, J = 9.5 Hz, 1H), 2.58-2.68 (m, 1H), 2.33 (d, J = 8.5 Hz, 2H), 1.92-2.01 (m, 3H), 1.84-1.92 (m, 3H), 1.76 (br. s., 1H), 1.68 (br. s.,1H), 1.43-1.54 (m, 3H), 1.33 (d, J = 9.2 Hz, 1H). |

-continued

| Structure | Name | LCMS and NMR |
|---|---|---|
| 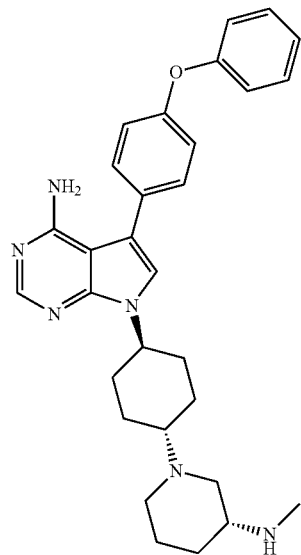 [SMILES: CN[C@@H]1CCCN([C@H]2CC[C@H](n3cc(-c4ccc(Oc5ccccc5)cc4)c4c(N)ncnc43)CC2)C1] | EXAMPLE 60<br>7-((trans)-4-((R)-3-(methylamino)piperidin-1-yl)cyclohexyl)-5-(4-phenoxyphenyl)-7H-pyrrolo[2,3-d]pyrimidin-4-amine | LCMS: Calculated Exact Mass = 496.3; Found [M + H]$^+$ (ESI) = 497.16; $^1$H NMR (DMSO-d$_6$) δ ppm: 8.14 (s, 1H), 7.39-7.50 (m, 5H), 7.17 (t, J = 7.4 Hz, 1H), 7.07-7.13 (m, 4H), 6.11 (br. s., 2H), 4.51-4.60 (m, 1H), 4.11 (br. s., 1H), 2.88 (d, J = 8.9 Hz, 1H), 2.66-2.70 (m, 1H), 2.41-2.47 (m, 1H), 2.33 (s, 3H), 2.24 (t, J = 9.3 Hz, 1H), 1.94-2.09 (m, 4H), 1.89 (t, J = 13.3 Hz, 3H), 1.76-1.81 (m, 1H), 1.63 (dd, J = 8.6, 4.3 Hz, 1H), 1.51 (d, J = 12.4 Hz, 2H), 1.37-1.48 (m, 2H). |
| 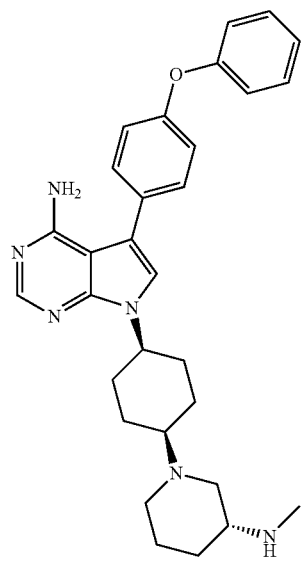 [SMILES: CN[C@@H]1CCCN([C@H]2CC[C@@H](n3cc(-c4ccc(Oc5ccccc5)cc4)c4c(N)ncnc43)CC2)C1] | EXAMPLE 61<br>7-((cis)-4-((R)-3-(methylamino)piperidin-1-yl)cyclohexyl)-5-(4-phenoxyphenyl)-7H-pyrrolo[2,3-d]pyrimidin-4-amine | LCMS: Calculated Exact Mass = 496.3; Found [M + H]$^+$ (ESI) = 497.09; $^1$H NMR (DMSO-d$_6$) δ ppm: 8.13 (s, 1H), 7.49 (d, J = 8.5 Hz, 2H), 7.42 (t, J = 7.8 Hz, 2H), 7.33 (s, 1H), 7.16 (t, J = 7.3 Hz, 1H), 7.09 (t, J = 7.6 Hz, 4H), 6.10 (br.s., 1H), 4.69 (t, J = 10.7 Hz, 1H), 2.81 (br. s., 1H), 2.63 (br. s., 2H), 2.35 (s, 3H), 2.23 (br. s., 1H), 1.97-2.17 (m, 6H), 1.65-1.78 (m, 4H), 1.45-1.61 (m, 3H), 1.17 (d, J = 7.0 Hz, 1H). |

| Structure | Name | LCMS and NMR |
|---|---|---|
| 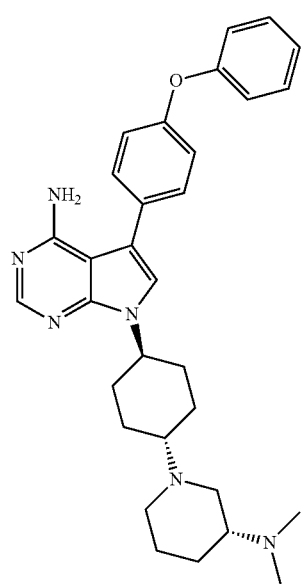 [SMILES: CN(C)[C@@H]1CCCN([C@H]2CC[C@H](n3cc(-c4ccc(Oc5ccccc5)cc4)c4c(N)ncnc43)CC2)C1] | EXAMPLE 62<br>7-((trans)-4-((R)-3-(dimethylamino)piperidin-1-yl)cyclohexyl)-5-(4-phenoxyphenyl)-7H-pyrrolo[2,3-d]pyrimidin-4-amine | LCMS: Calculated Exact Mass = 510.31; Found [M + H]$^+$ (ESI) = 511.3; $^1$H NMR (DMSO-d$_6$) δ ppm: 8.13 (s, 1H), 7.38-7.48 (m, 5H), 7.14-7.20 (m, 1H), 7.09 (dd, J = 7.9, 4.9 Hz, 4H), 6.10 (br. s., 1H), 4.57 (br. s., 1H), 3.01 (br. s.,1H), 2.77 (br. s., 1H), 2.44 (br. s., 6H), 2.33 (br. s., 2H), 1.98 (br. s., 3H), 1.92 (d, J = 9.2 Hz, 5H), 1.70-1.78 (m, 1H), 1.57 (br. s., 2H), 1.46 (br. s., 1H), 1.32(d, J = 10.4 Hz, 1H). |
| 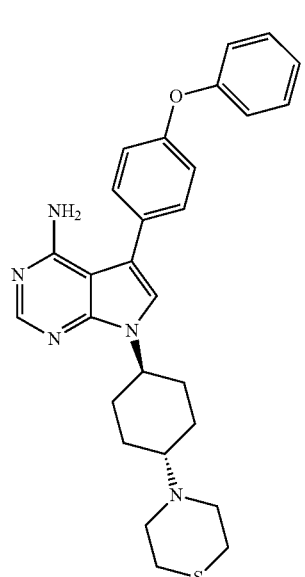 | EXAMPLE 63<br>5-(4-phenoxyphenyl)-7-((trans)-4-thiomorpholinocyclohexyl)-7H-pyrrolo[2,3-d]pyrimidin-4-amine | LCMS: Calculated Exact Mass = 485.2; Found [M + H]$^+$ (ESI) = 486.7; $^1$H NMR (400 MHz, DMSO-d6) δ ppm: 9.63 (s, 1H) 8.38 (s, 1H) 7.66 (s, 1H) 7.39-7.52 (m, 4H) 7.19 (t, J = 7.39 Hz, 1H) 7.11 (d, J = 7.79 Hz, 2H) 7.14 (d, J = 8.60 Hz, 2H) 4.69 (t, J = 11.82 Hz, 1H) 3.75 (d, J = 11.28 Hz, 2H) 3.22-3.40 (m, 2H) 3.10 (t, J = 13.03 Hz, 3H) 2.91 (d, J = 13.43 Hz, 2H) 2.18 (d, J = 10.75 Hz, 2H) 1.97-2.13 (m, 4H) 1.79-1.91 (m, 2H). |

| Structure | Name | LCMS and NMR |
|---|---|---|
| 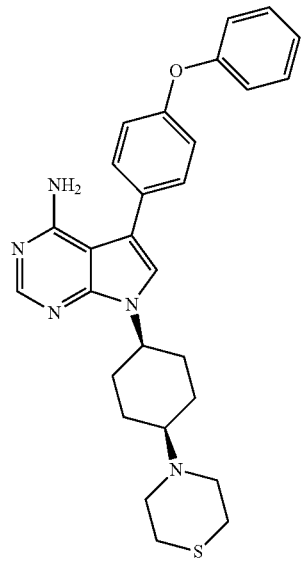 [SMILES: Nc1ncnc2c1c(-c1ccc(Oc3ccccc3)cc1)cn2[C@H]1CC[C@@H](N2CCSCC2)CC1] | EXAMPLE 64 5-(4-phenoxyphenyl)-7-((cis)-4-thiomorpholinocyclohexyl)-7H-pyrrolo[2,3-d]pyrimidin-4-amine | LCMS: Calculated Exact Mass = 485.2; Found [M + H]$^+$ (ESI) = 486.7; 1H NMR (400 MHz, DMSO-d6) δ ppm: 9.54 (s, 1H) 8.42 (s, 1H) 7.67 (s, 1H) 7.48-7.56 (m, 2H) 7.41-7.48 (m, 2H) 7.19 (t, J = 7.39 Hz, 1H) 7.11 (d, J = 7.79 Hz, 2H) 7.14 (d, J = 8.60 Hz, 2H) 4.90 (br. s., 1H) 3.77-3.85 (m, 3H) 3.54 (br. s., 2H) 3.27 (s, 2H) 3.00-3.11 (m, 2H) 2.88-2.98 (m, 2H) 2.33 (d, J = 7.79 Hz, 2H) 1.89-2.08 (m, 6H). |
| 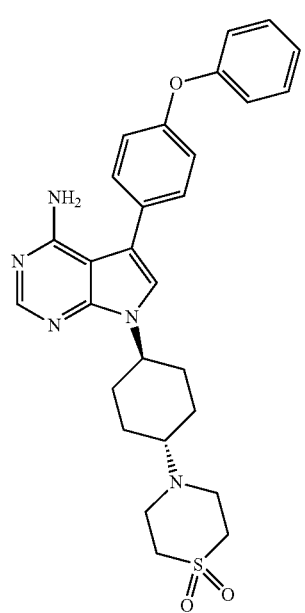 [SMILES: Nc1ncnc2c1c(-c1ccc(Oc3ccccc3)cc1)cn2[C@H]1CC[C@H](N2CCS(=O)(=O)CC2)CC1] | EXAMPLE 65 4-((trans)-4-(4-amino-5-(4-phenoxyphenyl)-7H-pyrrolo[2,3-d]pyrimidin-7-yl)cyclohexyl)thiomorpholine 1,1-dioxide | LCMS: Calculated Exact Mass = 517.2; Found [M + H]$^+$ (ESI) = 518.2; $^1$H NMR (400 MHz, DMSO-d$_6$) δ 8.34-8.44 (m, 1H), 7.67-7.75 (m, 1H), 7.39-7.53 (m, 5H), 7.06-7.22 (m, 5H), 4.74 (br. s., 1H), 4.17-4.26 (m, 2H), 3.91 (br. s.,1H), 3.84 (d, J = 13.0 Hz, 3H), 3.40-3.51 (m, 3H), 3.19 (d, J = 14.0 Hz, 2H), 2.13-2.26 (m, 2H), 1.96-2.13 (m, 8H). |

-continued

| Structure | Name | LCMS and NMR |
|---|---|---|
| 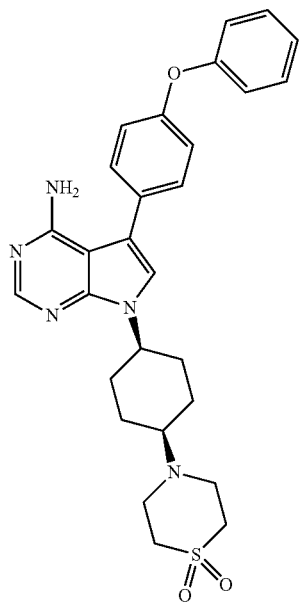 [SMILES: Nc1ncnc2c1c(-c1ccc(Oc3ccccc3)cc1)cn2[C@H]1CC[C@@H](N2CCS(=O)(=O)CC2)CC1] | EXAMPLE 66<br>4-((cis)-4-(4-amino-5-(4-phenoxyphenyl)-7H-pyrrolo[2,3-d]pyrimidin-7-yl)cyclohexyl)thiomorpholine 1,1-dioxide | LCMS: Calculated Exact Mass = 517.2; Found [M + H]$^+$ (ESI) = 518.0; $^1$H NMR (400 MHz, DMSO-d$_6$) δ ppm: 8.40 (s, 1H) 7.74 (s, 1H) 7.54 (d, J = 8.33 Hz, 2H) 7.43 (t, J = 7.72 Hz, 2H) 7.18 (t, J = 7.52 Hz, 1H) 7.09 (d, J = 8.33 Hz, 2H) 7.13 (d, J = 8.33 Hz, 2H) 4.94 (s, 1H) 4.21 (t, J = 12.89 Hz, 3H) 4.01-4.03 (m, 2H) 3.83 (d, J = 13.16 Hz, 4H) 3.42 (t, J = 13.50 Hz, 3H) 3.16 (d, J = 14.24 Hz, 2H) 2.21-2.29 (m., 2H) 2.00-2.14 (m, 6H). |
| 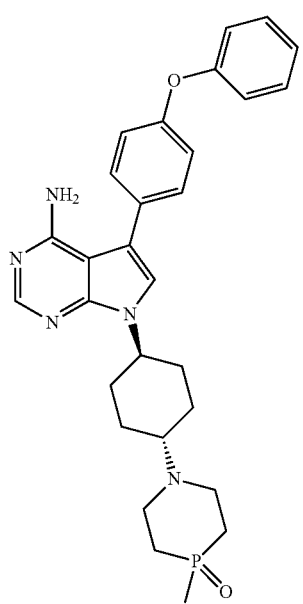 [SMILES: CP1(=O)CCN([C@H]2CC[C@H](n3cc(-c4ccc(Oc5ccccc5)cc4)c4c(N)ncnc43)CC2)CC1] | EXAMPLE 67<br>1-((trans)-4-(4-amino-5-(4-phenoxyphenyl)-7H-pyrrolo[2,3-d]pyrimidin-7-yl)cyclohexyl)-4-methyl-1,4-azaphosphinane 4-oxide | $^1$H NMR (400 MHz, DMSO-d$_6$) δ ppm: 8.47 (s, 1H), 7.74 (s, 1H), 7.36-7.59 (m, 4H), 7.07-7.26 (m, 5H), 4.66-4.82 (m, 1H), 3.32-3.82 (m, 5H), 2.00-2.37 (m, 10H), 1.72-1.93 (m, 2H), 1.56-1.70 (m, 3H). |

-continued

| Structure | Name | LCMS and NMR |
|---|---|---|
| | EXAMPLE 68<br>1-((cis)-4-(4-amino-5-(4-phenoxyphenyl)-7H-pyrrolo[2,3-d]pyrimidin-7-yl)cyclohexyl)-4-methyl-1,4-azaphosphinane 4-oxide | LCMS: Calculated Exact Mass = 515.2; Found [M + H]+ (ESI) = 515.9; $^1$H NMR (400 MHz, DMSO-$d_6$) δ ppm: 8.46 (s, 1H), 7.71 (br. s., 1H), 7.51 (d, J = 8.6 Hz, 2H), 7.39-7.47 (m, 2H), 7.03-7.27 (m, 5H), 4.93 (br. s., 1H), 3.49-3.68 (m, 5H), 2.25-2.35 (m, 6H), 1.81-2.23 (m, 6H), 1.52-1.54 (m, 3H). |
| | EXAMPLE 69<br>1-((trans)-4-(4-amino-5-(4-phenoxyphenyl)-7H-pyrrolo[2,3-d]pyrimidin-7-yl)cyclohexyl)piperidine-4-sulfonamide | LCMS: Calculated Exact Mass = 546.2; Found [M + H]$^+$ (ESI) = 547.0; $^1$H NMR (400 MHz, DMSO-$d_6$) δ ppm 9.18 (br. s., 1H) 8.77 (br. s., 1H) 8.31 (br. s., 1H) 7.47-7.58 (m, 2H) 7.38-7.47 (m, 2H) 7.02-7.23 (m, 5H) 4.84 (br. s., 1H) 3.76 (d, J = 11.82 Hz, 2H) 3.06 (br. s., 3H) 2.89 (d, J = 4.57 Hz, 2H) 2.34 (br. s., 1H) 2.24 (d, J = 12.09 Hz, 2H) 2.12 (br. s., 2H) 1.86-2.07 (m, 6H). |

| Structure | Name | LCMS and NMR |
|---|---|---|
| 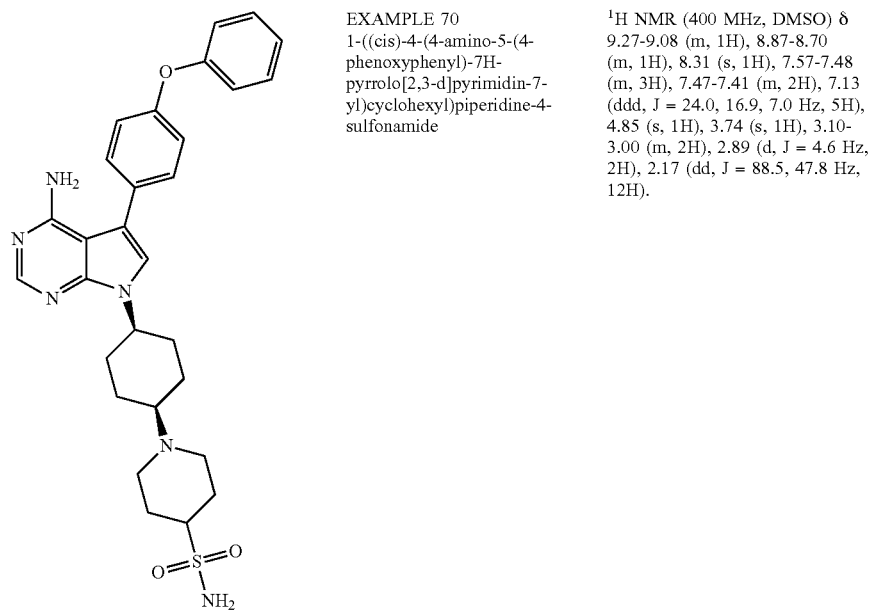 | EXAMPLE 70<br>1-((cis)-4-(4-amino-5-(4-phenoxyphenyl)-7H-pyrrolo[2,3-d]pyrimidin-7-yl)cyclohexyl)piperidine-4-sulfonamide | $^1$H NMR (400 MHz, DMSO) δ 9.27-9.08 (m, 1H), 8.87-8.70 (m, 1H), 8.31 (s, 1H), 7.57-7.48 (m, 3H), 7.47-7.41 (m, 2H), 7.13 (ddd, J = 24.0, 16.9, 7.0 Hz, 5H), 4.85 (s, 1H), 3.74 (s, 1H), 3.10-3.00 (m, 2H), 2.89 (d, J = 4.6 Hz, 2H), 2.17 (dd, J = 88.5, 47.8 Hz, 12H). |
| 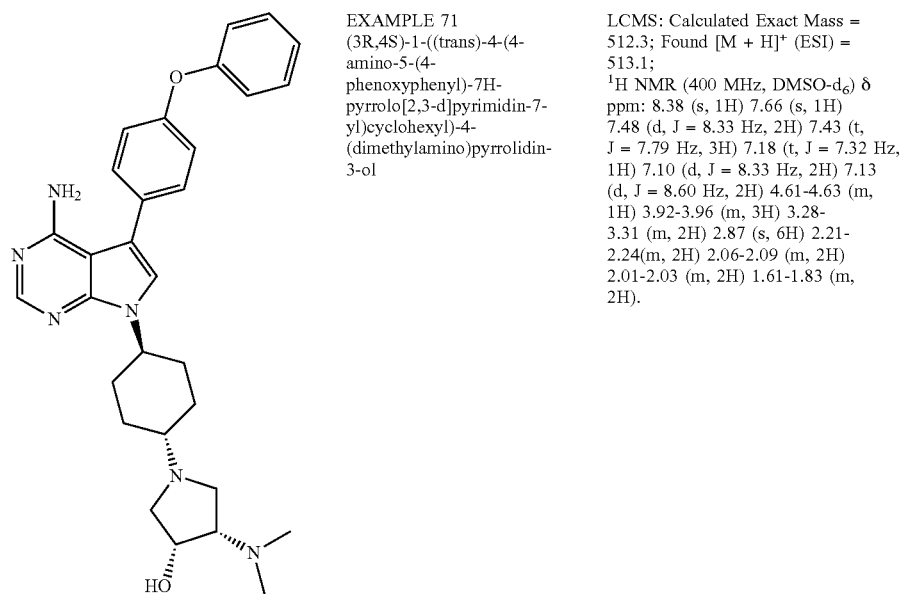 | EXAMPLE 71<br>(3R,4S)-1-((trans)-4-(4-amino-5-(4-phenoxyphenyl)-7H-pyrrolo[2,3-d]pyrimidin-7-yl)cyclohexyl)-4-(dimethylamino)pyrrolidin-3-ol | LCMS: Calculated Exact Mass = 512.3; Found [M + H]$^+$ (ESI) = 513.1;<br>$^1$H NMR (400 MHz, DMSO-d$_6$) δ ppm: 8.38 (s, 1H) 7.66 (s, 1H) 7.48 (d, J = 8.33 Hz, 2H) 7.43 (t, J = 7.79 Hz, 3H) 7.18 (t, J = 7.32 Hz, 1H) 7.10 (d, J = 8.33 Hz, 2H) 7.13 (d, J = 8.60 Hz, 2H) 4.61-4.63 (m, 1H) 3.92-3.96 (m, 3H) 3.28-3.31 (m, 2H) 2.87 (s, 6H) 2.21-2.24(m, 2H) 2.06-2.09 (m, 2H) 2.01-2.03 (m, 2H) 1.61-1.83 (m, 2H). |

| Structure | Name | LCMS and NMR |
|---|---|---|
| 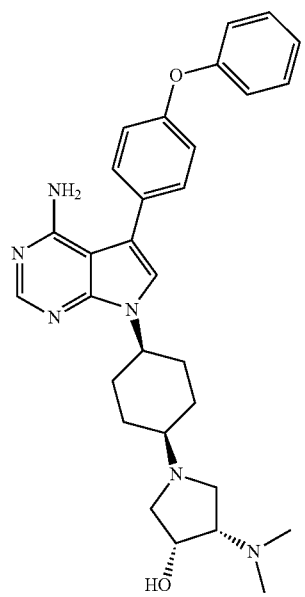 [SMILES: CN(C)[C@H]1CN([C@H]2CC[C@@H](n3cc(-c4ccc(Oc5ccccc5)cc4)c4c(N)ncnc43)CC2)C[C@H]1O] | EXAMPLE 72 (3R,4S)-1-((cis)-4-(4-amino-5-(4-phenoxyphenyl)-7H-pyrrolo[2,3-d]pyrimidin-7-yl)cyclohexyl)-4-(dimethylamino)pyrrolidin-3-ol | LCMS: Calculated Exact Mass = 512.3; Found [M + H]+ (ESI) = 513.1; $^1$H NMR (400 MHz, DMSO-d$_6$) δ ppm: 8.38 (s, 1H) 7.58 (br. s., 1H) 7.48 (d, J = 7.92 Hz, 2H) 7.43 (t, J = 7.72 Hz, 3H) 7.18 (t, J = 7.45 Hz, 1H) 7.09 (d, J = 8.19 Hz, 2H) 7.13 (d, J = 8.33 Hz, 2H) 4.81-4.86 (m, 1H) 4.56-4.59 (m, 1H) 2.86 (s, 6H) 2.21-2.23 (m, 2H) 2.00-2.06 (m, 3H) 1.85-1.89 (m, 3H). |
| 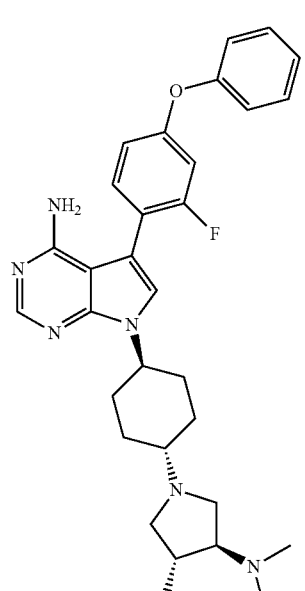 | EXAMPLE 73 (3R,4R)-1-((trans)-4-(4-amino-5-(2-fluoro-4-phenoxyphenyl)-7H-pyrrolo[2,3-d]pyrimidin-7-yl)cyclohexyl)-4-(dimethylamino)pyrrolidin-3-ol | LCMS: Calculated Exact Mass = 530.3; Found [M + H]+ (ESI) = 531.2; $^1$H NMR (400 MHz, DMSO-d6) δ ppm: 8.44 (br. s., 1H), 7.73 (br. s., 1H), 7.36-7.53 (m, 3H), 7.23 (t, J = 6.8 Hz, 1H), 7.16 (d, J = 7.8 Hz, 2H), 7.03 (d, J = 10.9 Hz, 1H), 6.94 (d, J = 8.3 Hz, 1H), 3.12-3.96 (m, 5H), 2.89 (s, 6H), 2.18-2.32 (m, 2H), 1.93-2.14 (m, 5H), 1.69 (br. s., 2H). |

| Structure | Name | LCMS and NMR |
|---|---|---|
| 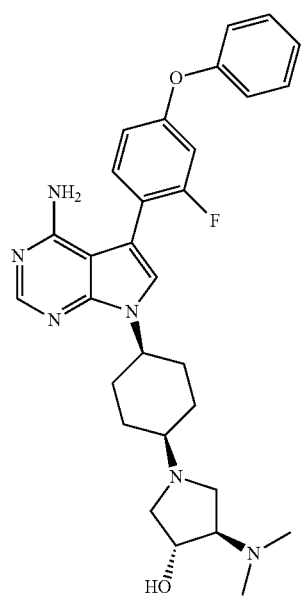 [SMILES: CN(C)[C@@H]1CN([C@H]2CC[C@@H](n3cc(-c4ccc(Oc5ccccc5)cc4F)c4c(N)ncnc43)CC2)C[C@H]1O] | EXAMPLE 74 (3R,4R)-1-((cis)-4-(4-amino-5-(2-fluoro-4-phenoxyphenyl)-7H-pyrrolo[2,3-d]pyrimidin-7-yl)cyclohexyl)-4-(dimethylamino)pyrrolidin-3-ol | $^1$H NMR (400 MHz, DMSO) δ 11.36-9.49 (m, 1H), 8.40 (s, 1H), 7.59 (s, 1H), 7.51-7.38 (m, 3H), 7.23 (s, 1H), 7.15 (d, J = 7.8 Hz, 2H), 7.03 (d, J = 11.4 Hz, 1H), 6.93 (d, J = 8.3 Hz, 1H), 4.81 (s, 1H), 4.55 (s, 1H), 3.83 (s, 2H), 3.64 (s, 2H), 3.43-3.15 (m, 2H), 2.87 (s, 6H), 2.04 (dd, J = 75.7, 52.3 Hz, 8H). |
| 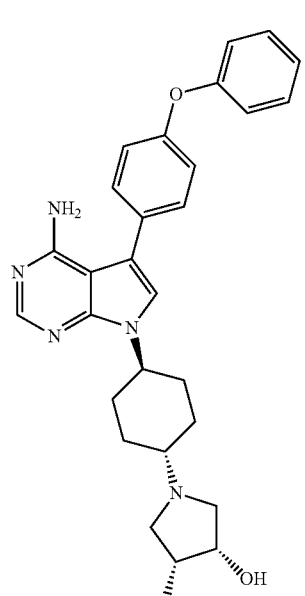 | EXAMPLE 75 (3R,4S)-1-((trans)-4-(4-amino-5-(4-phenoxyphenyl)-7H-pyrrolo[2,3-d]pyrimidin-7-yl)cyclohexyl)pyrrolidine-3,4-diol | LCMS: Calculated Exact Mass = 485.2; Found [M + H]$^+$ (ESI) = 486.0; $^1$H NMR (400 MHz, DMSO-d$_6$) δ ppm: 10.16 (s., 1H) 8.37 (s., 1H) 7.64 (s, 1H) 7.40-7.52 (m, 4H) 7.19 (t, J = 7.39 Hz, 1H) 7.06-7.16 (m, 4H) 5.59 (br. s., 2H) 4.56-4.76 (m, 1H) 4.25 (br. s., 2H) 4.09 (br. s., 1H) 3.57 (d, J = 5.37 Hz, 2H) 3.39-3.48 (m, 2H) 3.13-3.29 (m, 3H) 2.28 (br. s., 1H) 2.21 (d, J = 10.48 Hz, 2H) 1.90-2.12 (m, 4H) 1.59-1.78 (m, 2H). |

| Structure | Name | LCMS and NMR |
|---|---|---|
| | EXAMPLE 76<br>(3R,4S)-1-((cis)-4-(4-amino-5-(4-phenoxyphenyl)-7H-pyrrolo[2,3-d]pyrimidin-7-yl)cyclohexyl)pyrrolidine-3,4-diol | $^1$H NMR (400 MHz, DMSO-d$_6$) δ 9.84 (br. s., 1H), 8.37 (br. s., 1H), 7.62 (br. s., 1H), 7.40-7.57 (m, 4H), 7.09-7.20 (m, 4H), 5.59 (br. s., 1H), 4.90 (br. s., 1H), 4.85(br. s., 1H), 4.27 (br. s., 1H), 4.16 (br. s., 1H), 3.69 (br. s., 2H), 3.42 (d, J = 5.4 Hz, 2H), 3.08-3.26 (m, 2H), 2.10-2.23 (m, 2H), 1.99 (d, J = 4.3 Hz, 3H), 1.90 (d, J = 7.5 Hz, 2H). |
| | EXAMPLE 77<br>7-((trans)-4-(3-aminoazetidin-1-yl)cyclohexyl)-5-(4-phenoxyphenyl)-7H-pyrrolo[2,3-d]pyrimidin-4-amine | LCMS: Calculated Exact Mass = 454.3, Found [M + H]$^+$ (ESI) = 454.8; $^1$HNMR (400 MHz, DMSO-d6) δ ppm: 8.51 (br. s., 2H), 8.37 (s, 1H), 7.65 (s, 1H), 7.48 (d, J = 8.5 Hz, 2H), 7.43 (t, J = 8.1 Hz, 2H), 7.17 (t, J = 7.3 Hz, 1H), 7.10 (d, J = 7.6 Hz, 2H), 7.13 (d, J = 8.5 Hz, 2H), 4.58-4.68 (m, 1H), 4.29-4.46 (m, 2H), 4.11-4.28 (m, 3H), 3.19-3.36 (m, 1H), 2.14-2.22 (m, 2H), 1.91-2.12 (m, 4H), 1.37-1.51 (m, 2H). |

| Structure | Name | LCMS and NMR |
|---|---|---|
| 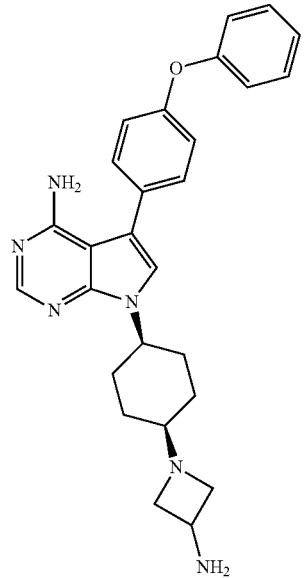 [SMILES: Nc1ncnc2c1c(-c1ccc(Oc3ccccc3)cc1)cn2[C@H]1CC[C@@H](N2CC(N)C2)CC1] | EXAMPLE 78<br>7-((cis)-4-(3-aminoazetidin-1-yl)cyclohexyl)-5-(4-phenoxyphenyl)-7H-pyrrolo[2,3-d]pyrimidin-4-amine | LCMS: Calculated Exact Mass = 454.3, Found [M + H]$^+$ (ESI) = 454.8; $^1$HNMR (400 MHz, DMSO-d6) δ ppm: 8.50 (br. s., 2H), 8.46 (s, 1H), 7.66 (br. s., 1H), 7.38-7.47 (m, 4H), 7.17 (t, J = 7.2 Hz, 1H), 7.10 (t, J = 7.6 Hz, 4H), 4.78-4.91 (m, 1H), 4.41-4.55 (m, 2H), 4.06-4.36 (m, 3H), 3.51-3.74 (m, 1H), 1.87-2.14 (m, 6H), 1.73-1.86 (m, 2H). |
| 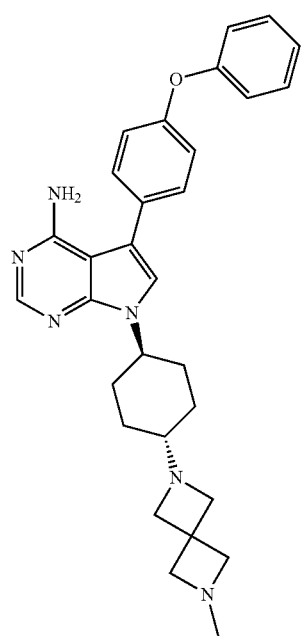 [SMILES: CN1CC2(C1)CN([C@H]1CC[C@H](n3cc(-c4ccc(Oc5ccccc5)cc4)c4c(N)ncnc43)CC1)C2] | EXAMPLE 79<br>7-((trans)-4-(6-methyl-2,6-diazaspiro[3.3]heptan-2-yl)cyclohexyl)-5-(4-phenoxyphenyl)-7H-pyrrolo[2,3-d]pyrimidin-4-amine | LCMS: Calculated Exact Mass = 494.3, Found [M + H]$^+$ (ESI) = 494.8; $^1$HNMR (400 MHz, DMSO-d6) δ ppm: 10.87 (br. s., 1H), 10.04 (br. s., 1H), 8.43 (s, 1H), 7.71 (s, 1H), 7.48 (d, J = 8.4 Hz, 2H), 7.43 (t, J = 7.8 Hz, 2H), 7.17 (t, J = 7.2 Hz, 1H), 7.10 (d, J = 7.6 Hz, 2H), 7.13 (d, J = 8.4 Hz, 2H), 4.58-4.69 (m, 1H), 4.26-4.49 (m, 6H), 4.17-4.26 (m, 1H), 4.06-4.17 (m, 1H), 3.18-3.29 (m, 1H), 2.02-2.16 (m, 4H), 1.87-2.03 (m, 2H), 1.33-1.48 (m, 2H). |

-continued

| Structure | Name | LCMS and NMR |
|---|---|---|
| 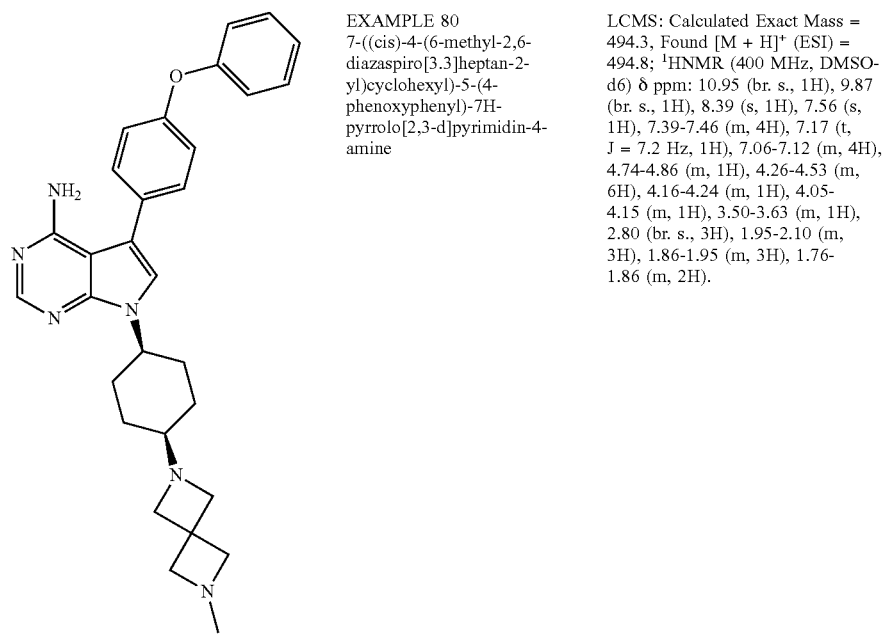 | EXAMPLE 80 7-((cis)-4-(6-methyl-2,6-diazaspiro[3.3]heptan-2-yl)cyclohexyl)-5-(4-phenoxyphenyl)-7H-pyrrolo[2,3-d]pyrimidin-4-amine | LCMS: Calculated Exact Mass = 494.3, Found [M + H]$^+$ (ESI) = 494.8; $^1$HNMR (400 MHz, DMSO-d6) δ ppm: 10.95 (br. s., 1H), 9.87 (br. s., 1H), 8.39 (s, 1H), 7.56 (s, 1H), 7.39-7.46 (m, 4H), 7.17 (t, J = 7.2 Hz, 1H), 7.06-7.12 (m, 4H), 4.74-4.86 (m, 1H), 4.26-4.53 (m, 6H), 4.16-4.24 (m, 1H), 4.05-4.15 (m, 1H), 3.50-3.63 (m, 1H), 2.80 (br. s., 3H), 1.95-2.10 (m, 3H), 1.86-1.95 (m, 3H), 1.76-1.86 (m, 2H). |
| 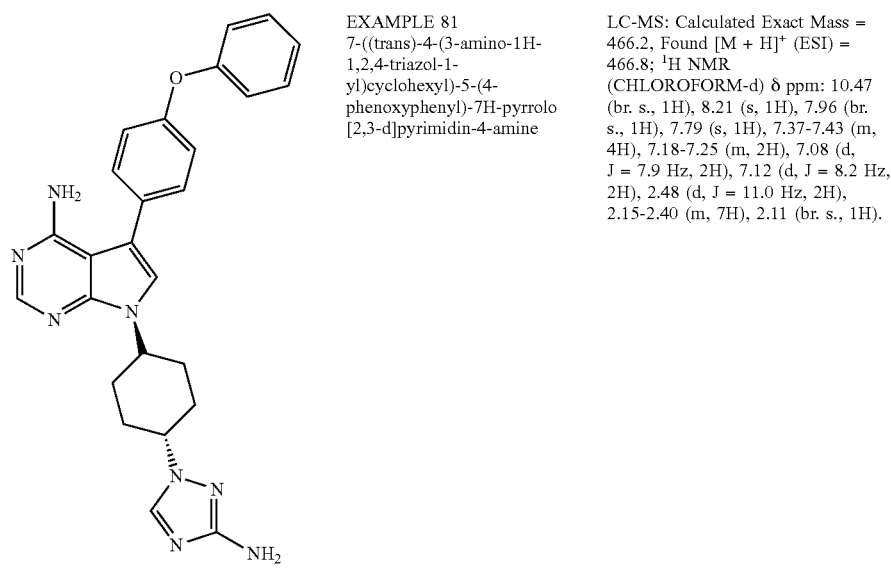 | EXAMPLE 81 7-((trans)-4-(3-amino-1H-1,2,4-triazol-1-yl)cyclohexyl)-5-(4-phenoxyphenyl)-7H-pyrrolo[2,3-d]pyrimidin-4-amine | LC-MS: Calculated Exact Mass = 466.2, Found [M + H]$^+$ (ESI) = 466.8; $^1$H NMR (CHLOROFORM-d) δ ppm: 10.47 (br. s., 1H), 8.21 (s, 1H), 7.96 (br. s., 1H), 7.79 (s, 1H), 7.37-7.43 (m, 4H), 7.18-7.25 (m, 2H), 7.08 (d, J = 7.9 Hz, 2H), 7.12 (d, J = 8.2 Hz, 2H), 2.48 (d, J = 11.0 Hz, 2H), 2.15-2.40 (m, 7H), 2.11 (br. s., 1H). |

-continued

| Structure | Name | LCMS and NMR |
|---|---|---|
| | EXAMPLE 82<br>7-((cis)-4-(3-amino-1H-1,2,4-triazol-1-yl)cyclohexyl)-5-(4-phenoxyphenyl)-7H-pyrrolo[2,3-d]pyrimidin-4-amine | LC-MS: Calculated Exact Mass = 466.2, Found [M + H]$^+$ (ESI) = 466.8; $^1$H NMR (CHLOROFORM-d) δ ppm: 10.72 (br. s., 1H), 8.20 (s, 1H), 7.36-7.42 (m, 4H), 7.16-7.22 (m, 2H), 7.08 (d, J = 8.2 Hz, 3H), 7.11 (d, J = 8.2 Hz, 1H), 2.53 (br. s., 2H), 2.15-2.28 (m, 6H), 2.12 (br. s., 2H). |
| | EXAMPLE 83<br>7-((trans)-4-(azetidin-3-ylamino)cyclohexyl)-5-(4-phenoxyphenyl)-7H-pyrrolo[2,3-d]pyrimidin-4-amine | LCMS: Calculated Exact Mass = 454.3, Found: [M + H]$^+$ (ESI) = 454.9; $^1$HNMR (400 MHz, DMSO-d6) δ ppm: 9.76 (br. s., 1H), 9.37 (br. s., 1H), 9.16 (br. s., 1H), 8.45 (s, 1H), 8.18 (br. s., 1H), 7.71 (s, 1H), 7.48 (d, J = 8.4 Hz, 2H), 7.43 (t, J = 7.8 Hz, 2H), 7.18 (t, J = 7.4 Hz, 1H), 7.11 (d, J = 8.4 Hz, 2H), 7.13 (d, J = 8.8 Hz, 2H), 4.61-4.71 (m, 1H), 4.37-4.47 (m, 1H), 4.22 (br. s., 4H), 3.13-3.25 (m, 1H), 2.01-2.15 (m, 5H), 1.92-2.01 (m, 1H), 1.53-1.70 (m, 2H). |
| | EXAMPLE 84<br>7-((cis)-4-(azetidin-3-ylamino)cyclohexyl)-5-(4-phenoxyphenyl)-7H-pyrrolo[2,3-d]pyrimidin-4-amine | LCMS: Calculated Exact Mass = 454.3, Found: [M + H]$^+$ (ESI) = 454.9; $^1$H NMR (400 MHz, DMSO-d6) δ ppm: 9.82 (br. s., 1H), 9.34 (br. s., 1H), 9.15 (br. s., 1H), 8.48 (s, 1H), 8.19 (br. s., 1H), 7.73 (s, 1H), 7.48 (d, J = 8.4 Hz, 2H), 7.43 (t, J = 7.8 Hz, 2H), 7.18 (t, J = 7.4 Hz, 1H), 7.10 (d, J = 8.4 Hz, 2H), 7.12 (d, J = 8.8 Hz, 2H), 4.77-4.93 (m, 1H), 4.37-4.51 (m, 1H), 4.25-4.36 (m, 2H), 4.14-4.25 (m, 2H), 3.46 (br. s., 1H), 2.11-2.36 (m, 2H), 1.77-2.07 (m, 6H). |

| Structure | Name | LCMS and NMR |
|---|---|---|
| 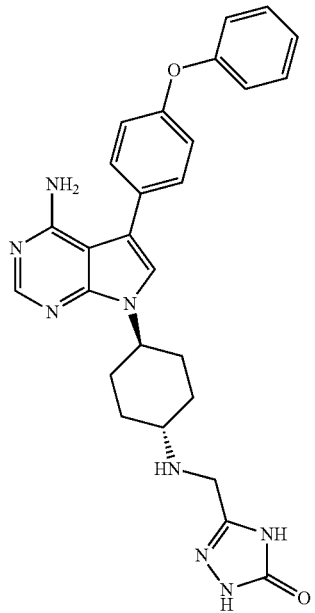 [SMILES: Nc1ncnc2c1c(-c1ccc(Oc3ccccc3)cc1)cn2[C@H]1CC[C@H](NCc2n[nH]c(=O)[nH]2)CC1] | EXAMPLE 85<br>3-((((trans)-4-(4-amino-5-(4-phenoxyphenyl)-7H-pyrrolo[2,3-d]pyrimidin-7-yl)cyclohexyl)amino)methyl)-1H-1,2,4-triazol-5(4H)-one | LCMS: Calculated Exact Mass = 496.2; Found [M + H]⁺ (ESI) = 497.2; ¹H NMR (400 MHz, DMSO-d₆) δ ppm: 11.78 (s, 1H), 11.73 (br. s., 1H), 9.40 (br. s., 1H), 8.44 (d, J = 4.6 Hz, 1H), 7.74 (d, J = 3.2 Hz, 1H), 7.34-7.52 (m, 4H), 7.04-7.26 (m, 5H), 4.65 (d, J = 5.1 Hz, 1H), 4.17 (br. s., 2H), 3.25 (br. s., 1H), 2.27 (d, J = 11.0 Hz, 2H), 1.89-2.15 (m, 4H), 1.65 (d, J = 8.6 Hz, 2H). |

Example 86

6-Bromo-7-((trans)-4-(4-methylpiperazin-1-yl)cyclohexyl)-5-(4-phenoxyphenyl)-7H-pyrrolo[2,3-d]pyrimidin-4-amine

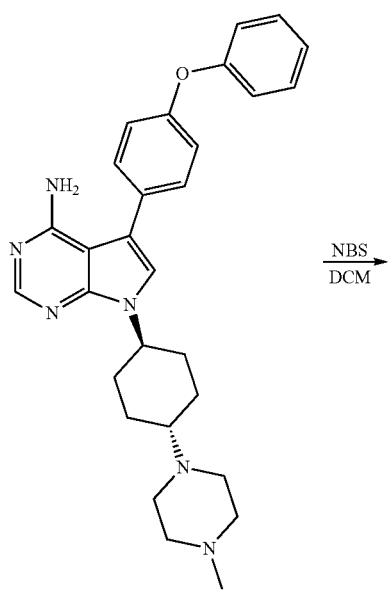

NBS
DCM

-continued

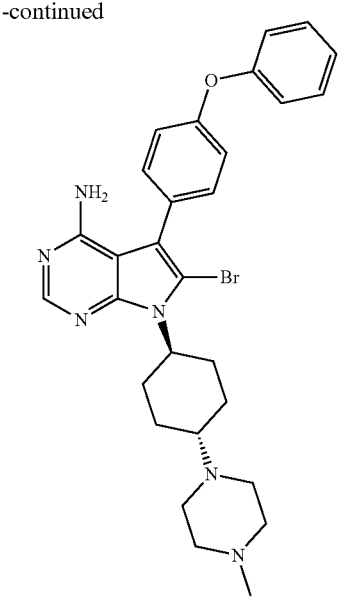

To the solution of 7-((trans)-4-(4-methylpiperazin-1-yl)cyclohexyl)-5-(4-phenoxyphenyl)-7H-pyrrolo[2,3-d]pyrimidin-4-amine (500 mg, 10.4 mmol) in dichloromethane (15 mL) was added NBS (368.8 mg, 2.07 mmol) by portions at room temperature. Then, the mixture was continued to stir for 16 hours. The mixture was concentrated to purify by flash chromatography (DCM:MeOH=15:1) to obtain yellow solid (280 mg, 48.3% yield). LCMS: Calculated Exact Mass=560.2; Found [M+H]+ (ESI)=561.8; ¹H NMR (400 MHz, CHLOROFORM-d) δ ppm: 8.23 (br. s., 1H), 7.33-7.45 (m, 4H), 7.16-7.23 (m, 1H), 7.11 (dd, J=7.8, 5.3 Hz, 4H), 5.48 (br. s., 2H), 4.61 (br. s., 1H), 3.12-3.35 (m, 6H), 2.81-3.08 (m, 2H), 2.75-2.80 (m, 2H), 2.66 (br. s., 3H), 2.24 (br. s., 2H), 2.03 (d, J=11.3 Hz, 2H), 1.69-1.77 (m, 2H).
Example 87
7-((trans)-4-(4-Methylpiperazin-1-yl)cyclohexyl)-5-(4-phenoxyphenyl)-7H-pyrrolo[2,3-d]pyrimidin-4-ol
And
Example 88
7-((cis)-4-(4-Methylpiperazin-1-yl)cyclohexyl)-5-(4-phenoxyphenyl)-7H-pyrrolo[2,3-d]pyrimidin-4-ol
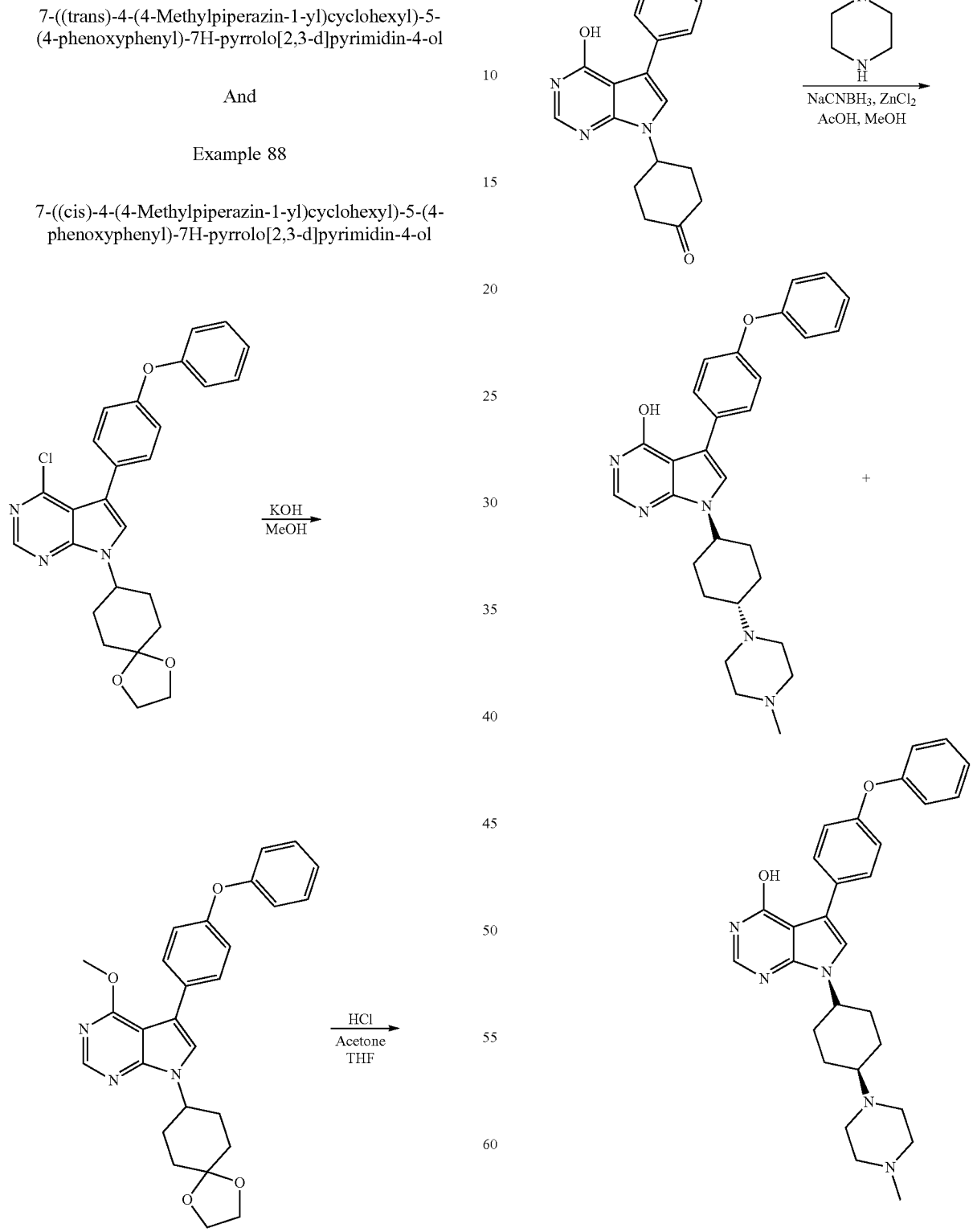
The solution of 4-chloro-5-(4-phenoxyphenyl)-7-(1,4-dioxaspiro[4.5]decan-8-yl)-7H-pyrrolo [2,3-d]pyrimidine (885 mg, 1.92 mmol) in MeOH (20 mL) at room temperature, KOH (215 mg, 3.83 mmol) was added under N₂ atmosphere and stirred at 80° C. for 4 hours. TLC (PE: EA=4:1) showed complete consumption of the starting material. The reaction mixture was cooled to room temperature, poured into ice water (50 mL) and extracted with EA (50 mL×2). The organic layer was washed with brine, dried with anhydrous Na₂SO4, and concentrated in vacuo to give the crude product as a yellow solid which was used in next step without further purification (623 mg, 71% yield).

LCMS: Calculated Exact Mass=457.20, Found [M+H]⁺ (ESI)=458.2.

4-(4-Hydroxy-5-(4-phenoxyphenyl)-7H-pyrrolo[2,3-d]pyrimidin-7-yl)cyclohexanone The solution of 4-methoxy-5-(4-phenoxyphenyl)-7-(1,4-dioxaspiro[4.5]decan-8-yl)-7H-pyrrolo[2,3-d] (623 mg, 1.36 mmol) in THF (3 mL), acetone (15 mL) and 6M HCL (11 mL) was stirred at 80° C. for 4 hours. TLC (EA:PE=1:2) showed complete consumption of the starting material. The mixture was cooled in ice bath. A 1M NaOH (80 mL, aq) was added until pH 8. The light brown solid product was collected by filtration (465 mg, 85.5% yield) and was used in next step without further purification. LCMS: Calculated Exact Mass=399.16, Found [M+H]⁺ (ESI)=400.1.

7-((cis)-4-(4-methylpiperazin-1-yl)cyclohexyl)-5-(4-phenoxyphenyl)-7H-pyrrolo[2,3-d]pyrimidin-4-ol and

7-((trans)-4-(4-Methylpiperazin-1-yl)cyclohexyl)-5-(4-phenoxyphenyl)-7H-pyrrolo[2,3-d]pyrimidin-4-ol The solution of compound 4-(4-hydroxy-5-(4-phenoxyphenyl)-7H-pyrrolo[2,3-d] pyrimidin-7-yl) cyclohexanone (100 mg, 0.25 mmol), 1-methylpiperazine (200 mg, 2.00 mmol) and ZnCl₂ (102 mg, 0.75 mmol) in MeOH (20 mL) was added NaBH₃CN (47 mg, 0.75 mmol) at room temperature and AcOH (0.1 mL) under N₂ atmosphere. Then the reaction was stirred at 40° C. for 16 hours. After concentration, the residue was extracted by DCM (150 mL×2) and water. The combined organic layer was washed with aqueous solution of NH₄Cl (200 mL), dried over anhydrous Na₂SO₄ and concentrated in vacuo. The residue was purified by Prep-TLC and then Prep-HPLC to get 7-((cis)-4-(4-methylpiperazin-1-yl)cyclohexyl)-5-(4-phenoxyphenyl)-7H-pyrrolo[2,3-d]pyrimidin-4-ol as a white solid (10 mg, 8.3% yield). LCMS: Calculated Exact Mass=483.26, Found [M+H]⁺ (ESI)=484.2; ¹H NMR (400 MHz, DMSO) δ 11.99 (s, 1H), 10.40 (s, 1H), 7.94 (dd, J=17.1, 5.5 Hz, 3H), 7.41 (dd, J=14.4, 5.9 Hz, 3H), 7.14 (t, J=7.4 Hz, 1H), 7.02 (dd, J=7.9, 6.6 Hz, 4H), 4.64 (s, 1H), 3.05 (s, 2H), 2.65 (s, 3H), 2.27 (d, J=17.6 Hz, 2H), 2.03 (dd, J=23.5, 9.1 Hz, 4H), 1.71 (s, 2H), 1.59 (s, 2H), 1.30-1.19 (m, 5H). Data for 7-((trans)-4-(4-methylpiperazin-1-yl)cyclohexyl)-5-(4-phenoxyphenyl)-7H-pyrrolo [2,3-d]pyrimidin-4-ol: ¹H NMR (400 MHz, DMSO) δ 8.92 (s, 1H), 7.95 (s, 1H), 7.42-7.32 (m, 7H), 7.18-7.07 (m, 2H), 7.05-6.93 (m, 7H), 6.85 (d, J=8.1 Hz, 4H), 4.83 (s, 1H), 3.54-3.45 (m, 2H), 2.79 (s, 3H), 2.12 (d, J=23.4 Hz, 7H), 1.69 (s, 2H), 1.23 (s, 5H).

Example 89

1-(4-((trans)-4-(4-amino-5-(4-phenoxyphenyl)-7H-pyrrolo[2,3-d]pyrimidin-7-yl)cyclohexyl)piperazin-1-yl)-2-methylpropan-2-ol

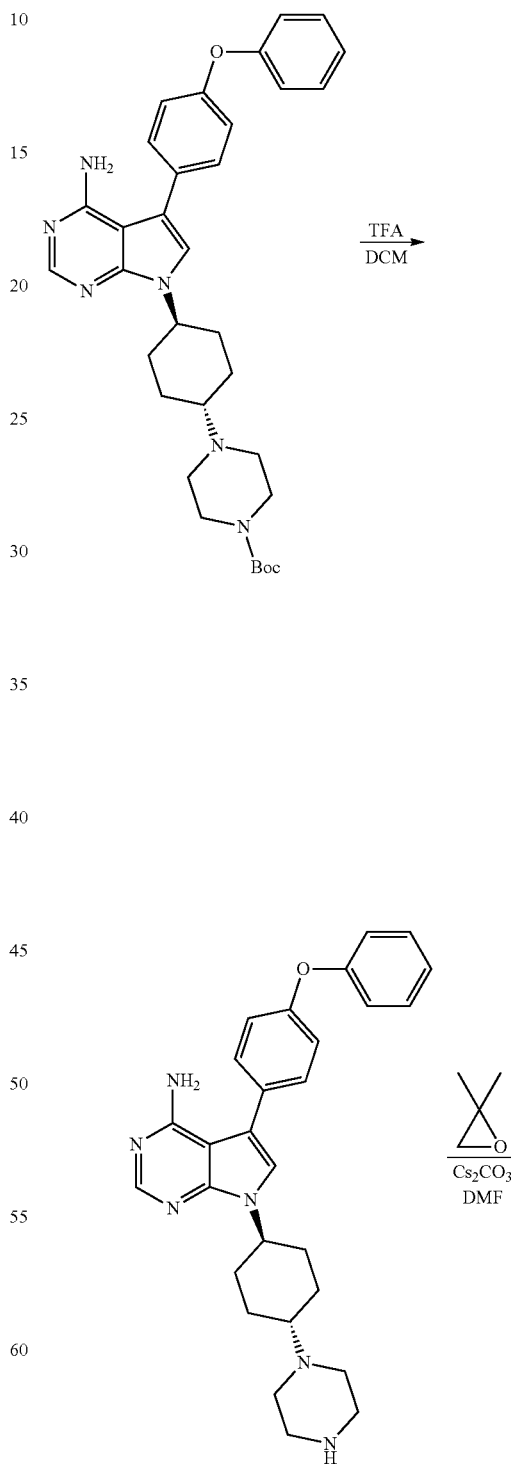

5-(4-phenoxyphenyl)-7-((trans)-4-(piperazin-1-yl)cyclohexyl)-7H-pyrrolo[2,3-d]pyrimidin-4-amine

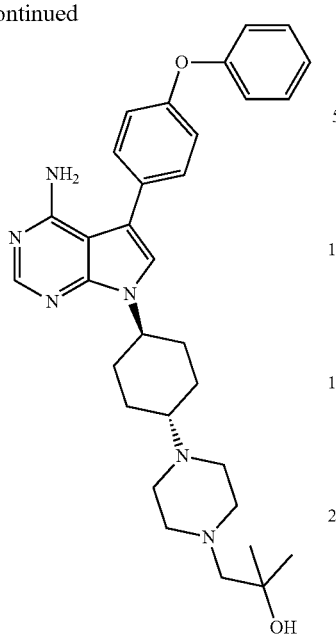

To a solution of tert-butyl 4-((trans)-4-(4-amino-5-(4-phenoxyphenyl)-7H-pyrrolo [2,3-d]pyrimidin-7-yl)cyclohexyl)piperazine-1-carboxylate (170 mg, 0.3 mmol) in DCM (4 mL) was added TFA (2 mL) dropwise. The reaction mixture was stirred at room temperature for 1 hours. The reaction mixture was concentrated to afford the product (50 mg, 35% yield) LCMS: Calculated Exact Mass=568.3; Found [M+H]$^+$ (ESI)=569.2.

1-(4-((trans)-4-(4-Amino-5-(4-phenoxyphenyl)-7H-pyrrolo[2,3-d]pyrimidin-7-yl)cyclohexyl)piperazin-1-yl)-2-methylpropan-2-ol A reaction mixture of 5-(4-phenoxyphenyl)-7-((trans)-4-(piperazin-1-yl)cyclohexyl)-7H-pyrrolo[2,3-d] pyrimidin-4-amine (100 mg, 0.21 mmol), 2,2-dimethyloxirane (30 mg, 0.43 mmol) and Cs$_2$CO$_3$ (208 mg, 00.64 mmol) in DMF (8 mL) was stirred at room temperature for 2 hours. NaBH$_3$CN (47 mg, 0.75 mol) was added. It was stirred at was stirred at 100° C. for overnight. After cooling to room temperature, DCM (20 mL) was added, the mixture was washed by water (20 mL×2). The organic layers were collected and concentrated. The reside was purified by Prep-TLC (DCM:MeOH=10:1) to afford the desired products (6 mg, 5% yield). LCMS: Calculated Exact Mass=540.2; Found [M+H]$^+$ (ESI)=540.3; $^1$H NMR (400 MHz, DMSO-d$_6$) δ ppm: 10.46 (br. s., 1H) 8.14 (s, 1H) 7.38-7.50 (m, 6H) 7.16 (t, J=7.38 Hz, 2H) 7.10 (dd, J=8.07, 6.07 Hz, 6H) 6.15 (s, 1H) 4.58-4.61 (m, 1H) 4.21-4.26 (m, 1H) 3.01-3.09 (m, 4H) 2.57-2.71 (m, 2H) 2.20-2.36 (m, 4H) 1.88-2.08 (m, 4H) 1.75-1.82 (m, 2H) 1.10 (s, 6H).

Example 90

1-((trans)-4-(4-Amino-5-(4-phenoxyphenyl)-7H-pyrrolo[2,3-d]pyrimidin-7-yl)cyclohexyl)piperazin-2-one and

Example 91

1-((cis)-4-(4-Amino-5-(4-phenoxyphenyl)-7H-pyrrolo[2,3-d]pyrimidin-7-yl)cyclohexyl)piperazin-2-one

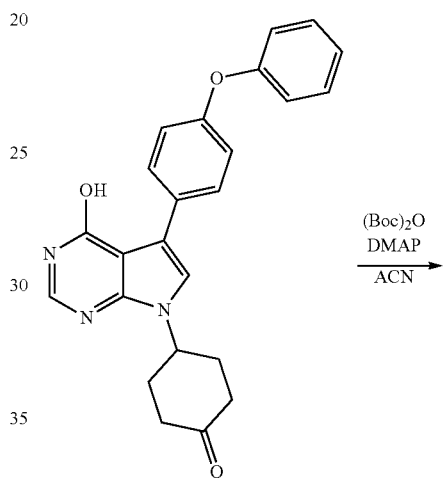

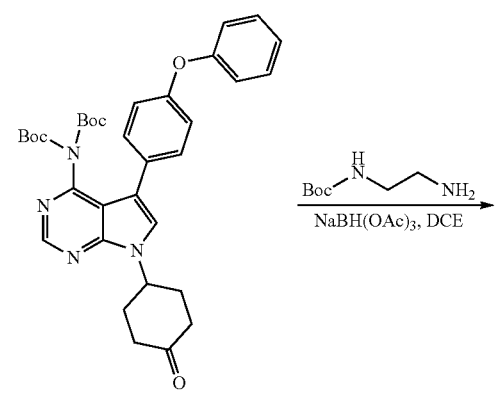

177
-continued

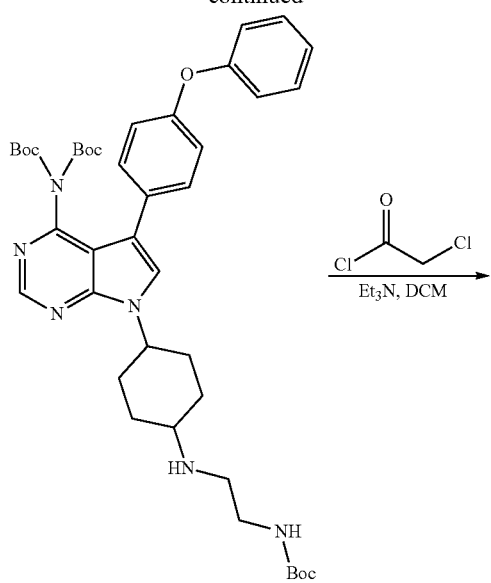

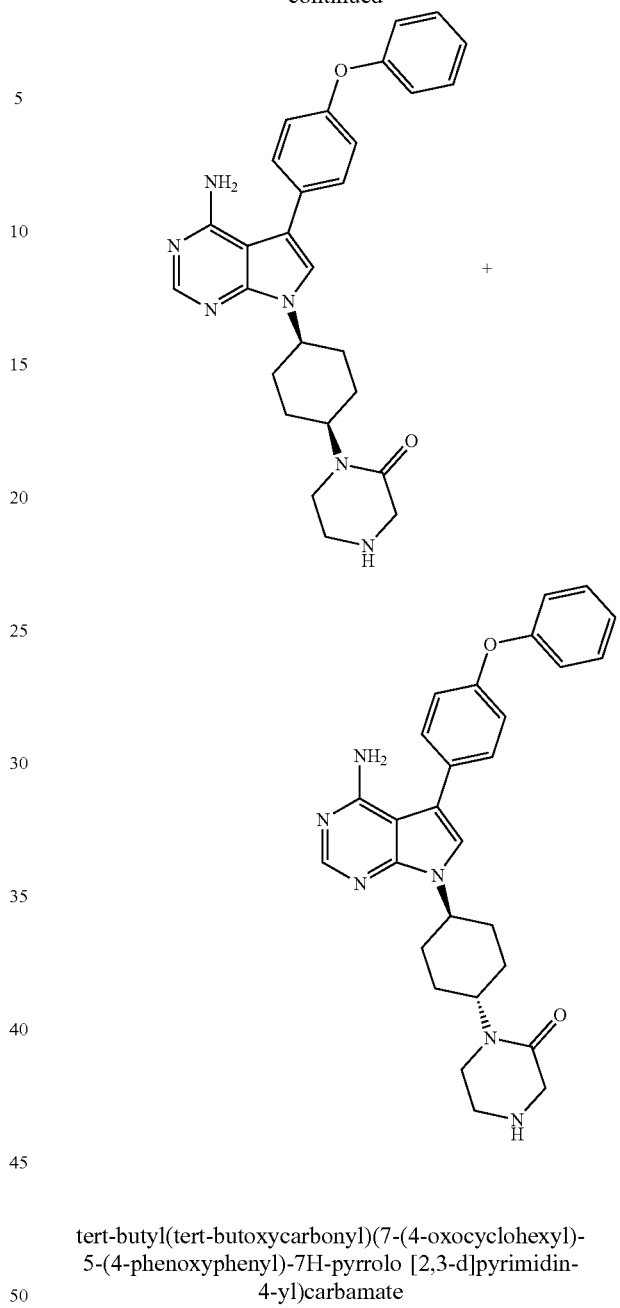

178
-continued tert-butyl(tert-butoxycarbonyl)(7-(4-oxocyclohexyl)-5-(4-phenoxyphenyl)-7H-pyrrolo [2,3-d]pyrimidin-4-yl)carbamate To a solution of 4-(4-amino-5-(4-phenoxyphenyl)-7H-pyrrolo[2,3-d]pyrimidin-7-yl)cyclo hexan-1-one (2 g, 5.01 mmol) in THF (10 mL) was added Et$_3$N (1.5 g, 15.06 mmol) and (Boc)$_2$O (2.2 g, 10 mmol). The mixture was stirred at room temperature overnight. DMAP (122 mg, 1 mmol), Et$_3$N (1.5 g, 15.06 mmol) and (Boc)$_2$O (2.2 g, 10 mmol) was added, the mixture was refluxed for 3 hours. The reaction was monitored via TLC and LCMS until complete consumption of starting material. It was then concentrated and washed with saturated NaHCO$_3$, and extracted with DCM, concentrated the organic layer obtained the crude product. The crude was purified by flash column chromatography (0-0.5% MeOH in DCM) to obtain product as a yellow solid (1.5 g, 50% yield). LCMS: Calculated Exact Mass=598.69; Found [M+H]$^+$ (ESI)=599.11.

tert-butyl(tert-butoxycarbonyl)(7-(4-((2-((tert-butoxycarbonyl)amino)ethyl)amino)cyclohexyl)-5-(4-phenoxyphenyl)-7H-pyrrolo[2,3-d]pyrimidin-4-yl)carbamate To a solution of tert-butyl (tert-butoxycarbonyl)(7-(4-oxocyclohexyl)-5-(4-phenoxyphenyl)-7H-pyrrolo[2,3-d]pyrimidin-4-yl)carbamate (1250 mg, 2.088 mmol) and tert-butyl (2-aminoethyl)carbamate (2007 mg, 12.52 mmol) in DCE (15 mL) was stirred at 50° C. under $N_2$ atmosphere for 2 hours. After it was cooled to room temperature, NaBH(OAc)$_3$ (2655 mg, 12.527 mmol) was added portion-wise, the mixture was stirred at room temperature under $N_2$ atmosphere overnight. The reaction was monitored via TLC and LCMS until complete consumption of starting material. It was then filtrated and concentrated, the crude was purified by flash column chromatography (2-3% MeOH in DCM) obtain product as a white solid (1 g, 64.5% yield).
LCMS: Calculated Exact Mass=742.41; Found [M+H]$^+$ (ESI)=742.92.

tert-butyl(tert-butoxycarbonyl)(7-(4-(N-(2-((tert-butoxycarbonyl)amino)ethyl)-2-chloroacetamido)cyclohexyl)-5-(4-phenoxyphenyl)-7H-pyrrolo[2,3-d]pyrimidin-4-yl)carbamate To a solution of tert-butyl (tert-butoxycarbonyl)(7-(4-((2-((tert-butoxycarbonyl)amino) ethyl)amino) cyclohexyl)-5-(4-phenoxyphenyl)-7H-pyrrolo[2,3-d]pyrimidin-4-yl)carbamate (500 mg, 0.67 mmol) in DCM (5 mL) was added Et$_3$N (430 mg, 2.05 mmol) and 2-chloroacetyl chloride (98.82 mg, 0.875 mmol) in DCM (0.5 mL) drop-wise at 0° C. The mixture was warmed up to room temperature for 2 hours. The reaction was monitored via LCMS until complete consumption of starting material. The reaction was quenched with ice/water, extracted with DCM (20 mL×2). It was then concentrated to obtained crude product. The crude was purified by flash column chromatography (1-1.5% MeOH in DCM) to obtain product as a colorless solid (175 mg, 31.7% yield). LCMS: Calculated Exact Mass=818.38; Found [M+H]$^+$ (ESI)=818.9.

tert-butyl(tert-butyl)4-(4-(4-((tert-butoxycarbonyl)amino)-5-(4-phenoxyphenyl)-7H-pyrrolo [2,3-d]pyrimidin-7-yl)cyclohexyl)-3-oxopiperazine-1-carboxylate To a solution of tert-butyl (tert-butoxycarbonyl)(7-(4-(N-(2-((tert-butoxycarbonyl)amino) ethyl)-2-chloroacetamido) cyclohexyl)-5-(4-phenoxyphenyl)-7H-pyrrolo[2,3-d]pyrimidin-4-yl)carbamate (175 mg, 0.214 mmol) in DMF (2 mL) was added NaH (33 mg, 60% in oil, 0.854 mmol) at 0° C., then warmed up to room temperature for 2 hours. The reaction was monitored via TLC and LCMS until complete consumption of starting material. The reaction was quenched with ice/water, extracted with DCM (50 mL×5), concentrated the organic layer to obtain product as a yellow solid (150 mg, 89.5% yield). LCMS: Calculated Exact Mass=782.4; Found [M+H]$^+$ (ESI)=682.62.

1-((trans)-4-(4-amino-5-(4-phenoxyphenyl)-7H-pyrrolo[2,3-d]pyrimidin-7-yl)cyclohexyl)piperazin-2-one and

1-((cis)-4-(4-amino-5-(4-phenoxyphenyl)-7H-pyrrolo[2,3-d]pyrimidin-7-yl)cyclohexyl)piperazin-2-one To a solution of tert-butyl (tert-butyl)4-(4-(4-((tert-butoxycarbonyl)amino)-5-(4-phenoxyphenyl)-7H-pyrrolo[2,3-d]pyrimidin-7-yl)cyclohexyl)-3-oxopiperazine-1-carboxylate (150 mg, 0.19 mmol) in DCM (2 mL) as added TFA (2 mL). The mixture was stirred at room temperature for 3 hours. The reaction was monitored via TLC and LCMS until complete consumption of starting material. Concentrated and added 20 mL 7.0 N NH$_3$ in MeOH, the mixture was stirred at room temperature for 15 min. Concentrated and prep-TLC to obtained 1-((trans)-4-(4-amino-5-(4-phenoxyphenyl)-7H-pyrrolo[2,3-d] pyrimidin-7-yl)cyclohexyl)piperazin-2-one as a yellow solid (45 mg, 48.6% yield). LCMS: Calculated Exact Mass=482.24; Found [M+H]$^+$ (ESI)=482.8; $^1$H NMR (DMSO-d$_6$) δ ppm: 8.14 (s, 1H), 7.38-7.52 (m, 5H), 7.16 (t, J=7.3 Hz, 1H), 7.06-7.12 (m, 4H), 6.03-6.24 (m, 1H), 4.62 (t, J=11.7 Hz, 1H), 4.41-4.51 (m, 1H), 3.25 (s, 2H), 3.21 (t, J=5.0 Hz, 2H), 2.88 (t, J=5.2 Hz, 2H), 2.05 (d, J=9.5 Hz, 2H), 1.99 (br. s., 2H), 1.72-1.86 (m, 2H), 1.66 (d, J=10.7 Hz, 2H)

Data for 1-((cis)-4-(4-amino-5-(4-phenoxyphenyl)-7H-pyrrolo[2,3-d]pyrimidin-7-yl)cyclohexyl) piperazin-2-one (300 mg, 48.6% yield). LCMS: Calculated Exact Mass=482.24; Found [M+H]$^+$ (ESI)=482.79; $^1$H NMR (DMSO-d$_6$) δ ppm: 8.14 (s, 1H), 7.48-7.56 (m, 3H), 7.38-7.46 (m, 2H), 7.06-7.20 (m, 5H), 6.12 (br. s., 1H), 4.80 (d, J=3.7 Hz, 1H), 4.30-4.40 (m, 1H), 3.23-3.28 (m, 4H), 2.89 (t, J=5.2 Hz, 2H), 2.37 (d, J=11.0 Hz, 2H), 1.95-2.04 (m, 2H), 1.80-1.91 (m, 2H), 1.57 (d, J=9.2 Hz, 2H).

Example 92

7-(3-Amino-1,5-dioxaspiro[5.5]undecan-9-yl)-5-(4-phenoxyphenyl)-7H-pyrrolo [2,3-d]pyrimidin-4-amine

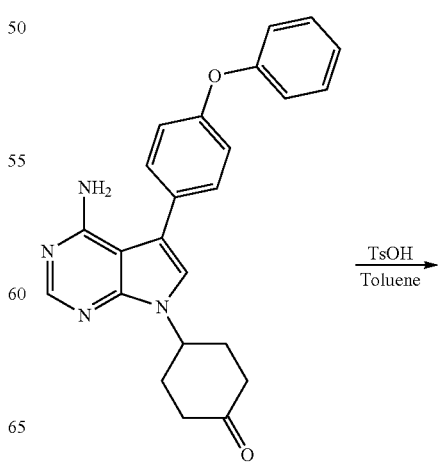

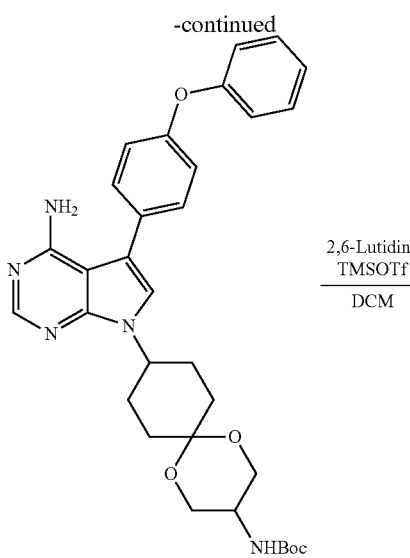

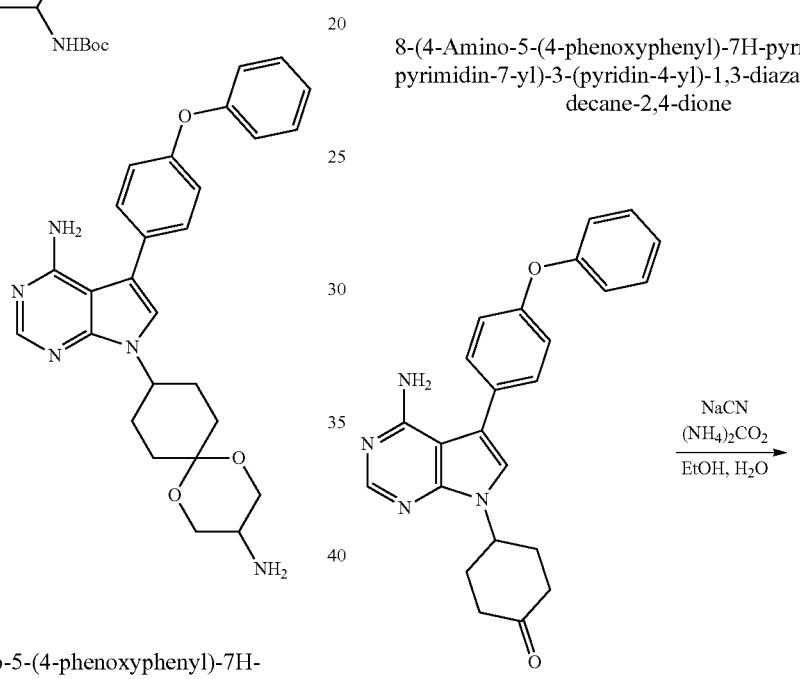

tert-butyl (9-(4-amino-5-(4-phenoxyphenyl)-7H-pyrrolo[2,3-d] pyrimidin-7-yl)-1,5-dioxaspiro [5.5] undecan-3-yl)carbamate To a solution of 4-(4-amino-5-(4-phenoxyphenyl)-7H-pyrrolo[2,3-d]pyrimidin-7-yl) cyclohexanone (400 mg, 1 mmol) in 10 mL toluene was added tert-butyl (1,3-dihydroxypropan-2-yl) carbamate (191 mg, 1 mmol), TsOH (12 mg, 0.06 mmol), and molecular sieve. The reaction mixture was heated to 150° C. and reacted for 2 hours under microwave irradiation. Solvent was removed under reduced pressure. The crude was purified by flash column chromatography (EA 100%) to give the product as white solid (160 mg, 28% yield). LC-MS: calculated Exact Mass=571.3, Found [M+H]$^+$ (ESI)=572.12.

7-(3-Amino-1,5-dioxaspiro[5.5]undecan-9-yl)-5-(4-phenoxyphenyl)-7H-pyrrolo [2,3-d]pyrimidin-4-amine To a solution of tert-butyl (9-(4-amino-5-(4-phenoxyphenyl)-7H-pyrrolo[2,3-d] pyrimidin-7-yl)-1,5-dioxaspiro [5.5] undecan-3-yl)carbamate (260 mg, 0.45 mmol) in 20 mL DCM at −78° C. was added 2,6-lutidine (72 mg, 0.675 mmol) and TMSOTf (130 mg, 0.585 mmol). The dry ice/acetone bath was replaced by an ice water bath, the reaction mixture was stirred for 2 hours before NaHCO$_3$ (aq 20 mL) was added and extracted with EA (20 mL×3). The organic layers were combined and dried over Na$_2$SO$_4$. After concentration, the crude was purified by Prep-TLC (DCM:CH$_3$OH=10:1) to give the product as white solid (19 mg, 8.6% yield). LC-MS: Calculated Exact Mass=471.2, Found [M+H]$^+$ (ESI)=472.11; $^1$H NMR (DMSO-d$_6$) δ ppm: 8.14 (s, 1H), 7.48 (d, J=8.7 Hz, 2H), 7.39-7.44 (m, 2H), 7.36 (s, 1H), 7.16 (t, J=7.3 Hz, 1H), 7.06-7.11 (m, 4H), 4.60-4.73 (m, 1H), 3.97 (dd, J=11.7, 3.4 Hz, 2H), 3.59-3.68 (m, 2H), 2.96 (br. s., 1H), 2.45 (d, J=13.5 Hz, 1H), 2.37 (d, J=13.5 Hz, 1H), 1.92-2.03 (m, 3H), 1.86 (d, J=9.8 Hz, 2H), 1.54 (ddt, J=17.3, 13.6, 3.7 Hz, 2H)

Example 93

8-(4-Amino-5-(4-phenoxyphenyl)-7H-pyrrolo[2,3-d]pyrimidin-7-yl)-3-(pyridin-4-yl)-1,3-diazaspiro [4.5] decane-2,4-dione

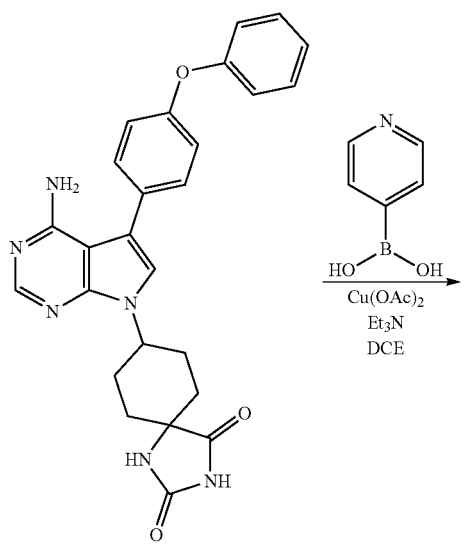

183

-continued

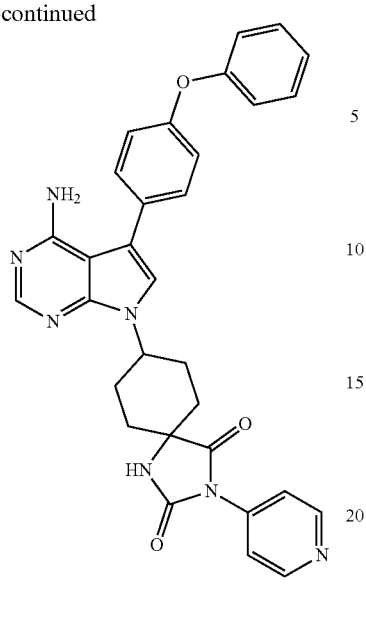

8-(4-Amino-5-(4-phenoxyphenyl)-7H-pyrrolo[2,3-d]pyrimidin-7-yl)-1,3-diazaspiro[4.5]decane-2,4-dione To a solution of 4-(4-amino-5-(4-phenoxyphenyl)-7H-pyrrolo[2,3-d]pyrimidin-7-yl) cyclohexan-1-one (5 g, 12.6 mmol) in EtOH (50 mL) and water (50 mL) was added NaCN (926 mg, 18.9 mmol) and $(NH_4)_2CO_3$ (3.63 g, 37.8 mmol). The mixture was stirred at 80° C. overnight. Then cooled to room temperature and concentrated to removed EtOH, filtered and washed with water (10 mL), dried the solid and to give product (4.5 g, 76% yield). LCMS: Calculated Exact Mass=468.2; Found $[M+H]^+$ (ESI)=469.2.

8-(4-Amino-5-(4-phenoxyphenyl)-7H-pyrrolo[2,3-d]pyrimidin-7-yl)-3-(pyridin-4-yl)-1,3-diazaspiro[4.5]decane-2,4-dione To a solution of 8-(4-amino-5-(4-phenoxyphenyl)-7H-pyrrolo[2,3-d]pyrimidin-7-yl)-1,3-diazaspiro [4.5]decane-2,4-dione (230 mg, 0.5 mmol) and pyridin-4-ylboronic acid (95 mg, 0.75 mmol) in 15 mL DCE was added $Cu(OAc)_2$ (97 mg, 0.5 mmol) and $Et_3N$ (0.15 mL, 1 mmol). The reaction was stirred at room temperature overnight under O2 atmosphere. The reaction was filtered through Celite and the solid was washed with 10 mL MeOH. The filtrate was concentrated and was purified by Prep-TLC (DCM:$CH_3OH$=10:1) to give 70 mg crude product that was further purified by Prep-HPLC to give the product as white solid in (11 mg 4% yield). LC-MS: Calculated Exact Mass=545.2, Found $[M+H]^+$ (ESI)=545.8; $^1H$ NMR (METHANOL-$d_4$) δ ppm: 8.78 (br. s., 2H), 8.48 (d, J=5.8 Hz, 2H), 8.27 (s, 1H), 7.53 (s, 1H), 7.42 (d, J=8.5 Hz, 2H), 7.28-7.35 (m, 2H), 6.96-7.12 (m, 6H), 1.97-2.25 (m, 9H), 1.93 (d, J=6.1 Hz, 1H).

184

Example 94

2-(4-(4-Amino-5-(4-phenoxyphenyl)-7H-pyrrolo[2,3-d]pyrimidin-7-yl)cyclohexylidene)acetamide and Example 95

Methyl 2-(1-amino-4-(4-amino-5-(4-phenoxyphenyl)-7H-pyrrolo[2,3-d]pyrimidin-7-yl)cyclohexyl) acetate and Example 96

2-(1-Amino-4-(4-amino-5-(4-phenoxyphenyl)-7H-pyrrolo[2,3-d]pyrimidin-7-yl)cyclohexyl)acetamide

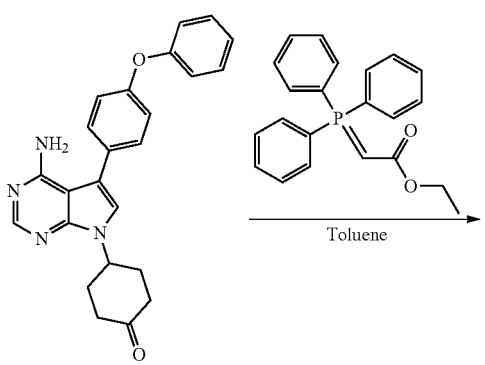

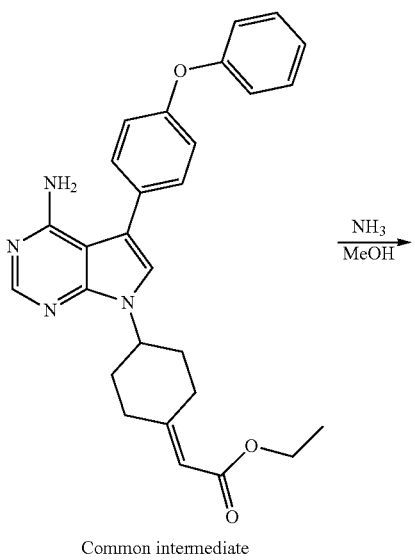

Common intermediate

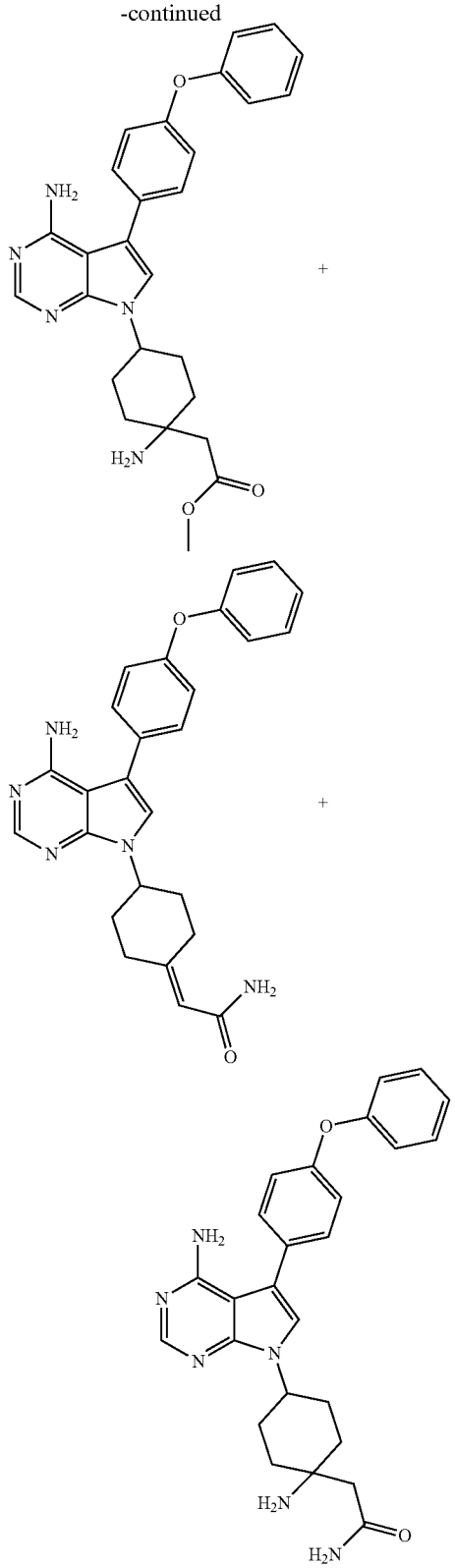

Ethyl 2-(4-(4-amino-5-(4-phenoxyphenyl)-7H-pyrrolo[2,3-d]pyrimidin-7-yl) cyclohexylidene)acetate A reaction mixture of 4-(4-amino-5-(4-phenoxyphenyl)-7H-pyrrolo[2,3-d] pyrimidin-7-yl)cyclohexanone (1.5 g, 3.76 mmol) and ethyl 2-(triphenylphosphoranylidene)acetate (1.3 g, 3.76 mmol) in Toluene (100 mL) was stirred at 110° C. overnight. The reaction mixture was cooled and concentrated. The reside was purified by flash column chromatography (DCM:EtOAc=1:1) to afford the product (900 mg, 51% yield)

LCMS: Calculated Exact Mass=468.2; Found [M+H]$^+$ (ESI)=468.6.

2-(4-(4-Amino-5-(4-phenoxyphenyl)-7H-pyrrolo[2,3-d]pyrimidin-7-yl)cyclohexylidene)acetamide and Methyl 2-(1-amino-4-(4-amino-5-(4-phenoxyphenyl)-7H-pyrrolo [2,3-d]pyrimidin-7-yl)cyclohexyl) acetate and 2-(1-Amino-4-(4-amino-5-(4-phenoxyphenyl)-7H-pyrrolo[2,3-d]pyrimidin-7-yl)cyclohexyl)acetamide To a solution of ethyl 2-(4-(4-amino-5-(4-phenoxyphenyl)-7H-pyrrolo[2,3-d] pyrimidin-7-yl) cyclohexylidene)acetate (350 mg, 0.75 mmol) in NH$_3$-MeOH (14 mL) was reacted in microwave reactor at 100° C. under for 48 hours. After cooled to room temperature, the reaction mixture was concentrated. The reside was purified by column chromatography (DCM:MeOH=10:1) to afford three products: 2-(4-(4-amino-5-(4-phenoxyphenyl)-7H-pyrrolo[2,3-d]pyrimidin-7-yl)cyclohexylidene)acetamide (2 mg, 0.6% yield) LCMS: Calculated Exact Mass=439.2; Found [M+H]$^+$ (ESI) =439.6; $^1$H NMR (400 MHz, DMSO-d$_6$) δ ppm: 8.13 (s, 1H) 7.47 (d, J=8.55 Hz, 2H) 7.38-7.45 (m, 3H) 7.32 (br. s., 1H) 7.16 (t, J=7.48 Hz, 1H) 7.05-7.13 (m, 4H) 6.85 (br. s., 1H) 5.50-5.60 (m, 1H) 4.83 (br. s., 1H) 2.80 (s, 2H) 2.45 (br. s., 1H) 2.33 (br. s., 1H) 2.24 (br. s., 1H) 2.15 (d, J=14.65 Hz, 2H) 1.89-2.06 (m, 2H) 1.81 (br. s., 1H).

2-(1-amino-4-(4-amino-5-(4-phenoxyphenyl)-7H-pyrrolo[2,3-d]pyrimidin-7-yl)cyclohexyl)acetate (2 mg, 0.6% yield) LCMS: Calculated Exact Mass=471.2; Found [M+H]+(ESI)=471.6; $^1$H NMR (400 MHz, DMSO-d$_6$) δ ppm: 8.13 (s, 1H) 7.67 (s, 1H) 7.48 (d, J=8.54 Hz, 2H) 7.42 (t, J=7.93 Hz, 2H) 7.16 (t, J=7.48 Hz, 1H) 7.08 (d, J=7.93 Hz, 2H) 7.11 (d, J=8.54 Hz, 2H) 6.14 (br. s., 1H) 4.61 (br. s., 1H) 3.68 (s, 3H) 3.01 (s, 2H) 1.95-2.14 (m, 4H) 1.72-1.92 (m, 4H).

2-(1-amino-4-(4-amino-5-(4-phenoxyphenyl)-7H-pyrrolo[2,3-d]pyrimidin-7-yl)cyclohexyl)acetamide (2 mg, 6% yield) LCMS: Calculated Exact Mass=456.2; Found [M+H]$^+$ (ESI)=456.8; $^1$H NMR (400 MHz, DMSO-d$_6$) δ ppm: 8.13 (s, 1H) 7.95 (s, 2H) 7.99 (s, 1H) 7.56-7.63 (m, 1H) 7.48 (d, J=8.24 Hz, 3H) 7.42 (t, J=7.78 Hz, 2H) 7.17 (d, J=7.32 Hz, 1H) 7.03-7.15 (m, 4H) 6.16 (br. s., 1H) 4.62 (br. s., 1H) 2.89 (s, 1H) 2.70-2.80 (m, 2H) 1.75-2.05 (m, 7H).

Example 97

2-(4-(4-amino-5-(4-phenoxyphenyl)-7H-pyrrolo[2,3-d]pyrimidin-7-yl)cyclohexylidene)-N-methylacetamide and

Example 98

2-(4-(4-amino-5-(4-phenoxyphenyl)-7H-pyrrolo[2,3-d]pyrimidin-7-yl)-1-(methylamino)cyclohexyl)-N-methylacetamide

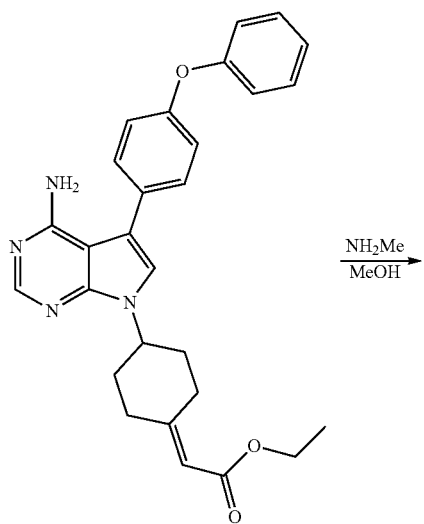

$\xrightarrow{\text{NH}_2\text{Me}}{\text{MeOH}}$

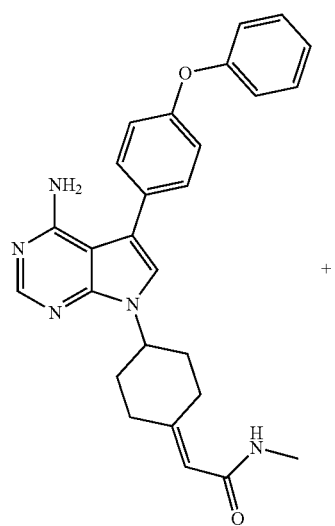

+

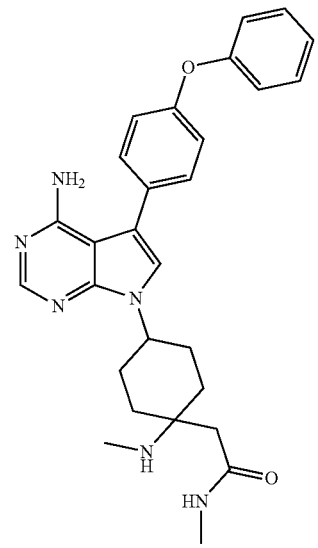

To a solution of ethyl 2-(4-(4-amino-5-(4-phenoxyphenyl)-7H-pyrrolo[2,3-d] pyrimidin-7-yl)cyclohexylidene) acetate (40 mg, 0.085 mmol) and Methylamine (40% in water, 0.5 mL) in MeOH (2 mL) was reacted in microwave reactor at 100° C. for 2 hours. After cooled to room temperature, the reaction mixture was concentrated. The reside was purified by column chromatography (DCM: MeOH=10:1) to afford two products: 2-(4-(4-amino-5-(4-phenoxyphenyl)-7H-pyrrolo[2,3-d]pyrimidin-7-yl)cyclohexylidene)-N-methylacetamide (3 mg, 7.8% yield) LCMS: Calculated Exact Mass=453.2; Found [M+H]$^+$ (ESI)=453.8; $^1$H NMR (400 MHz, DMSO-d$_6$) δ ppm: 8.13 (s, 1H) 7.79 (d, J=4.27 Hz, 1H) 7.44-7.50 (m, 3H) 7.37-7.44 (m, 3H) 7.16 (t, J=7.17 Hz, 2H) 7.09 (dd, J=8.09, 4.43 Hz, 5H) 7.01 (br. s., 1H) 5.55 (br. s., 1H) 4.81 (br. s., 1H) 2.81 (s, 2H) 2.56-2.61 (m, 3H) 2.44 (br. s., 2H) 2.22 (br. s., 1H) 2.04-2.18 (m, 2H) 1.89-2.04 (m, 3H); and 2-(4-(4-amino-5-(4-phenoxyphenyl)-7H-pyrrolo[2,3-d]pyrimidin-7-yl)-1-(methylamino)cyclohexyl)-N-methylacetamide (3 mg, 7.2% yield) LCMS: Calculated Exact Mass=484.2; Found [M+H]$^+$ (ESI)=484.8; $^1$H NMR (400 MHz, DMSO-d$_6$) δ ppm: 8.50 (s, 1H) 8.14 (s, 1H) 7.55 (s, 1H) 7.49 (d, J=8.54 Hz, 2H) 7.42 (t, J=7.63 Hz, 2H) 7.03-7.21 (m, 5H) 4.63 (br. s., 1H) 2.85 (br. s., 2H) 2.68 (d, J=4.27 Hz, 3H) 2.60 (s, 3H) 1.90 (s, 2H) 1.94 (s, 3H) 1.81 (br. s., 2H) 1.75 (s, 1H).

Example 99

Ethyl 6-(4-amino-5-(4-phenoxyphenyl)-7H-pyrrolo[2,3-d]pyrimidin-7-yl)spiro[2.5]octane-1-carboxylate

Example 100

4-(4-Amino-5-(4-phenoxyphenyl)-7H-pyrrolo[2,3-d]pyrimidin-7-yl)-1-((4-methylpiperazin-1-yl)methyl)cyclohexanol

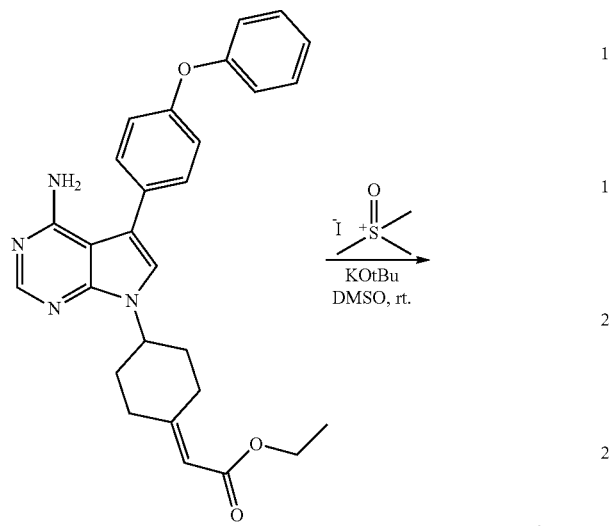

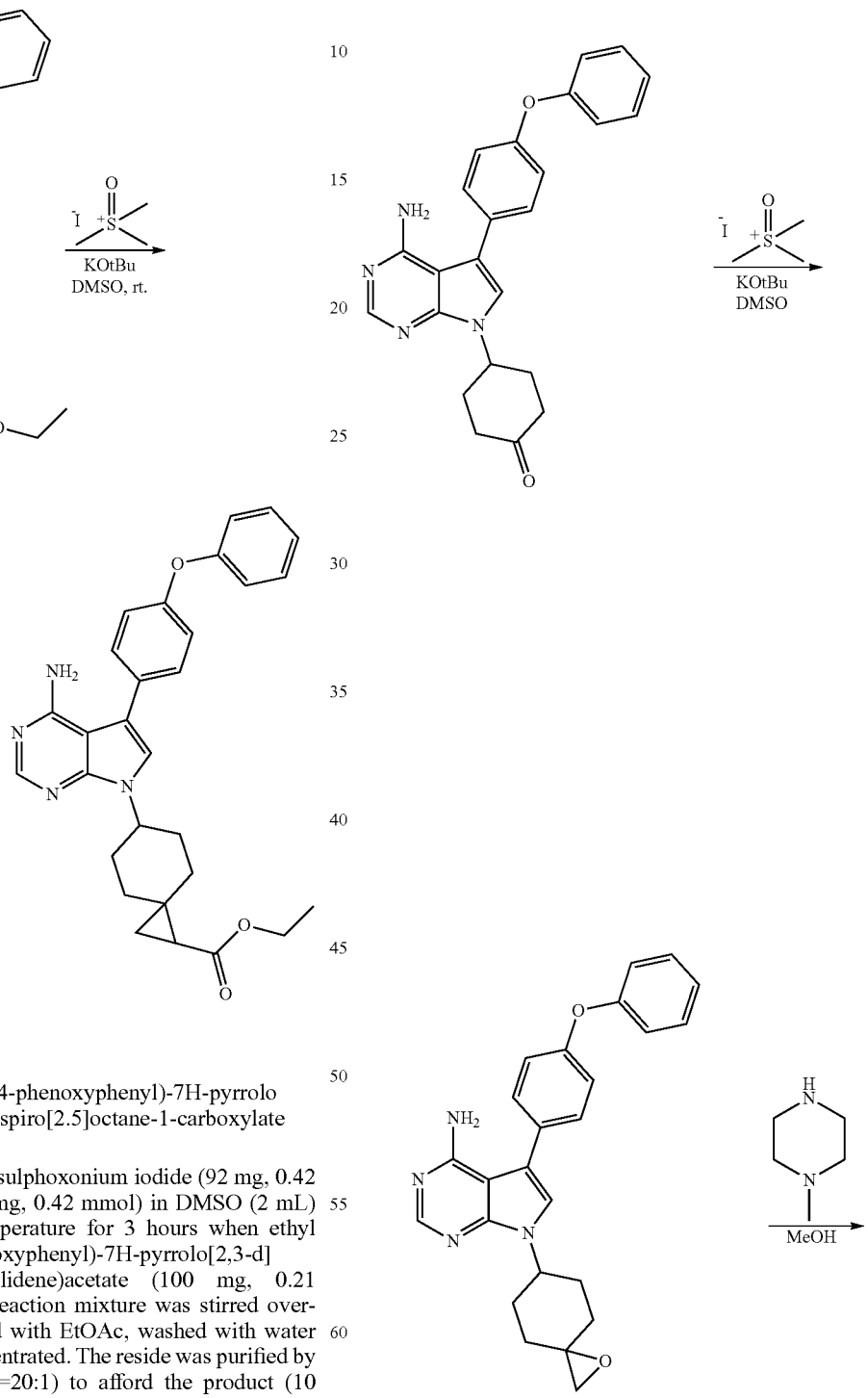

Ethyl 6-(4-amino-5-(4-phenoxyphenyl)-7H-pyrrolo[2,3-d]pyrimidin-7-yl)spiro[2.5]octane-1-carboxylate A solution of trimethylsulphoxonium iodide (92 mg, 0.42 mmol) and t-BuOK (47 mg, 0.42 mmol) in DMSO (2 mL) was stirred at room temperature for 3 hours when ethyl 2-(4-(4-amino-5-(4-phenoxyphenyl)-7H-pyrrolo[2,3-d]pyrimidin-7-yl)cyclohexylidene)acetate (100 mg, 0.21 mmol) was added. The reaction mixture was stirred overnight. It was then diluted with EtOAc, washed with water and brine, dried and concentrated. The reside was purified by Prep-TLC (DCM:MeOH=20:1) to afford the product (10 mg, 4.9% yield). LCMS: Calculated Exact Mass=482.2; Found [M+H]+ (ESI)=483.1; $^1$H NMR (400 MHz, CDCl$_3$-d$_6$) δ ppm: 8.30 (s, 1H) 7.40-7.46 (m, 4H) 2.15-2.19 (m, 3H) 1.95-1.99 (m, 3H) 1.57-1.60 (m, 2H) 1.33 (s, 3H) 1.10-1.31 (m, 3H).

Common Intermediate 5-(4-Phenoxyphenyl)-7-(1-oxaspiro[2.5]octan-6-yl)-
7H-pyrrolo[2,3-d]pyrimidin-4-amine To a solution of trimethylsulphoxonium iodide (220 mg, 1.00 mmol) and t-BuOK (110 mg, 1.00 mmol) in DMSO (10 mL) was stirred at room temperature for 0.5 hour when ethyl 2-(4-(4-amino-5-(4-phenoxyphenyl)-7H-pyrrolo[2,3-d]pyrimidin-7-yl)cyclohexylidene)acetate (200 mg, 0.50 mmol) was added. The reaction mixture was stirred overnight. The reaction was quenched with ice water, extracted with DCM, dried and concentrated to afford the crude product (250 mg) that was used without further purification. LCMS: Calculated Exact Mass=412.1; Found [M+H]+ (ESI)=412.8.

4-(4-amino-5-(4-phenoxyphenyl)-7H-pyrrolo[2,3-d]
pyrimidin-7-yl)-1-((4-methylpiperazin-1-yl)methyl)
cyclohexanol

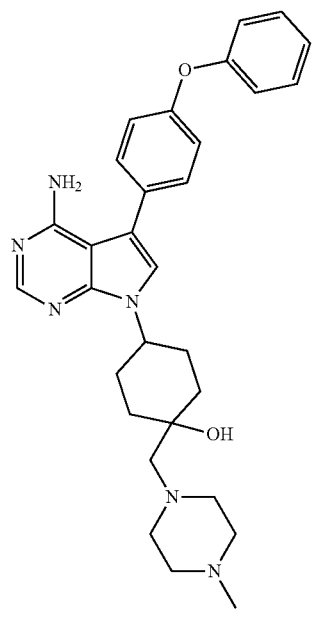

To a solution of 5-(4-phenoxyphenyl)-7-(1-oxaspiro[2.5]octan-6-yl)-7H-pyrrolo[2,3-d]pyrimidin-4-amine (50 mg, 0.12 mmol) and 1-methylpiperazine (50 mg, 0.50 mmol) in MeOH (10 mL) was heated at 70° C. under for 5 hours. After cooled to room temperature, the reaction mixture was concentrated. The residue was purified by flash column chromatography (DCM:MeOH=10:1) to afford products (20 mg, 39% yield over two steps). LCMS: Calculated Exact Mass=512.2; Found [M+H]$^+$ (ESI)=512.8; $^1$H NMR (400 MHz, CDCl$_3$-d$_6$) δ ppm: 8.13 (s, 1H) 7.48 (d, J=8.55 Hz, 2H) 7.39-7.45 (m, 2H) 7.37 (s, 1H) 7.13-7.19 (m, 1H) 7.09 (d, J=8.55 Hz, 4H) 6.12 (br. s., 1H) 4.53 (t, J=12.21 Hz, 1H) 4.11 (s, 1H) 2.54 (br. s., 3H) 2.35 (br. s., 4H) 2.26 (s, 3H) 2.08-2.20 (m, 5H) 1.63-1.79 (m, 4H) 1.49-1.63 (m, 2H).

Example 101

1-((1H-Imidazol-1-yl)methyl)-4-(4-amino-5-(4-phenoxyphenyl)-7H-pyrrolo[2,3-d]pyrimidin-7-yl)cyclohexanol

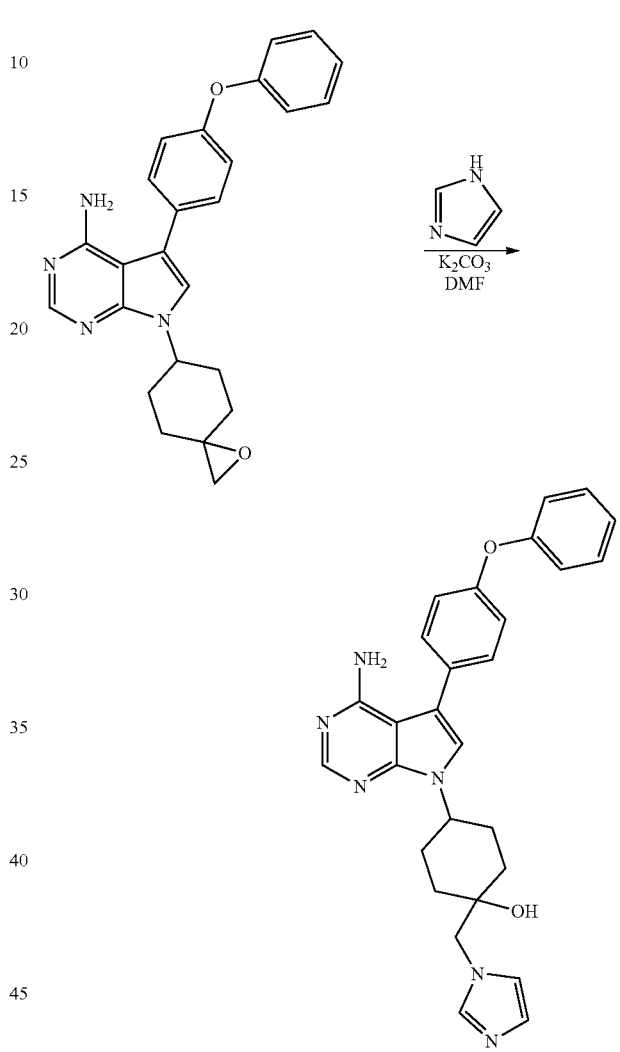

1-((1H-Imidazol-1-yl)methyl)-4-(4-amino-5-(4-phenoxyphenyl)-7H-pyrrolo[2,3-d]pyrimidin-7-yl)cyclohexanol To a solution of 5-(4-phenoxyphenyl)-7-(1-oxaspiro[2.5]octan-6-yl)-7H-pyrrolo [2,3-d]pyrimidin-4-amine (40 mg, 0.10 mmol), 1H-imidazole (27 mg, 0.40 mmol) and K$_2$CO$_3$ (50 mg, 0.40 mmol) in DMF (5 mL) was heated at 100° C. for 18 hours. After cooled to room temperature, the reaction mixture was concentrated. The reside was dissolved in DCM, washed with water, dried over Na$_2$SO$_4$, concentrated and purified by Prep-TLC (DCM:MeOH=10:1) to afford the product (10 mg, 20.8% yield). LCMS: Calculated Exact Mass=480.2; Found [M+H]$^+$ (ESI)=480.8; $^1$H NMR (400 MHz, CDCl$_3$-d$_6$) δ ppm: 8.05 (s, 1H) 7.60 (s, 1H) 7.33-7.43 (m, 4H) 7.32 (s, 1H) 7.08-7.16 (m, 2H) 7.01 (d, J=7.63 Hz, 2H) 7.04 (d, J=8.54 Hz, 3H) 6.89 (s, 1H) 4.5 (s, 3H) 3.94 (s, 2H) 1.87-2.07 (m, 3H) 1.73 (d, J=11.29 Hz, 2H) 1.60 (t, J=12.05 Hz, 2H) 1.50 (d, J=12.51 Hz, 3H).

Example 102

1-((1H-Tetrazol-1-yl)methyl)-4-(4-amino-5-(4-phenoxyphenyl)-7H-pyrrolo[2,3-d]pyrimidin-7-yl)cyclohexanol

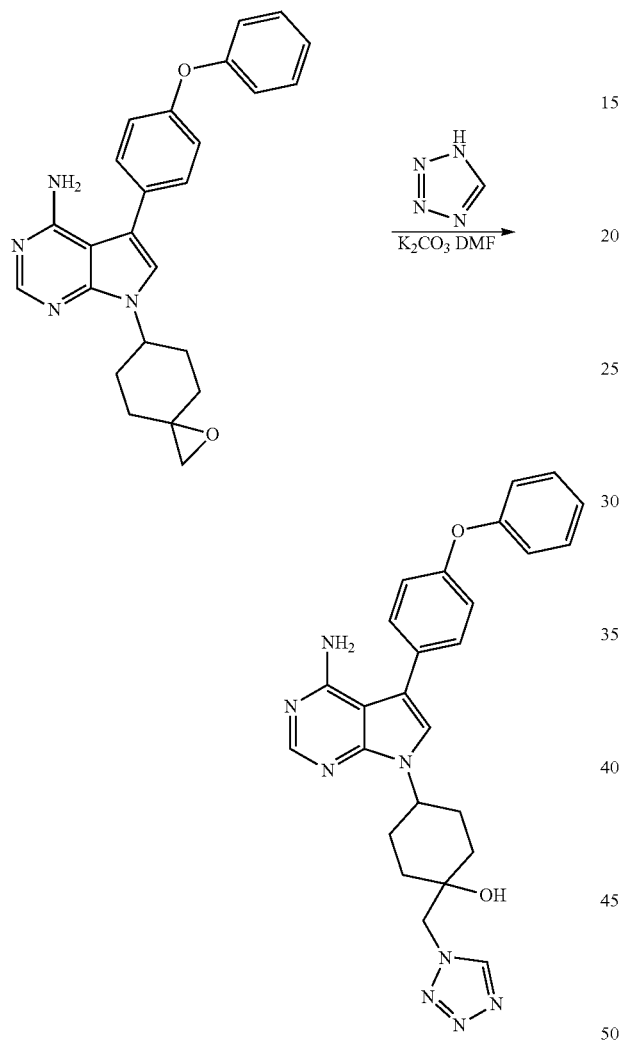

1-((1H-Tetrazol-1-yl)methyl)-4-(4-amino-5-(4-phenoxyphenyl)-7H-pyrrolo[2,3-d]pyrimidin-7-yl)cyclohexanol To a solution of 5-(4-phenoxyphenyl)-7-(1-oxaspiro[2.5]octan-6-yl)-7H-pyrrolo [2,3-d]pyrimidin-4-amine (50 mg, 0.12 mmol), 1H-tetrazole (34 mg, 0.48 mmol) and K₂CO₃ (66 mg, 0.48 mmol) in DMF (5 mL) was heated at 100° C. under for 4 hours. After cooled to room temperature, the reaction mixture was concentrated. The reside was dissolved in DCM, washed with water, dried over Na₂SO₄, concentrated and purified by Prep-TLC (DCM:MeOH=10:1) to afford the product (3 mg, 5% yield). LCMS: Calculated Exact Mass=482.2; Found [M+H]⁺ (ESI)=482.8; ¹H NMR (400 MHz, METHANOL-d₄) δ ppm: 9.07 (s, 1H) 8.05 (s, 1H) 7.37 (d, J=8.85 Hz, 2H) 7.28 (t, J=7.93 Hz, 2H) 7.17 (s, 1H) 7.04 (t, J=7.48 Hz, 1H) 6.96 (d, J=7.93 Hz, 2H) 6.99 (d, J=8.85 Hz, 2H) 4.58 (t, J=12.66 Hz, 1H) 4.45 (s, 2H) 1.99-2.14 (m, 3H) 1.92 (s, 1H) 1.84 (s, 2H) 1.67-1.83 (m, 4H) 1.58 (d, J=13.12 Hz, 3H).

Example 103

3-(2-Fluoro-4-phenoxyphenyl)-1-((trans)-4-(4-methylpiperazin-1-yl) cyclohexyl)-1H-pyrazolo [3,4-d]pyrimidin-4-amine

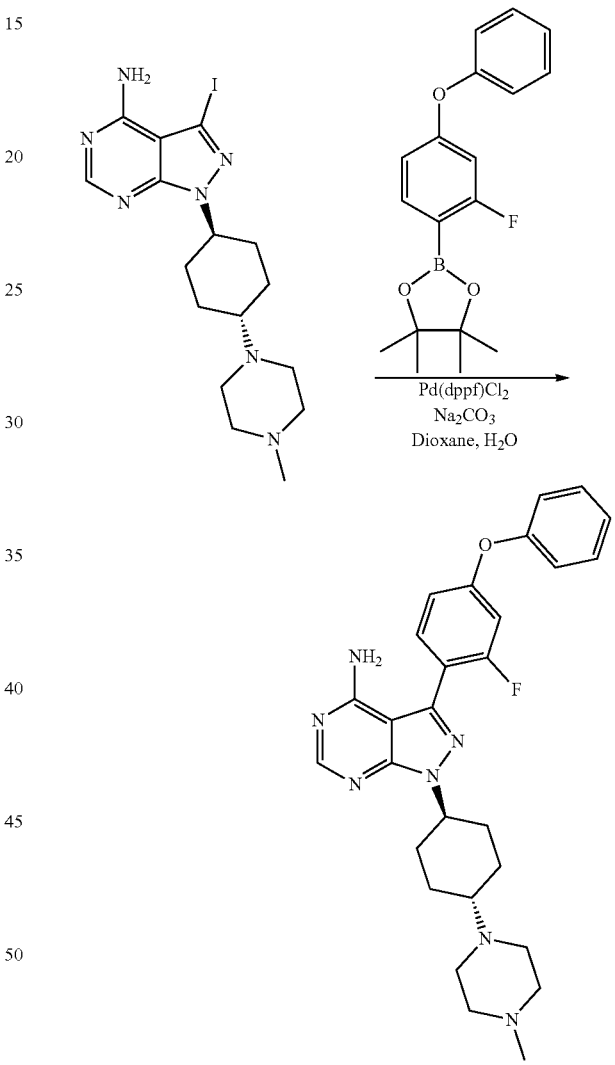

3-(2-Fluoro-4-phenoxyphenyl)-1-((trans)-4-(4-methylpiperazin-1-yl)cyclohexyl)-1H-pyrazolo[3,4-d]pyrimidin-4-amine To a 500 mL round-bottom flask was added 3-iodo-1-((trans)-4-(4-methylpiperazin-1-yl)cyclohexyl)-1H-pyrazolo[3,4-d]pyrimidin-4-amine (25 g, 56.6 mmol), 2-(2-fluoro-4-phenoxyphenyl)-4,4,5,5-tetramethyl-1,3,2-dioxaborolane (21.35 g, 67.9 mmol), Pd(dppf)Cl₂ (4.14 g, 5.6 mmol), Na₂CO₃ (24 g, 226.5 mmol), dioxane-water (9-1, 300 mL). The reaction was stirred at 85° C. overnight. It was cooled to the room temperature, filtrated and concentrated, the crude was purified by flash column chromatography (MeOH in DCM, 0 to 15% gradient) to obtain the product as a white solid (15 g) that was further purified by Prep-HPLC (Acetonitrile-water gradient with 0.1% TFA). After freeze-drying, it was obtained the product as a white powder (10.3 g, 41.2% yield). LC-MS: Calculated Exact Mass: 501.27; Found [M+H]$^+$ (ESI)=502.32; $^1$H NMR (400 MHz, DMSO-d6) δ ppm: 8.32 (s, 1H), 7.54 (t, J=8.6 Hz, 1H), 7.45-7.51 (m, 2H), 7.22-7.29 (m, 1H), 7.15-7.22 (m, 2H), 7.03 (dd, J=11.3, 2.4 Hz, 1H), 6.96 (dd, J=8.5, 2.4 Hz, 1H), 4.75 (dd, J=9.8, 4.8 Hz, 1H), 3.51 (br. s., 4H), 3.18 (br. s., 5H), 2.82 (s, 3H), 1.98-2.24 (m, 6H), 1.69 (d, J=6.6 Hz, 2H)

Using similar procedures, the following compounds may be prepared:

| Structure | Name | LCMS/NMR |
|---|---|---|
| | EXAMPLE 104<br>7-((trans)-4-(4-methylpiperazin-1-yl)cyclohexyl)-5-(4-pentadeuteriophenoxyphenyl)-7H-pyrrolo[2,3-d]pyrimidin-4-amine | LCMS: Calculated Exact Mass = 487.3; Found [M + H]$^+$ (ESI) = 488.2; $^1$H NMR (400 MHz, DMSO-d$_6$) δ ppm: 8.13 (s, 1H), 7.44-7.52 (m, J = 8.3 Hz, 2H), 7.41 (s, 1H), 7.05-7.15 (m, J = 8.3 Hz, 2H), 6.09 (br. s., 2H), 4.55 (t, J = 11.4 Hz, 1H), 2.53-2.68 (m, 4H), 2.31-2.48 (m, 5H), 2.20 (s, 3H), 1.80-2.04 (m, 6H), 1.37-1.58 (m, 2H). |
| | EXAMPLE 105<br>5-(2-fluoro-4-phenoxyphenyl)-7-((trans)-4-(4-methylpiperazin-1-yl)cyclohexyl)-7H-pyrrolo[2,3-d]pyrimidin-4-amine | LCMS: Calculated Exact Mass = 500.27; Found [M + H]+ (ESI) = 500.90; $^1$H NMR (DMSO-d6) δ ppm: 8.27 (s, 1H), 7.42 (t, J = 7.8 Hz, 2H), 7.32 (t, J = 8.4 Hz, 1H), 7.22 (t, J = 7.5 Hz, 1H), 7.11 (m, 3H), 6.87 (m, 2H), 4.68 (s, 1H), 2.55-3.18 (m, 9H), 1.84-2.34 (m, 8H), 1.25 (s, 3H). |

| Structure | Name | LCMS/NMR |
|---|---|---|
| 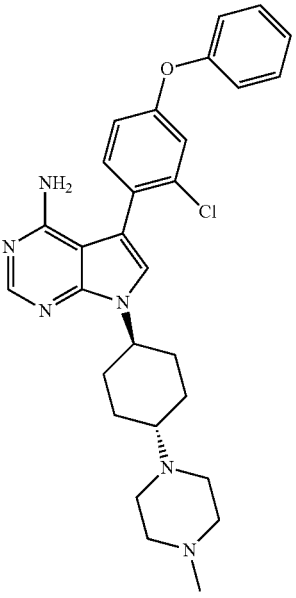 [SMILES: CN1CCN([C@H]2CC[C@H](n3cc(-c4ccc(Oc5ccccc5)cc4Cl)c4c(N)ncnc43)CC2)CC1] | EXAMPLE 106 5-(2-chloro-4-phenoxyphenyl)-7-((trans)-4-(4-methylpiperazin-1-yl)cyclohexyl)-7H-pyrrolo[2,3-d]pyrimidin-4-amine | LCMS: Calculated Exact Mass = 516.2; Found [M + H]$^+$ (ESI) = 517.9; $^1$H NMR (400 MHz, DMSO-d$_6$) δ ppm: 8.40 (s, 1H) 7.67 (s, 1H) 7.41-7.51 (m, 4H) 7.20-7.26 (m, 2H) 7.17 (d, J = 7.79 Hz, 2H) 7.05 (dd, J = 8.53, 2.48 Hz, 1H) 4.62-4.67 (m,1H) 3.70-3.75 (m, 1H) 3.40-3.45 (m, 2H) 3.27-3.29 (m, 1H) 2.97 (s, 1H) 2.77 (br. s., 3H) 2.06 (d, J = 7.39 Hz, 4H) 1.98 (d, J = 12.63 Hz, 2H) 1.59-1.64 (m, 2H). |
| 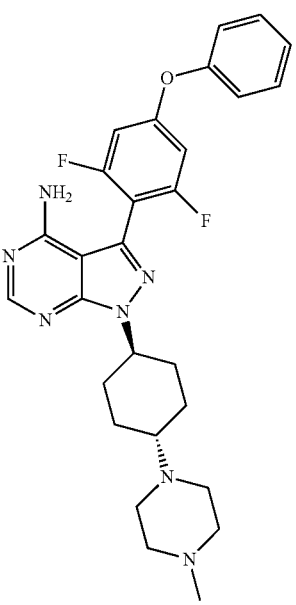 [SMILES: CN1CCN([C@H]2CC[C@H](n3nc(-c4c(F)cc(Oc5ccccc5)cc4F)c4c(N)ncnc43)CC2)CC1] | EXAMPLE 107 3-(2,6-difluoro-4-phenoxyphenyl)-1-((trans)-4-(4-methylpiperazin-1-yl)cyclohexyl)-1H-pyrazolo[3,4-d]pyrimidin-4-amine | LC-MS: Calculated Exact Mass: 519.3 Found: [M + H]$^+$ (ESI) = 520.2; $^1$H NMR (400 MHz, CDCl$_3$) δ 11.55 (s, 1H), 8.25 (s, 1H), 7.58 (d, J = 10.9 Hz, 3H), 7.42 (t, J = 7.8 Hz, 2H), 7.22 (t, J = 7.4 Hz, 1H), 7.16 (d, J = 7.9 Hz, 2H), 7.10 (d, J = 7.9 Hz, 2H), 6.26 (s, 1H), 5.05 (s, 1H), 4.63 (s, 2H), 4.47 (s, 1H), 2.61 (s, 2H), 2.44 (s, 2H), 2.14 (dd, J = 20.5, 9.7 Hz, 4H), 1.26 (s, 1H). |

-continued

| Structure | Name | LCMS/NMR |
|---|---|---|
| 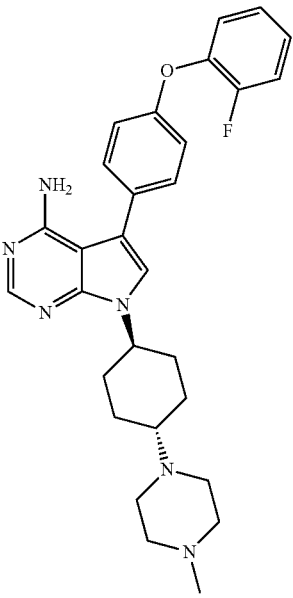 [SMILES: CN1CCN([C@H]2CC[C@H](n3cc(-c4ccc(Oc5ccccc5F)cc4)c4c(N)ncnc43)CC2)CC1] | EXAMPLE 108<br>5-(4-(2-fluorophenoxy)phenyl)-7-((trans)-4-(4-methylpiperazin-1-yl)cyclohexyl)-7H-pyrrolo[2,3-d]pyrimidin-4-amine | LC-MS: Calculated Exact Mass: 500.1 Found: [M + H]$^+$ (ESI) = 501.2; $^1$H NMR (400 MHz, CDCl$_3$) δ 11.55 (s, 1H), 8.25 (s, 1H), 7.58 (d, J = 10.9 Hz, 4H), 7.42 (t, J = 7.8 Hz, 2H), 7.22 (t, J = 7.4 Hz, 1H), 7.16 (d, J = 7.9 Hz, 2H), 7.10 (d, J = 7.9 Hz, 2H), 6.26 (s, 1H), 5.05 (s, 1H), 4.63 (s, 2H), 4.47 (s, 1H), 2.61 (s, 2H), 2.44 (s, 2H), 2.14 (dd, J = 20.5, 9.7 Hz, 4H), 1.26 (s, 1H). |
| 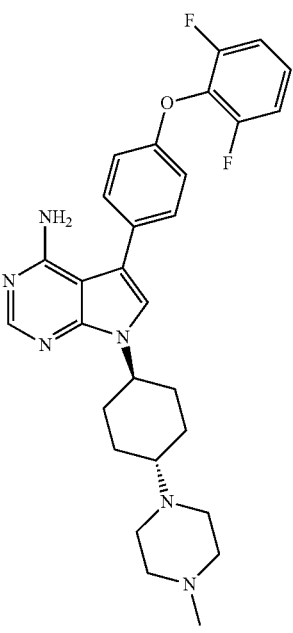 [SMILES: CN1CCN([C@H]2CC[C@H](n3cc(-c4ccc(Oc5c(F)cccc5F)cc4)c4c(N)ncnc43)CC2)CC1] | EXAMPLE 109<br>5-(4-(2,6-difluorophenoxy)phenyl)-7-((trans)-4-(4-methylpiperazin-1-yl)cyclohexyl)-7H-pyrrolo[2,3-d]pyrimidin-4-amine | LC-MS: Calculated Exact Mass: 518.3 Found: [M + H]$^+$ (ESI) = 519.2; $^1$H NMR (400 MHz, DMSO) δ 8.14 (s, 1H), 7.47 (s, 1H), 7.41-7.29 (m, 4H), 7.07-7.14(m, 3H), 627 (m, 2H), 4.60-4.54(m, 1H), 2.90-2.70 (m, 9H), 2.47 (s, 3H), 1.90-1.85 (m, 6H), 1.57-1.43 (m, 2H). |

| Structure | Name | LCMS/NMR |
|---|---|---|
| | EXAMPLE 110<br>5-(3-methoxy-4-phenoxyphenyl)-7-((trans)-2-(1-methylpiperidin-4-yl)-1,3-dioxan-5-yl)-7H-pyrrolo[2,3-d]pyrimidin-4-amine | LCMS: Calculated Exact Mass = 513.29; Found [M + H]+ (ESI) = 514.13; ¹H NMR (DMSO-d6) δ ppm: 8.24 (s, 1H), 7.32-7.36 (m, 3H), 7.23 (dd, J = 8.2, 1.9 Hz, 1H), 7.15 (d, J = 8.2 Hz, 1H), 7.06 (t, 7.3 Hz 1H), 6.97 (d, J = 7.7 Hz, 2H), 4.68 (s, 1H), 3.81 (s, 3H), 2.67 (m, 10H), 2.03 (m, 6H), 1.52 (s, 2H). |
| | EXAMPLE 111<br>7-((trans)-4-(4-methylpiperazin-1-yl)cyclohexyl)-5-(4-(p-tolyloxy)phenyl)-7H-pyrrolo[2,3-d]pyrimidin-4-amine | LCMS: Calculated Exact Mass = 496.3; Found [M + H]+ (ESI) = 497.2; ¹H NMR (400 MHz, DMSO-d₆) δ ppm: 8.45 (s, 1H), 7.72 (s, 1H), 7.46 (d, J = 8.6 Hz, 2H), 7.19-7.30 (m, J = 8.3 Hz, 2H), 7.05-7.16 (m, J = 8.6 Hz, 2H), 7.00 (d, J = 8.5 Hz, 2H), 4.63-4.77 (m, 1H), 3.39-3.68 (m, 7H), 2.95-3.24 (m, 2H), 2.31 (s, 3H), 1.93-2.22 (m, 6H), 1.67 (d, J = 9.4 Hz, 2H). |

-continued

| Structure | Name | LCMS/NMR |
|---|---|---|
| | EXAMPLE 112<br>2-(4-(4-amino-7-((trans)-4-(4-methylpiperazin-1-yl)cyclohexyl)-7H-pyrrolo[2,3-d]pyrimidin-5-yl)phenoxy)benzonitrile | LCMS: Calculated Exact Mass = 507.27; Found [M + H]$^+$ (ESI) = 508.1; $^1$H NMR (DMSO-d$_6$) δ ppm: 8.45 (s, 1H), 7.93 (d, J = 7.6 Hz, 1H), 7.77 (s, 1H), 7.71 (t, J = 7.7 Hz, 1H), 7.56 (d, J = 8.5 Hz, 2H), 7.27-7.35 (m, 3H), 7.14 (d, J = 8.5 Hz, 1H), 4.69 (br. s., 1H), 3.58-3.62 (m, 7H), 3.04 (br. s., 2H), 2.80 (s, 3H), 2.05-2.14 (m, 4H), 2.03 (d, J = 10.8 Hz, 2H), 1.76 (dt, J = 6.2, 3.2 Hz, 1H), 1.67 (d, J = 10.8 Hz, 2H). |
| | EXAMPLE 113<br>(4-(4-amino-7-((trans)-4-(4-methylpiperazin-1-yl)cyclohexyl)-7H-pyrrolo[2,3-d] pyrimidin-5-yl)phenyl)(phenyl)methanone | LC-MS: Calculated Exact Mass = 494.3, Found [M + H]$^+$ (ESI) = 494.8; $^1$H NMR (METHANOL-d$_4$) δ ppm: 8.40 (s, 1H), 7.95 (d, J = 8.2 Hz, 2H), 7.84-7.89 (m, 2H), 7.79 (s, 1H), 7.67-7.74 (m, 3H), 7.55-7.62 (m, 2H), 3.59 (br. s., 8H), 2.98 (s, 3H), 2.25-2.39 (m, 4H), 2.10-2.25 (m, 2H), 2.05 (s, 1H), 1.87 (d, J = 10.7 Hz, 2H). |

| Structure | Name | LCMS/NMR |
|---|---|---|
| | EXAMPLE 114<br>(4-(4-amino-7-((trans)-4-(4-methylpiperazin-1-yl)cyclohexyl)-7H-pyrrolo[2,3-d]pyrimidin-5-yl)phenyl)(phenyl)methanol | LCMS: Calculated Exact Mass = 496.3; Found [M + H]$^+$ (ESI) = 496.8; $^1$H NMR (400 MHz, CDCl$_3$-d$_6$) δ ppm: 8.05 (s, 1H) 7.37-7.42 (m, 2H) 7.30-7.37 (m, 4H) 7.19-7.27 (m, 3H) 7.12-7.17 (m, 1H) 5.74 (s, 1H) 4.53 (t, J = 11.90 Hz, 2H) 3.31 (s, 3H) 2.65 (br. s., 6H) 2.60 (br. s., 1H) 2.04 (br. s., 4H) 1.81-1.97 (m, 3H) 1.57 (d, J = 10.38 Hz, 3H). |
| | EXAMPLE 115<br>5-(4-benzylphenyl)-7-((trans)-4-(4-methylpiperazin-1-yl)cyclohexyl)-7H-pyrrolo[2,3-d]pyrimidin-4-amine | LCMS: Calculated Exact Mass = 480.3; Found [M + H]$^+$ (ESI) = 481.0; $^1$H NMR (DMSO-d$_6$) δ ppm: 8.48 (s, 1H), 7.74 (s, 1H), 7.35-7.46 (m, 4H), 7.32-7.35 (m, 1H), 7.28-7.32 (m, 3H), 7.22 (td, J = 6.2, 2.7 Hz, 1H), 4.70 (br. s.,1H), 4.02 (s, 2H), 3.68 (br. s., 2H), 3.57 (s, 1H), 3.27-3.54 (m, 4H), 3.21 (br. s., 2H), 2.86 (br. s., 3H), 2.06-2.20 (m, 4H), 2.02 (d, J = 12.6 Hz, 2H), 1.73 (d, J = 7.8 Hz, 2H). |

| Structure | Name | LCMS/NMR |
|---|---|---|
| | EXAMPLE 116<br>7-((trans)-4-(4-methylpiperazin-1-yl)cyclohexyl)-5-(4-(pyridazin-3-yloxy)phenyl)-7H-pyrrolo[2,3-d]pyrimidin-4-amine | LC-MS: Calculated Exact Mass = 484.3, Found [M + H]$^+$ (ESI) = 484.8; $^1$H NMR (METHANOL-d$_4$) δ 8.96-9.03 (m, 1H), 8.35 (s, 1H), 7.84 (td, J = 8.9, 4.5 Hz, 1H), 7.66 (s, 1H), 7.56-7.64 (m, 3H), 7.44 (d, J = 8.5 Hz, 1H), 7.35-7.41 (m, 1H), 3.37 (s, 3H), 2.93 (s, 1H), 2.88 (s, 2H), 2.85 (s, 2H), 2.14-2.28 (m, 5H), 2.11 (d, J = 12.8 Hz, 2H), 2.05 (q, J = 6.4 Hz, 3H), 1.62 (d, J = 7.1 Hz, 2H), 1.56 (d, J = 14.0 Hz, 1H). |
| | EXAMPLE 117<br>1-(4-(4-amino-7-((trans)-4-(4-methylpiperazin-1-yl)cyclohexyl)-7H-pyrrolo[2,3-d]pyrimidin-5-yl)phenyl)-3-(5-ethylisoxazol-3-yl)urea | LCMS: Calculated Exact Mass = 543.1; Found [M + H]$^+$ (ESI) = 544.1; $^1$H NMR (400 MHz, DMSO-d$_6$) δ ppm 9.52 (s, 1H) 8.93 (s, 1H) 8.13 (s, 1H) 7.55 (d, J = 8.60 Hz, 2H) 7.33-7.45 (m, 3H) 6.56 (s, 1H) 6.04 (br. s., 2H) 4.55 (br. s., 1H) 2.65-2.81 (m, 4H) 2.24-2.42 (m, 6H) 2.16 (s, 3H) 1.86-2.04 (m, 7H) 1.40-1.53 (m, 3H) 1.14-1.28 (m, 3H). |

| Structure | Name | LCMS/NMR |
|---|---|---|
| 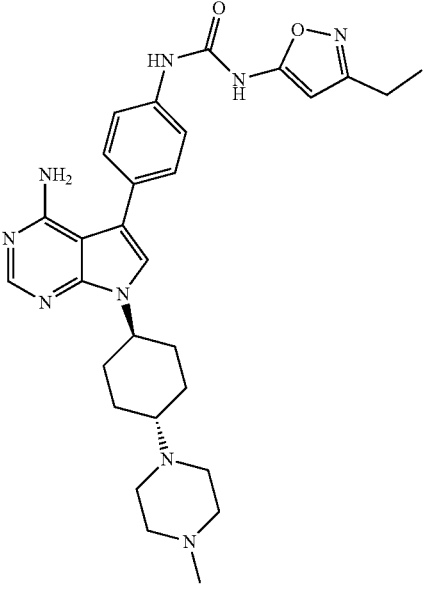 [SMILES: CCc1cc(NC(=O)Nc2ccc(-c3cn([C@H]4CC[C@H](N5CCN(C)CC5)CC4)c4ncnc(N)c34)cc2)on1] | EXAMPLE 118 1-(4-(4-amino-7-((trans)-4-(4-methylpiperazin-1-yl)cyclohexyl)-7H-pyrrolo[2,3-d]pyrimidin-5-yl)phenyl)-3-(3-ethylisoxazol-5-yl)urea | LCMS: Calculated Exact Mass = 543.31; Found [M + H]$^+$ (ESI) = 544.3; $^1$H NMR (400 MHz, DMSO-d$_6$) δ ppm 10.33 (s, 1H) 9.22 (s, 1H) 8.38 (s, 1H) 7.67 (s, 1H) 7.61 (d, J = 8.46 Hz, 2H) 7.42 (d, J = 8.33 Hz, 2H) 6.01 (s, 1H) 4.65 (br. s., 1H) 1.93-2.09 (m, 7H) 1.60 (br. s., 2H) 1.24 (br. s., 3H) 1.12-1.20 (m, 3H). |
| 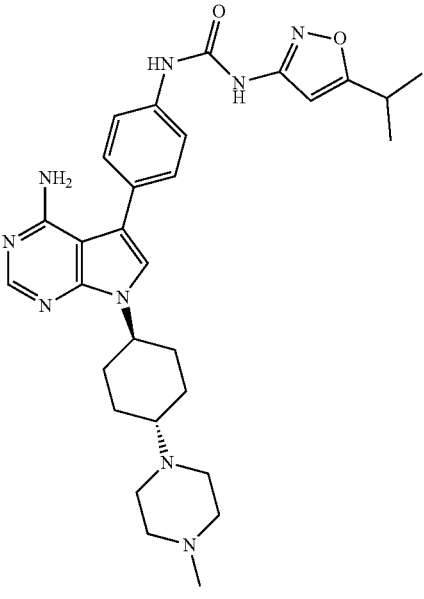 [SMILES: CC(C)c1cc(NC(=O)Nc2ccc(-c3cn([C@H]4CC[C@H](N5CCN(C)CC5)CC4)c4ncnc(N)c34)cc2)no1] | EXAMPLE 119 1-(4-(4-amino-7-((trans)-4-(4-methylpiperazin-1-yl)cyclohexyl)-7H-pyrrolo[2,3-d]pyrimidin-5-yl)phenyl)-3-(5-isopropylisoxazol-3-yl)urea | LCMS: Calculated Exact Mass = 557.3; Found [M + H]$^+$ (ESI) = 557.8; $^1$H NMR (400 MHz, DMSO-d$_6$) δ ppm: 9.67 (s, 1H), 9.11 (s, 1H), 8.38 (s, 1H), 7.68 (s, 1H), 7.60 (d, J = 8.5 Hz, 2H), 7.41 (d, J = 8.2 Hz, 2H), 6.53 (s, 1H), 4.65 (m, 1H), 3.01-3.24 (m, 8H), 2.67-2.98 (m., 3H), 1.99-2.21 (m., 7H), 1.52-1.69 (m., 2H), 1.25 (d, J = 7.0 Hz, 6H). |

-continued

| Structure | Name | LCMS/NMR |
|---|---|---|
| 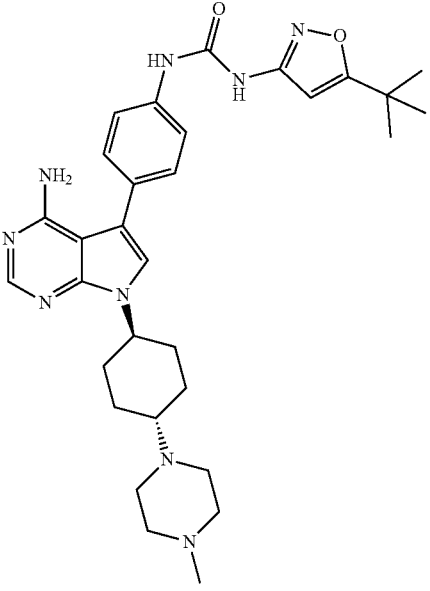 [SMILES: CN1CCN([C@H]2CC[C@H](n3cc(-c4ccc(NC(=O)Nc5cc(C(C)(C)C)on5)cc4)c4c(N)ncnc43)CC2)CC1] | EXAMPLE 120<br>1-(4-(4-amino-7-((trans)-4-(4-methylpiperazin-1-yl)cyclohexyl)-7H-pyrrolo[2,3-d]pyrimidin-5-yl)phenyl)-3-(5-(tert-butyl)isoxazol-3-yl)urea | LCMS: Calculated Exact Mass = 571.3; Found [M + H]$^+$ (ESI) = 571.7; $^1$H NMR (400 MHz, DMSO-d$_6$) δ ppm: 8.50 (s, 1H) 7.77 (s, 1H) 7.64 (m, J = 8.54 Hz, 2H) 7.44 (m, J = 8.85 Hz, 2H) 6.53 (s, 1H) 4.67-4.82 (m, 1H) 3.84 (s. 4H) 3.45 (d, J = 11.60 Hz, 4H) 2.95 (s, 3H) 2.25 (d, J = 9.46 Hz, 2H) 2.01-2.20 (m, 4H) 1.82 (d, J = 8.85 Hz, 2H) 1.31 (s, 9H). |
| 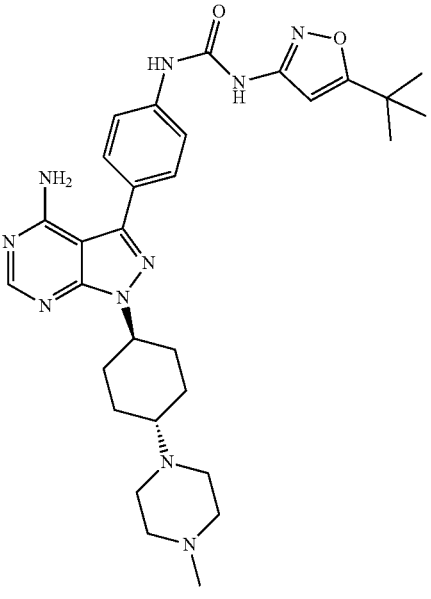 [SMILES: CN1CCN([C@H]2CC[C@H](n3nc(-c4ccc(NC(=O)Nc5cc(C(C)(C)C)on5)cc4)c4c(N)ncnc43)CC2)CC1] | EXAMPLE 121<br>1-(4-(4-amino-7-((trans)-4-(4-methylpiperazin-1-yl)cyclohexyl)-7H-pyrrolo[2,3-d]pyrimidin-5-yl)phenyl)-3-(5-(tert-butyl)isoxazol-3-yl)urea | LCMS: Calculated Exact Mass = 571.3; Found [M + H]$^+$ (ESI) = 572.9; $^1$H NMR (400 MHz, DMSO-d$_6$) δ ppm: 9.61 (s, 1H), 9.07 (s, 1H), 8.23 (s, 1H), 7.53-7.70 (m, 4H), 6.53 (s, 1H), 4.67 (br. s., 1H), 2.50-3.17 (m, 11H), 1.82-2.17 (m, 7H), 1.46-1.68 (m, 7H), 1.30 (s, 9H). |

| Structure | Name | LCMS/NMR |
|---|---|---|
| 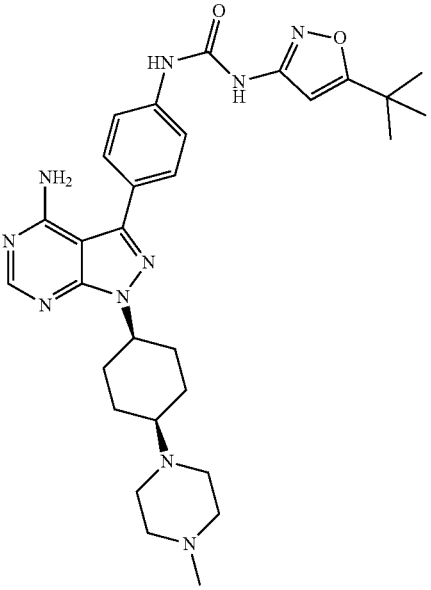 [SMILES: CN1CCN([C@H]2CC[C@@H](n3nc(-c4ccc(NC(=O)Nc5cc(C(C)(C)C)on5)cc4)c4c(N)ncnc43)CC2)CC1] | EXAMPLE 122<br>1-(4-(4-amino-7-((cis)-4-(4-methylpiperazin-1-yl)cyclohexyl)-7H-pyrrolo[2,3-d]pyrimidin-5-yl)phenyl)-3-(5-(tert-butyl)isoxazol-3-yl)urea | LCMS: Calculated Exact Mass = 571.3; Found [M + H]$^+$ (ESI) = 572.9; $^1$H NMR (400 MHz, DMSO-d$_6$) δ ppm: 9.59 (s, 1H), 9.05 (s, 1H), 8.23 (s, 1H), 7.52-7.70 (m, 4H), 6.54 (s, 1H), 4.71-4.86 (m, 1H), 3.17 (d, J = 3.4 Hz, 2H), 2.28-2.50 (m, 5H), 2.16-2.25 (m, 7H), 2.06-2.14 (m, 2H), 1.61-1.73 (m, 2H), 1.30 (s, 9H). |
| 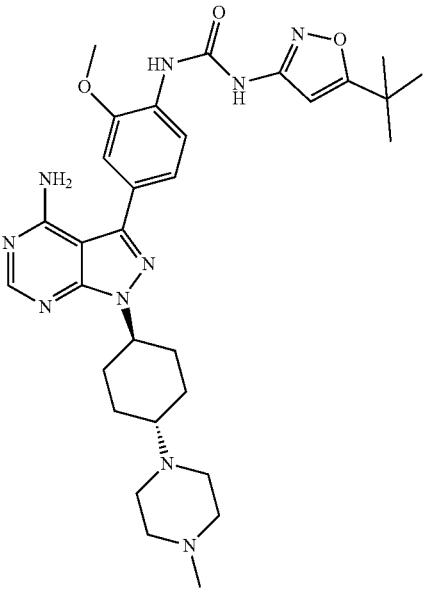 [SMILES: COc1cc(-c2nn([C@H]3CC[C@H](N4CCN(C)CC4)CC3)c3ncnc(N)c23)ccc1NC(=O)Nc1cc(C(C)(C)C)on1] | EXAMPLE 123<br>1-(4-(4-amino-1-((trans)-4-(4-methylpiperazin-1-yl)cyclohexyl)-1H-pyrazolo[3,4-d]pyrimidin-3-yl)-2-methoxyphenyl)-3-(5-(tert-butyl)isoxazol-3-yl)urea | LCMS: Calculated Exact Mass = 602.3; Found [M + H]$^+$ (ESI) = 603.1; $^1$H NMR (400 MHz, DMSO-d$_6$) δ ppm: 10.14 (s, 1H) 8.84 (br. s., 1H) 8.22-8.36 (m, 2H) 7.17-7.32 (m, 2H) 6.49 (s, 1H) 4.71-4.76 (m, 1H) 3.95 (s, 1H) 3.48-3.53 (m, 3H) 3.01-3.07 (m, 2H) 2.79 (s, 3H) 1.98-2.22 (m, 6H) 1.69 (s, 2H) 1.30 (s, 9H). |

| Structure | Name | LCMS/NMR |
|---|---|---|
| 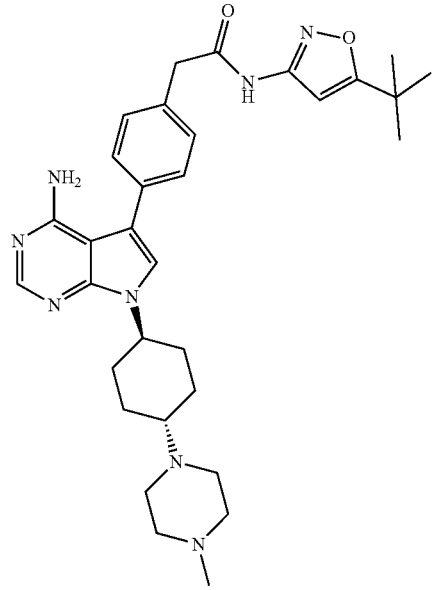 [SMILES: CN1CCN([C@H]2CC[C@H](n3cc(-c4ccc(CC(=O)Nc5cc(C(C)(C)C)on5)cc4)c4c(N)ncnc43)CC2)CC1] | EXAMPLE 124<br>2-(4-(4-amino-7-((trans)-4-(4-methylpiperazin-1-yl)cyclohexyl)-7H-pyrrolo[2,3-d]pyrimidin-5-yl)phenyl)-N-(5-(tert-butyl)isoxazol-3-yl)acetamide | LC-MS: Calculated exact mass = 570.3 Found [M + H]$^+$ (ESI) = 571.1; $^1$H NMR (400 MHz, DMSO-d6) δ ppm: 11.2 (s, 1H), 8.44 (s, 1H), 7.73 (s, 1H), 7.46 (m, 4H), 6.59 (s, 1H), 4.66 (m, 1H), 3.60-3.40 (m, 5H), 3.40-2.82 (m, 4H), 2.80(s, 3H), 2.20- 2.03 (m, 6H), 1.60-1.67 (m, 2H), 1.29 (m, 9H). |
| 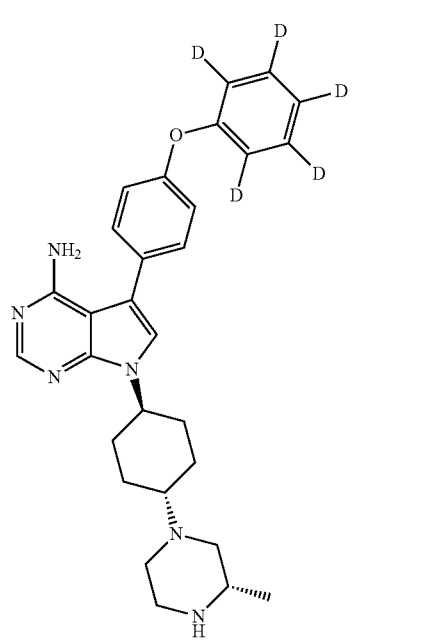 [SMILES: [2H]c1c([2H])c([2H])c(Oc2ccc(-c3cn([C@H]4CC[C@H](N5CCN[C@@H](C)C5)CC4)c4ncnc(N)c34)cc2)c([2H])c1[2H]] | EXAMPLE 125<br>7-((trans)-4-((S)-3-methylpiperazin-1-yl)cyclohexyl)-5-(4-pentadeuteriophenoxyphenyl)-7H-pyrrolo[2,3-d]pyrimidin-4-amine | LCMS: Calculated Exact Mass = 487.3; Found [M + H]$^+$ (ESI) = 488.0; $^1$H NMR (400 MHz, DMSO-d$_6$) δ ppm: 8.93 (br. s., 1H), 8.48 (br. s., 1H), 8.20 (s, 1H), 7.47 (d, J = 7.0 Hz, 3H), 7.12 (d, J = 8.3 Hz, 2H), 6.42 (br. s., 2H), 4.60 (br. s., 1H), 2.71-3.29 (m, 7H), 1.82-2.12 (m, 6H), 1.42-1.69 (m, 2H), 1.15-1.37 (m, 4H). |

| Structure | Name | LCMS/NMR |
|---|---|---|
| 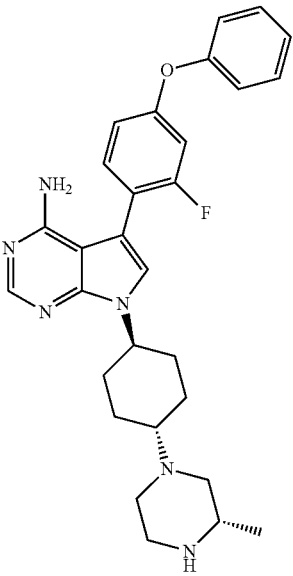 [SMILES: C[C@H]1CN([C@H]2CC[C@H](n3cc(-c4ccc(Oc5ccccc5)cc4F)c4c(N)ncnc43)CC2)CCN1] | EXAMPLE 126 5-(2-fluoro-4-phenoxyphenyl)-7-((trans)-4-((S)-3-methylpiperazin-1-yl)cyclohexyl)-7H-pyrrolo[2,3-d]pyrimidin-4-amine | LCMS: Calculated Exact Mass = 500.27; Found [M + H]+ (ESI) = 500.90; $^1$H NMR (DMSO-d6) δ ppm: 8.40 (s, 1H), 7.70 (s, 1H), 7.40 (m, 2H), 7.24 (t, J = 7.4 Hz, 1H), 7.17 (d, J = 7.7 Hz, 1H), 7.01-7.06 (m, 1H), 6.94 (d, J = 10.7 Hz, 1H), 4.68 (s, 1H), 2.83-3.24 (m, 8H), 1.94-2.14 (m, 6H), 1.67 (s, 2H), 1.25 (d, J = 5 Hz, 3H). |
| 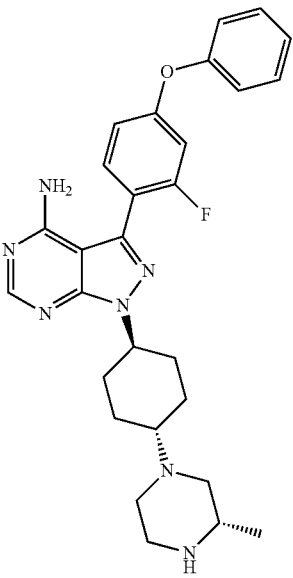 [SMILES: C[C@H]1CN([C@H]2CC[C@H](n3nc(-c4ccc(Oc5ccccc5)cc4F)c4c(N)ncnc43)CC2)CCN1] | EXAMPLE 127 3-(2-fluoro-4-phenoxyphenyl)-1-((trans)-4-((S)-3-methylpiperazin-1-yl)cyclohexyl)-1H-pyrazolo[3,4-d]pyrimidin-4-amine | LCMS: Calculated Exact Mass = 501.60; Found [M + H]$^+$ (ESI) = 502.2; $^1$H NMR (DMSO-d6) δ ppm: 9.29-9.53 (m, 1H), 8.96-9.16 (m, 1H), 8.30-8.36 (m, 1H), 7.45-7.59 (m, 3H), 7.25 (t, J = 7.4 Hz, 1H), 7.16-7.23 (m, 2H), 7.04 (dd, J = 11.3, 2.4 Hz, 1H), 6.96 (dd, J = 8.5, 2.3 Hz, 1H), 4.77 (dd, J = 10.2, 4.6 Hz, 1H), 3.60 (br. s., 3H), 3.52 (br. s., 1H), 3.36 (br. s., 1H), 3.25 (br. s., 1H), 3.12 (br. s., 1H), 2.97 (br. s., 1H), 2.05-2.22 (m, 5H), 1.76 (br. s., 2H), 1.28 (d, J = 6.4 Hz, 3H) |

| Structure | Name | LCMS/NMR |
|---|---|---|
| 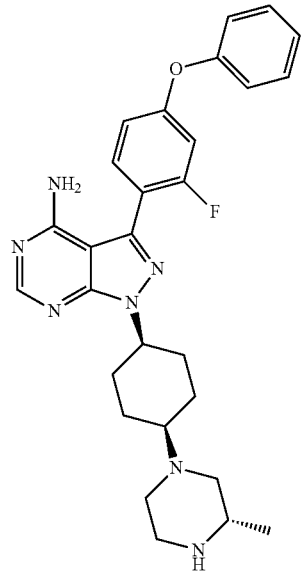 [SMILES: C[C@H]1CN([C@H]2CC[C@@H](n3nc(-c4ccc(Oc5ccccc5)cc4F)c4c(N)ncnc43)CC2)CCN1] | EXAMPLE 128<br>3-(2-fluoro-4-phenoxyphenyl)-1-((cis)-4-((S)-3-methylpiperazin-1-yl)cyclohexyl)-1H-pyrazolo[3,4-d]pyrimidin-4-amine | LCMS: Calculated Exact Mass = 501.60; Found [M + H]$^+$ (ESI) = 502.2; $^1$H NMR (DMSO-d$_6$) δ ppm: 9.39 (br. s., 1H), 9.00 (br. s., 1H), 8.35 (s, 1H), 7.59 (t, J = 8.6 Hz, 1H), 7.45-7.51 (m, 2H), 7.26 (t, J = 7.4 Hz, 1H), 7.19 (dd, J = 8.5, 0.9 Hz, 2H), 7.04 (dd, J = 11.3, 2.4 Hz, 1H), 6.96 (dd, J = 8.5, 2.3 Hz, 1H), 4.97 (br. s., 1H), 3.57 (d, J = 10.2 Hz, 3H), 3.48 (br. s., 1H), 3.22 (br. s., 2H), 3.00 (br. s., 1H), 2.85 (br. s., 1H), 2.34 (br. s., 2H), 2.09 (d, J = 9.4 Hz, 2H), 1.95 (br. s., 4H), 1.25 (d, J = 6.4 Hz, 3H). |
| 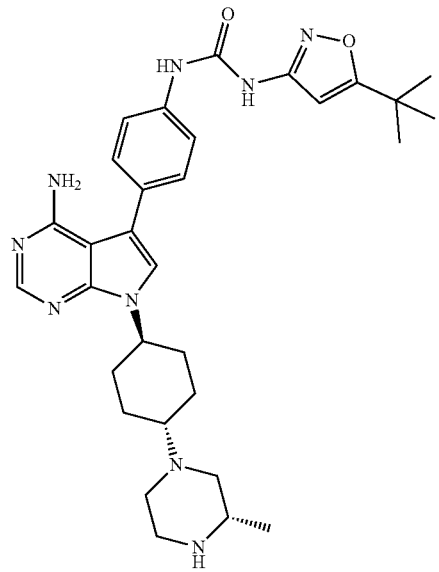 [SMILES: C[C@H]1CN([C@H]2CC[C@H](n3cc(-c4ccc(NC(=O)Nc5cc(C(C)(C)C)on5)cc4)c4c(N)ncnc43)CC2)CCN1] | EXAMPLE 129<br>1-(4-(4-amino-7-((trans)-4-((S)-3-methylpiperazin-1-yl)cyclohexyl)-7H-pyrrolo[2,3-d]pyrimidin-5-yl)phenyl)-3-(5-(tert-butyl)isoxazol-3-yl)urea | LCMS: Calculated Exact Mass = 571.34, Found [M + H]$^+$ (ESI) = 572.2; $^1$H NMR (DMSO-d$_6$) δ ppm: 9.70 (s, 1H), 9.15 (s, 1H), 8.41 (s, 1H), 7.41-7.69 (m, 5H), 6.51 (s, 1H), 4.70 (s, 1H), 3.40-3.60 (m, 4H), 2.07 (br.s., 5H), 1.60-1.70 (br.s., 3H), 1.31 (s, 11H). |

| Structure | Name | LCMS/NMR |
|---|---|---|
| 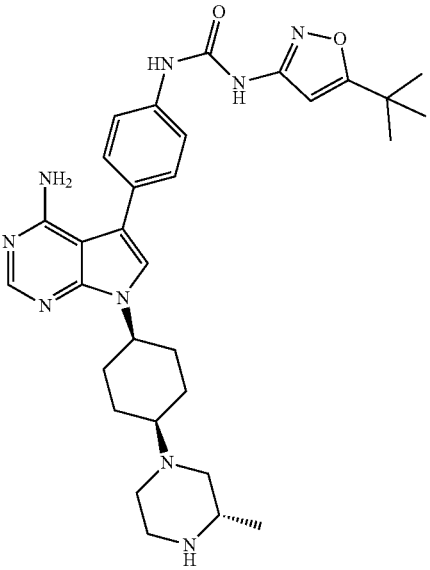 [SMILES: C[C@H]1CN([C@H]2CC[C@@H](n3cc(-c4ccc(NC(=O)Nc5cc(C(C)(C)C)on5)cc4)c4c(N)ncnc43)CC2)CCN1] | EXAMPLE 130 1-(4-(4-amino-7-((cis)-4-((S)-3-methylpiperazin-1-yl)cyclohexyl)-7H-pyrrolo[2,3-d]pyrimidin-5-yl)phenyl)-3-(5-(tert-butyl)isoxazol-3-yl)urea | LCMS: Calculated Exact Mass = 571.34, Found [M + H]$^+$ (ESI) = 572.2; $^1$H NMR (DMSO-d$_6$) δ ppm: 9.77 (m, 1H), 9.23 (m, 1H), 8.42 (s, 1H), 7.42-7.63 (m, 5H), 6.52 (s, 1H), 4.81 (s, 1H), 3.12-3.42 (m, 5H), 2.11 (br.s., 4H), 1.76 (br.s., 3H), 1.31 (s, 10H). |
| 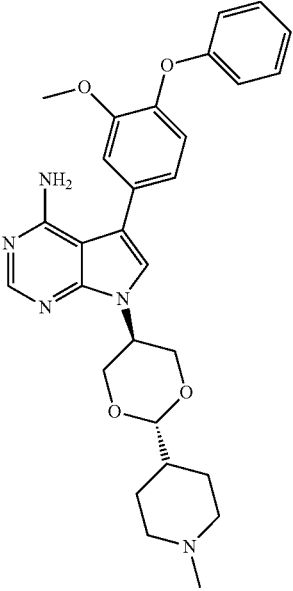 [SMILES: COc1cc(-c2cn([C@H]3CO[C@H](C4CCN(C)CC4)OC3)c3ncnc(N)c23)ccc1Oc1ccccc1] | EXAMPLE 131 5-(3-methoxy-4-phenoxyphenyl)-7-((trans)-2-(1-methylpiperidin-4-yl)-1,3-dioxan-5-yl)-7H-pyrrolo[2,3-d]pyrimidin-4-amine | LCMS: Calculated Exact Mass = 515.25; Found [M + H]$^+$ (ESI) = 515.82; $^1$H NMR (DMSO-d$_6$) δ ppm: 9.17 (s, 1H), 8.38 (s, 1H), 7.76 (s, 1H), 7.35 (t, J = 7.9 Hz, 2H), 7.21 (d, J = 1.7 Hz, 1H), 7.13 (d, J = 8.1 Hz, 1H), 7.07 (t, J = 7.8 Hz, 2H), 6.97 (d, J = 7.8 Hz, 2H), 4.83 (s, 1H), 4.72 (d, J = 4.5 Hz, 1H), 4.41-4.20 (m, 5H), 3.81 (s, 4H), 2.91 (m, 3H), 2.73 (d, J = 4.5 Hz, 3H), 1.91 (t, J = 17.6 Hz, 4H), 1.49-1.61 (m, 2H). |

-continued
| Structure | Name | LCMS/NMR |
|---|---|---|
| 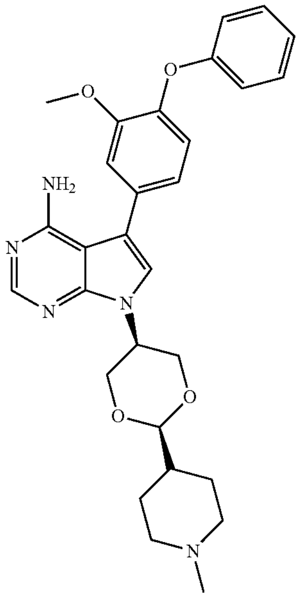 [SMILES: COc1cc(-c2cn([C@H]3CO[C@@H](C4CCN(C)CC4)OC3)c3ncnc(N)c23)ccc1Oc1ccccc1] | EXAMPLE 133 5-(3-methoxy-4-phenoxyphenyl)-7-((cis)-2-(1-methylpiperidin-4-yl)-1,3-dioxan-5-yl)-7H-pyrrolo[2,3-d]pyrimidin-4-amine | LCMS: Calculated Exact Mass = 515.25; Found [M + H]+ (ESI) = 515.82; 1H NMR (DMSO-d6) δ ppm: 9.19 (s, 1H), 8.32 (s, 1H), 7.65 (s, 1H), 7.30-7.36 (m, 2H), 7.21 (s, 1H), 7.13 (d, J = 8.1 Hz, 1H), 7.05 (t, J = 8.1 Hz, 2H), 6.94 (d, J = 7.8 Hz, 2H), 4.91 (s, 2H), 4.91 (s, 1H), 4.60 (d, J = 4.7 Hz, 2H), 4.23-4.25 (m, 4H), 3.45 (d, J = 11.1 Hz, 2H), 2.93 (m, 2H), 2.76 (d, J = 4.5 Hz, 4H), 1.90 (m, 3H), 1.56 (d, J = 10.7 Hz, 2H). |
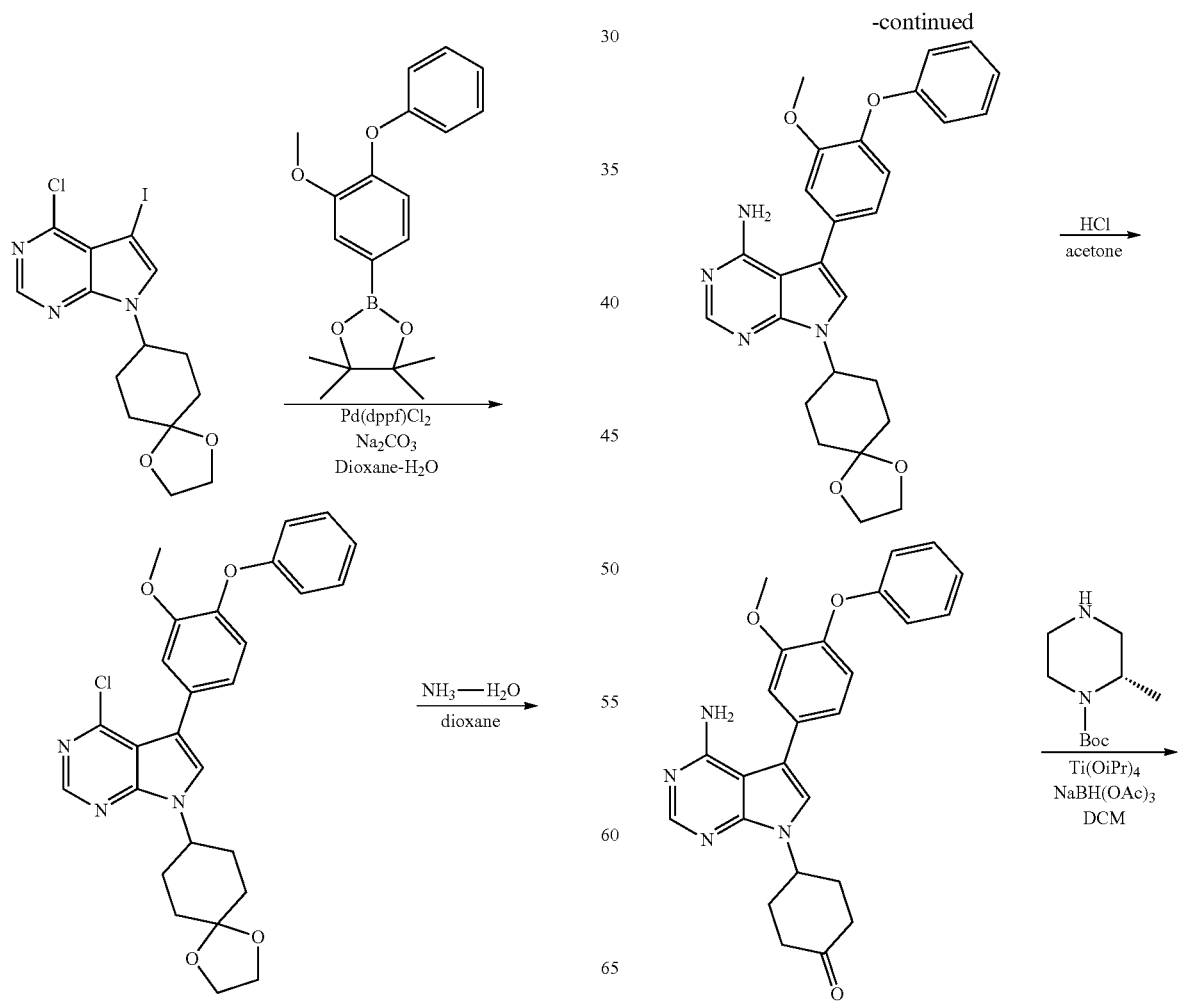

-continued

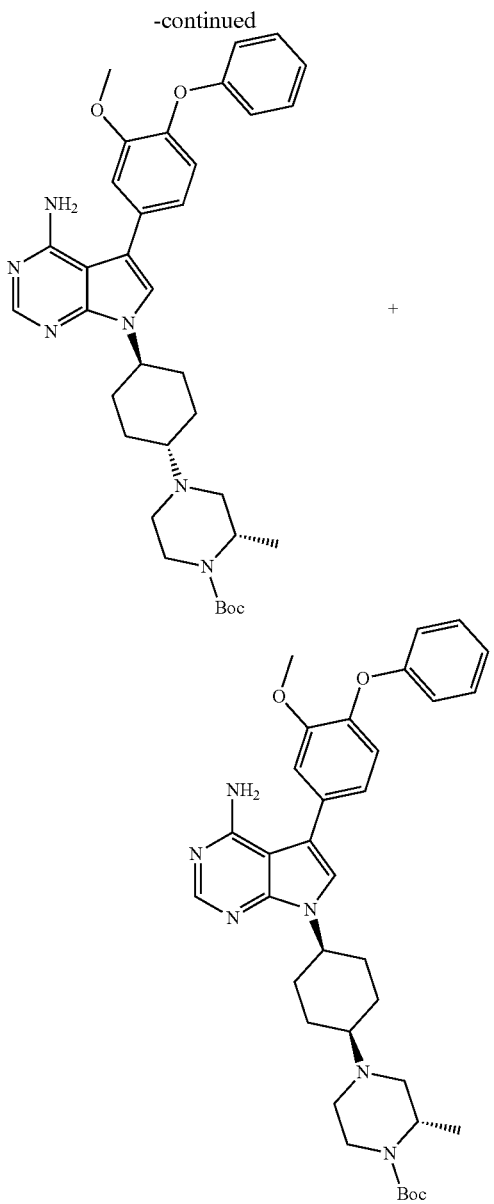

4-Chloro-5-(3-methoxy-4-phenoxyphenyl)-7-(1,4-dioxaspiro[4.5]decan-8-yl)-7H-pyrrolo[2,3-d]pyrimidine A mixture of 4-chloro-5-iodo-7-(1,4-dioxaspiro[4.5]decan-8-yl)-7H-pyrrolo[2,3-d]pyrimidine (800 mg, 1.9 mmol), 2-(3-methoxy-4-phenoxyphenyl)-4,4,5,5-tetramethyl-1,3,2-dioxaborolane (1.3 g, 3.98 mmol), Pd(dppf)Cl$_2$ (140 mg, 0.19 mmol) and Na$_2$CO$_3$ (600 mg, 5.7 mmol) in dioxane-H$_2$O (50 mL-5 mL) was heated at 80° C. under inert atmosphere for 3 hours. After cooled to room temperature, the reaction mixture was concentrated and purified by flash column chromatography (EA in PE, 0 to 33% gradient) to afford the product as a brown solid (350 mg, 37% yield).

5-(3-Methoxy-4-phenoxyphenyl)-7-(1,4-dioxaspiro[4.5]decan-8-yl)-7H-pyrrolo[2,3-d]pyrimidin-4-amine A mixture of 4-chloro-5-(3-methoxy-4-phenoxyphenyl)-7-(1,4-dioxaspiro[4.5]decan-8-yl)-7H-pyrrolo [2,3-d]pyrimidine (150 mg, 0.30 mmol) and NH$_3$—H$_2$O (5 mL) in dioxane (5 mL) was heated under microwave at 120° C. for 16 hours. After cooled to room temperature, the mixture was concentrated to afford the title compound (170 mg, 100% yield). LC-MS: Calculated Exact Mass: 472.5; Found [M+H]$^+$ (ESI)=473.1.

4-(4-Amino-5-(3-methoxy-4-phenoxyphenyl)-7H-pyrrolo[2,3-d]pyrimidin-7-yl)cyclohexanone To a suspension of 5-(3-methoxy-4-phenoxyphenyl)-7-(1,4-dioxaspiro[4.5]decan-8-yl)-7H-pyrrolo [2,3-d]pyrimidin-4-amine (340 mg, 0.6 mmol) in acetone (20 mL) and THF (6 mL) was added 6N HCl (3 mL, 18 mmol). The reaction was heated at 40° C. for 3 hours. Neutralized with 1 N NaOH solution. Extracted with DCM, dried with sodium sulfate, evaporated and purified with column chromatography (EA) to obtain the desired product as a light yellow solid (200 mg, 78% yield).

(S)-tert-butyl 4-((trans)-4-(4-amino-5-(3-methoxy-4-phenoxyphenyl)-7H-pyrrolo[2,3-d]pyrimidin-7-yl)cyclohexyl)-2-methylpiperazine-1-carboxylate A reaction mixture of 4-(4-amino-5-(3-methoxy-4-phenoxyphenyl)-7H-pyrrolo[2,3-d]pyrimidin-7-yl) cyclohexanone (40 mg, 0.09 mol), (S)-tert-butyl 2-methylpiperazine-1-carboxylate (37 mg, 0.18 mol) and Ti(OiPr)$_4$ (6 drops) in DCM (10 mL) was stirred at room temperature for 30 min. NaBH(OAc)$_3$ (76 mg, 0.36 mol) was added. The reaction was stirred at room temperature for overnight before it was quenched with MeOH. Then NaHCO$_3$aq and DCM were added. After filtration, the filtrate was extracted with DCM. The organic layers were collected and concentrated. The reside was purified by Prep-TLC (DCM:MeOH=20:1) to afford the product (30 mg, 54% yield). LCMS: Calculated Exact Mass=612.3; Found [M+H]$^+$ (ESI)=613.2.

Example 134

5-(3-Methoxy-4-phenoxyphenyl)-7-((trans)-4-((S)-3-methylpiperazin-1-yl)cyclohexyl)-7H-pyrrolo[2,3-d]pyrimidin-4-amine

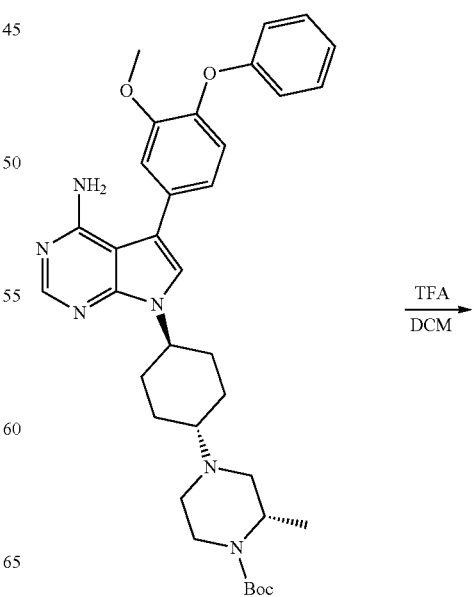

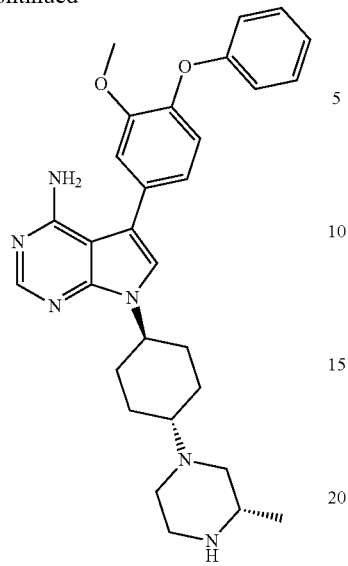

To a solution of (S)-tert-butyl-4-((trans)-4-(4-amino-5-(3-methoxy-4-phenoxyphenyl)-7H-pyrrolo [2,3-d]pyrimidin-7-yl)cyclohexyl)-2-methylpiperazine-1-carboxylate (30 mg, 0.05 mmol) in DCM (10 mL) was added TFA (1 mL) dropwise. The reaction mixture was stirred at room temperature for 3 hours before it was concentrated, the reside was purified by Prep-HPLC to afford the product as white solid (18 mg, 70% yield). LCMS: Calculated Exact Mass=512.2; Found [M+H]$^+$ (ESI)=513.2; $^1$H NMR (600 MHz, DMSO-$d_6$) δ ppm 8.14 (s, 1H) 7.46-7.52 (m, 1H) 7.33 (t, J=7.78 Hz, 2H) 7.19-7.23 (m, 1H) 7.10 (d, J=8.24 Hz, 1H) 7.01-7.08 (m, 2H) 6.92 (d, J=8.47 Hz, 2H) 6.22 (br. s., 1H) 4.58 (t, J=11.79 Hz, 1H) 3.80 (s, 3H) 3.20 (d, J=11.22 Hz, 1H) 3.12 (br. s., 1H) 2.85-3.00 (m, 3H) 239 (br. s., 1H) 2.25 (t, J=10.99 Hz, 1H) 1.98-2.05 (m, 2H) 1.87-1.98 (m, 4H) 1.44-1.58 (m, 2H) 1.13-1.21 (m, 3H)

Example 135

(2S)-tert-butyl-4-(3-(4-amino-3-(4-phenoxyphenyl)-1H-pyrazolo[3,4-d]pyrimidin-1-yl)cyclopentyl)-2-methylpiperazine-1-carboxylate

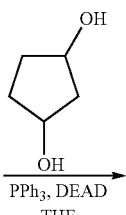

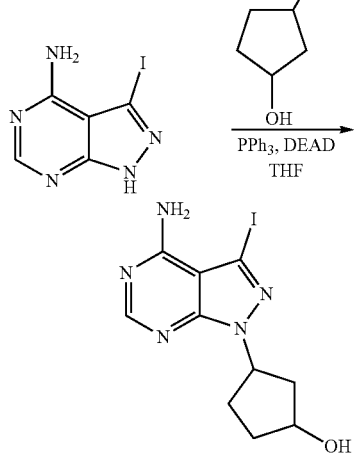

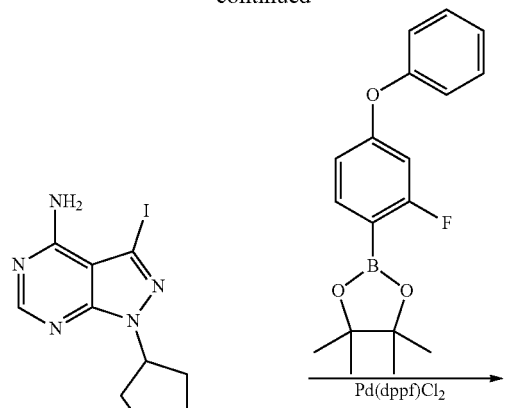

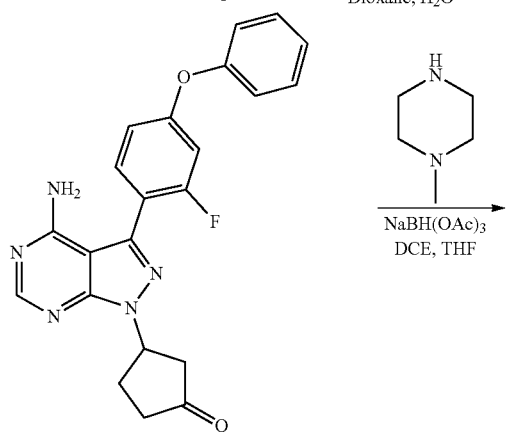

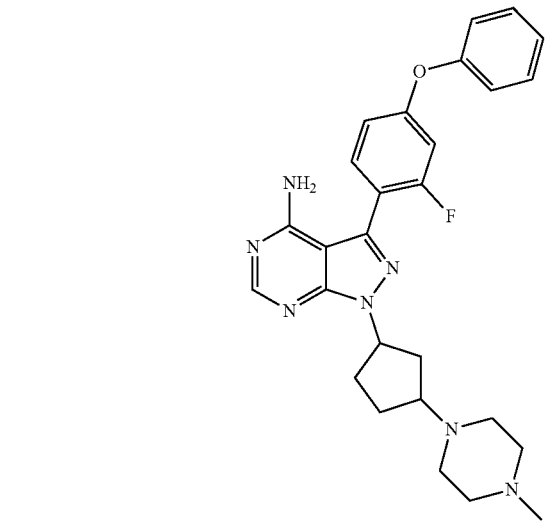 [SMILES: CN1CCN(C2CCC(n3nc(-c4ccc(Oc5ccccc5)cc4F)c4c(N)ncnc43)C2)CC1]

3-(4-Amino-3-iodo-1H-pyrazolo[3,4-d]pyrimidin-1-yl)cyclopentanol

Into a 250 mL round-bottom flask, was added with 3-iodo-1H-pyrazolo[3,4-d] pyrimidin-4-amine (2 g, 7.64 mmol), cyclopentane-1,3-diol (3.9 g, 38.2 mmol), triphenylphosphine (6.0 g, 22.9 mmol), THF (50 mL). The mixture was stirred, to the mixture was added with DEAD (3.98 g, 22.9 mmol) dropwise under ice bath. The resulting solution was stirred at room temperature overnight. The mixture was filtered, the filter was concentrated under vacuum. The residue was loaded onto a silica gel column and eluted with DCM-MeOH (100:1-10:1) to give the product as a brown solid (400 mg, 24% yield).

3-(4-Amino-3-iodo-1H-pyrazolo[3,4-d]pyrimidin-1-yl)cyclopentanone

Into a 100 mL round-bottom flask, was added 3-(4-amino-3-iodo-1H-pyrazolo[3,4-d] pyrimidin-1-yl)cyclopentanol (316 mg, 0.92 mmol), PCC (236 mg, 1.1 mmol), DCM (10 mL). The mixture was stirred overnight. The mixture was filtered, the filter was concentrated under vacuum. The residue was loaded onto a silica gel column and eluted with DCM-MeOH (100:1-20:1) to give the product as a white solid (100 mg, 31.8% yield).

3-(4-Amino-3-(2-fluoro-4-phenoxyphenyl)-1H-pyrazolo[3,4-d]pyrimidin-1-yl)cyclopentanone Into a 100 mL round-bottom flask, was added with 3-(4-amino-3-iodo-1H-pyrazolo[3,4-d]pyrimidin-1-yl)cyclopentanone (100 mg, 0.291 mmol), 3-(4-amino-3-iodo-1H-pyrazolo[3,4-d]pyrimidin-1-yl)cyclopentanone (137 mg, 0.437 mmol), sodium carbonate (92.5 mg, 0.87 mmol), Pd(dppf)Cl$_2$ (42.6 mg, 0.058 mmol, 0.2 eq) and dioxane-H$_2$O (10 mL-1 mL). The resulting mixture was stirred at 85° C. overnight. The mixture was filtered, the filter was concentrated. The residue was loaded onto a silica gel column and eluted with DCM/MeOH (50:1-20:1) to give the product (52 mg, 44% yield).

(2S)-tert-butyl-4-(3-(4-amino-3-(4-phenoxyphenyl)-1H-pyrazolo[3,4-d]pyrimidin-1-yl)cyclopentyl)-2-methylpiperazine-1-carboxylate Into a 20 mL round-bottom flask, was added with 3-(4-amino-3-(2-fluoro-4-phenoxyphenyl)-1H-pyrazolo[3,4-d]pyrimidin-1-yl)cyclopentanone (52 mg, 0.129 mmol), 1-methylpiperazine (25.8 mg, 0.258 mmol), and DCE (3 mL). The mixture was stirred at room temperature overnight. To the mixture was added with sodium triacetoxyborohydride (41 mg, 0.193 mmol), then the mixture was stirred for 3 hours at RT. Then the mixture was filtered with celite and concentrated. The residue was loaded onto a silica gel column and eluted with DCM-MeOH (50:1-10:1), then purified by prep-HPLC to give the product as a white solid (3.0 mg, 4.7% yield). LCMS: Calculated Exact Mass=487.25; Found [M+H]$^+$ (ESI)=488.20; $^1$H NMR (CDCl$_3$) δ ppm: 8.32 (s, 1H), 7.56 (t, J=8.5 Hz, 1H), 7.44 (t, J=8.0 Hz, 2H), 7.23 (s, 1H), 7.12 (d, J=7.7 Hz, 2H), 6.96 (dd, J=8.5, 2.2 Hz, 1H), 6.86 (dd, J=11.4, 2.2 Hz, 1H), 5.29-5.43 (m, 1H), 3.13-3.39 (m, 8H), 2.75 (s, 3H), 2.08-2.56 (m, 7H)

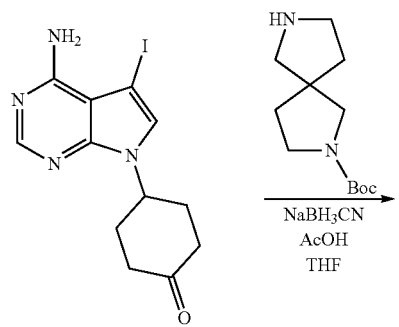

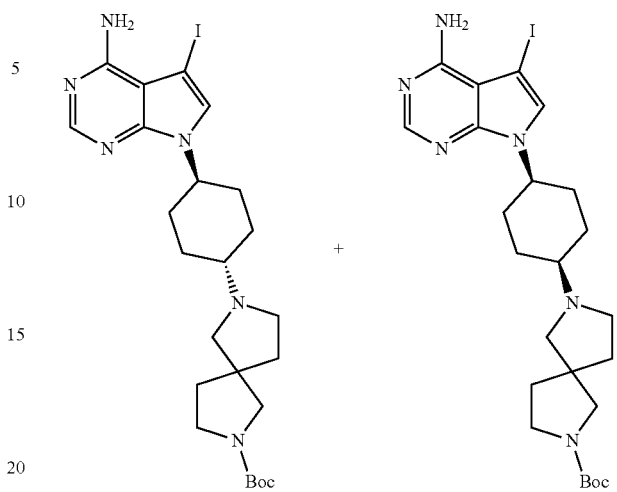

tert-butyl 7-((cis)-4-(4-amino-5-iodo-7H-pyrrolo[2,3-d]pyrimidin-7-yl)cyclohexyl)-2,7-diazaspiro[4.4]nonane-2-carboxylate and tert-butyl 7-((trans)-4-(4-amino-5-iodo-7H-pyrrolo[2,3-d]pyrimidin-7-yl)cyclohexyl)-2,7-diazaspiro[4.4] nonane-2-carboxylate A reaction mixture of 4-(4-amino-5-iodo-7H-pyrrolo[2,3-d]pyrimidin-7-yl)cyclohexanone (1.0 g, 2.81 mmol), tert-butyl 2,7-diazaspiro[4.4]nonane-2-carboxylate (1.9 g, 8.43 mmol) and acetic acid (101 mg, 1.68 mmol) in THF (50 mL) was stirred at room temperature for 2 hours. NaBH$_3$CN (529 mg, 8.43 mol) was added. It was stirred at room temperature for 3 hours when it was quenched with MeOH (10 mL). Then NaHCO$_3$aq and DCM were added, and it was filtered. The filtrate was extracted with DCM. The organic layers were collected and concentrated. The reside was purified by column chromatography on silica (DCM:MeOH=10:1) to afford tert-butyl7-((trans)-4-(4-amino-5-iodo-7H-pyrrolo[2,3-d]pyrimidin-7-yl) cyclohexyl)-2,7-diazaspiro [4.4] nonane-2-carboxylate (300 mg, 18% yield). LCMS: Calculated Exact Mass=566.2; Found [M+H]$^+$ (ESI)=567.0 and tert-butyl 7-((cis)-4-(4-amino-5-iodo-7H-pyrrolo[2,3-d]pyrimidin-7-yl) cyclohexyl)-2,7-diazaspiro[4.4]nonane-2-carboxylate (330 mg, 21% yield). LCMS: Calculated Exact Mass=566.2; Found [M+H]$^+$ (ESI)=567.0.

Example 136

7-((trans)-4-(2,7-diazaspiro[4.4]nonan-2-yl)cyclohexyl)-5-(4-phenoxyphenyl)-7H-pyrrolo[2,3-d]pyrimidin-4-amine

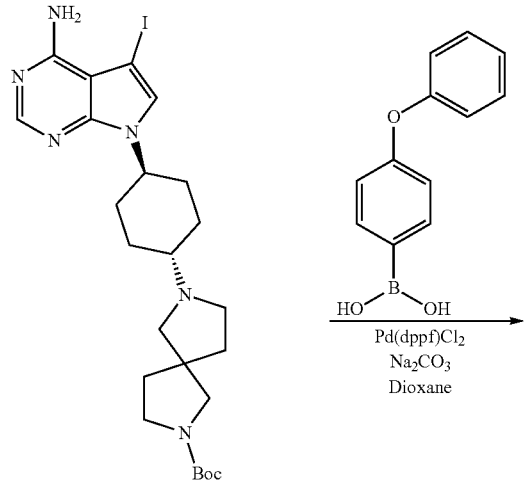

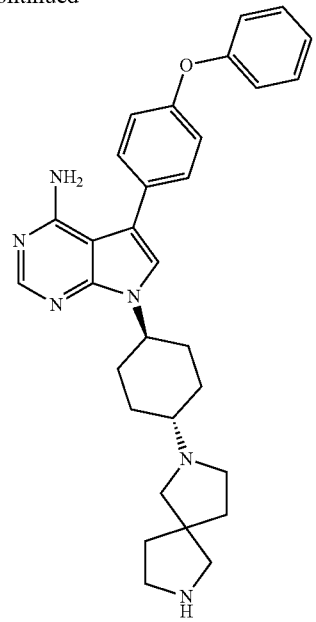

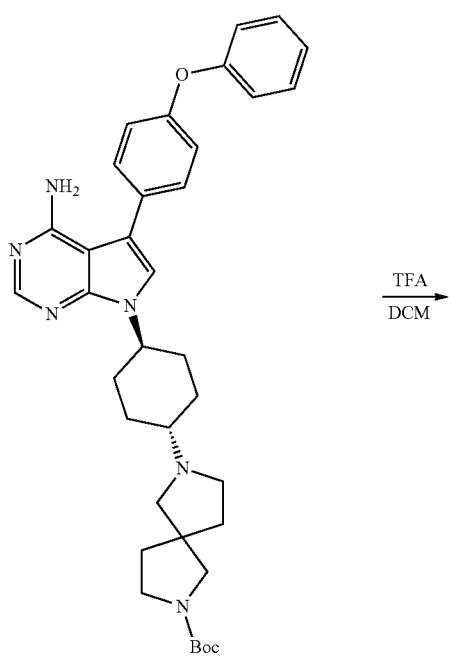

tert-butyl 7-((trans)-4-(4-amino-5-(4-phenoxyphenyl)-7H-pyrrolo[2,3-d]pyrimidin-7-yl)cyclohexyl)-2,7-diazaspiro[4.4]nonane-2-carboxylate A mixture of tert-butyl 7-((trans)-4-(4-amino-5-iodo-7H-pyrrolo[2,3-d]pyrimidin-7-yl)cyclohexyl)-2,7-diazaspiro[4.4]nonane-2-carboxylate (40 mg, 0.071 mmol), (4-phenoxyphenyl)boronic acid (18 mg, 0.085 mmol), Pd(dppf)Cl$_2$ (15 mg, 0.013 mol) and Na$_2$CO$_3$ (15 mg, 0.14 mmol) in dioxane (6 mL) and H$_2$O (0.6 mL) was heated at 85° C. under Argon atmosphere for 2 hours. After cooled to room temperature, the reaction mixture was concentrated and extracted with DCM (500 mL×4). The organic layers were concentrated and purified by Prep-TLC (DCM:MeOH=10:1) to afford the product as a light yellow solid (10 mg, 23% yield). LCMS: Calculated Exact Mass=608.4; Found [M+H]$^+$ (ESI)=609.1.

7-((trans)-4-(2,7-diazaspiro[4.4]nonan-2-yl)cyclohexyl)-5-(4-phenoxyphenyl)-7H-pyrrolo[2,3-d]pyrimidin-4-amine To a solution of tert-butyl 7-((trans)-4-(4-amino-5-(4-phenoxyphenyl)-7H-pyrrolo[2,3-d]pyrimidin-7-yl) cyclohexyl)-2,7-diazaspiro[4.4]nonane-2-carboxylate (20.0 mg, 0.03 mmol) in DCM (2 mL) was added TFA (1 mL) dropwise. The reaction mixture was stirred at room temperature for 2 hours. The reaction mixture was concentrated and was purified by Prep-HPLC to afford the product as white solid (3 mg, 17% yield). LCMS: Calculated Exact Mass=508.3; Found [M+H]$^+$ (ESI)=509.1; $^1$H NMR (400 MHz, DMSO-d$_6$) δ ppm: 9.06 (br. s., 2H) 8.25 (br. s., 1H) 7.52 (br. s., 1H) 7.39-7.49 (m, 5H) 7.23 (s, 2H) 7.14-7.21 (m, 2H) 7.07-7.14 (m, 6H) 6.98 (s, 1H) 5.33 (t, J=4.63 Hz, 1H) 4.58-4.63 (m, 1H) 3.57-3.62 (m, 6H) 2.77 (d, J=4.84 Hz, 1H) 2.63-2.69 (m, 1H) 2.31-2.37 (m, 1H) 2.26 (br. s., 1H) 2.18 (br. s., 2H) 1.89-2.15 (m, 13H) 1.77 (br. s., 3H) 1.41-1.51 (m, 2H).

Example 137

7-((cis)-4-(2,7-diazaspiro[4.4]nonan-2-yl)cyclohexyl)-5-(4-phenoxyphenyl)-7H-pyrrolo[2,3-d]pyrimidin-4-amine

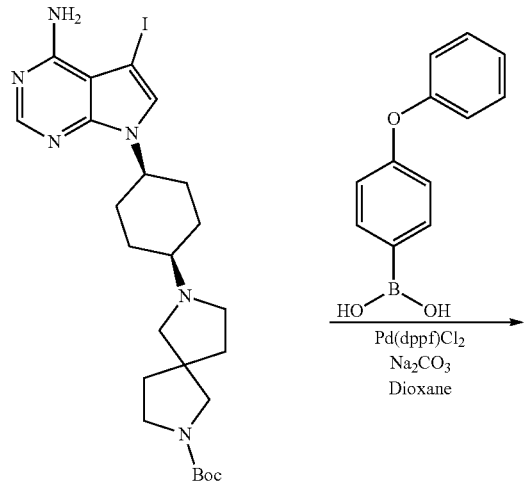

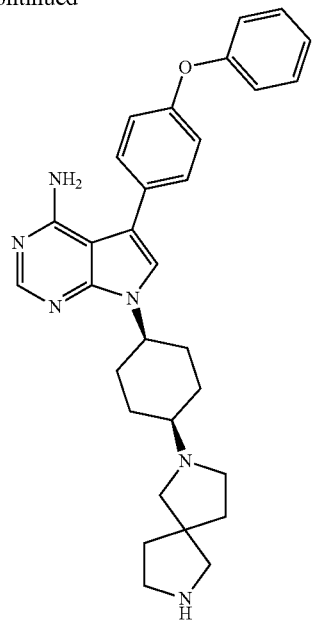

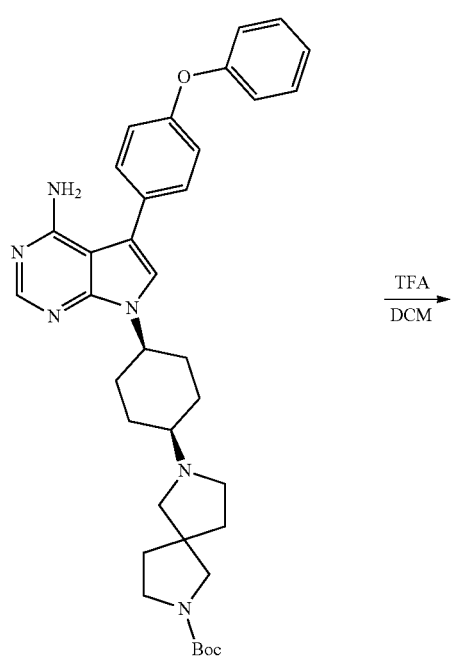

tert-butyl 7-((cis)-4-(4-amino-5-(4-phenoxyphenyl)-7H-pyrrolo[2,3-d]pyrimidin-7-yl) cyclohexyl)-2,7-diazaspiro[4.4]nonane-2-carboxylate A mixture of tert-butyl 7-((cis)-4-(4-amino-5-iodo-7H-pyrrolo[2,3-d]pyrimidin-7-yl)cyclohexyl)-2,7-diazaspiro[4.4]nonane-2-carboxylate (450 mg, 0.80 mmol), (4-phenoxyphenyl)boronic acid (204 mg, 0.95 mmol), Pd(dppf)Cl$_2$ (116 mg, 0.16 mmol) and Na$_2$CO$_3$ (169 mg, 0.59 mmol) in dioxane (30 mL) and H$_2$O (3 mL) was heated at 85° C. under Argon atmosphere for 2.5 hours. After cooled to room temperature, the reaction mixture was concentrated and purified by column chromography (DCM:MeOH=20:1) to afford the product (20 mg, 4% yield). LCMS: Calculated Exact Mass=608.4; Found [M+H]$^+$ (ESI)=609.1.

7-((cis)-4-(2,7-diazaspiro[4.4]nonan-2-yl)cyclohexyl)-5-(4-phenoxyphenyl)-7H-pyrrolo[2,3-d]pyrimidin-4-amine To a solution of tert-butyl 7-((cis)-4-(4-amino-5-(4-phenoxyphenyl)-7H-pyrrolo[2,3-d]pyrimidin-7-yl)cyclohexyl)-2,7-diazaspiro[4.4]nonane-2-carboxylate (20 mg, 0.033 mmol) in DCM (2 mL) was added TFA (1 mL) dropwise. The reaction mixture was stirred at room temperature for 0.5 hour. The reaction mixture was concentrated and was purified by Prep-HPLC to afford the product as white solid (2 mg, 12% yield). LCMS: Calculated Exact Mass=508.3; Found [M+H]$^+$ (ESI)=509.1; $^1$H NMR (400 MHz, DMSO-d$_6$) δ 10.06 (br. s., 2H), 8.92 (br. s., 2H), 8.31 (br. s., 1H), 7.52 (br. s., 1H), 7.39-7.50 (m, 3H), 7.18 (t, J=7.3 Hz, 1H), 7.04-7.16 (m, 3H), 4.84 (br. s., 1H), 3.79 (br. s., 2H), 3.29 (br. s., 5H), 2.34 (br. s., 2H), 2.25 (br. s., 2H), 2.05 (d, J=8.1 Hz, 4H), 1.94 (br. s., 3H).

235
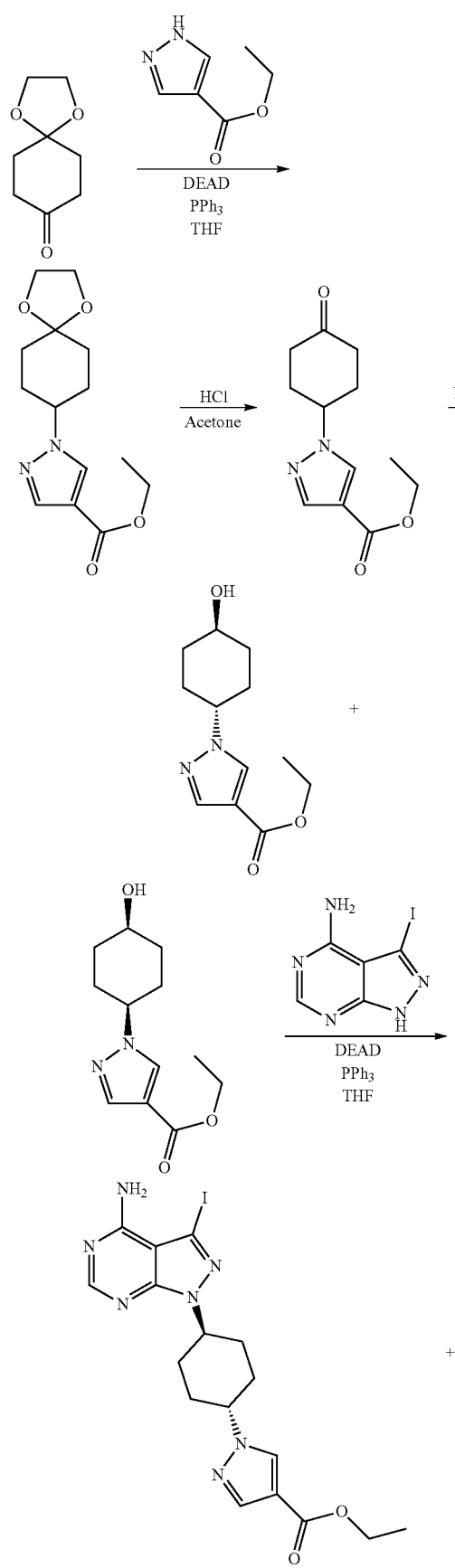
236
-continued
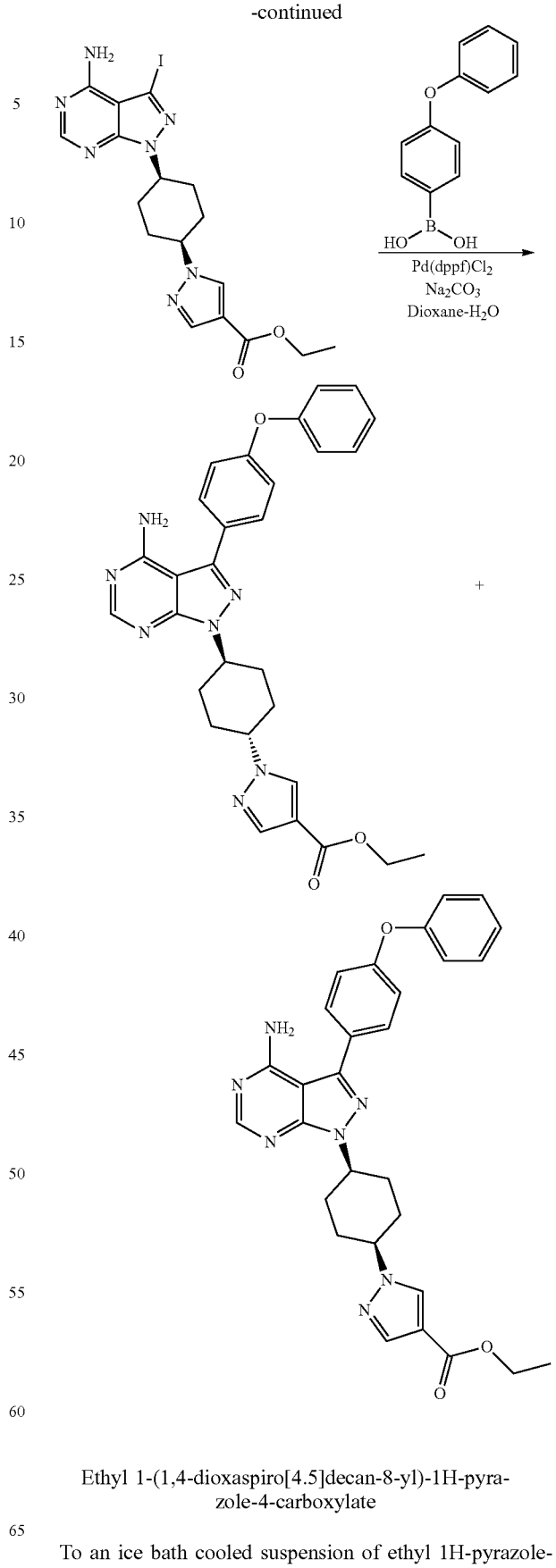
Ethyl 1-(1,4-dioxaspiro[4.5]decan-8-yl)-1H-pyrazole-4-carboxylate
To an ice bath cooled suspension of ethyl 1H-pyrazole-4-carboxylate (1 g, 7.14 mmol) in THF (10 mL) was added 1,4-dioxaspiro[4.5]decan-8-one (2.26 g, 14.3 mmol), PPh₃ (3.75 g, 14.3 mmol), followed by dropwise addition of DEAD (2.49 g, 14.3 mmol) over a period of 20 minutes. The reaction was stirred at room temperature overnight. The mixture was filtered. The filtrate was concentrated in vacuo. The residue was purified with column chromatography (EA in PE, 0 to 20% gradient) to obtain the desired product as colorless oil (1.0 g, 50% yield).

Ethyl 1-(4-oxocyclohexyl)-1H-pyrazole-4-carboxylate

To a suspension of ethyl 1-(1,4-dioxaspiro[4.5]decan-8-yl)-1H-pyrazole-4-carboxylate (1 g, 3.57 mmol) in acetone (15 mL) was added 6N HCl (15 mL, 9 mmol). The reaction was heated at 50° C. for 1 hour. Neutralized with 1 N NaOH aq. Extracted with EA (100 mL×2), washed with brine, dried with sodium sulfate, evaporated and purified with column chromatography (EA in PE, 0 to 30% gradient) to obtain the desired product as colorless oil (470 mg, 56% yield).

Ethyl 1-((trans)-4-hydroxycyclohexyl)-1H-pyrazole-4-carboxylate and ethyl 1-((cis)-4-hydroxycyclohexyl)-1H-pyrazole-4-carboxylate To a stirred mixture of ethyl 1-(4-oxocyclohexyl)-1H-pyrazole-4-carboxylate (470 mg, 1.99 mmol) in MeOH (15 mL) was added NaBH₄ (91 mg, 2.39 mmol). After stirring for 1 hour, the mixture was concentrated in vacuo. The residue was diluted with water (20 mL), extracted with DCM (20 mL). The organic layer was concentrated in vacuo to afford a mixture of ethyl 1-((trans)-4-hydroxycyclohexyl)-1H-pyrazole-4-carboxylate and ethyl 1-((cis)-4-hydroxycyclohexyl)-1H-pyrazole-4-carboxylate as colorless oil (400 mg, 84% yield).

Ethyl 1-((trans)-4-(4-amino-3-iodo-1H-pyrazolo[3,4-d]pyrimidin-1-yl)cyclohexyl)-1H-pyrazole-4-carboxylate and Ethyl 1-((cis)-4-(4-amino-3-iodo-1H-pyrazolo[3,4-d]pyrimidin-1-yl)cyclohexyl)-1H-pyrazole-4-carboxylate To an ice bath cooled suspension of 3-iodo-1H-pyrazolo[3,4-d]pyrimidin-4-amine (240 mg, 0.924 mmol) in THF (5 mL) was added the mixture of ethyl 1-((trans)-4-hydroxycyclohexyl)-1H-pyrazole-4-carboxylate and ethyl 1-((cis)-4-hydroxycyclohexyl)-1H-pyrazole-4-carboxylate (220 mg, 0.924 mmol), PPh₃ (363 mg, 1.38 mmol), followed by dropwise addition of DEAD (241 mg, 1.38 mmol) over a period of 5 minutes. The reaction was stirred at room temperature overnight. The mixture was filtrated. The filtrate was concentrated in vacuo. The residue was purified with column chromatography (MeOH in DCM, 0 to 10% gradient) to obtain a crude (540 mg). The crude was purified with Prep-HPLC to afford a mixture of ethyl 1-((trans)-4-(4-amino-3-iodo-1H-pyrazolo[3,4-d]pyrimidin-1-yl)cyclohexyl)-1H-pyrazole-4-carboxylate and ethyl 1-((cis)-4-(4-amino-3-iodo-1H-pyrazolo[3,4-d]pyrimidin-1-yl) cyclohexyl)-1H-pyrazole-4-carboxylate as a white solid (160 mg, 36% yield)

Ethyl 1-((trans)-4-(4-amino-3-(4-phenoxyphenyl)-1H-pyrazolo[3,4-d]pyrimidin-1-yl) cyclohexyl)-1H-pyrazole-4-carboxylate and Ethyl 1-((cis)-4-(4-amino-3-(4-phenoxyphenyl)-1H-pyrazolo[3,4-d]pyrimidin-1-yl) cyclohexyl)-1H-pyrazole-4-carboxylate A mixture of ethyl 1-((trans)-4-(4-amino-3-iodo-1H-pyrazolo[3,4-d]pyrimidin-1-yl)cyclohexyl)-1H-pyrazole-4-carboxylate and ethyl 1-((cis)-4-(4-amino-3-iodo-1H-pyrazolo[3,4-d] pyrimidin-1-yl)cyclohexyl)-1H-pyrazole-4-carboxylate as a white solid (50 mg, 0.104 mmol), (4-phenoxyphenyl)boronic acid (37 mg, 0.125 mmol), Pd(dppf)Cl₂ (15 mg, 0.0208 mmol) and Na₂CO₃ (33 mg, 0.312 mmol) in dioxane-H₂O (3 mL-0.3 mL) was heated at 85° C. under inert atmosphere overnight. After cooled to room temperature, the reaction mixture was filtrated and the filtrate was concentrated in vacuo and purified by Prep-HPLC to get ethyl 1-((trans)-4-(4-amino-3-(4-phenoxyphenyl)-1H-pyrazolo[3,4-d] pyrimidin-1-yl) cyclohexyl)-1H-pyrazole-4-carboxylate as a white solid (20 mg, 37% yield) LC-MS: Calculated Exact Mass: 523.2 Found: [M+H]⁺ (ESI)=524.1 and ethyl 1-((cis)-4-(4-amino-3-(4-phenoxyphenyl)-1H-pyrazolo[3,4-d]pyrimidin-1-yl)cyclohexyl)-1H-pyrazole-4-carboxylate as a white solid (6 mg, 11% yield) LC-MS: Calculated Exact Mass: 523.2 Found: [M+H]⁺ (ESI)=524.1.

Example 138

(1-((trans)-4-(4-Amino-3-(4-phenoxyphenyl)-1H-pyrazolo[3,4-d]pyrimidin-1-yl)cyclohexyl)-1H-pyrazol-4-yl)methanol

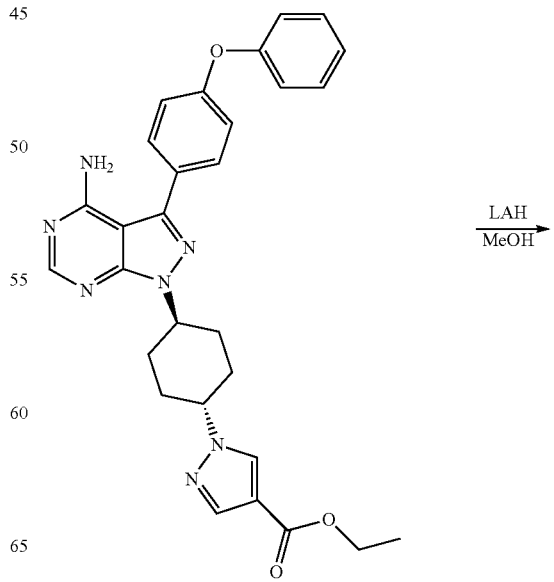

239

-continued

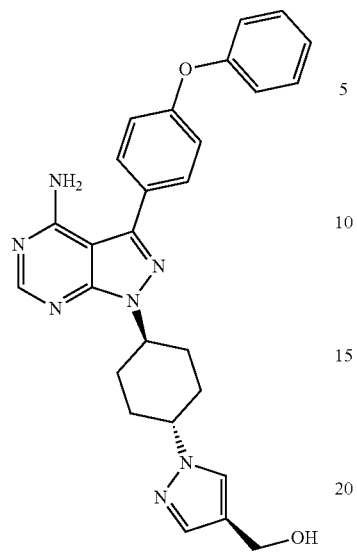

To an ice bath cooled stirred mixture of ethyl 1-((trans)-4-(4-amino-3-(4-phenoxyphenyl)-1H-pyrazolo[3,4-d]pyrimidin-1-yl)cyclohexyl)-1H-pyrazole-4-carboxylate (15 mg, 0.0287 mmol) in THF (2 mL) was added LAH (2 mg, 0.0574 mmol). The mixture was purged with $N_2$. After stirring for 2 hours, LAH (10 mg, 0.263 mmol) was added to the mixture. Monitored by TLC, after the starting material was completely disappeared, the mixture was quenched by $H_2O$ (2 mL), extracted by DCM (5 mL). The organic layer was concentrated in vacuo and purified with Prep-HPLC to afford the title compound as a white solid (3 mg, 21.7% yield) LC-MS: Calculated Exact Mass: 481.2; Found [M+H]$^+$ (ESI)=482.1; $^1$H NMR (400 MHz, CDCl$_3$) δ 11.55 (s, 1H), 8.25 (s, 1H), 7.58 (d, J=10.9 Hz, 3H), 7.42 (t, J=7.8 Hz, 2H), 7.22 (t, J=7.4 Hz, 1H), 7.16 (d, J=7.9 Hz, 2H), 7.10 (d, J=7.9 Hz, 2H), 6.26 (s, 1H), 5.05 (s, 1H), 4.63 (s, 2H), 4.47 (s, 1H), 2.61 (s, 2H), 2.44 (s, 2H), 2.14 (dd, J=20.5, 9.7 Hz, 4H), 1.26 (s, 1H).

Example 139

N-(4-(4-Amino-7-(4-(5-amino-1,3-dioxan-2-yl)cyclohexyl)-7H-pyrrolo[2,3-d]pyrimidin-5-yl)phenyl)-3-phenylpropanamide

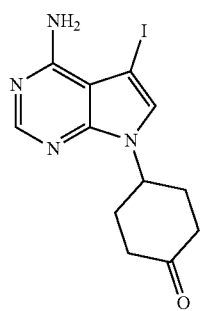

240

-continued

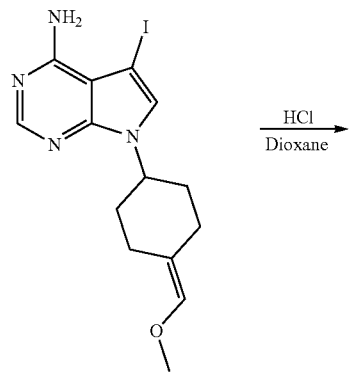

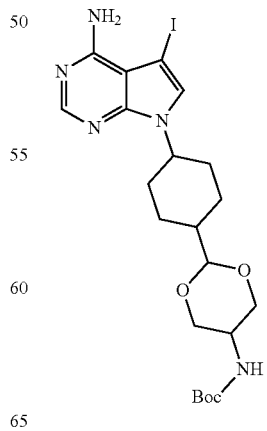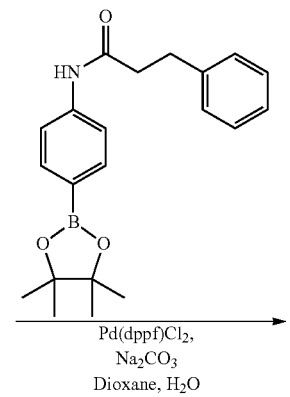

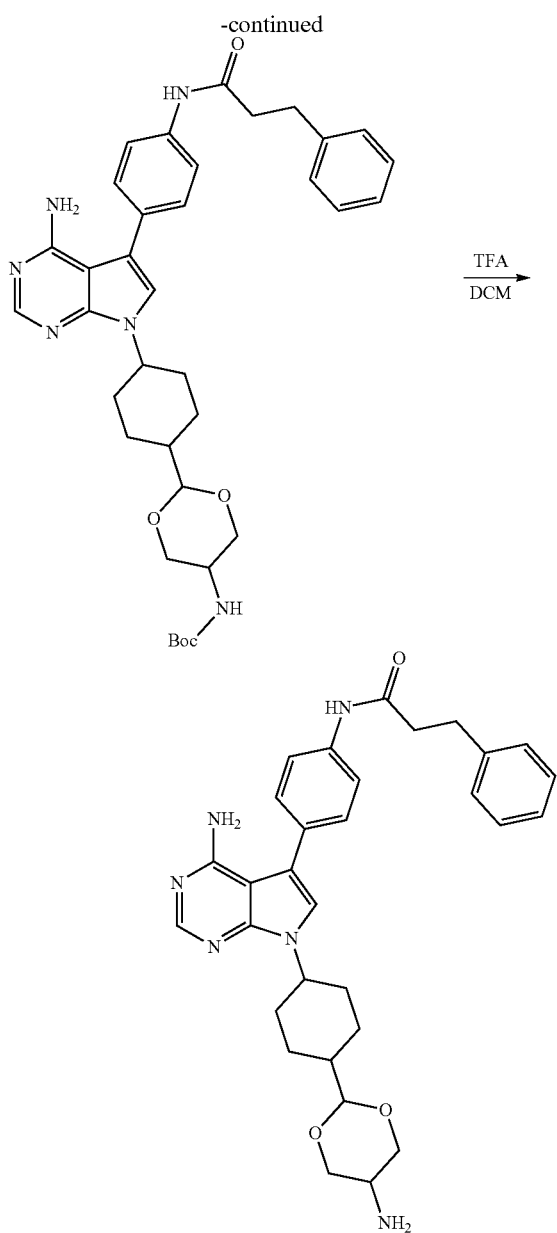

5-Iodo-7-(4-(methoxymethylene)cyclohexyl)-7H-pyrrolo[2,3-d]pyrimidin-4-amine

To a solution of (methoxymethyl)triphenylphosphonium chloride (3451 mg, 11.231 mmol) in THF (15 mL) was added Potassium tert-butanolate (1.26 g, 11.2 mmol) in THF (10 mL) drop-wise at 0° C. for 30 min. 4-(4-amino-5-iodo-7H-pyrrolo[2,3-d]pyrimidin-7-yl) cyclohexan-1-one (2.0 g, 5.61 mmol) added to the mixture and then stirred at room temperature overnight. The reaction was monitored via TLC and LCMS until complete consumption of starting material. It was then filtered. The filtrate was concentrated to obtain a crude product. The crude product was purified by flash column chromatography (0-3% MeOH in DCM) to obtain product as a yellow solid (1.9 g, 88% yield). LCMS: Calculated Exact Mass=384.04; Found [M+H]$^+$ (ESI)= 385.61; $^1$H NMR (DMSO-d$_6$) δ ppm: 8.08 (s, 1H), 7.54 (s, 1H), 6.59 (br. s., 1H), 5.95 (s, 1H), 4.56-4.67 (m, 1H), 3.51 (s, 3H), 2.78 (d, J=11.3 Hz, 1H), 2.14-2.24 (m, 1H), 2.00-2.11 (m, 1H), 1.89 (t, J=12.1 Hz, 2H), 1.68-1.79 (m, 3H).

4-(4-Amino-5-iodo-7H-pyrrolo[2,3-d]pyrimidin-7-yl)cyclohexane-1-carbaldehyde

To a solution of 5-iodo-7-(4-(methoxymethylene)cyclohexyl)-7H-pyrrolo[2,3-d] pyrimidin-4-amine (1900 mg, 4.945 mmol) in THF (15 mL) was added 6 N HCl (20 mL, 120 mmol) at room temperature. The mixture was stirred at room temperature for 3 hours. It was then filtrated, the filtrate was adjusted to pH=10, then extracted with EtOAC (30 mL×3). The organic layer was dried with brine and anhydrous Na$_2$SO$_4$. It was then concentrated to give crude product as a yellow solid (1.15 g 62.8% yield). LCMS: Calculated Exact Mass=307.03; Found [M+H]$^+$ (ESI) =307.6; $^1$H NMR (DMSO-d$_6$) δ ppm: 9.62 (s, 1H), 8.44 (s, 1H), 7.94 (s, 1H), 4.57 (br. s., 1H), 2.37 (br. s., 1H), 2.08 (d, J=12.5 Hz, 2H), 1.89-2.01 (m, 4H), 1.41 (dd, J=12.7, 4.1 Hz, 2H).

tert-butyl (2-(4-(4-amino-5-iodo-7H-pyrrolo[2,3-d]pyrimidin-7-yl)cyclohexyl)-1,3-dioxan-5-yl) carbamate To a solution of 4-(4-amino-5-iodo-7H-pyrrolo[2,3-d]pyrimidin-7-yl)cyclohexane-1-carbaldehyde (1.1 g, 2.97 mmol), tert-butyl (1,3-dihydroxypropan-2-yl)carbamate (5.68 g, 29.7 mmol), p-Toluenesulfonic acid monohydrate (5.65 g, 29.7 mmol), Na$_2$CO$_3$ (8.43 mg, 59.4 mmol), in chloroform (50 mL) was refluxed overnight. It was then cooled to room temperature and filtrated, the solid was washed with DCM (10 mL×3), the filtrate was concentrated, the crude product was purified by flash column chromatography (0.5-2.5% MeOH in DCM) to obtain product as a white solid (350 mg, 21.7% yield). LCMS: Calculated Exact Mass=543.13; Found [M+H]$^+$ (ESI)=543.7.

tert-butyl (2-(4-(4-amino-5-(4-(3-phenylpropanamido)phenyl)-7H-pyrrolo[2,3-d] pyrimidin-7-yl) cyclohexyl)-1,3-dioxan-5-yl)carbamate To a 50 mL round-bottom flask was added tert-butyl (2-((trans)-4-(4-amino-5-iodo-7H-pyrrolo[2,3-d]pyrimidin-7-yl)cyclohexyl)-1,3-dioxan-5-yl)carbamate (150 mg, 0.27 mmol), 3-phenyl-N-(4-(4,4,5,5-tetramethyl-1,3,2-dioxaborolan-2-yl)phenyl)propanamide (193 mg, 0.55 mmol), Pd(dppf)Cl$_2$ (101 mg, 0.13 mmol), Na$_2$CO$_3$ (143 mg, 0.82 mmol), 1,4 Dioxane with 10% water (5 mL). The mixture was stirred at 80° C. overnight. The reaction was monitored via TLC and LCMS until complete consumption of starting material. The mixture was cooled to the room temperature, filtrated and concentrated the filtrate. The crude was purified by flash column chromatography (MeOH in DCM, 5-25%) to obtain crude product as a yellow solid (150 mg, 80% yield). LCMS: Calculated Exact Mass=640.34; Found [M+H]$^+$ (ESI)=640.81.

N-(4-(4-Amino-7-(4-(5-amino-1,3-dioxan-2-yl)cyclohexyl)-7H-pyrrolo[2,3-d]pyrimidin-5-yl)phenyl)-3-phenylpropanamide To a solution of tert-butyl (2-((trans)-4-(4-amino-5-(4-(3-phenylpropanamido)phenyl)-7H-pyrrolo[2,3-d]pyrimidin-7-yl)cyclohexyl)-1,3-dioxan-5-yl)carbamate (150 mg, 0.22 mmol) in DCM (5 mL) was added TFA (2 mL), the mixture was stirred at room temperature for 40 min. The reaction was monitored via TLC and LCMS until complete consumption of starting material. It was then concentrated, the crude was purified by flash column chromatography (MeOH in DCM, 1-5%) and Prep-HPLC (Acetonitrile/water, 0.1% TFA), freeze-dried, obtained the title compound as a white solid (55 mg, 43% yield). LCMS: Calculated Exact Mass=540.28; Found [M+H]+ (ESI)=540.79; ¹H NMR (DMSO-d₆) δ ppm: 10.10 (s, 1H), 8.43 (s, 1H), 8.19 (br. s., 3H), 7.70-7.77 (m, 3H), 7.37-7.45 (m, 2H), 7.23-7.31 (m, 4H), 7.20 (d, J=6.7 Hz, 1H), 4.53-4.67 (m, 1H), 4.46 (d, J=5.8 Hz, 1H), 3.94-4.05 (m, 3H), 3.29 (br. s., 1H), 2.93 (t, J=7.5 Hz, 2H), 2.67 (t, J=7.6 Hz, 2H), 1.97 (d, J=7.6 Hz, 4H), 1.80-1.93 (m, 2H), 1.67 (br. s., 1H), 1.30 (d, J=11.0 Hz, 2H).

Benzyl 9-(4-amino-5-(4-phenoxyphenyl)-7H-pyrrolo[2,3-d]pyrimidin-7-yl)-3-azaspiro[5.5]undecane-3-carboxylate

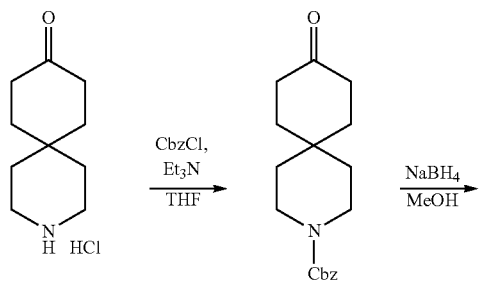

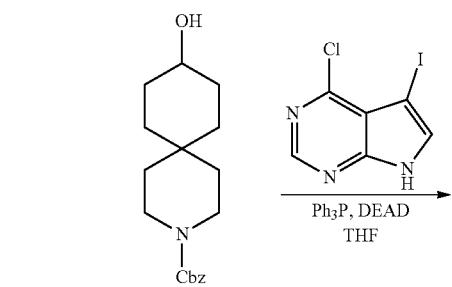

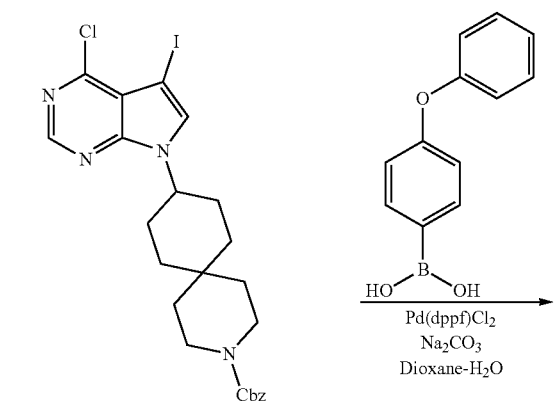

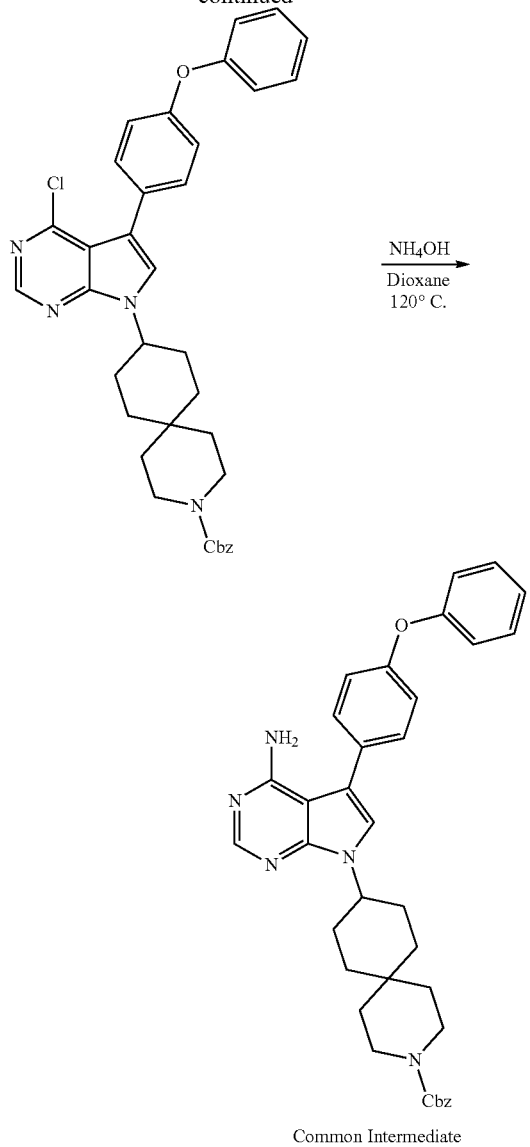

Common Intermediate

Benzyl 9-oxo-3-azaspiro[5.5]undecane-3-carboxylate

A solution of 3-azaspiro[5.5]undecan-9-one hydrochloride (260 mg, 1.28 mmol) and triethylamine (0.4 mL, 3.19 mmol) in THF (40 mL) was stirred at room temperature for 10 minutes. Then, the mixture was cooled to 0° C., benzyl carbonochloridate (0.4 mL, 2.55 mmol) was added dropwise. After addition, the mixture was stirred at room temperature for 12 hours. The reaction was diluted with ethyl acetate (120 mL), washed with water (50 mL), dried over sodium sulfate and concentrated. The crude was purified by flash chromatography (PE:EA=3:1) to obtain the product as yellow solid (350 mg, 91.1% yield). LCMS: Calculated Exact Mass=301.2; Found [M+H]+ (ESI)=302.1.

Benzyl 9-hydroxy-3-azaspiro[5.5]undecane-3-carboxylate

A stirred solution of benzyl 9-oxo-3-azaspiro[5.5]undecane-3-carboxylate (350 mg, 1.16 mmol) in methanol (15 mL), maintained at 0° C., was treated with sodium borohydride (66.3 mg, 1.74 mmol). After 10 minutes, the reaction mixture was warmed to room temperature and stirred at this temperature for additional 1.5 hour. The solvent was then removed under reduced pressure and the resulting residue was partitioned between water (50 mL) and dichloromethane (50 mL). The separated aqueous phase was extracted with dichloromethane (50 mL) and the combined organic fractions were then dried over sodium sulfate, filtered and concentrated under reduced pressure to afford the product as a colorless oil (400 mg, quant.). LCMS: Calculated Exact Mass=303.2; Found [M+H]+ (ESI)=304.1; $^1$H NMR (400 MHz, CHLOROFORM-d) δ ppm: 7.30-7.45 (m, 5H), 5.14 (s, 2H), 3.63-3.76 (m, 1H), 3.43-3.50 (m, 4H), 1.74-1.83 (m, 2H), 1.65-1.73 (m, 2H), 1.40-1.60 (m, 4H), 1.35-1.40 (m, 2H), 1.17-1.31 (m, 2H).

Benzyl 9-(4-chloro-5-iodo-7H-pyrrolo[2,3-d]pyrimidin-7-yl)-3-azaspiro[5.5] undecane-3-carboxylate Diethyl azodicarboxylate (0.5 mL, 3.45 mmol) was added dropwise to a tetrahydrofuran (15 mL) solution of triphenylphosphine (904.9 mg, 3.45 mmol) under ice cooling. Then, the mixture was brought to room temperature, and a tetrahydrofuran (10 mL) solution of 4-chloro-5-iodo-7H-pyrrolo[2,3-d] pyrimidine (338.5 mg, 1.21 mmol) and benzyl 9-hydroxy-3-azaspiro[5.5]undecane-3-carboxylate (350 mg, 1.21 mmol) was added dropwise. After completion of the addition, the mixture was stirred for 2 hours at room temperature. And the solvent was evaporated in an evaporator. The residue was purified by flash chromatography (PE:EA=3:1) to obtain the product as yellow solid (260 mg, 39.9% yield). LCMS: Calculated Exact Mass=564.1; Found [M+H]+ (ESI)=564.9.

Benzyl 9-(4-chloro-5-(4-phenoxyphenyl)-7H-pyrrolo[2,3-d]pyrimidin-7-yl)-3-azaspiro[5.5]undecane-3-carboxylate The solution of benzyl 9-(4-chloro-5-iodo-7H-pyrrolo[2,3-d]pyrimidin-7-yl)-3-azaspiro[5.5]undecane-3-carboxylate (240 mg, 0.43 mmol), (4-phenoxyphenyl) boronic acid (182.8 mg, 0.85 mmol), Pd(dppf)Cl$_2$ (30.3 mg, 0.04 mmol) and Sodium carbonate (135.8 mg, 1.28 mmol) in dioxane-water (27.5 mL, 10:1) was stirred at 80° C. under nitrogen atmosphere for 4 hours. After cooling to room temperature, the reaction was diluted with ethyl acetate (120 mL), washed with water (200 mL) and brine (50 mL), dried over Sodium sulfate and concentrated. The crude was purified by flash column chromatography (PE:EA=3:1) to obtain the product as yellow solid (220 mg, 85.3% yield). LCMS: Calculated Exact Mass=606.2; Found [M+H]+ (ESI)=607.2.

Benzyl 9-(4-amino-5-(4-phenoxyphenyl)-7H-pyrrolo[2,3-d]pyrimidin-7-yl)-3-azaspiro [5.5]undecane-3-carboxylate A mixture of benzyl 9-(4-chloro-5-(4-phenoxyphenyl)-7H-pyrrolo[2,3-d] pyrimidin-7-yl)-3-azaspiro[5.5] undecane-3-carboxylate (100 mg, 0.16 mmol), 1,4-dioxane (1.5 mL) and a concentrated aqueous ammonia solution (1.5 mL) was reacted in microwave reactor at 120° C. for 9 hours. The mixture was cooled to room temperature, and the solvent was distilled off under reduced pressure and the residue was purified by Prep-TLC (DCM:MeOH=15:1) to obtain the title compound as yellow solid (70 mg, 72.8% yield).

LCMS: Calculated Exact Mass=587.3; Found [M+H]+ (ESI)=588.2.

Example 140

4-(9-(4-amino-5-(4-phenoxyphenyl)-7H-pyrrolo[2,3-d]pyrimidin-7-yl)-3-azaspiro[5.5]undecan-3-yl)butan-1-ol

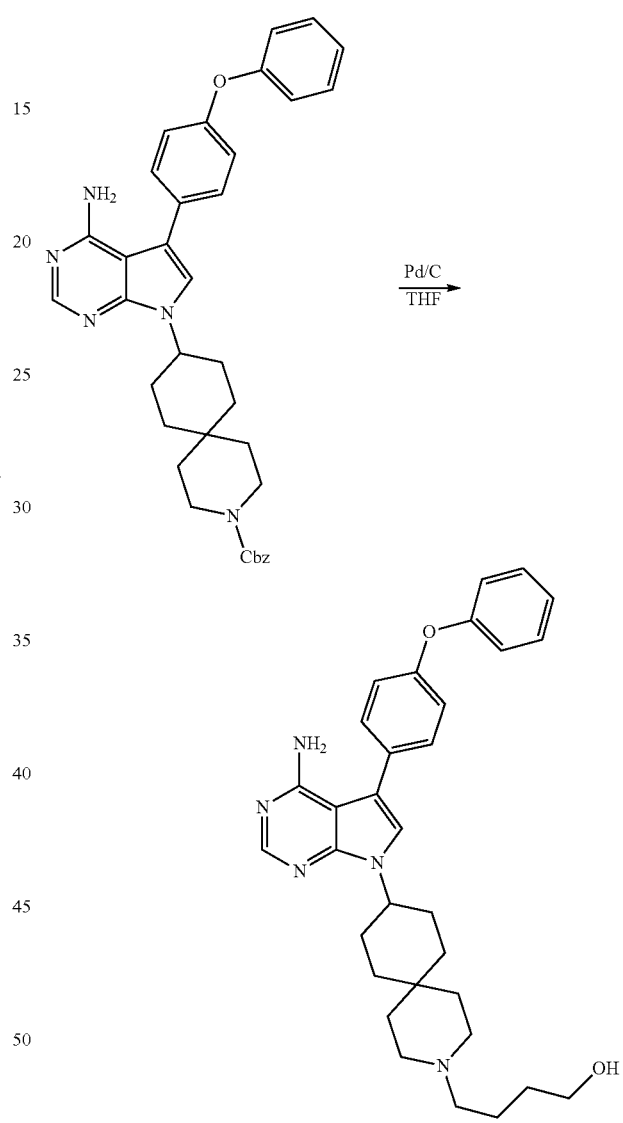

4-(9-(4-Amino-5-(4-phenoxyphenyl)-7H-pyrrolo[2,3-d]pyrimidin-7-yl)-3-azaspiro[5.5]undecan-3-yl)butan-1-ol A mixture of benzyl 9-(4-amino-5-(4-phenoxyphenyl)-7H-pyrrolo[2,3-d] pyrimidin-7-yl)-3-azaspiro[5.5]undecane-3-carboxylate (70 mg, 0.12 mmol) and Pd/C (70 mg, 1.0 eq. w/w) in tetrahydrofuran (10 mL) was stirred at room temperature under Hydrogen atmosphere for 12 hours. Then, the solution was filtered and concentrated to purify by Prep-TLC (DCM:MeOH=15:1) to obtain the product as a yellow solid (23 mg, 36.7% yield). LCMS: Calculated Exact Mass=525.3; Found [M+H]+ (ESI)=526.2; ¹H NMR (400 MHz, CHLOROFORM-d) δ ppm: 8.30 (s, 1H), 7.33-7.53 (m, 4H), 6.94-7.24 (m, 6H), 5.25 (br. s., 2H), 4.66 (t, J=11.6 Hz, 1H), 3.64 (t, J=5.2 Hz, 2H), 2.78 (br. s., 4H), 2.69 (t, J=6.0 Hz, 2H), 1.77-2.05 (m, 10H), 1.61-1.76 (m, 4H), 1.44 (t, J=12.1 Hz, 2H).

Example 141

5-(4-phenoxyphenyl)-7-(3-azaspiro[5.5]undecan-9-yl)-7H-pyrrolo[2,3-d]pyrimidin-4-amine

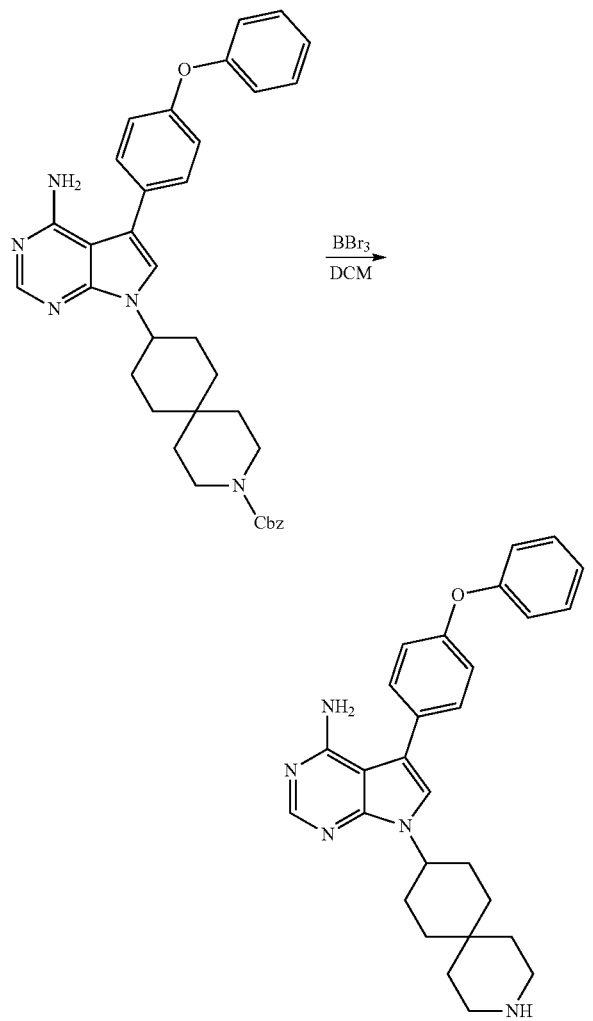

5-(4-phenoxyphenyl)-7-(3-azaspiro[5.5]undecan-9-yl)-7H-pyrrolo[2,3-d]pyrimidin-4-amine The solution of benzyl 9-(4-amino-5-(4-phenoxyphenyl)-7H-pyrrolo[2,3-d] pyrimidin-7-yl)-3-azaspiro[5.5]undecane-3-carboxylate (50 mg, 0.09 mmol) in dichloromethane (10 mL) was cooled to 0° C. Then, tribromoborane (1.0 mL, 1.0 M in dichloromethane) was added dropwise. After addition, the mixture was continued to stir at 0° C. for 0.5 hour. The reaction was quenched with methanol (2 mL) and concentrated to purify by Prep-TLC (DCM:MeOH: 15:1) to give the product as a yellow solid (36 mg, 93.2% yield).

LCMS: Calculated Exact Mass=453.3; Found [M+H]+ (ESI)=454.2; ¹H NMR (400 MHz, DMSO-d₆) δ ppm: 8.47 (br. s., 2H), 8.14 (s, 1H), 7.56 (s, 1H), 7.37-7.51 (m, 4H), 7.05-7.22 (m, 5H), 6.14 (br. s., 2H), 4.51-4.66 (m, 1H), 3.08 (br. s., 4H), 1.96-2.14 (m, 2H), 1.82-1.93 (m, 4H), 1.75 (d, J=9.9 Hz, 2H), 1.54 (br. s., 2H), 1.32-1.46 (m, 2H).

Example 142

7-(3-methyl-3-azaspiro[5.5]undecan-9-yl)-5-(4-phenoxyphenyl)-7H-pyrrolo[2,3-d]pyrimidin-4-amine

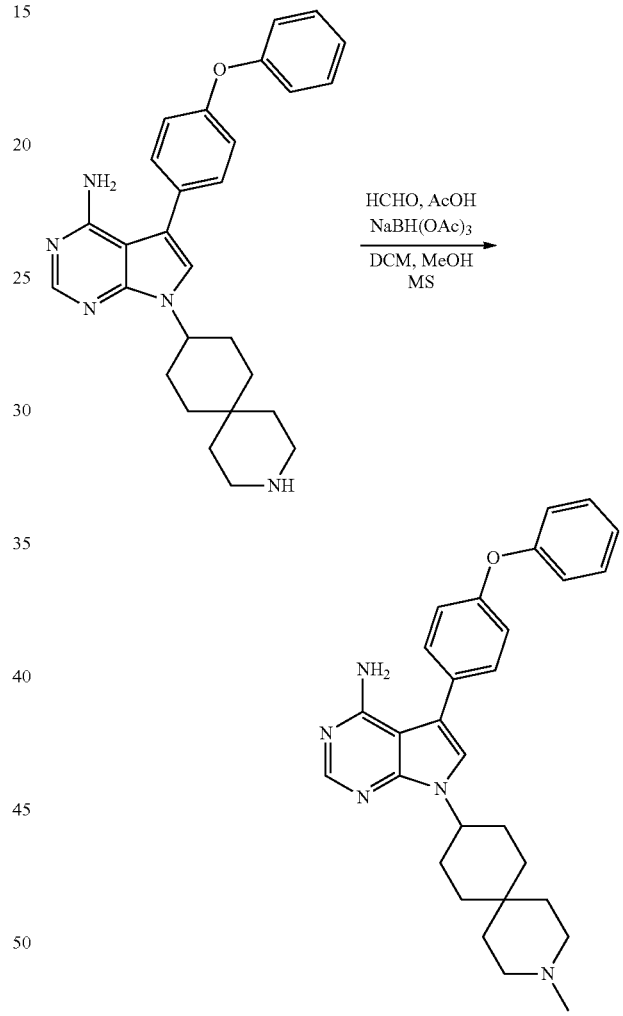

7-(3-Methyl-3-azaspiro[5.5]undecan-9-yl)-5-(4-phenoxyphenyl)-7H-pyrrolo[2,3-d]pyrimidin-4-amine The solution of 5-(4-phenoxyphenyl)-7-(3-azaspiro[5.5] undecan-9-yl)-7H-pyrrolo[2,3-d]pyrimidin-4-amine (20 mg, 0.04 mmol), Formaldehyde (7.9 mg, 0.26 mmol), acetic acid (2.4 mg, 0.04 mmol) and molecular sieves (300 mg) in dichloroethane/methanol (5 mL/2 mL) was stirred at room temperature for 1 hours. Then, Sodium triacetoxyborohydride (55.1 mg, 0.26 mmol) was added and continued to stir for 16 hours at room temperature. Water (50 mL) and dichloromethane (50 mL) were added to the reaction mixture, a saturated aqueous solution of Sodium bicarbonate (25 mL) was further added thereto, and the mixture was partitioned. The organic layer was washed with brine (25 mL) and dried over Sodium sulfate and concentrated to purify by Prep-TLC (DCM:MeOH=15:1) to obtain title compound as white solid (9 mg, 43.7% yield). LCMS: Calculated Exact Mass=467.3; Found [M+H]+ (ESI)=468.2; $^1$H NMR (400 MHz, DMSO-$d_6$) δ ppm: 8.13 (s, 1H), 7.56-7.61 (m, 1H), 7.37-7.52 (m, 4H), 7.04-7.22 (m, 5H), 6.13 (br. s., 1H), 4.59 (t, J=12.1 Hz, 1H), 2.95-3.20 (m, 4H), 2.71 (s, 3H), 2.01 (d, J=12.2 Hz, 2H), 1.75 (d, J=11.0 Hz, 2H).

Example 143

2-(4-(4-Amino-5-(4-phenoxyphenyl)-7H-pyrrolo[2,3-d]pyrimidin-7-yl)cyclohexyl)-4-methylmorpholin-3-one and Example 144

7-(4-(4-Methylmorpholin-2-yl)cyclohexyl)-5-(4-phenoxyphenyl)-7H-pyrrolo[2,3-d]pyrimidin-4-amine

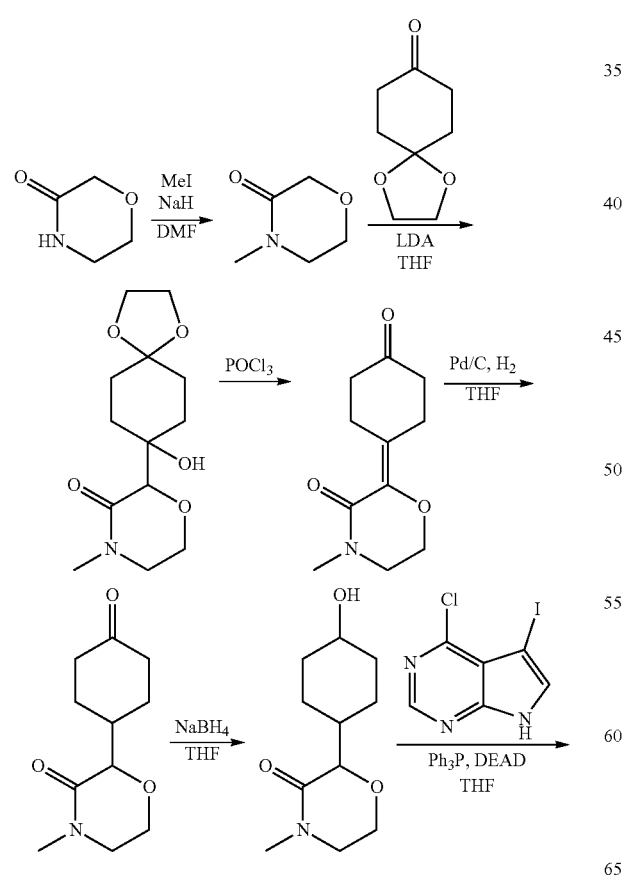

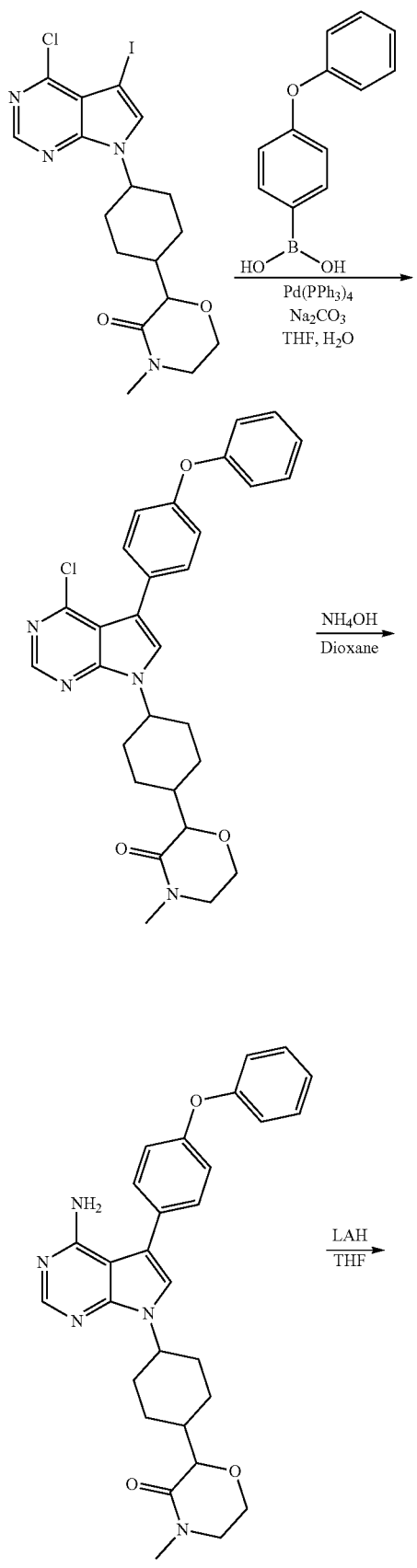

-continued

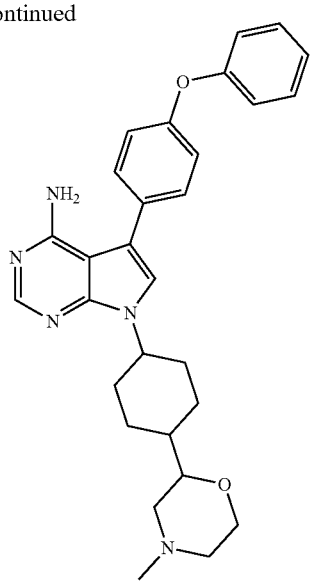

2-(8-Hydroxy-1,4-dioxaspiro[4.5]decan-8-yl)-4-methylmorpholin-3-one

To a solution of 4-methylmorpholin-3-one (1.88 g, 16.3 mmol) in THF (20 mL) was added LDA (2 mmol/l, 19.6 mmol, 9.8M) at −78° C. under $N_2$ atmosphere. Then the reaction was stirred at −78° C. for 60 minutes. After that, 1,4-dioxaspiro[4.5]decan-8-one (92.5 g, 16.3 mmol) in THF (10 mL) was added dropwise at −78° C. The reaction was allowed to warm to room temperature slowly and stirred at 20° C. for 2 hours. Detected by LC-MS and TLC, the starting material was consumed up. It was quenched with saturated $NH_4Cl$ solution (20 mL) and extracted with EA (30 mL*3). The organic layer was washed with brine (40 mL), dried over $Na_2SO_4$, and concentrated in vacuo. The crude product was purified by flash column chromatography eluting with DCM-MeOH (200/1-50/1) to give the desired product as a yellow solid (2.8 g, 64%, yield). LC-MS: Calculated Exact Mass=271.14; Found [M+H]$^+$ (ESI)=272.1; $^1$H NMR (400 MHz, CHLOROFORM-d) δ ppm: 4.06 (dd, J=4.16, 11.69 Hz, 1H), 3.95-4.01 (m, 4H), 3.93 (s, 1H), 3.75-3.84 (m, 1H), 3.65 (dt, J=4.43, 11.75 Hz, 1H), 3.13 (dd, J=2.82, 11.95 Hz, 1H), 1.97-2.20 (m, 3H), 1.88 (dt, J=4.03, 13.43 Hz, 1H), 1.54-1.65 (m, 3H), 1.42-1.50 (m, 1H).

4-Methyl-2-(4-oxocyclohexylidene)morpholin-3-one

To a solution of 2-(8-hydroxy-1,4-dioxaspiro[4.5]decan-8-yl)-4-methylmorpholin-3-one (2.3 g, 8.5 mmol) and TEA (17.2 g, 170 mmol) in DCM (30 mL) was added $POCl_3$ (13.0 g, 85 mmol) at 0° C. under $N_2$ atmosphere. Then the reaction was stirred at 20° C. for 6 hours. The reaction was monitored by LC-MS and TLC until the starting material was consumed. The reaction was quenched with ice water (20 mL) and extracted with DCM (30 mL*3). The organic layer was washed with brine (50 mL), dried over $Na_2SO_4$, and concentrated in vacuo. The crude product was purified by flash column chromatography eluting with PE-EA (5/1-1/1) to give product as a colorless oil (1.0 g, 57%, yield). LC-MS: Calculated Exact Mass=209.11; Found [M+H]$^+$ (ESI)=210.1; $^1$H NMR (400 MHz, CHLOROFORM-d) δ ppm: 4.08 (t, J=5.04 Hz, 2H), 3.50 (t, J=5.04 Hz, 2H), 3.32 (t, J=6.87 Hz, 2H), 3.00-3.09 (m, 3H), 2.72 (t, J=6.87 Hz, 2H), 2.37-2.49 (m, 4H).

4-Methyl-2-(4-oxocyclohexyl)morpholin-3-one

To a solution of 4-methyl-2-(4-oxocyclohexylidene)morpholin-3-one (84 mg, 0.3 mmol), in THF (15 mL) was added Pd/C (100 mg, 10%). Then the reaction was hydrogenated at 20° C. for 4 hours at 30 psi. Detected by LC-MS and TLC, the starting material was consumed up. Filtered and concentrated in vacuo to give the desired product as a light yellow oil. (1.0 g, 98%, yield) LC-MS: Calculated Exact Mass=211.12; Found [M+H]$^+$ (ESI)=212.1; $^1$H NMR (400 MHz, CHLOROFORM-d) δ ppm: 4.11 (d, J=1.88 Hz, 1H), 4.02 (dd, J=3.76, 11.82 Hz, 1H), 3.78 (dt, J=3.09, 11.62 Hz, 1H), 3.58-3.71 (m, 1H), 3.13 (dd, J=2.55, 11.95 Hz, 1H), 2.99-3.05 (m, 3H), 2.57-2.70 (m, 1H), 2.31-2.48 (m, 4H), 1.73-2.05 (m, 4H).

2-(4-Hydroxycyclohexyl)-4-methylmorpholin-3-one

To a solution of compound 4-methyl-2-(4-oxocyclohexyl)morpholin-3-one (0.5 g, 2.5 mmol) in THF (20 mL) was added $NaBH_4$ (380 mg, 10 mmol) at 0° C. under $N_2$ atmosphere. Then the reaction was stirred at 20° C. for 2 hours. The reaction was monitored by LC-MS and TLC until the starting material was consumed. It was quenched with saturated $NH_4Cl$ solution (20 mL) and extracted with DCM (30 mL*5). The organic layer was washed with brine (20 mL), dried over $Na_2SO_4$, and concentrated. The crude product was purified by flash column chromatography eluting with PE-EA (10/1-1/5) to give the product as a colorless oil. (126 mg, 24%, yield) LC-MS: Calculated Exact Mass=213.14; Found [M+H]$^+$ (ESI)=214.1; $^1$H NMR (400 MHz, CHLOROFORM-d) δ ppm: 3.97-4.02 (m, 2H), 3.76 (dt, J=2.55, 11.48 Hz, 1H), 3.45-3.67 (m, 2H), 3.10 (d, J=11.28 Hz, 1H), 3.00 (s, 3H), 1.93-2.18 (m, 3H), 1.69-1.76 (m, 1H), 1.22-1.57 (m, 5H).

2-(4-(4-Chloro-5-iodo-7H-pyrrolo[2,3-d]pyrimidin-7-yl)cyclohexyl)-4-methylmorpholin-3-one To a solution of 2-(4-hydroxycyclohexyl)-4-methylmorpholin-3-one (84 mg, 0.3 mmol), 4-chloro-5-iodo-7H-pyrrolo[2,3-d]pyrimidine (63 mg, 0.3 mmol) and $PPh_3$ (236 mg, 0.9 mmol) in THF (12 mL) was added DIAD (182 mg, 0.9 mmol) dropwise at 0° C. under $N_2$ atmosphere. Then the reaction was stirred at 20° C. for 16 hours. Detected by LC-MS and TLC, the starting material was nearly consumed up. The reaction was concentrated and purified by Prep-TLC eluting with PE-EA (3:1) to give the desired product as a yellow solid (120 mg, 80%, yield). LC-MS: Calculated Exact Mass=474.03; Found [M+H]$^+$ (ESI)=475.0.

2-(4-(4-Chloro-5-(4-phenoxyphenyl)-7H-pyrrolo[2,3-d]pyrimidin-7-yl)cyclohexyl)-4-methylmorpholin-3-one A suspension of compound 2-(4-(4-chloro-5-iodo-7H-pyrrolo[2,3-d]pyrimidin-7-yl)cyclohexyl)-4-methylmorpholin-3-one (150 mg, 0.3 mmol) and (4-phenoxyphenyl) boronic acid (67 mg, 0.3 mmol), $Na_2CO_3$ (102 mg, 0.9 mmol) and Pd(dppf)$Cl_2$, (22 mg, 0.03 mmol) in THF and water (15 mL-3 mL) was stirred at 65° C. under $N_2$ atmosphere for 4 hours. Detected by LC-MS and TLC, the starting material was nearly consumed up. The reaction was concentrated and purified by flash column chromatography eluting with DCM-MeOH (100/1-20/1) to give the desired product as a yellow solid. (130 mg, 84% yield)

LC-MS: Calculated Exact Mass=516.19; Found [M+H]⁺ (ESI)=517.2; ¹H NMR (400 MHz, CHLOROFORM-d) δ ppm: 8.63 (s, 1H), 7.63-7.71 (m, 3H), 7.52-7.59 (m, 2H), 7.43-7.51 (m, 6H), 7.33-7.41 (m, 3H), 6.95-7.18 (m, 6H), 4.94-5.04 (m, 1H), 4.17 (d, J=4.03 Hz, 1H), 4.04 (td, J=2.08, 9.81 Hz, 1H), 3.77 (dt, J=3.22, 11.15 Hz, 1H), 3.61 (dt, J=4.30, 11.28 Hz, 1H), 3.16 (d, J=11.82 Hz, 1H), 3.00 (s, 3H), 2.45 (d, J=4.57 Hz, 1H), 2.18-2.35 (m, 2H), 1.91-2.09 (m, 3H), 1.77-1.90 (m, 2H).

2-(4-(4-Amino-5-(4-phenoxyphenyl)-7H-pyrrolo[2,3-d]pyrimidin-7-yl)cyclohexyl)-4-methylmorpholin-3-one To a solution of compound 2-(4-(4-chloro-5-(4-phenoxyphenyl)-7H-pyrrolo[2,3-d]pyrimidin-7-yl)cyclohexyl)-4-methylmorpholin-3-one (130 mg, 0.25 mmol) in 1,4-dioxane (5 mL) was added NH₃·H₂O (8 mL) in a sealed tube. Then the reaction was stirred at 120° C. for 48 hours. Detected by LC-MS and TLC, the starting material was nearly consumed up. Extracted with EA (30 mL*3), washed with brine (40 mL), dried over Na₂SO₄, concentrated in vacuo and purified by pre-TLC eluting with DCM/MeOH (20/1) to give of the desired product as a yellow solid. (100 mg, 80% yield) LC-MS: Calculated Exact Mass=497.24; Found [M+H]⁺ (ESI)=498.2; ¹H NMR (400 MHz, METHANOL-d₄) δ ppm: 8.29 (s, 1H), 7.57 (s, 1H), 7.47 (d, J=8.60 Hz, 2H), 7.32-7.40 (m, 2H), 7.02-7.16 (m, 5H), 4.21 (d, J=4.57 Hz, 1H), 3.98-4.10 (m, 1H), 3.70-3.84 (m, 1H), 3.52-3.66 (m, 1H), 3.29-3.31 (m, 1H), 3.22 (d, J=12.09 Hz, 1H), 2.95 (s, 3H), 2.21-2.43 (m, 3H), 1.74-2.08 (m, 5H), 1.49-1.65 (m, 1H).

7-(4-(4-Methylmorpholin-2-yl)cyclohexyl)-5-(4-phenoxyphenyl)-7H-pyrrolo[2,3-d]pyrimidin-4-amine To a solution of 2-(4-(4-amino-5-(4-phenoxyphenyl)-7H-pyrrolo[2,3-d]pyrimidin-7-yl)cyclohexyl)-4-methylmorpholin-3-one (50 mg, 0.1 mmol) in THF (5 mL) was added LAH (2 mL) at 0° C. under N₂ atmosphere. Then the reaction was stirred at 20° C. for 2 hours. Monitored by LC-MS and TLC, the starting material was consumed up. The reaction was quenched with saturated water (0.076 mL), NaOH (0.076 mL, 15%) and water (0.228 mL) in sequence. Then Na₂SO₄ was added and the mixture was stirred for 30 minutes. The mixture was filtered through celite and washed with MeOH (20 mL). The filtrate was concentrated and purified by Prep-HPLC to give of the desired product as a white solid (10 mg, 10% yield). LC-MS: Calculated Exact Mass=483.26; Found [M+H]⁺ (ESI)=484.3; ¹H NMR (600 MHz, METHANOL-d₄) δ ppm: 8.30 (s, 1H), 7.59 (s, 1H), 7.49 (d, J=8.59 Hz, 2H), 7.39 (t, J=8.01 Hz, 2H), 7.16 (t, J=7.43 Hz, 1H), 7.12 (d, J=8.59 Hz, 2H), 7.07 (d, J=7.76 Hz, 2H), 4.15 (d, J=11.06 Hz, 1H), 4.02-4.10 (m, 1H), 3.87 (t, J=12.39 Hz, 1H), 3.70 (d, J=12.06 Hz, 1H), 3.45 (d, J=12.22 Hz, 1H), 3.32-3.33 (m, 1H), 3.09 (t, J=10.82 Hz, 1H), 2.94 (s, 3H), 2.87 (t, J=11.48 Hz, 1H), 2.08-2.25 (m, 3H), 1.93 (dt, J=4.38, 8.30 Hz, 2H), 1.80-1.87 (m, 3H), 1.65-1.76 (m, 1H).

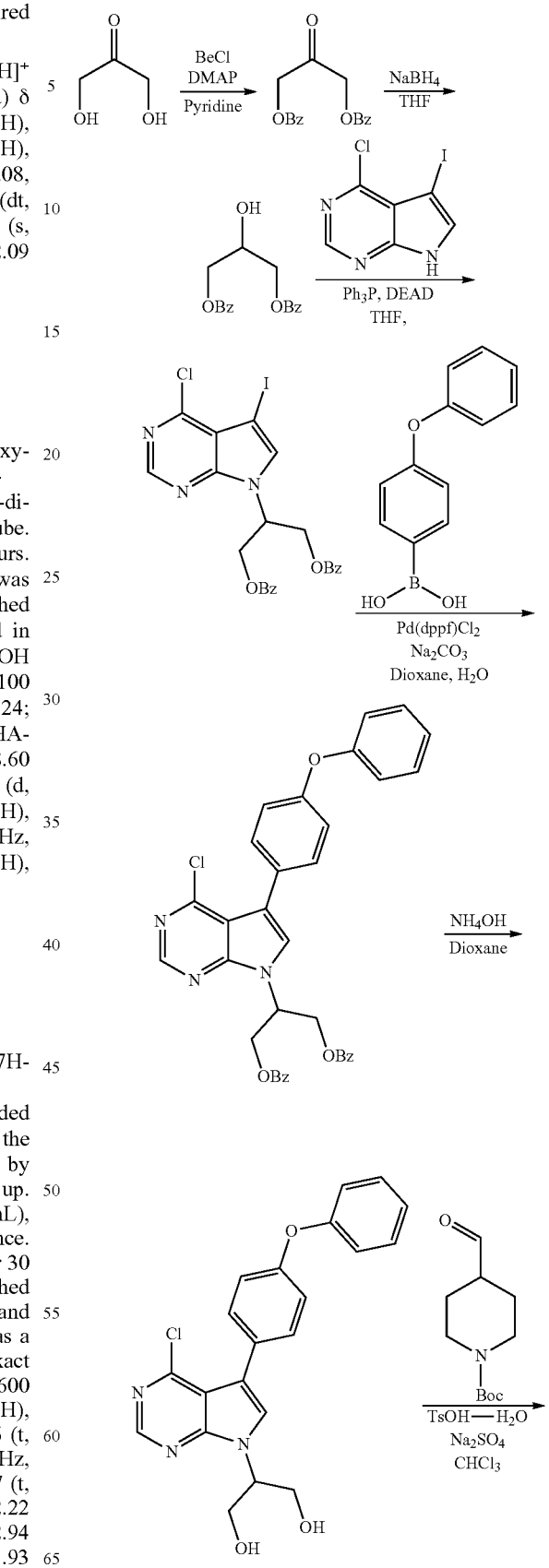

-continued

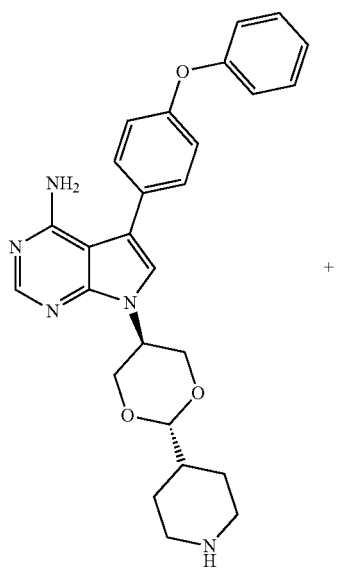

+

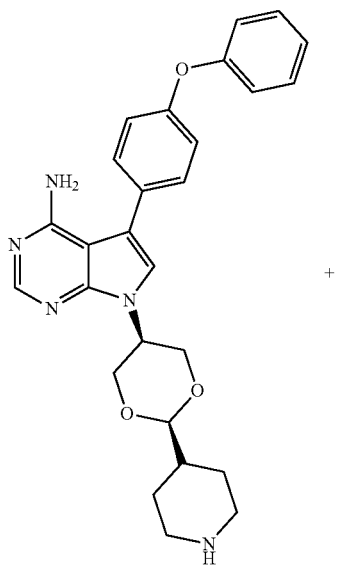

-continued

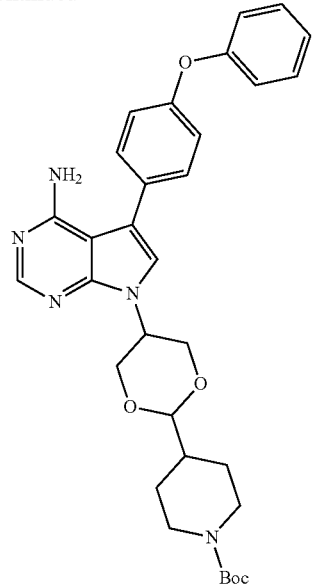

2-Hydroxypropane-1,3-diyl dibenzoate

To a solution of 2-oxopropane-1,3-diyl dibenzoate (2.5 g, 8.4 mmol) in THF (50 mL) was added NaBH$_4$ (352 mg, 9.6 mmol) at 0° C., and stirred for 10 minutes at 0° C. The reaction was monitored by TLC until the starting material was consumed. It was quenched with NH$_4$Cl solution and extracted with EA. The organic layer was washed with brine (40 mL), dried over Na$_2$SO$_4$, and concentrated. The crude was purified by flash column chromatography (PE:EA=10:1-3:1) to obtain the desired product as a colorless oil (1.8 g, 75.6% yield). $^1$H NMR (400 MHz, DMSO-d$_6$) δ ppm: 8.00 (d, J=7.25 Hz, 4H), 7.61-7.73 (m, 2H), 7.45-7.56 (m, 4H), 5.57 (d, J=5.64 Hz, 1H), 4.32-4.44 (m, 4H), 4.15-4.25 (m, 1H).

2-(4-Chloro-5-iodo-7H-pyrrolo[2,3-d]pyrimidin-7-yl)propane-1,3-diyldibenzoate To a solution of 2-hydroxypropane-1,3-diyl dibenzoate (1.4 g, 5 mmol), 4-chloro-5-iodo-7H-pyrrolo [2,3-d]pyrimidine (1.8 g, 6 mmol) and PPh$_3$ (3.93 g, 15 mmol) in THF (40 mL) was added DEAD (2.61 g, 15 mmol) dropwise at 0° C. under N$_2$ atmosphere. Then the reaction was stirred at 20° C. for 18 hours. The reaction was concentrated and the crude was purified by Prep-TLC eluting with PE/EA (100/1-3/1) to get the desired product as a white solid. (2 g, 71%, yield) LC-MS: Calculated Exact Mass=561.00; Found [M+H]$^+$ (ESI)=562.0.

2-(4-Chloro-5-(4-phenoxyphenyl)-7H-pyrrolo[2,3-d]pyrimidin-7-yl)propane-1,3-diyl dibenzoate A suspension of 2-(4-chloro-5-iodo-7H-pyrrolo[2,3-d]pyrimidin-7-yl)propane-1,3-diyldibenzoate (2.2 g, 3.9 mmol)) and (4-phenoxyphenyl)boronic acid (1.0 g, 4.7 mmol), Na$_2$CO$_3$ (2.48 g, 23.4 mmol) and Pd(dppf)Cl$_2$ (571 mg, 0.78 mmol) in THF and water (30 mL-6 mL) was stirred at 65° C. under N$_2$ atmosphere for 3 hours. The reaction was concentrated and the crude was purified by flash column chromatography (PE:EA=20:1-3:1) to get the desired product as a yellow solid. (2.0 g, 85% yield). LC-MS: Calculated Exact Mass=603.16; Found [M+H]+ (ESI)=604.2.

2-(4-Amino-5-(4-phenoxyphenyl)-7H-pyrrolo[2,3-d]pyrimidin-7-yl)propane-1,3-diol

To a solution of 2-(4-chloro-5-(4-phenoxyphenyl)-7H-pyrrolo[2,3-d]pyrimidin-7-yl)propane-1,3-diyl dibenzoate (2 g, 3.3 mmol) in 1,4-dioxane (30 mL) was added NH$_3$·H$_2$O (30 mL) in a sealed tube. Then the reaction was stirred at 120° C. for 60 hours. The reaction mixture was extracted with EA (30 mL*3). The organic layer was washed with brine (40 mL), dried over Na$_2$SO$_4$, and concentrated. The crude was purified by Prep-TLC (DCM:MeOH=100:1-10:1) to get the desired product as a yellow solid. (750 mg, 60% yield).

LC-MS: Calculated Exact Mass=376.15; Found [M+H]+ (ESI)=377.2; $^1$H NMR (400 MHz, DMSO-d$_6$) δ ppm: 8.13 (s, 1H), 7.47 (d, J=8.53 Hz, 2H), 7.41 (t, J=7.91 Hz, 2H), 7.32 (s, 1H), 7.16 (t, J=7.40 Hz, 1H), 7.07-7.13 (m, 4H), 5.93 (br. s., 2H), 4.69-4.90 (m, 3H), 3.84 (br. s., 4H).

5-(4-Phenoxyphenyl)-7-((2r,5r)-2-(piperidin-4-yl)-1,3-dioxan-5-yl)-7H-pyrrolo[2,3-d]pyrimidin-4-amine and 5-(4-Phenoxyphenyl)-7-((2s,5s)-2-(piperidin-4-yl)-1,3-dioxan-5-yl)-7H-pyrrolo[2,3-d]pyrimidin-4-amine A suspension of 2-(4-amino-5-(4-phenoxyphenyl)-7H-pyrrolo[2,3-d]pyrimidin-7-yl)propane-1,3-diol (50 mg, 0.13 mmol)) and tert-butyl 4-formylpiperidine-1-carboxylate (360 mg, 1.69 mmol), TSOH·H$_2$O (321 mg, 1.69 mmol) and Na$_2$SO$_4$ (1.85 g, 13 mmol) in CHCl$_3$ (15 mL) was stirred at reflux under N$_2$ atmosphere for 48 hours. The reaction was quenched with Na$_2$CO$_3$ solution (40 mL), and extracted with EA (40 mL*3). The organic layer was washed with brine (40 mL), dried over Na$_2$SO$_4$, and concentrated. The crude was purified by Prep-TLC (PE:EA=10:1) and Prep-HPLC to give 5-(4-phenoxyphenyl)-7-((2r,5r)-2-(piperidin-4-yl)-1,3-dioxan-5-yl)-7H-pyrrolo[2,3-d]pyrimidin-4-amine (10 mg, 16% yield) LC-MS: Calculated Exact Mass=471.23; Found [M+H]+ (ESI)=472.1; $^1$H NMR (600 MHz, METHANOL-d$_4$) δ ppm 8.26 (s, 1H), 7.84 (s, 1H), 7.50 (d, J=8.47 Hz, 2H), 7.40 (t, J=7.90 Hz, 2H), 7.17 (t, J=7.44 Hz, 1H), 7.13 (d, J=8.47 Hz, 2H), 7.08 (d, J=8.01 Hz, 2H), 4.83-4.84 (m, 1H), 4.74 (d, J=4.58 Hz, 1H), 4.38-4.46 (m, 2H), 4.31 (d, J=12.59 Hz, 2H), 3.41 (d, J=12.36 Hz, 2H), 2.98 (t, J=12.02 Hz, 2H), 2.01-2.08 (m, 3H), 1.57-1.72 (m, 2H); and 5-(4-phenoxyphenyl)-7-((2s,5s)-2-(piperidin-4-yl)-1,3-dioxan-5-yl)-7H-pyrrolo[2,3-d]pyrimidin-4-amine (5 mg, 8% yield) LC-MS: Calculated Exact Mass=603.16; Found [M+H]+ (ESI) =472.1; $^1$H NMR (600 MHz, METHANOL-d$_4$) δ ppm 8.34 (s, 1H), 7.55 (s, 1H), 7.48 (d, J=8.47 Hz, 2H), 7.39 (t, J=7.90 Hz, 2H), 7.16 (t, J=7.32 Hz, 1H), 7.12 (d, J=8.47 Hz, 2H), 7.07 (d, J=8.01 Hz, 2H), 5.08 (td, J=5.52, 10.70 Hz, 1H), 4.65 (d, J=4.35 Hz, 1H), 4.30-4.35 (m, 2H), 4.22-4.29 (m, 2H), 3.43 (d, J=12.59 Hz, 2H), 2.96-3.06 (m, 2H), 1.95-2.12 (m, 3H), 1.62-1.74 (m, 2H); and tert-butyl 4-(5-(4-amino-5-(4-phenoxyphenyl)-7H-pyrrolo [2,3-d]pyrimidin-7-yl)-1,3-dioxan-2-yl) piperidine-1-carboxylate.

Example 145

7-((2r,5r)-2-(1-Methylpiperidin-4-yl)-1,3-dioxan-5-yl)-5-(4-phenoxyphenyl)-7H-pyrrolo[2,3-d]pyrimidin-4-amine and Example 146

7-((2s,5s)-2-(1-Methylpiperidin-4-yl)-1,3-dioxan-5-yl)-5-(4-phenoxyphenyl)-7H-pyrrolo[2,3-d]pyrimidin-4-amine

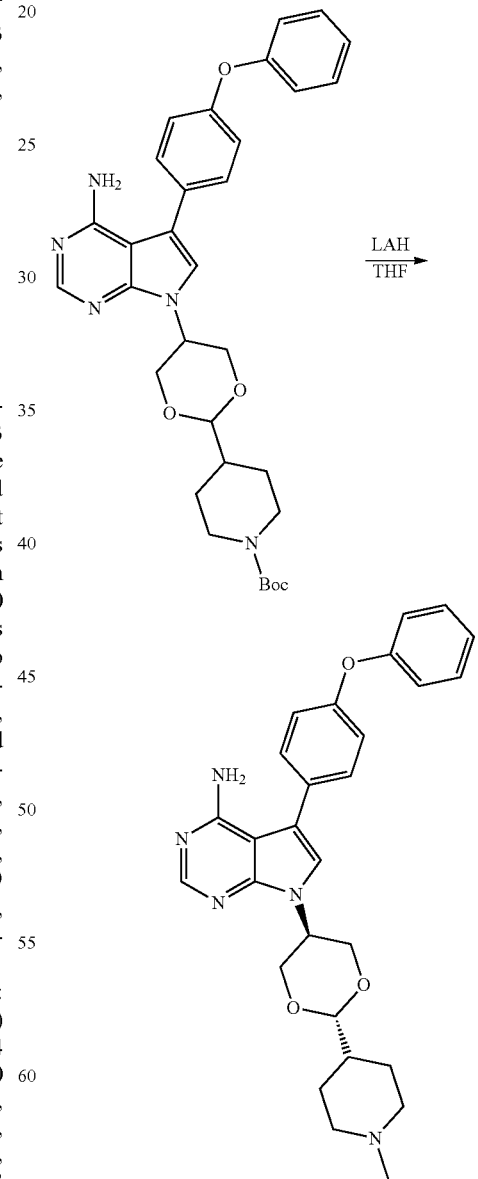

-continued

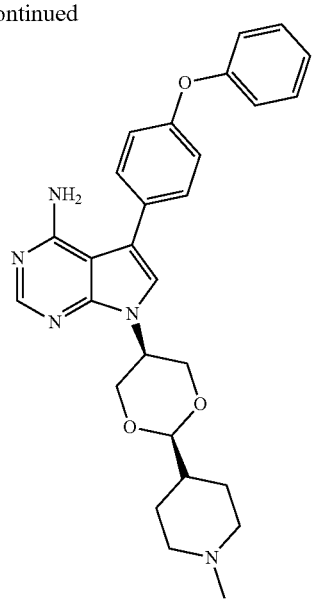

To a solution of tert-butyl 4-(5-(4-amino-5-(4-phenoxyphenyl)-7H-pyrrolo[2,3-d]pyrimidin-7-yl)-1,3-dioxan-2-yl)piperidine-1-carboxylate (130 mg, 0.28 mmol) in THF (5 mL) was added LAH (2 mL, 2 mmol) at 0° C. under $N_2$ atmosphere. Then the reaction was stirred at 20° C. for 16 hours. The reaction was quenched by the addition of saturated water (0.076 mL), NaOH (0.076 mL, 15%) and water (0.228 mL) in order. Then $Na_2SO_4$ was added and the mixture was stirred for 30 min. It was filtered through celite and wash with MeOH. The filtrate was concentrated. The crude was purified by Prep-HPLC to give 7-((2r,5r)-2-(1-methylpiperidin-4-yl)-1,3-dioxan-5-yl)-5-(4-phenoxyphenyl)-7H-pyrrolo[2,3-d]pyrimidin-4-amine (15 mg, 11% yield) LC-MS: Calculated Exact Mass=471.23; Found [M+H]$^+$ (ESI)=486.2; $^1$H NMR (600 MHz, METHANOL-$d_4$) ppm: 8.33 (s, 1H), 7.92 (s, 1H), 7.50 (d, J=8.47 Hz, 2H), 7.40 (t, J=7.90 Hz, 2H), 7.17 (t, J=7.44 Hz, 1H), 7.14 (d, J=8.47 Hz, 2H), 7.09 (d, J=8.24 Hz, 2H), 4.92 (br. s., 1H), 4.75 (d, J=4.58 Hz, 1H), 4.42 (d, J=12.36 Hz, 2H), 4.31 (d, J=12.36 Hz, 2H), 3.53 (d, J=12.36 Hz, 2H), 2.97 (t, J=12.13 Hz, 2H), 2.83 (s, 3H), 2.08 (d, J=13.96 Hz, 2H), 1.98 (ddd, J=3.89, 8.35, 16.14 Hz, 1H), 1.65-1.75 (m, 2H); and 7-((2s,5s)-2-(1-methylpiperidin-4-yl)-1,3-dioxan-5-yl)-5-(4-phenoxyphenyl)-7H-pyrrolo[2,3-d] pyrimidin-4-amine (10 mg, 7%) LC-MS: Calculated Exact Mass=471.23; Found [M+H]$^+$ (ESI)=486.2; $^1$H NMR (600 MHz, METHANOL-$d_4$) ppm: 8.34 (s, 1H), 7.56 (s, 1H), 7.48 (d, J=8.47 Hz, 2H), 7.39 (t, J=7.78 Hz, 2H), 7.17 (t, J=7.44 Hz, 1H), 7.12 (d, J=8.47 Hz, 2H), 7.07 (d, J=8.24 Hz, 2H), 5.05-5.14 (m, 1H), 4.66 (d, J=4.35 Hz, 1H), 4.30-4.35 (m, 2H), 4.23-4.29 (m, 2H), 3.55 (d, J=12.36 Hz, 2H), 3.00 (t, J=12.13 Hz, 2H), 2.86 (s, 3H), 2.09 (d, J=14.42 Hz, 2H), 1.97 (tdd, J=3.98, 8.13, 12.07 Hz, 1H), 1.66-1.77 (m, 2H).

5-Iodo-7-(piperidin-4-yl)-7H-pyrrolo[2,3-d]pyrimidin-4-amine

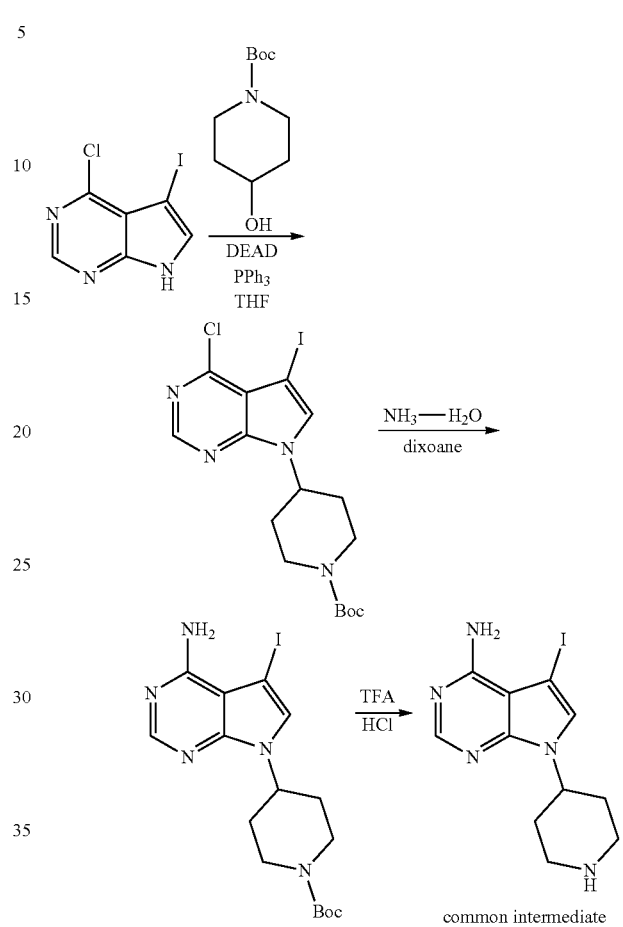

tert-butyl 4-(4-chloro-5-iodo-7H-pyrrolo[2,3-d]pyrimidin-7-yl)piperidine-1-carboxylate To an ice bath cooled suspension of 4-chloro-5-iodo-7H-pyrrolo[2,3-d]pyrimidine (50 g, 179 mmol) in THF (900 mL) was added tert-butyl 4-hydroxypiperidine-1-carboxylate (54.1 g, 269 mmol), PPh$_3$ (78 g, 448 mmol), followed by dropwise addition of DEAD (117.4 g, 448 mmol) over a period of 60 minutes. The reaction was stirred at room temperature overnight. The mixture was evaporated. The residue was diluted with EA (900 mL). A solid thus obtained was collected by filtration. Dried under reduced pressure to afford the title compound (35 g, 42% yield).

tert-butyl 4-(4-amino-5-iodo-7H-pyrrolo[2,3-d]pyrimidin-7-yl)piperidine-1-carboxylate A mixture of tert-butyl 4-(4-chloro-5-iodo-7H-pyrrolo[2,3-d]pyrimidin-7-yl)piperidine-1-carboxylate (25 g, 54.1 mmol) in dioxane (200 mL) NH$_3$—H$_2$O (200 mL) was reacted in a sealed vessel at 120° C. under for 8 hours. After cooled to room temperature, the reaction mixture was concentrated to afford the product as a light yellow solid (20 g, 84% yield). LCMS: Calculated Exact Mass=443.1; Found [M+H]$^+$ (ESI)=443.6.

5-Iodo-7-(piperidin-4-yl)-7H-pyrrolo[2,3-d]pyrimidin-4-amine

To a solution of tert-butyl tert-butyl 4-(4-amino-5-iodo-7H-pyrrolo[2,3-d]pyrimidin-7-yl)piperidine-1-carboxylate (15 g, 33.9 mmol) in DCM (80 mL) was added TFA (50 mL) dropwise. The reaction mixture was stirred at room temperature for 2 hours. The reaction mixture was concentrated, 1M sodium hydroxide was added to adjusted until pH 8. The formed solid was filtered to afford the product as white solid (12 g, 100% yield) LCMS: Calculated Exact Mass=343.0; Found [M+H]$^+$ (ESI)=343.6.

3-Iodo-1-(piperidin-4-yl)-1H-pyrazolo[3,4-d]pyrimidin-4-amine

Method-1

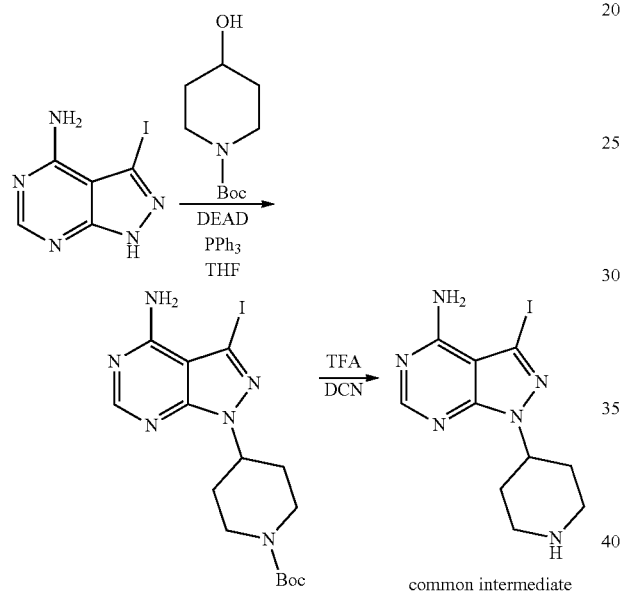

common intermediate tert-butyl 4-(4-amino-3-iodo-1H-pyrazolo[3,4-d]pyrimidin-1-yl)piperidine-1-carboxylate To an ice bath cooled suspension of 3-iodo-1H-pyrazolo[3,4-d]pyrimidin-4-amine (20.0 g, 76.6 mmol) in THF (600 mL) was added tert-butyl 4-hydroxypiperidine-1-carboxylate (38.5 g, 191.6 mmol), PPh$_3$ (50.2 mg, 191.6 mmol), followed by dropwise addition of DEAD (33.4 g, 191.6 mmol) over a period of 1 hours. The reaction was stirred at room temperature for 3 hour and was monitored by LCMS until complete conversion of the starting material. The reaction mixture was concentrated. The crude was washed by THF (100 mL), and then by EtOAc (250 mL) and filtrated to give the product (11.1 g, 32% yield). LCMS: Calculated Exact Mass=444.1; Found [M+H]$^+$ (ESI)=445.0.

3-Iodo-1-(piperidin-4-yl)-1H-pyrazolo[3,4-d]pyrimidin-4-amine

To a solution of tert-butyl 4-(4-amino-3-iodo-1H-pyrazolo[3,4-d]pyrimidin-1-yl)piperidine-1-carboxylate (11.1 g, 25.0 mmol) in DCM (100 mL) was added TFA (25 mL) dropwise. The reaction mixture was stirred at room temperature for 3 hours. The reaction mixture was concentrated and was purified by column chromography on silica (DCM:MeOH=10:1) to afford the product (7.5 g, 87% yield) LCMS: Calculated Exact Mass=344.0; Found [M+H]$^+$ (ESI)=344.9.

Method-2

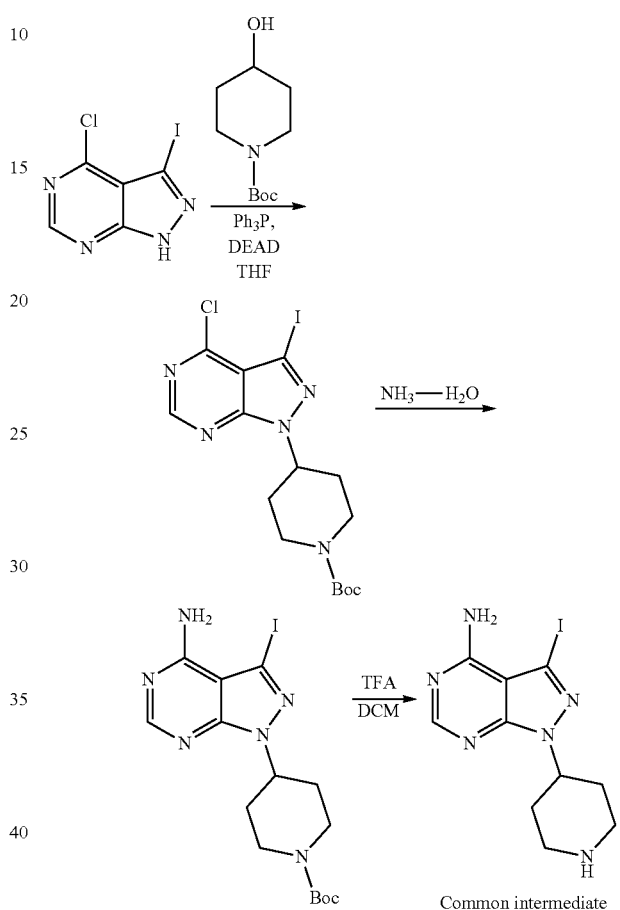

Common intermediate tert-butyl 4-(4-chloro-3-iodo-1H-pyrazolo[3,4-d]pyrimidin-1-yl)piperidine-1-carboxylate Diethyl azodicarboxylate (16.8 mL, 106.97 mmol) was added dropwise to a tetrahydrofuran (200 mL) solution of triphenylphosphine (28.1 g, 106.97 mmol) under ice cooling. Then, the mixture was brought to room temperature, and a tetrahydrofuran/dimethyl sulfoxide (150 mL/50 mL) solution of 4-chloro-3-iodo-1H-pyrazolo [3,4-d]pyrimidine (10 g, 35.66 mmol) and tert-butyl 4-hydroxypiperidine-1-carboxylate (9.3 g, 46.35 mmol) was added dropwise thereto. After completion of the dropwise addition, the mixture was continued to stir at room temperature for 2 hours. The mixture was diluted with ethyl acetate (200 mL), washed with water (350 mL) and brine (300 mL), dried over sodium sulfate and concentrated to purify by flash chromatography (PE:EA=3:1) to obtain tert-butyl 4-(4-chloro-3-iodo-1H-pyrazolo[3,4-d]pyrimidin-1-yl) piperidine-1-carboxylate as pink solid (2.4 g, 14% yield). LCMS: Calculated Exact Mass=463.0; Found [M+H]$^+$ (ESI)=463.6.

tert-butyl 4-(4-amino-3-iodo-1H-pyrazolo[3,4-d]pyrimidin-1-yl)piperidine-1-carboxylate A mixture of tert-butyl 4-(4-chloro-3-iodo-1H-pyrazolo[3,4-d]pyrimidin-1-yl) piperidine-1-carboxylate (2.4 g, 5.18 mmol), 1,4-dioxane (35 mL) and a concentrated aqueous ammonia solution (35 mL) heated in a pressure vessel at 120° C. for 16 hours. After cooling to room temperature, the mixture was concentrated by vacuum. The residue was suspended in water (20 mL), filtered and washed with water (10 mL) to get white solid (2.0 g, 87% yield). LCMS: Calculated Exact Mass=444.1; Found [M+H]+ (ESI)=444.6.

3-Iodo-1-(piperidin-4-yl)-1H-pyrazolo[3,4-d]pyrimidin-4-amine

The solution of tert-butyl 4-(4-amino-3-iodo-1H-pyrazolo[3,4-d]pyrimidin-1-yl) piperidine-1-carboxylate (2.0 g, 4.50 mmol) in TFA-DCM (4 mL-4 mL) was stirred at room temperature for 0.5 hour. The mixture was concentrated to get crude product for the next step without further purification. LCMS: Calculated Exact Mass=344.0; Found [M+H]+ (ESI)=344.6.

5-(4-Phenoxyphenyl)-7-(piperidin-4-yl)-7H-pyrrolo[2,3-d]pyrimidin-4-amine

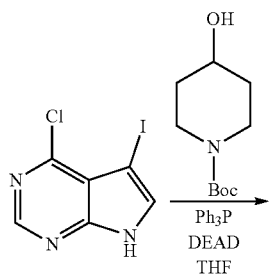

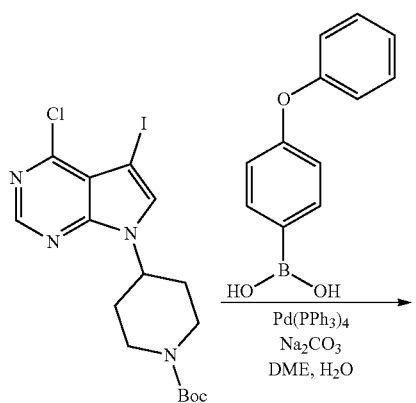

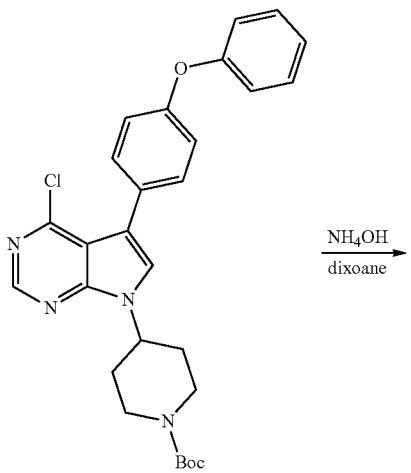

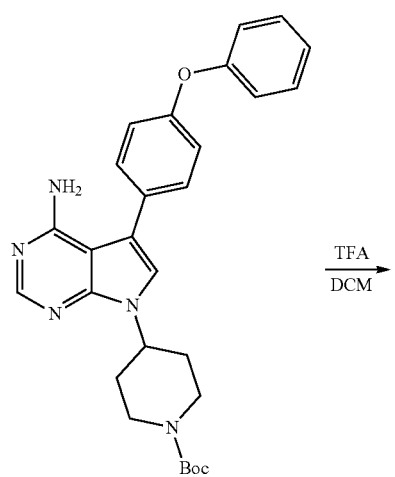

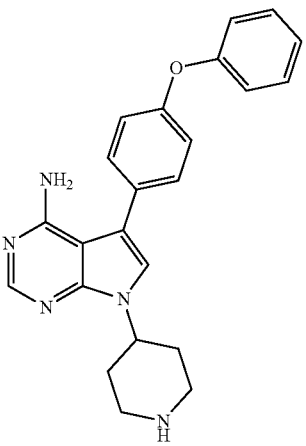

common intermediate tert-butyl 4-(4-chloro-5-iodo-7H-pyrrolo[2,3-d]pyrimidin-7-yl)piperidine-1-carboxylate To an ice bath cooled suspension of 4-chloro-5-iodo-7H-pyrrolo[2,3-d]pyrimidine (10.0 g, 35.8 mmol) in THF (250 mL) was added tert-butyl 4-hydroxypiperidine-1-carboxylate (11 g, 53.7 mmol), PPh$_3$ (21 mg, 82.3 mmol), followed by dropwise addition of DEAD (14.3 g, 82.3 mmol) over a period of 1 hours. The reaction was stirred at room temperature for 3 hour and was monitored by LCMS until complete conversion of the starting material. The reaction mixture was concentrated. The crude was washed by THF (100 mL), and then by EtOAc (250 mL) to give the product (9.3 g, 37% yield). LCMS: Calculated Exact Mass=462.0; Found [M+H]$^+$ (ESI)=463.1.

tert-butyl 4-(4-chloro-5-(4-phenoxyphenyl)-7H-pyrrolo[2,3-d]pyrimidin-7-yl)piperidine-1-carboxylate A mixture of tert-butyl 4-(4-chloro-5-iodo-7H-pyrrolo[2,3-d]pyrimidin-7-yl)piperidine-1-carboxylate (8.9 g, 19.26 mmol), (4-phenoxyphenyl)boronic acid (8.2 g, 38.52 mmol), Pd(dppf)Cl$_2$ (1.4 g, 1.93 mmol) and Na$_2$CO$_3$ (4.1 g, 38.52 mmol) in dioxane (150 mL) H$_2$O (15 mL) was heated at 85° C. under Argon atmosphere for 3 hours. After cooled to room temperature, the reaction mixture was concentrated and extracted with DCM (500 mL×4). The organic layers were concentrated and purified by flash column chromatography (PE:EA=6:1) to afford the product as a light yellow solid (6.2 g, 65% yield). LCMS: Calculated Exact Mass=504.2; Found [M+H]$^+$ (ESI)=505.0.

tert-butyl 4-(4-amino-5-(4-phenoxyphenyl)-7H-pyrrolo[2,3-d]pyrimidin-7-yl)piperidine-1-carboxylate A mixture of tert-butyl 4-(4-chloro-5-(4-phenoxyphenyl)-7H-pyrrolo[2,3-d]pyrimidin-7-yl) piperidine-1-carboxylate (500 mg, 0.99 mmol) in dioxane (2.5 mL) and NH$_4$OH (2.5 mL) was reacted in microwave reactor at 120° C. under for 8 hours. After cooled to room temperature, the reaction mixture was concentrated to afford the product as a light yellow solid (450 mg, 93% yield). LCMS: Calculated Exact Mass=485.2; Found [M+H]$^+$ (ESI)=486.0.

5-(4-Phenoxyphenyl)-7-(piperidin-4-yl)-7H-pyrrolo[2,3-d]pyrimidin-4-amine

To a solution of tert-butyl 4-(4-amino-5-(4-phenoxyphenyl)-7H-pyrrolo[2,3-d]pyrimidin-7-yl) piperidine-1-carboxylate (960 mg, 1.98 mmol) in DCM (8 mL) was added TFA (8 mL) dropwise. The reaction mixture was stirred at room temperature for 2 hours. The reaction mixture was concentrated, 2M sodium hydroxide was added there to adjust until pH 8 and the mixture was extracted with DCM (15 mL×2). The organic layer was concentrated to afford the product as white solid (890 mg). LCMS: Calculated Exact Mass=385.3; Found [M+H]$^+$ (ESI)=386.3; $^1$H NMR (400 MHz, DMSO-d$_6$) δ 8.95 (d, J=10.7 Hz, 1H), 8.68 (d, J=9.8 Hz, 1H), 8.50 (s, 1H), 7.65 (s, 1H), 7.51 (d, J=8.5 Hz, 2H), 7.41-7.47 (m, 2H), 7.07-7.22 (m, 5H), 4.92-5.06 (m, 2H), 3.48 (d, J=12.5 Hz, 2H), 2.23-2.36 (m, 2H), 2.11-2.23 (m, 2H), 2.02-2.11 (m, 3H).

Example 147

3-(2-fluoro-4-phenoxyphenyl)-1-(1'-methyl-[1,4'-bipiperidin]-4-yl)-1H-pyrazolo[3,4-d]pyrimidin-4-amine

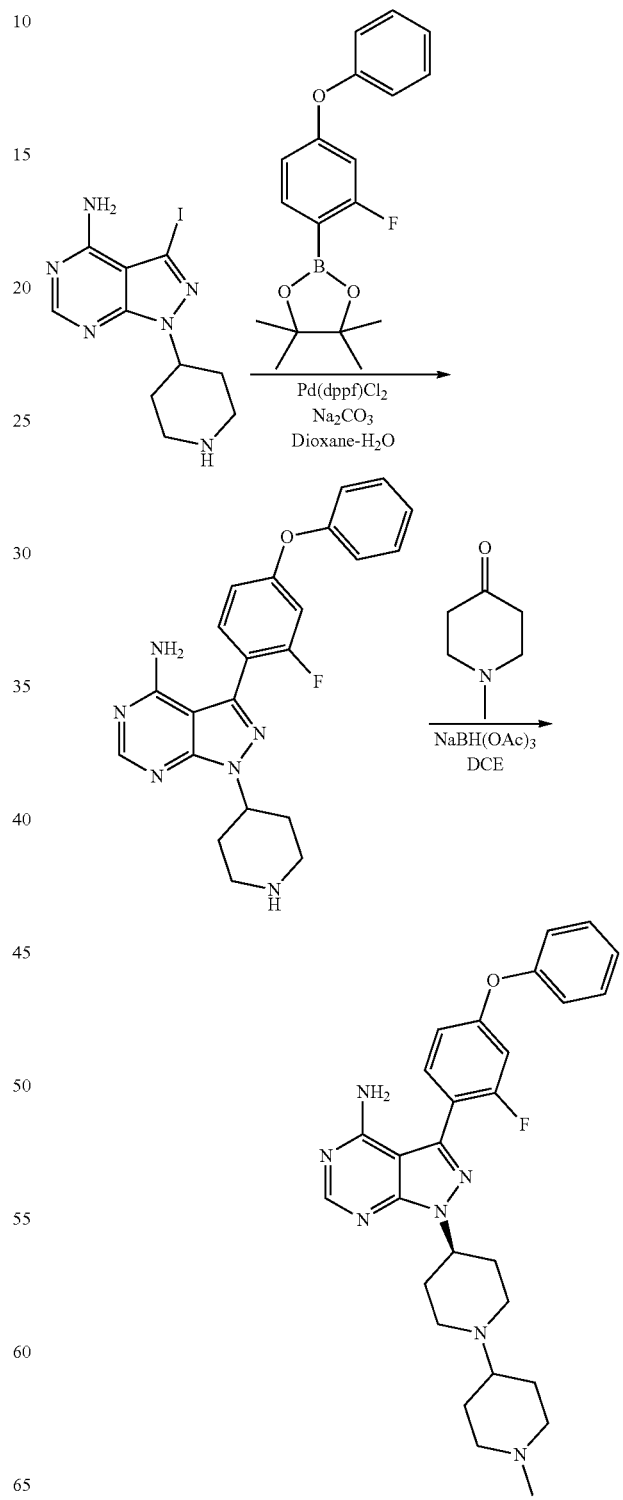

3-(2-Fluoro-4-phenoxyphenyl)-1-(piperidin-4-yl)-1H-pyrazolo[3,4-d]pyrimidin-4-amine A mixture of 3-iodo-1-(piperidin-4-yl)-1H-pyrazolo[3,4-d]pyrimidin-4-amine (500 mg, 1.453 mmol), 2-(2-fluoro-4-phenoxyphenyl)-4,4,5,5-tetramethyl-1,3,2-dioxaborolane (639 mg, 2.034 mmol), Pd(dppf)Cl$_2$ (212 mg, 0.291 mmol) and Na$_2$CO$_3$ (461 mg, 4.358 mmol) in dioxane-H$_2$O (8 mL-1 mL) was heated at 85° C. under inert atmosphere overnight. After cooled to room temperature, the reaction mixture was concentrated and purified by flash column chromatography (MeOH in DCM, 0 to 10% gradient) to afford the product as semi-solid (300 mg, 51% yield).

3-(2-Fluoro-4-phenoxyphenyl)-1-(1'-methyl-[1,4'-bipiperidin]-4-yl)-1H-pyrazolo[3,4-d]pyrimidin-4-amine To a mixture of 3-(2-fluoro-4-phenoxyphenyl)-1-(piperidin-4-yl)-1H-pyrazolo [3,4-d]pyrimidin-4-amine (150 mg, 0.37 mol) and 1-methylpiperidin-4-one (126 mg, 1.11 mmol) in DCE (6 mL) was added 5 g of 4 Å molecular sieve and 10 mL AcOH. The mixture was stirred at 50° C. under N$_2$ atmosphere for 50 min. After it was cooled to room temperature, NaBH(OAc)$_3$ (157 mg, 0.74 mmol) was added portion-wise, the mixture was stirred at room temperature overnight. The reaction was monitored via TLC and LCMS until complete consumption of starting material. It was then filtrated and concentrated, prep-TLC (15% MeOH in DCM) and Prep-HPLC obtained (Acetonitrile/water, 0.1% TFA) obtained product (10 mg, 5.4% yield). LCMS: Calculated Exact Mass=501.27; Found [M+H]$^+$ (ESI)=502.41; $^1$H NMR (DMSO-d$_6$) δ ppm: 10.01 (br. s., 1H), 8.29-8.35 (m, 1H), 7.44-7.58 (m, 3H), 7.25 (t, J=7.4 Hz, 1H), 7.19 (d, J=8.0 Hz, 2H), 7.04 (dd, J=11.3, 2.1 Hz, 1H), 6.96 (dd, J=8.4, 1.9 Hz, 1H), 5.13 (br. s., 1H), 4.39 (br. s., 3H), 3.59-3.67 (m, 4H), 3.34 (br. s., 2H), 3.02 (br. s., 2H), 2.79 (br. s., 3H), 2.17-2.39 (m, 4H), 1.94 (d, J=10.0 Hz, 2H).

Example 148

1-(4-(4-Amino-1-(1'-methyl-[1,4'-bipiperidin]-4-yl)-1H-pyrazolo[3,4-d]pyrimidin-3-yl)phenyl)-3-(5-(tert-butyl)isoxazol-3-yl)urea

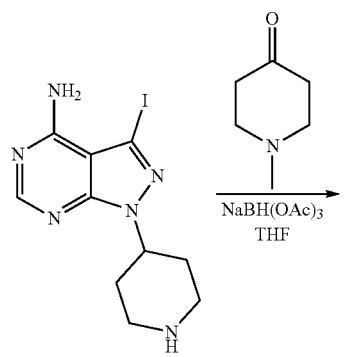

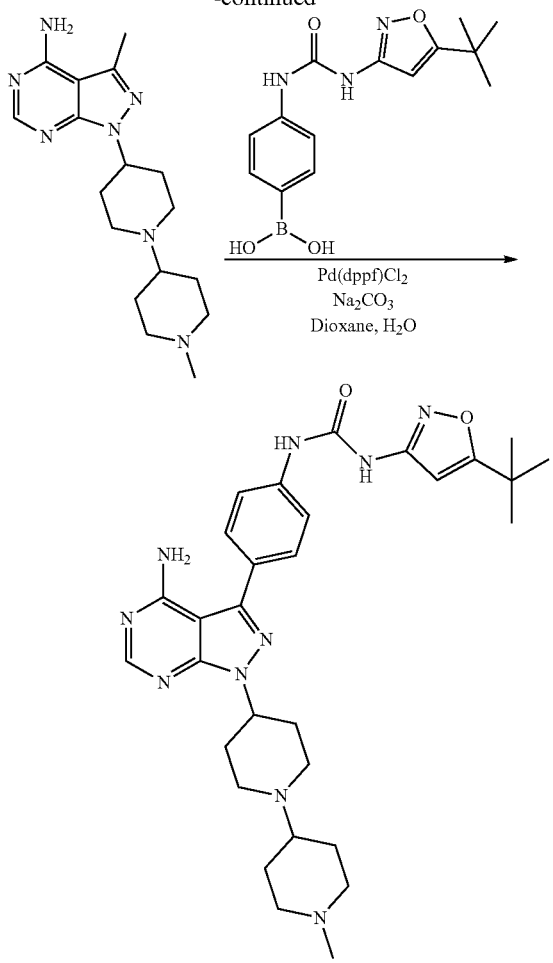

3-Iodo-1-(1'-methyl-[1,4'-bipiperidin]-4-yl)-1H-pyrazolo[3,4-d]pyrimidin-4-amine The solution of 3-iodo-1-(piperidin-4-yl)-1H-pyrazolo[3,4-d]pyrimidin-4-amine (500 mg, 1.45 mmol) and 1-methylpiperidin-4-one (493.2 mg, 4.36 mmol) in tetrahydrofuran (60 mL) was stirred at room temperature for 1 hour. Then, sodium triacetoxyborohydride (923.8 mg, 4.36 mmol) was added and continued to stir for 16 hours. The mixture was concentrated and diluted with DCM-MeOH (250 mL, 10:1). The solution was filtered and concentrated to purify by flash chromatography (DCM-MeOH—NH$_3$ (7.0 N in methanol): 100:10:1) to obtain the product as brown solid (400 mg, 62% yield). LCMS: Calculated Exact Mass=441.1; Found [M+H]$^+$ (ESI)=441.7.

1-(4-(4-Amino-1-(1'-methyl-[1,4'-bipiperidin]-4-yl)-1H-pyrazolo[3,4-d]pyrimidin-3-yl)phenyl)-3-(5-(tert-butyl)isoxazol-3-yl)urea The solution of 3-iodo-1-(1'-methyl-[1,4'-bipiperidin]-4-yl)-1H-pyrazolo[3,4-d] pyrimidin-4-amine (200 mg, 0.45 mmol), (4-(3-(5-(tert-butyl)isoxazol-3-yl)ureido) phenyl) boronic acid (206 mg, 0.68 mmol), Pd(dppf)Cl$_2$ (66 mg, 0.09 mmol) and sodium carbonate (96 mg, 0.91 mmol) in 1,4-dioxane (8 mL) and water (0.8 mL) was reacted in microwave reactor at 80° C. for 1 hour under nitrogen atmosphere.

After cooling to room temperature, the mixture was concentrated and purified by flash chromatography (DCM: MeOH:NH$_3$ (7.0 N in methanol)=100:10:1) to obtain yellow solid (250 mg, 80% purity) that was further purified by Prep-HPLC to get title compound as white solid (105 mg, 40% yield). LCMS: Calculated Exact Mass=572.3; Found [M+H]$^+$ (ESI)=572.8; $^1$H NMR (400 MHz, DMSO-d$_6$) δ ppm: 9.71 (s, 2H), 9.17 (s, 1H), 8.30 (s, 1H), 7.66 (d, J=8.5 Hz, 1H), 7.60 (d, J=8.5 Hz, 2H), 6.52 (s, 1H), 5.11-5.25 (m, 1H), 3.35-3.72 (m, 9H), 3.02 (d, J=8.9 Hz, 2H), 2.80 (s, 3H), 2.22-2.33 (m, 4H), 1.88-2.15 (m, 2H), 1.30 (s, 9H).

Using similar procedures, the following compounds were prepared:

| Structure | Name | LCMS/NMR |
|---|---|---|
| | EXAMPLE 149<br>5-(3-methoxy-4-phenoxyphenyl)-7-(1'-methyl-[1,4'-bipiperidin]-4-yl)-7H-pyrrolo[2,3-d]pyrimidin-4-amine | LCMS: Calculated Exact Mass = 512.3; Found [M + H]$^+$ (ESI) = 513.0; $^1$H NMR (400 MHz, DMSO-d$_6$) δ ppm: 8.14 (s, 1H) 7.57 (s, 1H) 7.33 (t, J = 7.93 Hz, 2H) 7.24 (s, 1H) 7.08-7.12 (m, 1H) 7.04 (d, J = 5.19 Hz, 2H) 6.92 (d, J = 7.93 Hz, 2H) 4.46-4.63 (m, 1H) 3.80 (s, 3H) 3.02 (d, J = 10.38 Hz, 2H) 2.82 (d, J = 10.07 Hz, 2H) 2.20-2.37 (m, 4H) 2.15 (br. s., 3H) 2.09 (s, 3H) 1.96-2.07 (m, 3H) 1.91 (d, J = 10.07 Hz, 4H) 1.73 (d, J = 10.99 Hz, 2H) 1.47 (d, J = 11.90 Hz, 2H). |
| | EXAMPLE 150<br>7-([1,4'-bipiperidin]-4-yl)-5-(3-methoxy-4-phenoxyphenyl)-7H-pyrrolo[2,3-d]pyrimidin-4-amine | LCMS: Calculated Exact Mass = 498.2; Found [M + H]$^+$ (ESI) = 498.8; $^1$H NMR (400 MHz, DMSO-d$_6$) δ ppm: 8.14 (s, 1H) 7.57 (s, 1H) 7.33 (t, J = 7.93 Hz, 3H) 7.24 (s, 1H) 7.08-7.13 (m, 1H) 7.04 (d, J = 4.58 Hz, 2H) 6.92 (d, J = 7.93 Hz, 2H) 4.57 (br. s., 1H) 3.80 (s, 3H) 3.15 (d, J = 12.51 Hz, 3H) 3.00 (d, J = 12.51 Hz, 3H) 2.59-2.72 (m, 3H) 2.29-2.40 (m, 3H) 1.97-2.05 (m, 3H) 1.93 (br. s., 2H) 1.81 (d, J = 10.99 Hz, 2H). |

-continued

| Structure | Name | LCMS/NMR |
|---|---|---|
| 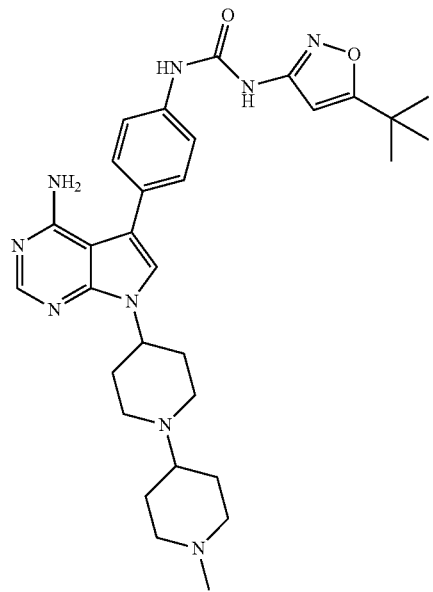 [SMILES: CN1CCC(N2CCC(n3cc(-c4ccc(NC(=O)Nc5cc(C(C)(C)C)on5)cc4)c4c(N)ncnc43)CC2)CC1] | EXAMPLE 151<br>1-(4-(4-amino-7-(1'-methyl-[1,4'-bipiperidin]-4-yl)-7H-pyrrolo[2,3-d]pyrimidin-5-yl)phenyl)-3-(5-(tert-butyl)isoxazole-3-yl)urea | LCMS: Calculated Exact Mass = 571.3; Found [M + H]$^+$ (ESI) = 571.7; $^1$H NMR (400 MHz, DMSO-d$_6$) δ ppm: 10.07 (s, 1H) 9.69 (br. s., 1H) 8.18 (s, 1H) 7.61 (m, J = 8.24 Hz, 2H) 7.39 (m, J = 8.24 Hz, 2H) 6.41-6.64 (m, 1H) 4.88 (br. s., 1H) 3.43 (br. s., 4H) 2.96 (br. s., 3H) 2.75 (br. s., 2H) 2.38 (br. s., 2H) 2.14 (br. s., 4H) 1.91 (br. s., 2H) 1.30 (s, 9H). |
| 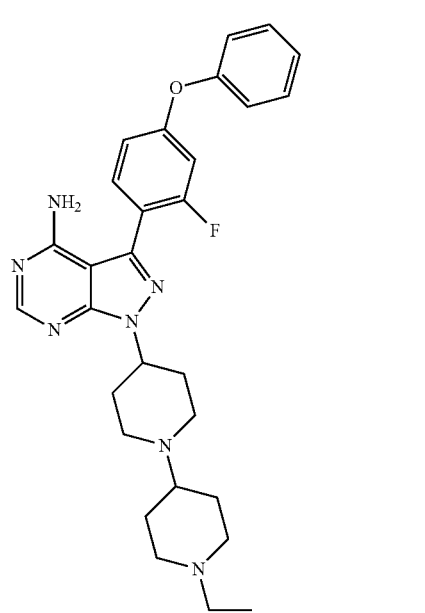 [SMILES: CCN1CCC(N2CCC(n3nc(-c4ccc(Oc5ccccc5)cc4F)c4c(N)ncnc43)CC2)CC1] | EXAMPLE 152<br>1-(1'-ethyl-[1,4'-bipiperidin]-4-yl)-3-(2-fluoro-4-phenoxyphenyl)-1H-pyrazolo[3,4-d]pyrimidin-4-amine | LCMS: Calculated Exact Mass = 515.3; Found [M + H]$^+$ (ESI) = 516.2; $^1$H NMR (400 MHz, DMSO-d$_6$) δ ppm: 9.91 (br. s., 1H) 9.74 (br. s., 1H) 8.30 (s, 1H) 7.44-7.59 (m, 4H) 7.25 (t, J = 7.38 Hz, 1H) 7.19 (d, J = 7.63 Hz, 2H) 7.03 (dd, J = 11.19, 2.19 Hz, 1H) 6.96 (dd, J = 8.50, 2.13 Hz, 1H) 5.12 (t, J = 11.94 Hz, 1H) 3.68 (br. s., 2H) 3.50 (d, J = 8.63 Hz, 3H) 3.34 (br. s., 2H) 3.12 (d, J = 6.00 Hz, 2H) 2.97 (d, J = 8.88 Hz, 2H) 2.22-2.40 (m, 5H) 1.88-2.03 (m, 2H) 1.18-1.30 (m, 3H). |

| Structure | Name | LCMS/NMR |
|---|---|---|
| | EXAMPLE 153<br>3-(2-fluoro-4-phenoxyphenyl)-1-(1'-isopropyl-[1,4'-bipiperidin]-4-yl)-1H-pyrazolo[3,4-d]pyrimidin-4-amine | LCMS: Calculated Exact Mass = 529.3; Found [M + H]$^+$ (ESI) = 530.2; $^1$H NMR (400 MHz, DMSO-d$_6$) δ ppm: 9.83 (br. s., 1H) 9.47 (br. s., 1H) 8.28 (s, 1H) 7.40-7.59 (m, 3H) 7.25 (t, J = 7.38 Hz, 1H) 7.19 (d, J = 7.75 Hz, 2H) 7.03 (dd, J = 11.19, 2.31 Hz, 1H) 6.96 (dd, J = 8.44, 2.19 Hz, 1H) 5.14 (t, J = 11.69 Hz, 1H) 3.56-3.66 (m, 3H) 3.35 (br. s., 2H) 3.04 (d, J = 10.51 Hz, 2H) 2.20-2.35 (m, 4H) 1.89-2.05 (m, 2H) 1.25 (d, J = 6.63 Hz, 6H). |
| | EXAMPLE 154<br>7-((2'S)-2'-methyl-[1,4'-bipiperidin]-4-yl)-5-(4-phenoxyphenyl)-7H-pyrrolo[2,3-d]pyrimidin-4-amine | LCMS: Calculated Exact Mass = 482.3; Found [M + H]$^+$ (ESI) = 482.9; $^1$H NMR (400 MHz, DMSO-d$_6$) δ ppm: 10.19 (br. s., 1H) 8.94 (br. s., 1H) 8.66 (br. s., 1H) 8.41 (br. s., 1H) 8.36 (br. s., 1H) 7.39-7.52 (m, 5H) 7.19 (t, J = 7.39 Hz, 1H) 7.13 (t, J = 8.33 Hz, 4H) 4.99 (br. s., 1H) 3.62 (br. s., 2H) 3.52 (d, J = 11.01 Hz, 2H) 3.33 (br. s., 3H) 2.99 (d, J = 11.28 Hz, 1H) 2.44 (br. s., 2H) 2.21-2.34 (m, 3H) 1.83 (br. s., 1H) 1.69 (br. s., 1H) 1.29 (d, J = 6.18 Hz, 3H). |

| Structure | Name | LCMS/NMR |
|---|---|---|
| 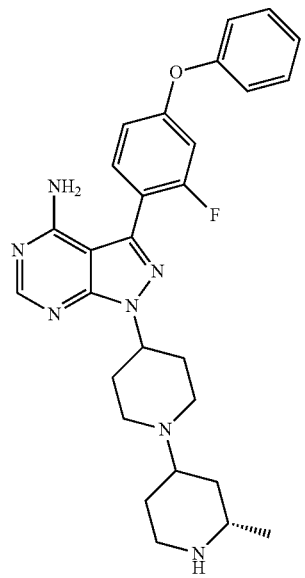 [SMILES: C[C@H]1CC(N2CCC(n3nc(-c4ccc(Oc5ccccc5)cc4F)c4c(N)ncnc43)CC2)CCN1] | EXAMPLE 155<br>3-(2-fluoro-4-phenoxyphenyl)-1-((2'S)-2'-methyl-[1,4'-bipiperidin]-4-yl)-1H-pyrazolo[3,4-d]pyrimidin-4-amine | LCMS: Calculated Exact Mass = 501.3; Found [M + H]+ (ESI) = 502.2; $^1$H NMR (400 MHz, DMSO-$d_6$) δ ppm: 9.76 (br. s., 1H) 8.90 (br. s., 1H) 8.55 (d, J = 10.76 Hz, 1H) 8.29 (s, 1H) 7.41-7.60 (m, 3H) 7.20-7.30 (m, 1H) 7.14-7.20 (m, 2H) 7.03 (dd, J = 11.26, 2.25 Hz, 1H) 6.96 (dd, J = 8.44, 2.31 Hz, 1H) 5.01-5.25 (m, 1H) 3.56-3.74 (m, 2H) 3.50 (d, J = 13.76 Hz, 2H) 3.31-3.42 (m, 2H) 3.26 (br. s., 1H) 2.90-3.07 (m, 1H) 2.17-2.37 (m, 4H) 1.72-1.87 (m, 1H) 1.58-1.72 (m, 1H) 1.19-1.34 (m, 3H). |
| 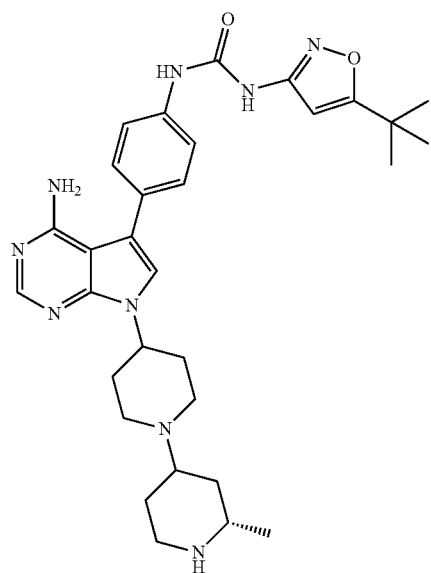 [SMILES: C[C@H]1CC(N2CCC(n3cc(-c4ccc(NC(=O)Nc5cc(C(C)(C)C)on5)cc4)c4c(N)ncnc43)CC2)CCN1] | EXAMPLE 156<br>1-(4-(4-amino-7-((2'S)-2'-methyl-[1,4'-bipiperidin]-4-yl)-7H-pyrrolo[2,3-d]pyrimidin-5-yl)phenyl)-3-(5-(tert-butyl)isoxazol-3-yl)urea | LCMS: Calculated Exact Mass = 571.3; Found [M + H]+ (ESI) = 571.9.; $^1$H NMR (400 MHz, DMSO-$d_6$) δ ppm: 10.39 (br. s., 1H) 9.78 (s, 1H) 9.26 (s, 1H) 9.03 (d, J = 9.13 Hz, 1H) 8.68 (d, J = 8.86 Hz, 1H) 8.47 (s, 1H) 7.63 (m, J = 8.33 Hz, 2H) 7.54 (s, 1H) 7.43 (m, J = 8.33 Hz, 2H) 6.52 (s, 1H) 5.04 (br. s., 1H) 3.64 (d, J = 10.21 Hz, 2H) 3.48-3.59 (m, 2H) 3.33 (br. s., 3H) 2.45 (br. s., 2H) 2.23-2.35 (m, 3H) 2.00 (dd, J = 14.91, 7.39 Hz, 1H) 1.77-1.89 (m, 1H) 1.61-1.77 (m, 1H) 1.27-1.32 (m, 12H). |

| Structure | Name | LCMS/NMR |
|---|---|---|
| | EXAMPLE 157<br>(4-(4-amino-5-(4-phenoxyphenyl)-7H-pyrrolo[2,3-d]pyrimidin-7-yl)-[1,4'-bipiperidin]-2'-yl)methanol | LCMS: Calculated Exact Mass = 498.3; Found [M + H]⁺ (ESI) = 499.8; ¹H NMR (400 MHz, DMSO-d₆) δ ppm: 10.47 (br. s., 1H) 9.05 (d, J = 9.40 Hz, 1H) 8.65 (d, J = 9.40 Hz, 1H) 8.50 (s, 1H) 7.58 (s, 1H) 7.49 (d, J = 8.33 Hz, 2H) 7.39-7.47 (m, 2H) 7.19 (t, J = 7.39 Hz, 1H) 7.13 (t, J = 8.06 Hz, 4H) 4.94-5.13 (m, 1H) 3.60-3.74 (m, 4H) 3.54 (dd, J = 11.55, 5.64 Hz, 1H) 3.47 (d, J = 12.09 Hz, 1H) 3.35 (br. s., 1H) 3.28 (br. s., 1H) 3.03 (d, J = 11.01 Hz, 1H) 2.39-2.49 (m, 1H) 2.29 (d, J = 11.01 Hz, 3H) 1.84-1.94 (m, 1H) 1.68-1.84 (m, 1H). |
| | EXAMPLE 158<br>methyl 4-(4-amino-5-(4-phenoxyphenyl)-7H-pyrrolo[2,3-d]pyrimidin-7-yl)-[1,4'-bipiperidine]-2'-carboxylate | LCMS: Calculated Exact Mass = 526.4; Found [M + H]⁺ (ESI) = 527.1; ¹H NMR (400 MHz, DMSO-d₆) δ ppm: 10.70 (br. s., 1H) 9.66 (br. s., 1H) 9.45 (br. s., 1H) 8.51 (s, 1H) 7.59 (br. s., 1H) 7.50 (d, J = 8.60 Hz, 2H) 7.39-7.47 (m, 2H) 7.19 (t, J = 7.39 Hz, 1H) 7.07-7.16 (m, 4H) 5.06 (br. s., 1H) 4.31 (d, J = 11.01 Hz, 1H) 3.77-3.89 (m, 3H) 3.51-3.68 (m, 3H) 3.39 (br. s., 2H) 3.02 (t, J = 12.49 Hz, 1H) 2.64 (d, J = 11.55 Hz, 1H) 2.46 (br. s., 2H) 2.28 (d, J = 11.01 Hz, 3H) 1.83-2.04 (m, 2H). |

| Structure | Name | LCMS/NMR |
|---|---|---|
| 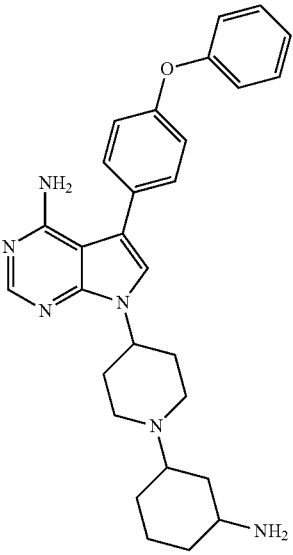 [SMILES: Nc1ncnc2c1c(-c1ccc(Oc3ccccc3)cc1)cn2C1CCN(C2CCCC(N)C2)CC1] | EXAMPLE 159<br>7-(1-(3-aminocyclohexyl)piperidin-4-yl)-5-(4-phenoxyphenyl)-7H-pyrrolo[2,3-d]pyrimidin-4-amine | LCMS: Calculated Exact Mass = 482.3; Found [M + H]$^+$ (ESI) = 483.4; $^1$H NMR (DMSO-d$_6$) δ ppm: 10.32 (br. s., 1H), 8.23 (s, 1H), 8.17 (br. s., 2H), 7.40-7.49 (m, 5H), 7.31 (br. s., 1H), 7.17 (t, J = 7.3 Hz, 1H), 7.09-7.12 (m, 5H), 5.00 (br. s., 1H), 3.70 (br. s., 2H), 3.50-3.58 (m, 4H), 2.54 (br. s., 2H), 2.41 (d, J = 18.5 Hz, 1H), 2.21 (br. s., 3H), 2.09 (br. s., 1H), 1.87-2.07 (m, 4H), 1.77 (br. s., 2H), 1.66 (br. s., 4H). |
| 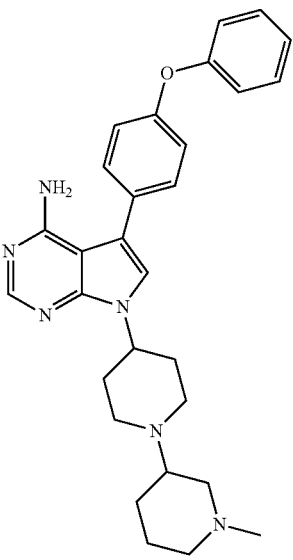 [SMILES: CN1CCCC(N2CCC(n3cc(-c4ccc(Oc5ccccc5)cc4)c4c(N)ncnc43)CC2)C1] | EXAMPLE 160<br>7-(1'-methyl-[1,3'-bipiperidin]-4-yl)-5-(4-phenoxyphenyl)-7H-pyrrolo [2,3-d] pyrimidin-4-amine | LC-MS: Calculated Exact Mass = 482.3, Found [M + H]$^+$ (ESI) = 483.3; $^1$H NMR (DMSO-d$_6$) δ ppm: 8.39 (s, 1H), 7.49 (d, J = 8.5 Hz, 2H), 7.43 (t, J = 7.8 Hz, 2H), 7.08-7.20 (m, 6H), 3.07 (br. s., 3H), 2.98 (br. s., 3H), 2.18 (br. s., 5H), 1.92-2.07 (m, 9H), 1.88 (br. s., 1H). |

Example 161

2-(4-(4-amino-5-(4-phenoxyphenyl)-7H-pyrrolo[2,3-d]pyrimidin-7-yl)piperidin-1-yl)propane-1,3-diol

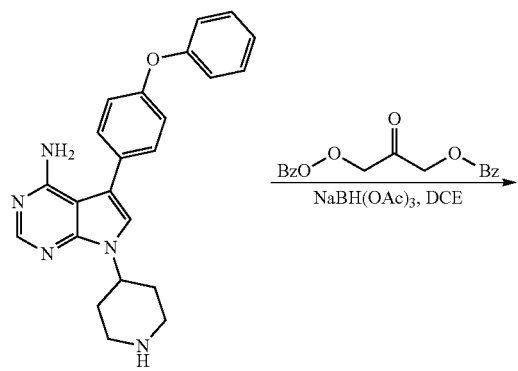

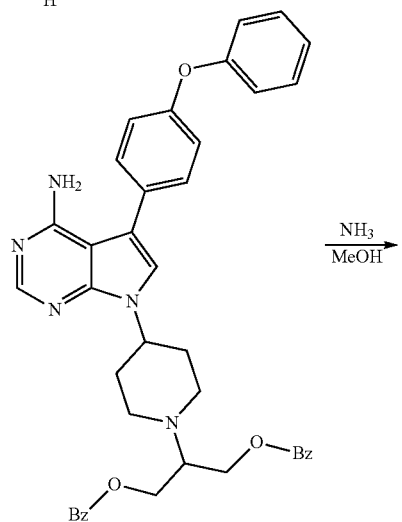

2-(4-(4-Amino-5-(4-phenoxyphenyl)-7H-pyrrolo[2,3-d]pyrimidin-7-yl)piperidin-1-yl)propane-1,3-diyl dibenzoate To a solution of 5-(4-phenoxyphenyl)-7-(piperidin-4-yl)-7H-pyrrolo[2,3-d]pyrimidin-4-amine (800 mg, 2.07 mmol) and 2-oxopropane-1,3-diyl dibenzoate (1.23 g, 4.15 mmol) in DCE (8 mL) was stirred at 50° C. under $N_2$ atmosphere for 2 hours. After it was cooled to room temperature, $NaBH(OAc)_3$ (1.3 g, 6.22 mmol) was added portion-wise, the mixture was stirred at room temperature overnight under $N_2$ atmosphere. The reaction was monitored via TLC and LCMS until complete consumption of starting material. It was then filtrated, the filtrate was added saturate $NaHCO_3$, extracted with DCM (30 mL×3). The organic layer was dried with anhydrous $Na_2SO_4$. Concentrated to obtained crude product. The crude was purified by flash column chromatography (2-5% MeOH in DCM) obtain product as a white solid (150 mg, 10.8%).

LCMS: Calculated Exact Mass=667.28; Found [M+H]$^+$ (ESI)=667.71.

2-(4-(4-Amino-5-(4-phenoxyphenyl)-7H-pyrrolo[2,3-d]pyrimidin-7-yl)piperidin-1-yl)propane-1,3-diol To a solution of 2-(4-(4-amino-5-(4-phenoxyphenyl)-7H-pyrrolo[2,3-d]pyrimidin-7-yl)piperidin-1-yl)propane-1,3-diyl dibenzoate (150 mg, 0.22 mmol) dissolved in 7.0 N $NH_3$/MeOH (10 mL) was stirred at 30° C. for 3 days. The reaction was monitored via TLC and LCMS until complete consumption of starting material. It was then concentrated and purified by flash column chromatography (5-10% MeOH in DCM) to obtain product as a white solid (75 mg, 72.5% yield). LCMS: Calculated Exact Mass=459.23; Found [M+H]$^+$ (ESI)=459.8; $^1$H NMR (DMSO-d$_6$) δ ppm: 8.13 (s, 1H), 7.38-7.49 (m, 5H), 7.13-7.19 (m, 1H), 7.06-7.12 (m, 4H), 6.12 (br. s., 1H), 4.55 (t, J=12.1 Hz, 1H), 4.29 (br. s., 2H), 3.43-3.57 (m, 4H), 2.97 (d, J=10.7 Hz, 2H), 2.67 (t, J=11.4 Hz, 2H), 2.55-2.62 (m, 1H), 1.98-2.06 (m, 2H), 1.87 (d, J=10.7 Hz, 2H).

Example 162

7-(1-(2-(aminomethyl)-1,3-dioxan-5-yl)piperidin-4-yl)-5-(4-phenoxyphenyl)-7H-pyrrolo[2,3-d]pyrimidin-4-amine

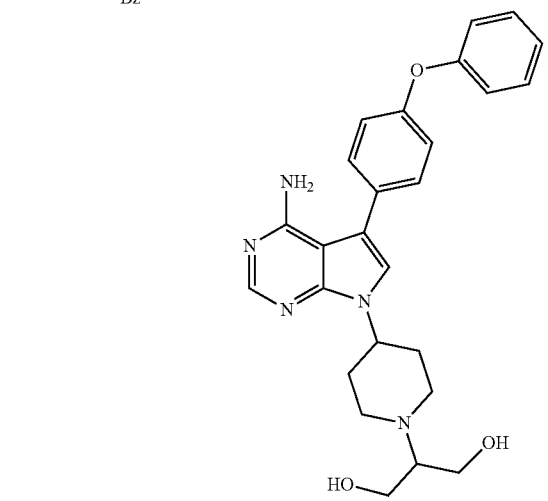

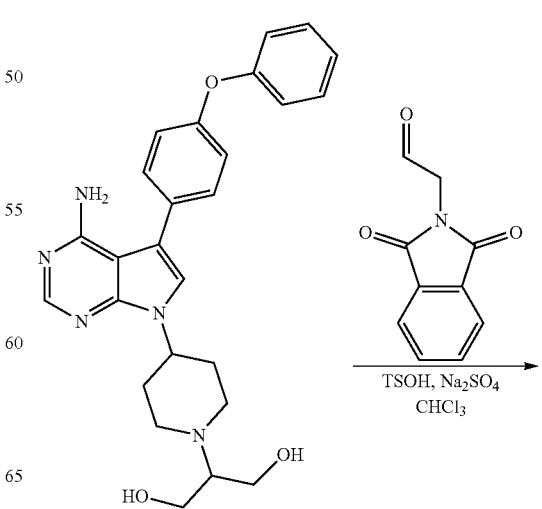

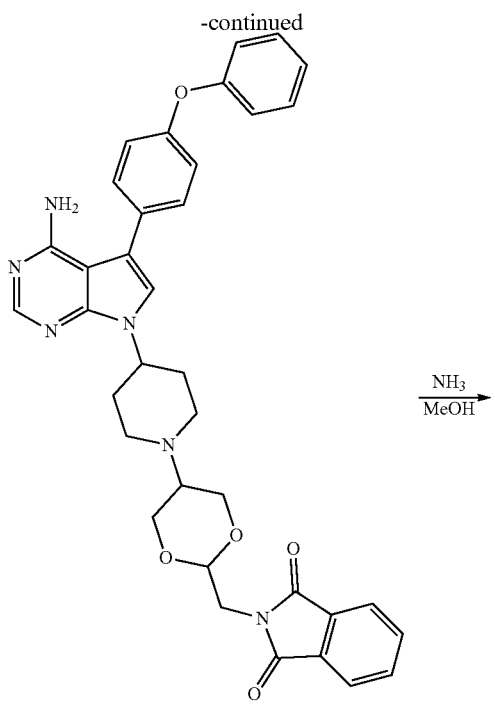

2-((5-(4-(4-Amino-5-(4-phenoxyphenyl)-7H-pyrrolo[2,3-d]pyrimidin-7-yl)piperidin-1-yl)-1,3-dioxan-2-yl)methyl)isoindoline-1,3-dione To a solution of 2-(4-(4-amino-5-(4-phenoxyphenyl)-7H-pyrrolo[2,3-d]pyrimidin-7-yl) piperidin-1-yl) propane-1,3-diol (100 mg, 0.218 mmol) and 2-(1,3-dioxoisoindolin-2-yl)acetaldehyde (411 mg, 2.17 mmol) in chloroform (5 mL) was added anhydrous $Na_2SO_4$ (927 mg, 6.53 mmol), and p-Toluenesulfonic acid monohydrate (414 mg, 2.17 mmol). The mixture was refluxed overnight. It was then cooled to room temperature and added saturated $NaHCO_3$, extracted with DCM (25 mL×3). The organic layer was concentrated to give a crude product. The crude was purified by flash column chromatography (3-7% MeOH in DCM) to obtain product as a white solid (30 mg, 21.8% yield). LCMS: Calculated Exact Mass=510.31; Found [M+H]$^+$ (ESI)=511.3.

7-(1-(2-(Aminomethyl)-1,3-dioxan-5-yl)piperidin-4-yl)-5-(4-phenoxyphenyl)-7H-pyrrolo[2,3-d]pyrimidin-4-amine To a solution of 2-((5-(4-(4-amino-5-(4-phenoxyphenyl)-7H-pyrrolo[2,3-d]pyrimidin-7-yl) piperidin-1-yl)-1,3-dioxan-2-yl)methyl)isoindoline-1,3-dione (30 mg, 0.048 mmol) in 7.0 N $NH_3$/MeOH (20 mL) was stirred at 30° C. overnight. The reaction was monitored via TLC and LCMS until complete consumption of starting material. It was then concentrated and prep-TLC (MeOH:DCM=40:3) to obtain product as a white solid (7 mg, 29% yield). LCMS: Calculated Exact Mass=500.25; Found [M+H]$^+$ (ESI)=500.81; $^1$H NMR (DMSO-$d_6$) δ ppm: 8.14 (s, 1H), 7.40-7.52 (m, 5H), 7.16 (t, J=7.3 Hz, 1H), 7.10 (t, J=6.9 Hz, 4H), 6.14 (br. s., 1H), 4.76 (d, J=5.5 Hz, 1H), 4.59 (br. s., 1H), 4.13 (br. s., 1H), 3.70-3.81 (m, 1H), 3.58 (d, J=6.7 Hz, 2H), 3.49 (d, J=11.9 Hz, 1H), 3.17 (s, 3H), 3.04 (d, J=10.4 Hz, 1H), 2.89-2.98 (m, 2H), 2.57-2.73 (m, 1H), 1.88-2.10 (m, 4H), 1.75 (s, 1H).

4-(4-Amino-5-(2-fluoro-4-phenoxyphenyl)imidazo[5,1-f][1,2,4] triazin-7-yl)cyclohexanone

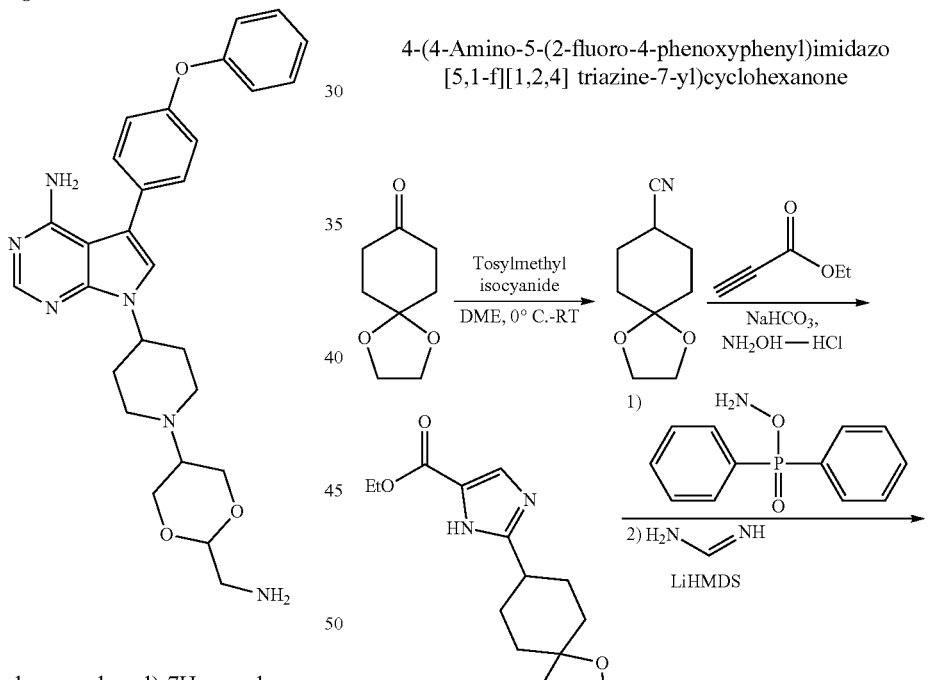

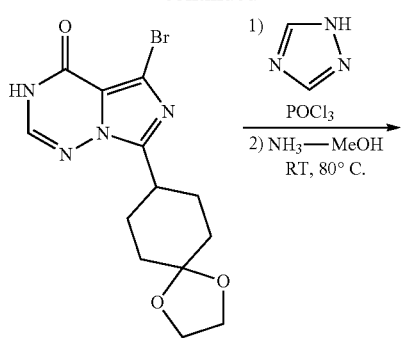

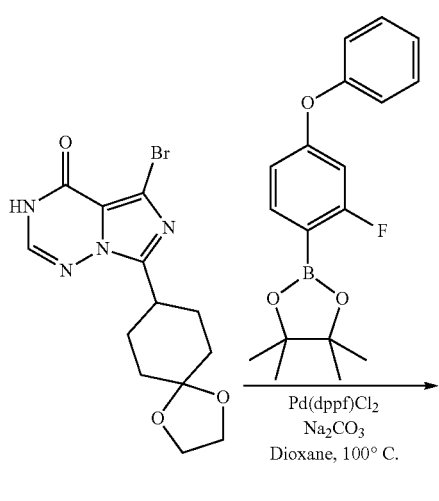

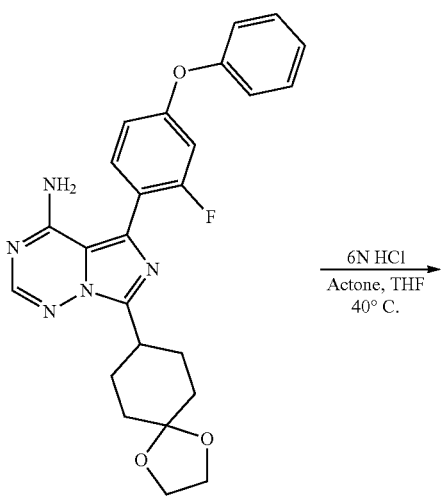

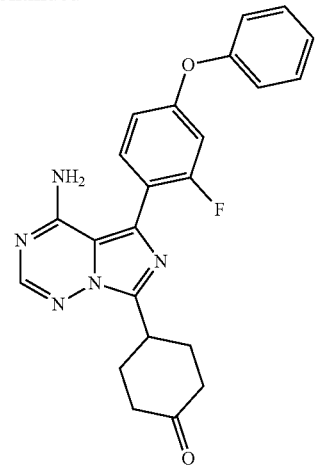

Common intermediate

Ethyl 2-(1,4-dioxaspiro[4.5]decan-8-yl)-1H-imidazole-5-carboxylate

To a solution of NH$_2$OH—HCl (447 g, 6.42 mol) in water (700 mL) was added NaHCO$_3$ (787 g, 9.41 mol) portionwise. Followed by 1,4-dioxaspiro[4.5]decane-8-carbonitrile (716 g, 4.28 mol) and EtOH (7 L). The mixture was stirred at room temperature for 1 hour before it was heated to 80° C. for 22 hours. It was then cooled to room temperature and ethyl propiolate (660 g, 6.73 mol) was added. The reaction was heated to 80° C. for 7.5 hours. After it was cooled to room temperature, the reaction was filtrated and the filtrate was concentrated and extracted with EtOAc. The organic layer was washed with brine and concentrated to afford orange color solid (1.4 kg). Diphenyl ether (7 kg) was added and the reaction was heated to 200° C. for 2 hours. The mixture was cooled to room temperature and PE (21 L) was added. After filtration it was obtained black color crude product (2 kg) that was purified by flash column chromatography (EtOAc 100%) to afford the product as a yellow solid (850 g, 62% yield). $^1$H NMR (400 MHz, CDCl$_3$) δ ppm: 7.63 (s, 1H), 4.34 (q, J=7.1 Hz, 2H), 3.90-4.02 (m, 5H), 2.89 (br. s., 1H), 2.09 (dd, J=13.2, 3.2 Hz, 2H), 1.86 (d, J=12.3 Hz, 3H), 1.63-1.71 (m, 2H), 1.36 (t, J=7.1 Hz, 3H).

7-(1,4-Dioxaspiro[4.5]decan-8-yl)imidazo[5,1-f][1,2,4]triazin-4 (3H)-one

To an ice bath cooled solution of ethyl 2-(1,4-dioxaspiro[4.5]decan-8-yl)-1H-imidazole-5-carboxylate (312 g, 1.11 mol) in DMF (5 L) was added LiHMDS (1.0 M, 1.11 L, 1.11 mol) dropwise. The mixture was stirred for 2 hours before diphenyl aminooxyphosphonate (260 g, 1.11 mol) was added. The reaction mixture was stirred at room temperature overnight. DCM was added and the mixture was filtrated. The filtrate was concentrated partially to afford a DMF solution. Formamidine acetate (1.16 kg, 11.1 mol) and ethanol (5 L) was added. The reaction was heated to 85° C. under N$_2$ atmosphere 2 days. The reaction was heated to 100° C. for 3.5 hours. The mixture was concentrated to obtain 1 kg crude product that was purified by flash column chromatography (MeOH in DCM, 0 to 10% gradient) to obtain a crude product as a pale yellow wax (255 g) that was used without further purification. LC-MS: Calculated Exact Mass: 276.12; Found [M+H]+ (ESI)=277.1.

5-Bromo-7-(1,4-dioxaspiro[4.5]decan-8-yl)imidazo[5,1-f][1,2,4]triazin-4 (3H)-one To an ice bath cooled solution of 7-(1,4-dioxaspiro[4.5]decan-8-yl)imidazo[5,1-f] [1,2,4]triazin-4 (3H)-one (100 g, 0.362 mol) in DMF (1.25 L) was added NBS (77.3 g, 0.434 mol) portion-wise. The reaction mixture was stirred at room temperature overnight. The reaction was monitored via TLC and LCMS until complete consumption of the starting material. The reaction was quenched by adding 1 L water. The solid was filtrated and washed with water (200 mL×3). The white solid was dried under reduced pressure to afford a white powder product (98 g, 76.2% yield). LC-MS: Calculated Exact Mass: 354.03; Found [M+H]+ (ESI)= 355.13; $^1$H NMR (400 MHz, DMSO-$d_6$) δ ppm: 11.85 (br. s., 1H), 7.90 (s, 1H), 3.83-3.92 (m, 4H), 3.17 (ddd, J=10.8, 6.6, 4.3 Hz, 1H), 1.81-1.90 (m, 3H), 1.73-1.81 (m, 3H), 1.56-1.65 (m, 2H)

5-Bromo-7-(1,4-dioxaspiro[4.5]decan-8-yl)imidazo[5,1-f][1,2,4]triazin-4-amine To an ice bath cooled suspension of 1H-1,2,4-triazole (97 g, 1.4 mol) in ACN (1.5 L) was added POCl$_3$ (64 g, 0.42 mol) dropwise, Then Et$_3$N (170 g, 1.68 mol) and 5-bromo-7-(1,4-dioxaspiro[4.5]decan-8-yl) imidazo[5,1-f] [1,2,4]triazin-4 (3H)-one (50 g, 0.14 mol) was added at room temperature. The reaction was stirred at room temperature for 6 hours. The solvent was removed under reduced pressure. NH$_3$ in MeOH (7.0 N, 1 L) was added and the reaction was heated to 80° C. for 1 hour, and then at room temperature overnight. It was filtrated and the residue was suspended in water and aqueous NaOH. After filtration, it was obtained a light yellow solid product (141 g, 82% yield). LC-MS: Calculated Exact Mass: 353.05; Found [M+H]+ (ESI)=354.2.

5-(2-Fluoro-4-phenoxyphenyl)-7-(1,4-dioxaspiro[4.5]decan-8-yl)imidazo[5,1-f][1,2,4]triazin-4-amine To a mixture of 5-bromo-7-(1,4-dioxaspiro[4.5]decan-8-yl)imidazo[5,1-f][1,2,4]triazin-4-amine (40 g, 0.11 mol), 2-(2-fluoro-4-phenoxyphenyl)-4,4,5,5-tetramethyl-1,3,2-dioxaborolane (48 g, 0.127 mol), Pd(dppf)Cl$_2$ (8 g, m 0.011 mol), Na$_2$CO$_3$ (35 g, 0.33 mol), 700 mL of 1,4-Dioxane (contain 10% water) was heated to 100° C. overnight. The mixture was cooled to the room temperature, filtrated and concentrated, the residue was extracted with DCM and H$_2$O (1 L), dried and concentrated. The crude was purified by flash column chromatography (MeOH in DCM, 0 to 2% gradient) to obtain the yellow solid product (42 g, 81% yield).
LC-MS: Calculated Exact Mass: 461.19; Found [M+H]+ (ESI)=462.1.

4-(4-Amino-5-(2-fluoro-4-phenoxyphenyl)imidazo[5,1-f][1,2,4]triazin-7-yl)cyclohexanone To a solution of 5-(2-fluoro-4-phenoxyphenyl)-7-(1,4-dioxaspiro[4.5]decan-8-yl)imidazo[5,1-f][1,2,4]triazin-4-amine (42 g, 0.091 mol) in acetone (400 mL) and THF (800 mL) was added 6 N HCl (400 mL). The reaction was stirred at 40° C. for 5 hours. The mixture was cooled to room temperature and neutralized with aqueous NaOH. After concentration, the residue was extracted with DCM (300 mL×3). The organic layer was washed with water, dried and concentrated. The crude was purified by flash column chromatography to obtain yellow solid product (14 g, 36.8% yield). LC-MS: Calculated Exact Mass: 417.16; Found [M+H]+ (ESI)=418.31.

Example 163

5-(2-Fluoro-4-phenoxyphenyl)-7-((trans)-4-(4-methylpiperazin-1-yl)cyclohexyl)imidazo[5,1-f][1,2,4]triazin-4-amine and

Example 164

5-(2-Fluoro-4-phenoxyphenyl)-7-((cis)-4-(4-methylpiperazin-1-yl)cyclohexyl)imidazo[5,1-f][1,2,4]triazin-4-amine

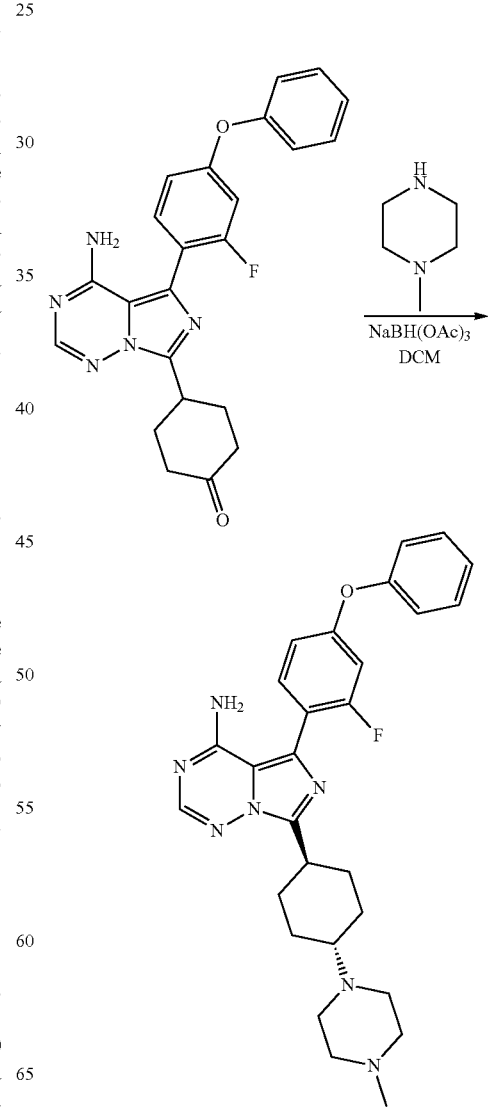

289
-continued

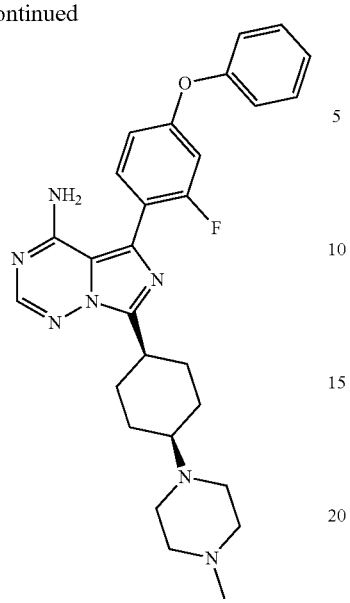

To a round bottom flask was added 4-(4-amino-5-(2-fluoro-4-phenoxyphenyl)imidazo[5,1-f][1,2,4] triazin-7-yl)cyclohexanone (150 mg, 0.36 mmol), 1-methylpiperazine (180 mg, 1.8 mmol), DCM (30 mL) and 4 Å molecular sieve. The mixture was stirred at room temperature for 15 min, NaBH(OAc)$_3$ (156 mg, 0.72 mol) was added portion-wise. The reaction was stirred at room temperature for 3 hours. Additional NaBH(AcO)$_3$ (156 mg, 0.72 mol) was added portion-wise. The reaction was stirred at room temperature for 3.5 hours. The reaction was quenched with saturated NaHCO$_3$aq. It was then filtrated and extracted with DCM. The organic layer was concentration and the crude was purified by flash column chromatography (MeOH in DCM, 0 to 10%) to obtain 5-(2-fluoro-4-phenoxyphenyl)-7-((trans)-4-(4-methylpiperazin-1-yl)cyclohexyl)imidazo[5,1-f][1,2,4]triazin-4-amine (10 mg, 5.5% yield) as a light yellow solid.

LC-MS: Calculated Exact Mass: 501.27; Found [M+H]$^+$ (ESI)=502.2; $^1$H NMR (DMSO-d$_6$) δ ppm: 7.89 (s, 1H), 7.41-7.53 (m, 3H), 7.15-7.25 (m, 3H), 6.97 (dd, J=11.1, 2.4 Hz, 1H), 6.91 (dd, J=8.5, 2.4 Hz, 1H), 3.12-3.20 (m, 1H), 2.63-2.78 (m, 2H), 2.60 (br. s., 2H), 2.53-2.57 (m, 1H), 2.21-2.44 (m, 5H), 1.94-2.16 (m, 4H), 1.91 (br. s., 2H), 1.59-1.74 (m, 2H), 1.42 (br. s., 2H), 1.34 (d, J=7.3 Hz, 1H); and 5-(2-fluoro-4-phenoxyphenyl)-7-((cis)-4-(4-methylpiperazin-1-yl)cyclohexyl)imidazo[5,1-f][1,2,4]triazin-4-amine (40 mg, 22% yield); $^1$H NMR (400 MHz, DMSO) δ 9.79 (s, 1H), 8.16 (s, 1H), 7.89 (s, 1H), 7.54-7.43 (m, 3H), 7.23 (t, J=7.4 Hz, 1H), 7.20-7.15 (m, 2H), 6.96 (ddd, J=10.8, 9.8, 2.3 Hz, 2H), 3.42 (s, 1H), 2.99 (s, 4H), 2.67 (s, 3H), 2.27 (d, J=47.5 Hz, 4H), 2.13-1.93 (m, 4H), 1.72 (s, 2H), 1.59 (s, 2H).

290
Example 165

5-(2-fluoro-4-phenoxyphenyl)-7-((trans)-4-((S)-3-methylpiperazin-1-yl)cyclohexyl)imidazo[5,1-f][1,2,4]triazin-4-amine and Example 166

5-(2-fluoro-4-phenoxyphenyl)-7-((cis)-4-((S)-3-methylpiperazin-1-yl)cyclohexyl)imidazo[5,1-f][1,2,4]triazin-4-amine

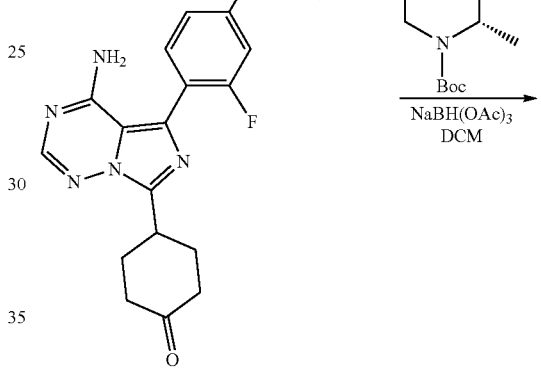

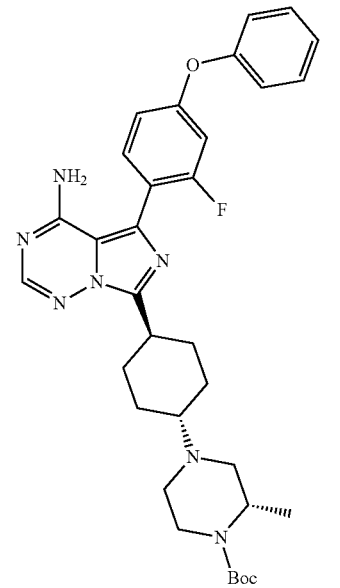

-continued

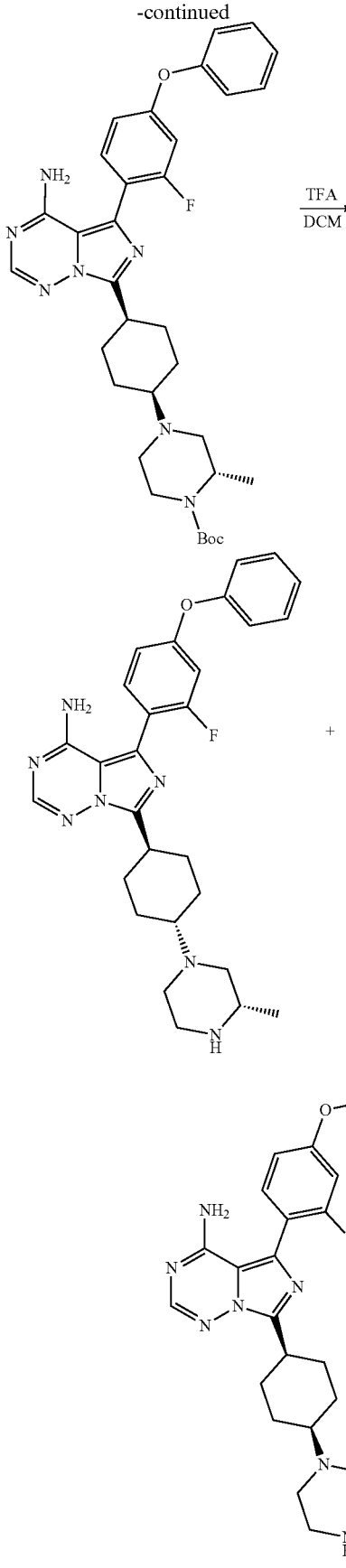

(S)-tert-butyl 4-((trans)-4-(4-amino-5-(2-fluoro-4-phenoxyphenyl)imidazo[5,1-f][1,2,4]triazine-7-yl)cyclohexyl)-2-methylpiperazine-1-carboxylate and (S)-tert-butyl 4-((cis)-4-(4-amino-5-(2-fluoro-4-phenoxyphenyl)imidazo[5,1-f][1,2,4]triazine-7-yl)cyclohexyl)-2-methylpiperazine-1-carboxylate To a mixture of 4-(4-amino-5-(2-fluoro-4-phenoxyphenyl)imidazo[5,1-f][1,2,4]triazin-7-yl) cyclohexanone (250 mg, 0.60 mmol) and tert-butyl (S)-2-methylpiperazine-1-carboxylate (250 mg, 1.2 mmol) in DCM (30 mL) was added 4 Å molecular sieve. The mixture was stirred at room temperature for 2 hours before NaBH(OAc)$_3$ (31.67 g, 0.50 mol) was added portion-wise. The reaction was stirred at room temperature overnight. The reaction was quenched by saturated NaHCO$_3$ aq. It was then filtrated and extracted with DCM. The organic layer was collected and concentrated. The crude was purified by flash column chromatography (MeOH in DCM, 0 to 5% gradient) to obtain a mixture of two product as a white solid (300 mg, 83% yield).

LC-MS: Calculated Exact Mass: 601.32; Found [M+H]$^+$ (ESI)=602.1.

5-(2-fluoro-4-phenoxyphenyl)-7-((trans)-4-((S)-3-methylpiperazin-1-yl)cyclohexyl)imidazo[5,1-f][1,2,4]triazin-4-amine and 5-(2-fluoro-4-phenoxyphenyl)-7-((cis)-4-((S)-3-methylpiperazin-1-yl)cyclohexyl)imidazo[5,1-f][1,2,4]triazin-4-amine To a solution of (S)-tert-butyl 4-(4-(4-amino-5-(2-fluoro-4-phenoxyphenyl)imidazo[5,1-f][1,2,4]triazin-7-yl)cyclohexyl)-2-methylpiperazine-1-carboxylate (300 mg, 0.50 mmol) a in DCM (10 mL) was added TFA (2 mL). The mixture was stirred at room temperature for 3 hours, after which it was concentrated. Saturated NaHCO$_3$ aq. and DCM was added and extracted. The organic layer was collected and dried and concentrated. The crude was purified by flash column chromatography (MeOH in DCM, 0 to 10% gradient) to obtain 5-(2-fluoro-4-phenoxyphenyl)-7-((trans)-4-((S)-3-methylpiperazin-1-yl) cyclohexyl) imidazo[5,1-f][1,2,4]triazin-4-amine (25 mg, 10% yield). LC-MS: Calculated Exact Mass: 501.27; Found [M+H]$^+$ (ESI)=502.1; $^1$H NMR (400 MHz, DMSO-d$_6$) δ ppm: 8.31 (br. s., 1H), 7.89 (s, 1H), 7.42-7.52 (m, 3H), 7.15-7.26 (m, 3H), 6.98 (dd, J=11.1, 2.4 Hz, 1H), 6.92 (dd, J=8.5, 2.3 Hz, 1H), 3.18 (d, J=12.5 Hz, 3H), 2.95 (br. s., 3H), 2.20-2.35 (m, 2H), 2.08 (d, J=12.9 Hz, 2H), 1.89 (d, J=9.6 Hz, 2H), 1.61-1.75 (m, 2H), 1.43 (d, J=12.0 Hz, 2H), 1.19 (d, J=6.5 Hz, 3H); and 5-(2-fluoro-4-phenoxyphenyl)-7-((cis)-4-((S)-3-methylpiperazin-1-yl)cyclohexyl)imidazo[5,1-f][1,2,4]triazin-4-amine (150 mg, 60% yield): $^1$H NMR (400 MHz, DMSO) δ 8.74 (s, 1H), 8.26 (s, 1H), 7.89 (s, 1H), 7.54-7.42 (m, 3H), 7.23 (t, J=7.4 Hz, 1H), 7.20-7.15 (m, 2H), 6.96 (ddd, J=10.9, 9.8, 2.4 Hz, 2H), 5.76 (s, 1H), 4.09 (s, 1H), 3.44 (s, 1H), 3.17 (s, 3H), 3.07-2.90 (m, 3H), 2.25 (s, 1H), 2.05 (d, J=11.4 Hz, 2H), 1.92 (s, 2H), 1.72 (s, 2H), 1.59 (s, 2H), 1.18 (d, J=6.5 Hz, 3H).

4-(4-amino-5-(4-phenoxyphenyl)pyrrolo[2,1-f][1,2,4]triazin-7-yl)cyclohexan-1-one

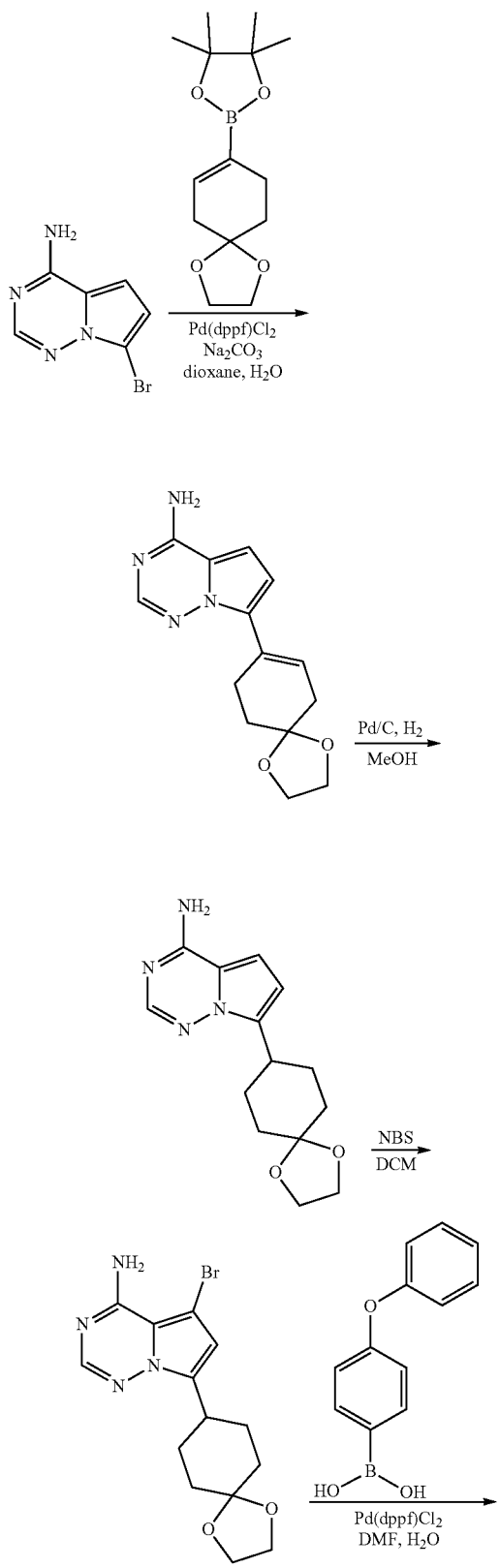

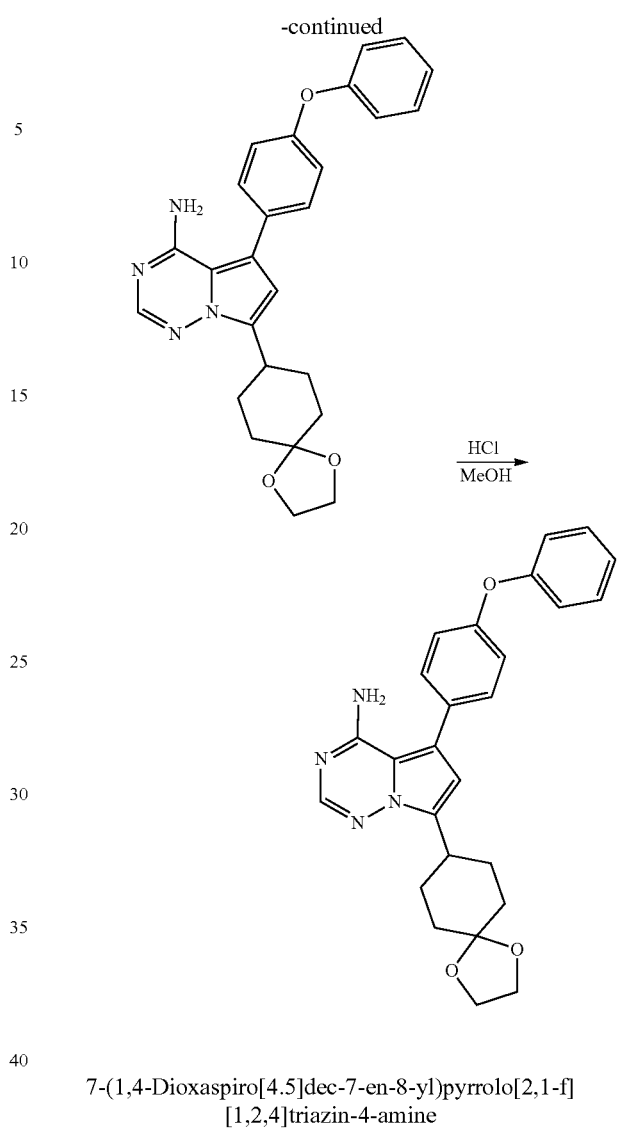

7-(1,4-Dioxaspiro[4.5]dec-7-en-8-yl)pyrrolo[2,1-f][1,2,4]triazin-4-amine

To a mixture of 7-bromopyrrolo[2,1-f][1,2,4]triazin-4-amine (0.6 g, 2.82 mmol), 4,4,5,5-tetramethyl-2-(1,4-dioxaspiro[4.5]dec-7-en-8-yl)-1,3,2-dioxaborolane (0.9 g, 3.38 mmol), Pd(dppf)Cl$_2$ (0.2 g, 0.28 mmol), Na$_2$CO$_3$ (0.9 g, 8.46 mmol) in 1,4 Dioxane with 10% water (50 mL). The mixture was stirred at 100° C. overnight. The mixture was cooled to the room temperature, filtrated and concentrated the filtrate. The crude was purified by flash column chromatography (PE:EtOAc=1:1) to obtain product (400 mg, 52% yield) as a yellow solid.

LCMS: Calculated Exact Mass=272.1; Found [M+H]$^+$ (ESI)=273.0.

7-(1,4-Dioxaspiro[4.5]decan-8-yl)pyrrolo[2,1-f][1,2,4]triazin-4-amine

To a mixture of 7-(1,4-dioxaspiro[4.5]dec-7-en-8-yl)pyrrolo[2,1-f][1,2,4]triazin-4-amine (400 mg, 1.47 mmol) in MeOH/EtOAc (100 mL) was added Pd (80 mg, 10% in activity carbon). The mixture was stirred at room temperature under H$_2$ atmosphere overnight. Then filtrated, the filtrate was concentrated to obtain product (290 mg, 72% yield) as a yellow solid. LCMS: Calculated Exact Mass=274.1; Found [M+H]$^+$ (ESI)=275.2.

5-Bromo-7-(1,4-dioxaspiro[4.5]decan-8-yl)pyrrolo[2,1-f][1,2,4]triazin-4-amine To a solution of 7-(1,4-dioxaspiro[4.5]decan-8-yl)pyrrolo[2,1-f][1,2,4]triazin-4-amine (290 mg, 1.06 mmol) in DCM (100 mL) was added NBS (226 mg, 1.27 mmol). The mixture was stirred at room temperature for 2.5 hours. The mixture was quenched with saturated NaHCO$_3$ aq., extracted with DCM, dried and concentrated. The residue was purified by flash column chromatography (PE:EtOAc=2:1) to obtain the product (250 mg, 67%) as a light yellow solid. LCMS: Calculated Exact Mass=352.0; Found [M+H]$^+$ (ESI)=353.1.

5-(4-Phenoxyphenyl)-7-(1,4-dioxaspiro[4.5]decan-8-yl)pyrrolo[2,1-f][1,2,4]triazin-4-amine To a mixture of 5-bromo-7-(1,4-dioxaspiro[4.5]decan-8-yl)pyrrolo[2,1-f][1,2,4]triazin-4-amine (230 mg, 0.65 mmol), (4-phenoxyphenyl)boronic acid (418 mg, 1.95 mmol), Pd(dppf)Cl$_2$ (95 mg, 0.13 mmol), Na$_2$CO$_3$ (276 mg, 2.6 mmol) in 1,4 Dioxane with 10% water (20 mL). The mixture was stirred at 100° C. overnight. The mixture was cooled to the room temperature, filtrated and concentrated the filtrate. The crude was purified by flash column chromatography (PE:EtOAc=1:1) to obtain product (125 mg, 42% yield) as a yellow solid. LCMS: Calculated Exact Mass=442.2; Found [M+H]$^+$ (ESI)=443.1.

4-(4-Amino-5-(4-phenoxyphenyl)pyrrolo[2,1-f][1,2,4]triazin-7-yl)cyclohexan-1-one To a mixture of 5-(4-phenoxyphenyl)-7-(1,4-dioxaspiro[4.5]decan-8-yl)pyrrolo[2,1-f][1,2,4]triazine-4-amine (120 mg, 0.27 mmol) in THF (2 mL), acetone (5 mL) and 6.0 N HCl (1 mL) was stirred at room temperature for 4 hours. Then quenched with NaOH aq. and extracted with DCM, dried, concentrated to obtain crude product (95 mg, 88% yield) as light yellow solid.

LCMS: Calculated Exact Mass=398.2; Found [M+H]$^+$ (ESI)=399.1.

4-(4-Amino-5-bromopyrrolo[2,1-f][1,2,4]triazin-7-yl)cyclohexanone

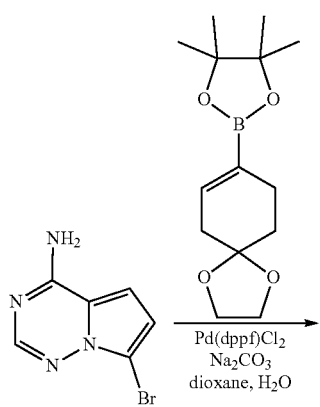

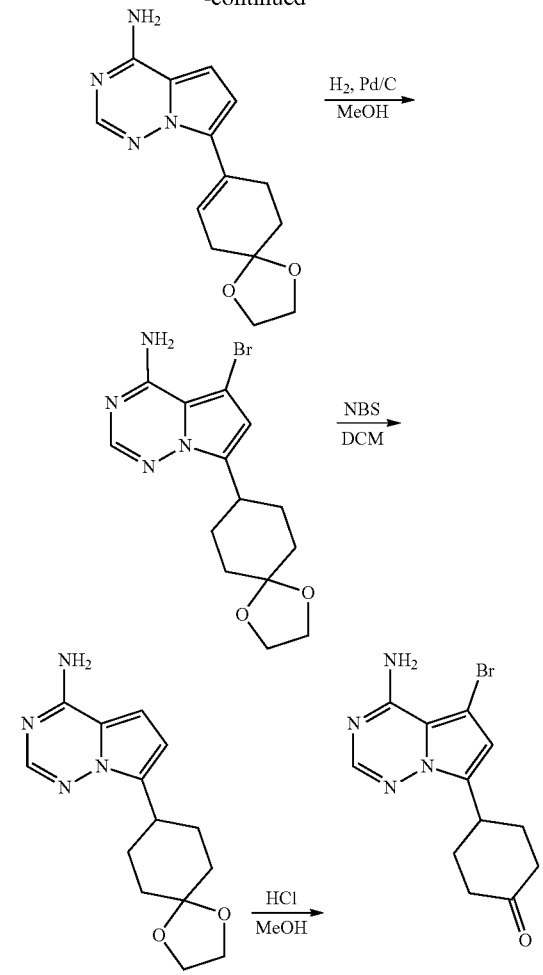

7-(1,4-Dioxaspiro[4.5]dec-7-en-8-yl)pyrrolo[2,1-f][1,2,4]triazin-4-amine

A mixture of 7-bromopyrrolo[2,1-f][1,2,4]triazin-4-amine (1.6 g, 7.5 mmol), 4,4,5,5-tetramethyl-2-(1,4-dioxaspiro[4.5]dec-7-en-8-yl)-1,3,2-dioxaborolane (2.4 g, 9.0 mmol), Pd(dppf)Cl$_2$ (550 mg, 0.75 mmol) and Na$_2$CO$_3$ (2.4 g, 22.5 mmol) in dioxane-H$_2$O (50 mL-5 mL) was heated at 100° C. under Ar atmosphere overnight. After cooled to the room temperature, the reaction mixture was concentrated and extracted with DCM (200 mL×4). The organic layers were concentrated. The crude was purified by flash column chromatography (PE:EA=1:1) to afford the product (900 mg, 36.7% yield). LCMS: Calculated Exact Mass=272.1; Found [M+H]$^+$ (ESI)=272.8.

7-(1,4-Dioxaspiro[4.5]decan-8-yl)pyrrolo[2,1-f][1,2,4]triazin-4-amine

A mixture of 7-(1,4-dioxaspiro[4.5]dec-7-en-8-yl)pyrrolo[2,1-f][1,2,4]triazin-4-amine (900 mg, 3.3 mmol), and Pd/C (180 mg) in MeOH-EtOAc (200 mL) was hydrogenated under balloon for overnight. The reaction mixture was filtered through celite, washed with (DCM/MeOH=10/1). The filtrate was concentrated to afford the product as light yellow solid (900 mg, 99% yield).

LCMS: Calculated Exact Mass=274.1; Found [M+H]+ (ESI)=274.8.

5-Bromo-7-(1,4-dioxaspiro[4.5]decan-8-yl)pyrrolo [2,1-f][1,2,4]triazin-4-amine

A mixture of 7-(1,4-dioxaspiro[4.5]decan-8-yl)pyrrolo[2,1-f][1,2,4]triazin-4-amine (900 mg, 3.3 mmol) in DCM (200 mL) was added NBS (700 mg, 3.9 mmol). The mixture was stirred at room temperature for 2 hours. The reaction mixture was quenched with NaHCO₃, extracted with DCM, dried and concentrated to afford a crude product (1.15 g) that was used without further purification. LCMS: Calculated Exact Mass=452.1; Found [M+H]+ (ESI)=452.8.

4-(4-Amino-5-bromopyrrolo[2,1-f][1,2,4]triazin-7-yl)cyclohexanone

To a suspension of 5-bromo-7-(1,4-dioxaspiro[4.5]decan-8-yl)pyrrolo[2,1-f] [1,2,4]triazine-4-amine (1.1 g, 3.1 mol) in THF (25 mL) and acetone (25 mL) was added 6N HCl (10 mL). The reaction was heated at 50° C. for 2 hours. It was neutralized with NaHCO₃aq., extracted with DCM, dried and concentrated. The reside was purified by flash column chromatography (PE:EA=1:1) to afford product (600 mg, 62.6% yield). LCMS: Calculated Exact Mass=308.0; Found [M+H]+ (ESI)=308.8.

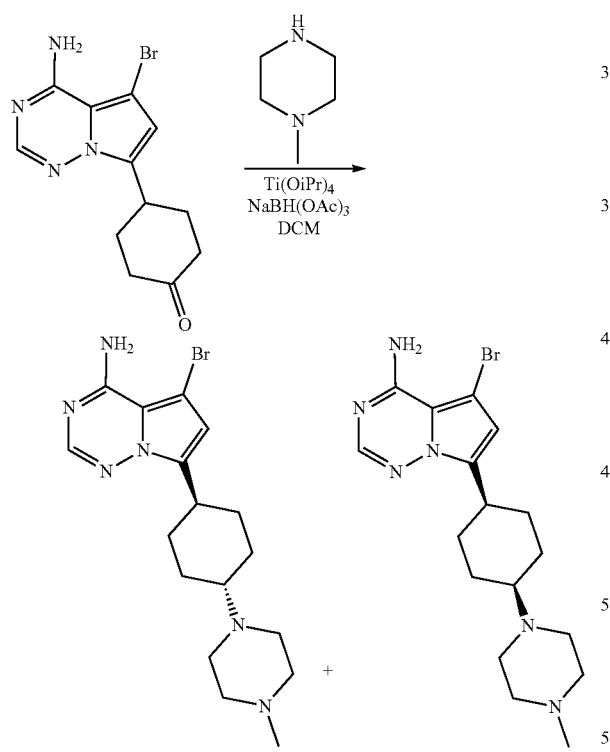

5-Bromo-7-((trans)-4-(4-methylpiperazin-1-yl)cyclohexyl)pyrrolo[2,1-f][1,2,4]triazin-4-amine and 5-Bromo-7-((cis)-4-(4-methylpiperazin-1-yl)cyclohexyl)pyrrolo[2,1-f][1,2,4]triazin-4-amine A mixture of 4-(4-amino-5-bromopyrrolo[2,1-f][1,2,4]triazin-7-yl)cyclohexanone (200 mg, 0.67 mmol), 1-methylpiperazine (134 mg, 1.34 mmol), titanium tetraisopropanolate (758 mg, 2.67 mmol) in DCM (30 mL) was stirred at room temperature. After 2 hours stirring, sodium tris(acetoxy)borohydride (560 mg, 2.67 mmol) was added. It was stirred at room temperature for 16 hours before it was diluted with DCM. Then NaHCO₃ solution was added. The mixture was filtered. The organic layer was dried and concentrated in vacuo. The residue was purified by flash column chromatography (DCM:MeOH=10:1) to afford 5-bromo-7-((cis)-4-(4-methylpiperazin-1-yl)cyclohexyl)pyrrolo[2,1-f][1,2,4] triazin-4-amine as a white solid (80 mg, 30% yield) and 5-bromo-7-((trans)-4-(4-methylpiperazin-1-yl) cyclohexyl)pyrrolo[2,1-f][1,2,4]triazin-4-amine as a light yellow solid (60 mg, 22% yield).

4-(4-Amino-5-(4-phenoxyphenyl)pyrrolo[2,1-f][1,2,4]triazin-7-yl)cyclohexanone

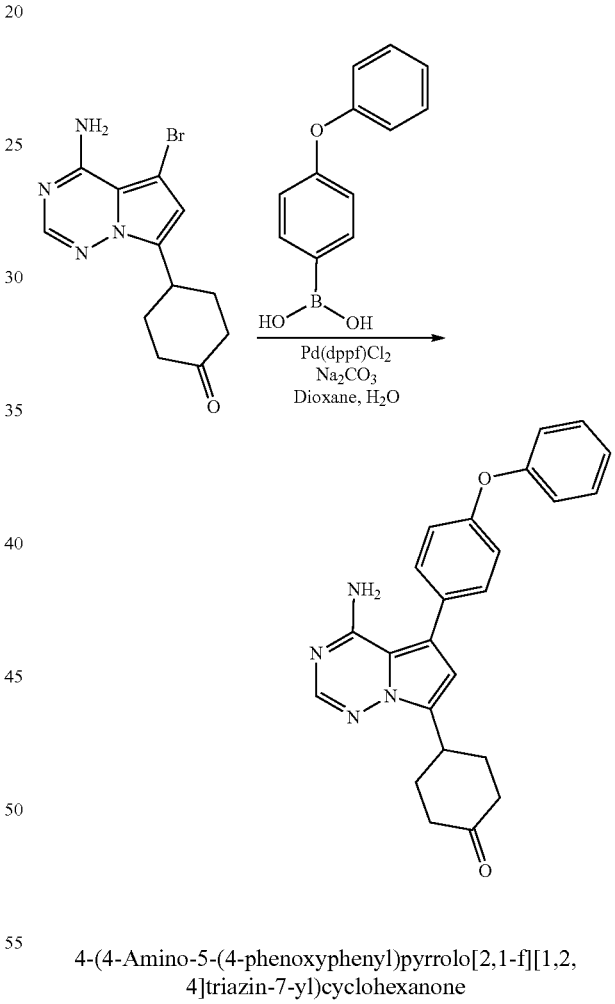

4-(4-Amino-5-(4-phenoxyphenyl)pyrrolo[2,1-f][1,2,4]triazin-7-yl)cyclohexanone

A mixture of tert-butyl 4-(4-amino-5-bromopyrrolo[2,1-f][1,2,4]triazin-7-yl) cyclohexanone (60 mg, 0.19 mmol), (4-phenoxyphenyl)boronic acid (82 g, 0.38 mmol), Pd(dppf)Cl₂ (14 mg, 0.019 mmol) and Na₂CO₃ (41 mg, 0.38 mmol) in dioxane-H₂O (10 mL-1 mL) was heated at 85° C. under Ar atmosphere for 2 hours. After cooled to room temperature, the reaction mixture was concentrated and extracted with DCM (50 mL×4). The organic layers were concentrated and purified by flash column chromatography (PE:EA=6:1)

to afford the product as a light yellow solid (60 mg, 79% yield). LCMS: Calculated Exact Mass=398.1; Found [M+H]+ (ESI)=398.9.

Example 167

7-((cis)-4-(4-Methylpiperazin-1-yl)cyclohexyl)-5-(4-phenoxyphenyl)pyrrolo[2,1-f][1,2,4]triazin-4-amine and Example 168

7-((trans)-4-(4-Methylpiperazin-1-yl)cyclohexyl)-5-(4-phenoxyphenyl)pyrrolo[2,1-f][1,2,4]triazin-4-amine

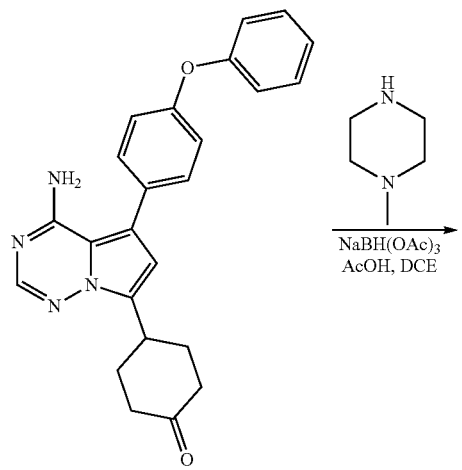

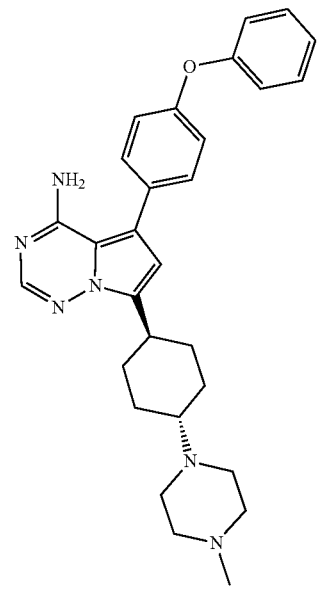

To a mixture of 4-(4-amino-5-(4-phenoxyphenyl)pyrrolo[2,1-f][1,2,4]triazin-7-yl)cyclohexan-1-one (90 mg, 0.22 mmol), 1-methylpiperazine (110 mg, 1.1 mmol) in 1,2-dichloroethane (5 mL) with AcOH (2 drops) was stirred at room temperature under $N_2$ atmosphere for 1 hours. Then $NaBH(OAc)_3$ (370 mg, 1.76 mmol) was added portion-wise. The mixture was stirred at room temperature under $N_2$ atmosphere for 3 hours. The reaction was monitored via TLC and LCMS until complete consumption of starting material. It was then filtrated and concentrated, the crude was purified via flash (1-10% MeOH in DCM) to obtain 7-((cis)-4-(4-methylpiperazin-1-yl)cyclohexyl)-5-(4-phenoxyphenyl)pyrrolo[2,1-f][1,2,4]triazin-4-amine (28 mg, 26% yield) as a colorless solid. LCMS: Calculated Exact Mass=442.2; Found [M+H]+ (ESI)=443.1; $^1$H NMR (DMSO-d6) δ 7.89 (s, 1H), 7.38-7.51 (m, 4H), 7.17 (t, J=7.3 Hz, 1H), 7.10 (dd, J=7.9, 3.7 Hz, 4H), 6.54 (br. s., 1H), 2.67 (br. s., 3H), 2.32 (br.s., 5H), 1.88 (br. s., 5H), 1.75 (br. s., 3H), 1.58 (br. s., 2H); and 7-((trans)-4-(4-methylpiperazin-1-yl)cyclohexyl)-5-(4-phenoxyphenyl)pyrrolo[2,1-f][1,2,4]triazin-4-amine (25 mg, 23% yield) as a colorless solid.

LCMS: Calculated Exact Mass=442.2; Found [M+H]+ (ESI)=443.1; $^1$H NMR (DMSO-d6) δ 7.89 (s, 1H), 7.39-7.47 (m, 4H), 7.17 (t, J=7.3 Hz, 1H), 7.09 (t, J=8.4 Hz, 4H), 6.50 (s, 1H), 3.04 (d, J=7.9 Hz, 1H), 2.58 (br. s., 3H), 2.33 (br. s., 4H), 2.18-2.28 (m, 4H), 2.13 (d, J=11.6 Hz, 3H), 1.92 (br. s., 2H), 1.37-1.56 (m, 4H).

301

7-((trans)-4-((S)-3-Methylpiperazin-1-yl)cyclohexyl)-5-(4-phenoxyphenyl)pyrrolo[2,1-f][1,2,4]triazin-4-amine

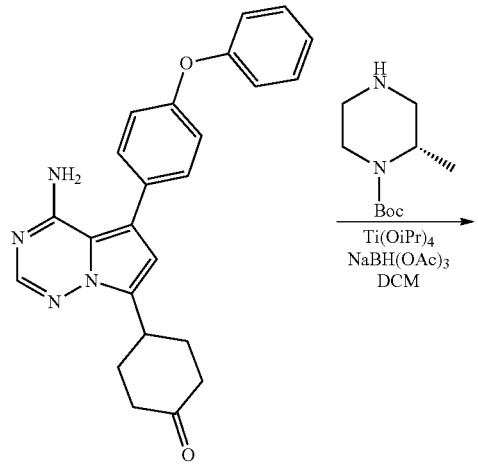

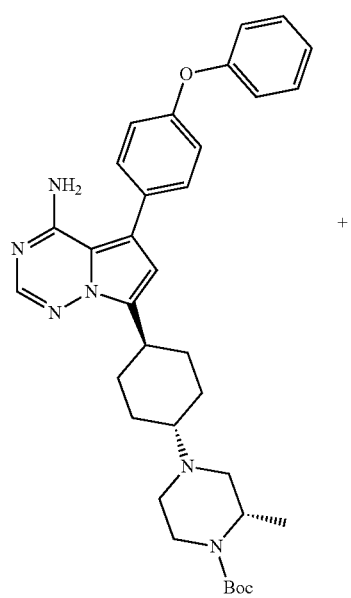

302

-continued

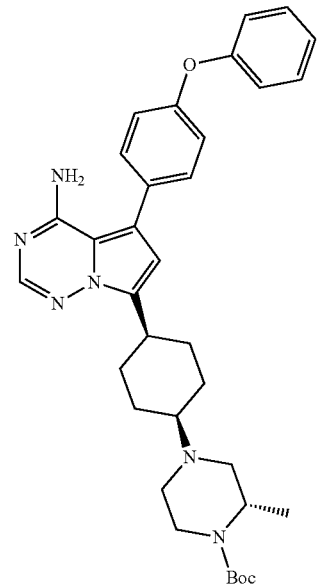

(S)-tert-butyl 4-((trans)-4-(4-amino-5-(4-phenoxyphenyl)pyrrolo[2,1-f] [1,2,4]triazin-7-yl)cyclohexyl)-2-methylpiperazine-1-carboxylate A reaction mixture of 4-(4-amino-5-(4-phenoxyphenyl)pyrrolo[2,1-f][1,2,4] triazin-7-yl)cyclohexanone (50 mg, 0.12 mol), (S)-tert-butyl-2-methylpiperazine-1-carboxylate (50 mg, 0.24 mol) and Ti(OiPr)$_4$ (142 mg, 0.48 mmol) in DCM (10 mL) was stirred at room temperature for 2 hours. NaBH (OAc)$_3$ (100 mg, 0.48 mol) was added. It was stirred at room temperature for overnight. it was quenched with MeOH. Then NaHCO$_3$aq and DCM were added, and it was filtrated. The filtrate was extracted with DCM. The organic layers were collected and concentrated. The reside was purified by flash column chromatography (DCM:MeOH=10:1) to afford (S)-tert-butyl 4-((trans)-4-(4-amino-5-(4-phenoxyphenyl)pyrrolo[2,1-f][1,2,4]triazin-7-yl)cyclohexyl)-2-methylpiperazine-1-carboxylate (25 mg, 36% yield) LCMS: Calculated Exact Mass=582.3; Found [M+H]$^+$ (ESI)=583.1; and (S)-tert-butyl 4-((cis)-4-(4-amino-5-(4-phenoxyphenyl)pyrrolo [2,1-f][1,2,4]triazin-7-yl)cyclohexyl)-2-methylpiperazine-1-carboxylate as a white solid (21 mg, 30% yield) LCMS: Calculated Exact Mass=582.3; Found [M+H]$^+$ (ESI)=583.1.

Example 169

7-((trans)-4-((S)-3-Methylpiperazin-1-yl)cyclohexyl)-5-(4-phenoxyphenyl)pyrrolo[2,1-f][1,2,4]triazin-4-amine

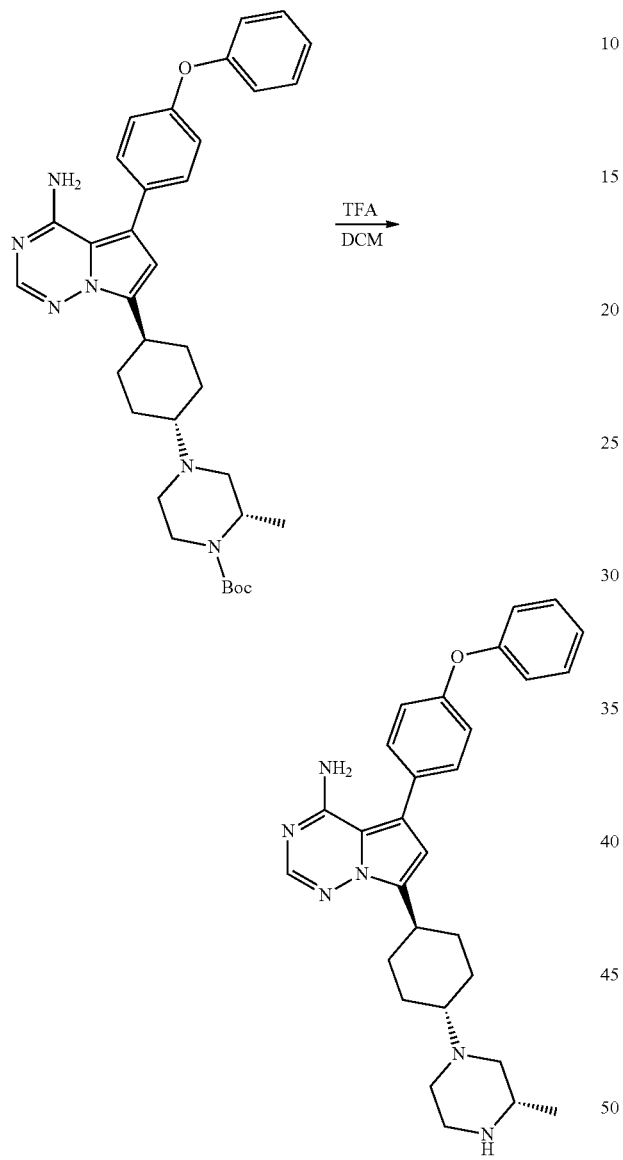

7-((trans)-4-((S)-3-Methylpiperazin-1-yl)cyclohexyl)-5-(4-phenoxyphenyl)pyrrolo[2,1-f][1,2,4]triazin-4-amine To a solution of (S)-tert-butyl 4-((trans)-4-(4-amino-5-(4-phenoxyphenyl)pyrrolo[2,1-f][1,2,4]triazine-7-yl)cyclohexyl)-2-methylpiperazine-1-carboxylate (25 mg, 0.04 mmol) in DCM (10 mL) was added TFA (0.5 mL) drowse. The reaction was stirred at room temperature for 3 hours before it was concentrated, the residue was purified by Prep-HPLC to afford the product as white solid (18 mg, 93% yield) LCMS: Calculated Exact Mass=482.3; Found [M+H]+ (ESI)=483.1; ¹H NMR (400 MHz, METHANOL-d₄) δ ppm 7.94 (s, 1H) 7.41 (d, J=8.54 Hz, 2H) 7.31 (t, J=7.93 Hz, 2H) 7.08 (t, J=7.32 Hz, 1H) 7.00 (d, J=7.93 Hz, 2H) 7.04 (d, J=8.55 Hz, 2H) 6.68 (s, 1H) 3.55-3.68 (m, 4H) 3.29-3.41 (m, 1H) 2.99 (t, J=12.05 Hz, 1H) 2.12-2.29 (m, 4H) 1.58-1.76 (m, 4H) 1.30-1.36 (m, 3H).

Example 170

7-((cis)-4-((S)-3-Methylpiperazin-1-yl)cyclohexyl)-5-(4-phenoxyphenyl)pyrrolo[2,1-f][1,2,4]triazin-4-amine

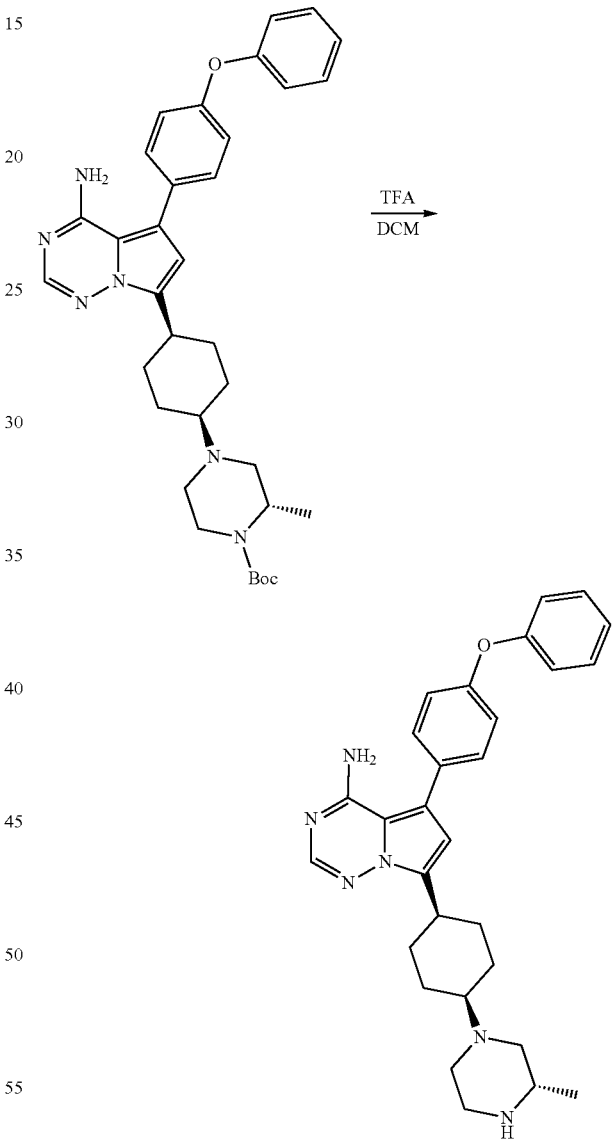

7-((cis)-4-((S)-3-Methylpiperazin-1-yl)cyclohexyl)-5-(4-phenoxyphenyl)pyrrolo[2,1-f][1,2,4]triazin-4-amine To a solution of (S)-tert-butyl 4-((cis)-4-(4-amino-5-(4-phenoxyphenyl)pyrrolo[2,1-f][1,2,4]triazine-7-yl)cyclohexyl)-2-methylpiperazine-1-carboxylate (21 mg, 0.04 mmol) in DCM (10 mL) was added TFA (0.5 mL) dropwise.

The reaction mixture was stirred at room temperature for 4 hours. The mixture was evaporated and dissolved with DCM, washed with NaHCO₃ solution and water. The organic layer was dried and concentrated in vacuo to afford the title compound as a light yellow solid (16 mg, 82% yield) LC-MS: Calculated Exact Mass: 482.3; Found [M+H]⁺ (ESI)=483.7; ¹H NMR (400 MHz, MeOD) δ 8.03 (s, 1H), 7.54 (d, J=8.7 Hz, 2H), 7.46-7.40 (m, 2H), 7.20 (t, J=7.4 Hz, 1H), 7.13 (dd, J=15.3, 8.1 Hz, 4H), 6.86 (s, 1H), 3.52 (d, J=14.0 Hz, 6H), 2.83 (s, 1H), 2.74-2.62 (m, 1H), 2.48 (s, 1H), 2.18 (s, 2H), 1.95 (d, J=19.6 Hz, 7H), 1.37 (d, J=6.5 Hz, 3H).

Example 171

1-(4-(4-Amino-7-((trans)-4-(4-methylpiperazin-1-yl) cyclohexyl)pyrrolo[2,1-f][1,2,4]triazin-5-yl)phenyl)-3-(5-(tert-butyl)furan-3-yl)urea and Example 172

1-(4-(4-Amino-7-((cis)-4-(4-methylpiperazin-1-yl) cyclohexyl)pyrrolo[2,1-f][1,2,4]triazin-5-yl)phenyl)-3-(5-(tert-butyl)furan-3-yl)urea

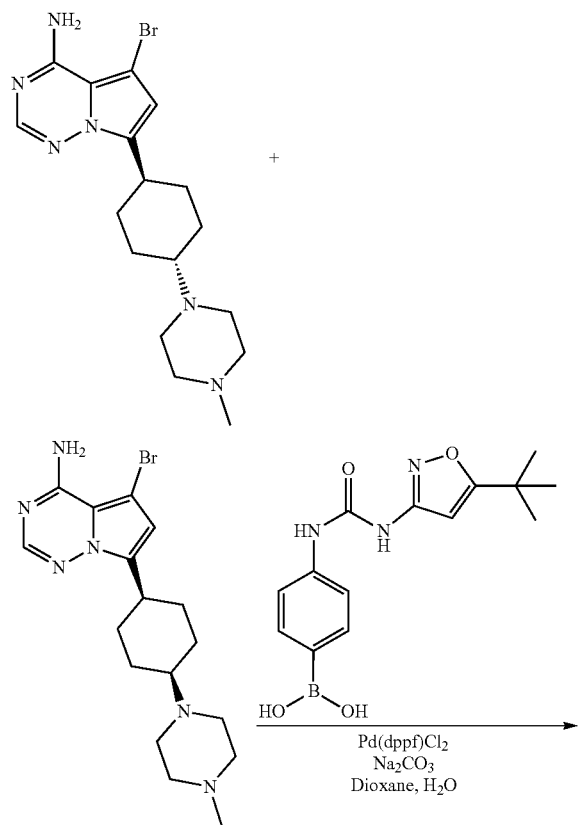

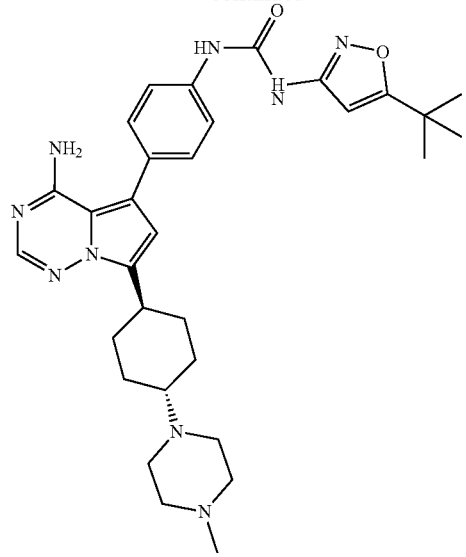 [SMILES: CN1CCN([C@H]2CC[C@@H](c3cc(-c4ccc(NC(=O)Nc5cc(C(C)(C)C)on5)cc4)c4c(N)ncnn43)CC2)CC1]

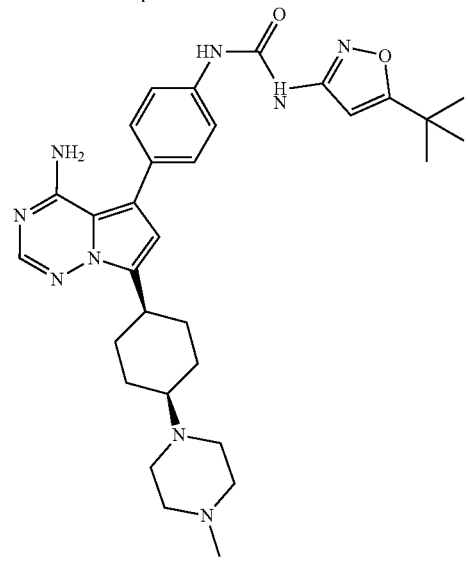

A mixture of a mixture of 5-bromo-7-((trans)-4-(4-methylpiperazin-1-yl)cyclohexyl)pyrrolo[2,1-f][1,2,4] triazin-4-amine and 5-bromo-7-((cis)-4-(4-methylpiperazin-1-yl)cyclohexyl)pyrrolo[2,1-f][1,2,4] triazin-4-amine (80 mg, 0.2 mmol), (4-(3-(5-(tert-butyl)furan-3-yl)ureido)phenyl)boronic acid (74 mg, 0.24 mmol), sodium carbonate (64 mg, 0.6 mmol) and Pd(dppf)Cl₂ (30 mg, 0.04 mmol) in dioxane-H₂O (10 mL-1 mL) was heated at 100° C. under inert atmosphere for 3 hours. The reaction was concentrated in vacuo. The residue was dissolved in DCM, washed with water, dried, evaporated and purified by Prep-TLC (DCM: MeOH=10:1) to give 1-(4-(4-amino-7-((trans)-4-(4-methylpiperazin-1-yl) cyclohexyl)pyrrolo[2,1-f][1,2,4]triazin-5-yl)phenyl)-3-(5-(tert-butyl)furan-3-yl)urea as a white solid (5 mg, 4% yield) LC-MS: Calculated Exact Mass: 571.3; Found [M+H]⁺ (ESI)=572.3; ¹H NMR (400 MHz, MeOD) δ 7.82 (s, 1H), 7.61 (d, J=8.5 Hz, 2H), 7.45 (d, J=8.5 Hz, 2H), 6.52 (s, 1H), 6.42 (s, 1H), 3.20 (s, 2H), 2.78 (d, J=65.6 Hz, 10H), 2.42 (s, 3H), 2.28 (d, J=10.8 Hz, 3H), 2.14 (d, J=10.2 Hz, 2H), 1.68-1.50 (m, 5H), 1.38 (s, 10H); and 1-(4-(4-amino-7-((cis)-4-(4-methylpiperazin-1-yl) cyclohexyl)pyrrolo[2,1-f] [1,2,4]triazin-5-yl)phenyl)-3-(5-(tert-butyl)furan-3-yl)urea as a white solid (21 mg, 18% yield) LC-MS: Calculated Exact Mass: 571.3; Found [M+H]⁺ (ESI)=572.3; ¹H NMR (400 MHz, MeOD) δ 7.70 (s, 1H), 7.50 (d, J=8.5 Hz, 2H), 7.34 (d, J=8.5 Hz, 2H), 6.52 (s, 1H), 6.30 (s, 1H), 3.37 (s, 1H), 2.72 (s, 8H), 2.40 (s, 4H), 2.07 (s, 2H), 1.82-1.67 (m, 6H), 1.26 (s, 9H).

8-Chloro-3-((trans)-4-(4-methylpiperazin-1-yl)cyclohexyl)imidazo[1,5-a]pyrazine and 8-Chloro-3-((cis)-4-(4-methylpiperazin-1-yl)cyclohexyl)imidazo[1,5-a]pyrazine

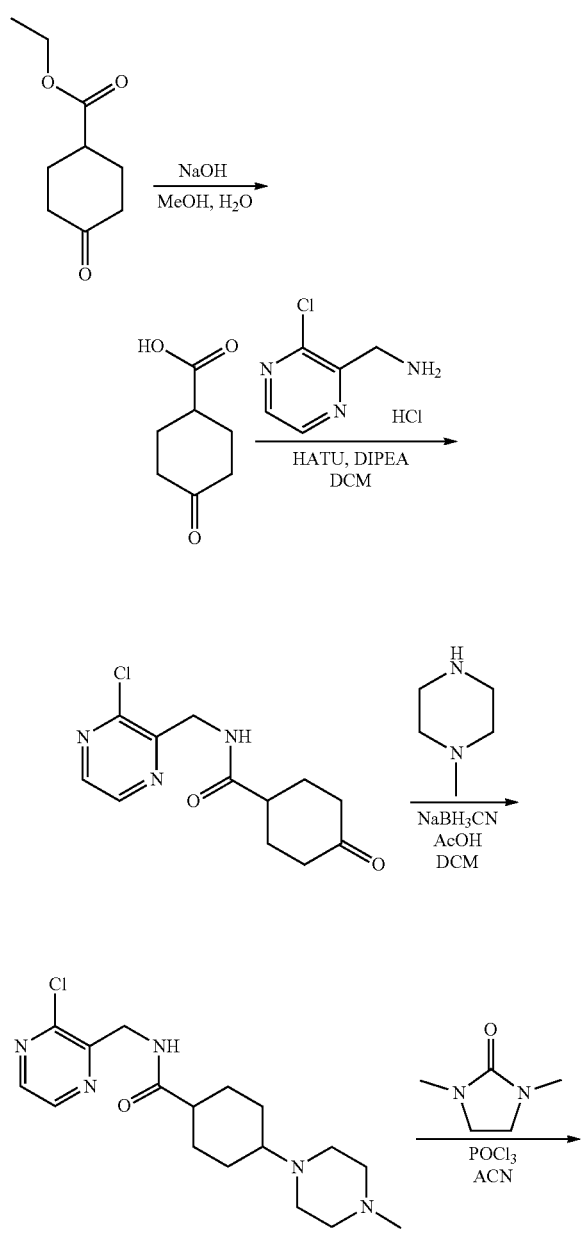

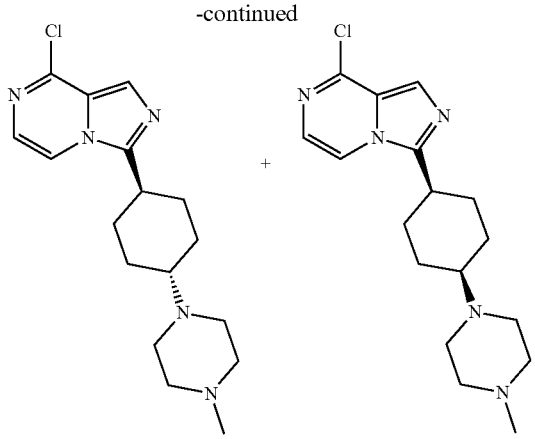

N-((3-Chloropyrazin-2-yl)methyl)-4-oxocyclohexanecarboxamide

To a solution of 4-oxocyclohexanecarboxylic acid (0.7 g, 3.9 mmol) and TEA (1.1 mL, 7.8 mmol) in DCM (10 mL) was added HATU (1.77 g, 4.67 mL) and (3-chloropyrazin-2-yl)methanamine (1.77 g, 4.67 mmol). The reaction was stirred at room temperature for 18 hours before it was quenched with water (20 mL) and extracted with DCM (20 mL×3). The organic layer was collected and washed with brine (20 mL) and dried over Na$_2$SO$_4$. After concentration the crude was purified by flash column chromatography (EA 100%) to give the desired product as a yellow solid (680 mg, 65% yield). LCMS: Calculated Exact Mass=267.08; Found [M+H]⁺ (ESI)=268.0; ¹H NMR (400 MHz, DMSO-d$_6$) δ ppm: 8.63 (d, J=2.42 Hz, 1H), 8.50 (t, J=5.24 Hz, 1H), 8.44 (d, J=2.42 Hz, 1H), 4.53 (d, J=5.37 Hz, 2H), 2.72 (tt, J=3.59, 10.64 Hz, 1H), 2.34-2.45 (m, 2H), 2.23-2.33 (m, 2H), 2.05 (dd, J=3.76, 13.16 Hz, 2H), 1.73-1.88 (m, 2H).

N-((3-chloropyrazin-2-yl)methyl)-4-(4-methylpiperazin-1-yl)cyclohexanecarboxamide To a solution of N-((3-chloropyrazin-2-yl)methyl)-4-oxocyclohexanecarboxamide (2.2 g, 8.1 mmol), 1-methylpiperazine (1.2 g, 10.6 mmol) in DCM (30 mL) was added NaBH$_3$CN (1023 mg, 16.2 mmol) and AcOH (292 mg, 4.87 mmol) at 0° C. under N$_2$ atmosphere. The reaction was stirred at 20° C. for 3 hours. The reaction was quenched by NaHCO$_3$ solution (20 mL) and extracted with DCM (20 mL×3). The organic layer was washed with brine (20 mL) and dried over Na$_2$SO$_4$. After it was concentrated the crude was purified by flash column chromatography (DCM: MeOH=100:1 to 5:1) to give the desired product as a yellow solid (1.4 g, 60% yield).

LCMS: Calculated Exact Mass=351.18; Found [M+H]⁺ (ESI)=352.0.

8-chloro-3-(4-(4-methylpiperazin-1-yl)cyclohexyl) imidazo[1,5-a]pyrazine

To a solution of N-((3-chloropyrazin-2-yl)methyl)-4-(4-methylpiperazin-1-yl)cyclohexanecarboxamide (1.4 g, 4 mmol) in ACN (30 mL) was added DMI (1.37 g, 12 mmol) and POCl$_3$ (2.5 g, 16 mmol) dropwise at 0° C. under N$_2$ atmosphere. The reaction was stirred under reflux for 3 hours. It was quenched with NH$_3$·H$_2$O (20 mL) and ice carefully and extracted with DCM (20 mL×3). The organic layer was washed with brine (20 mL) and dried over Na₂SO₄. After it was concentrated, the crude was purified by flash column chromatography (DCM:MeOH=100:1-10:1) to give 8-chloro-3-((trans)-4-(4-methylpiperazin-1-yl) cyclohexyl)imidazo[1,5-a] pyrazine (240 mg, 18% yield) LCMS: Calculated Exact Mass=333.17; Found [M+H]⁺ (ESI)=334.1 and 8-chloro-3-((cis)-4-(4-methylpiperazin-1-yl)cyclohexyl)imidazo[1,5-a]pyrazine (340 mg, 25% yield) LCMS: Calculated Exact Mass=333.17; Found [M+H]⁺ (ESI)=334.1.

Example 173

3-((trans)-4-(4-Methylpiperazin-1-yl)cyclohexyl)-1-(4-phenoxyphenyl)imidazo[1,5-a]pyrazin-8-amine

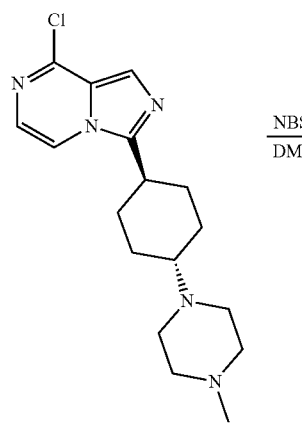

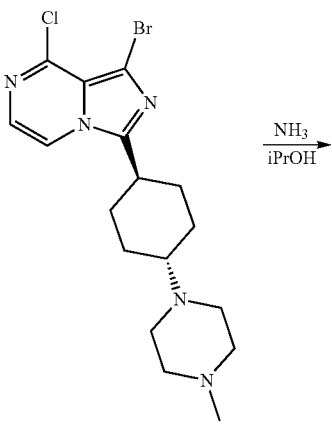

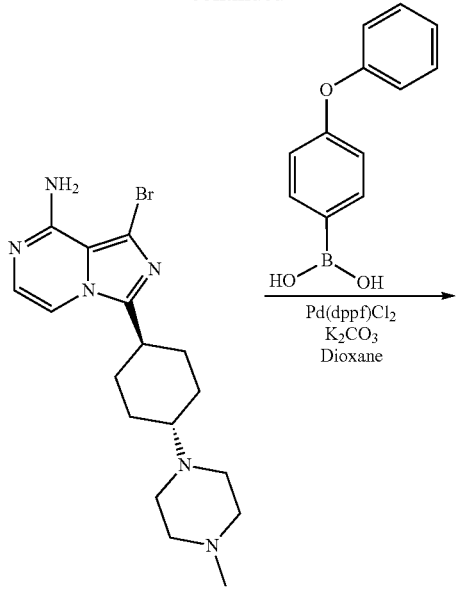

1-Bromo-8-chloro-3-((trans)-4-(4-methylpiperazin-1-yl)cyclohexyl)imidazo[1,5-a]pyrazine To a solution of 8-chloro-3-((trans)-4-(4-methylpiperazin-1-yl)cyclohexyl)imidazo [1,5-a]pyrazine (240 mg, 0.72 mmol) in DCM (10 mL) was added NBS (192 mg, 1.08 mmol) at 20° C. under N₂ atmosphere. Then the reaction was stirred at reflux for 3 hours. Detected by LC-MS and TLC, the starting material was consumed up. The reaction was quenched by NaHCO₃ (20 mL) and extracted with DCM (20 mL×3). The organic layer was washed with brine (20 mL), dried over Na₂SO₄ and concentrated in vacuo to give the desired product as a yellow solid which was used in next step without further purification (300 mg, 98% yield). LCMS: Calculated Exact Mass=411.08; Found [M+H]⁺ (ESI)=412.1.

311

1-Bromo-3-((trans)-4-(4-methylpiperazin-1-yl)cyclohexyl)imidazo[1,5-a]pyrazin-8-amine To a solution of 1-bromo-8-chloro-3-((trans)-4-(4-methylpiperazin-1-yl)cyclohexyl) imidazo[1,5-a]pyrazine (300 mg, 0.70 mmol) in 1,4-dioxane (10 mL) was added NH$_3$·H$_2$O (10 mL) in a sealed tube. Then the reaction was stirred at 120° C. for 48 hours. Detected by LC-MS and TLC, the starting material was nearly consumed up. It was extracted with EA (30 mL×3). The organic layer was washed with brine (40 mL), dried over Na$_2$SO$_4$, concentrated in vacuo and purified by silica gel chromatography (DCM:MeOH=100:1-10:1) to give the desired product as a yellow solid. (100 mg, 34% yield).

3-((trans)-4-(4-Methylpiperazin-1-yl)cyclohexyl)-1-(4-phenoxyphenyl)imidazo[1,5-a]pyrazin-8-amine A suspension of 1-bromo-3-((trans)-4-(4-methylpiperazin-1-yl)cyclohexyl)imidazo[1,5-a]pyrazin-8-amine (100 mg, 0.25 mmol) and 4-phenoxyphenylboronic acid (65 mg, 0.30 mmol), Na$_2$CO$_3$ (81 mg, 0.76 mmol) and Pd(dppf)Cl$_2$ (37 mg, 0.05 mmol) in THF (15 mL) and water (3 mL) was stirred at 80° C. under N$_2$ atmosphere for 3 hours. Detected by LC-MS and TLC, the starting material was consumed up. The reaction was concentrated in vacuo and purified by flash column chromatography (PE:EA=10:1-3:1) and Prep-HPLC to give the desired product as a white solid. (26 mg, 22% yield) LCMS: Calculated Exact Mass=482.28; Found [M+H]$^+$ (ESI)=483.3; $^1$H NMR (600 MHz, METHANOL-d$_4$) δ ppm: 7.74 (d, J=5.72 Hz, 1H), 7.62 (d, J=8.47 Hz, 2H), 7.41 (t, J=7.78 Hz, 2H), 7.19 (t, J=7.32 Hz, 1H), 7.15 (d, J=8.47 Hz, 2H), 7.10 (d, J=8.24 Hz, 2H), 6.99 (d, J=5.49 Hz, 1H), 3.35 (s, 1H), 3.32 (br. s., 4H), 3.18 (t, J=11.79 Hz, 1H), 2.71 (br. s., 3H), 2.15 (d, J=9.84 Hz, 4H), 1.85 (q, J=12.05 Hz, 2H), 1.58-1.70 (m, 2H), 1.26-1.37 (m, 2H).

Example 174

3-((cis)-4-(4-Methylpiperazin-1-yl)cyclohexyl)-1-(4-phenoxyphenyl)imidazo[1,5-a]pyrazin-8-amine

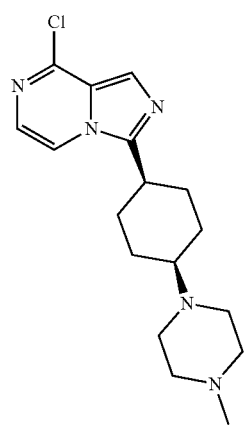

312

-continued

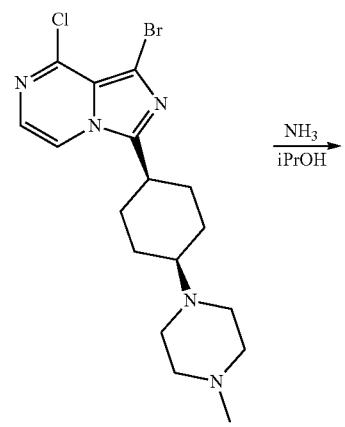

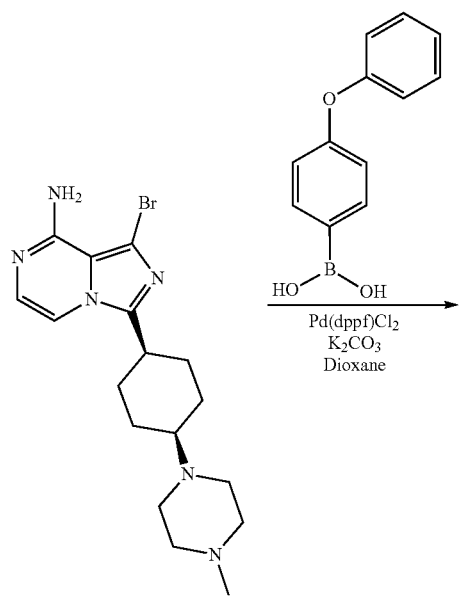

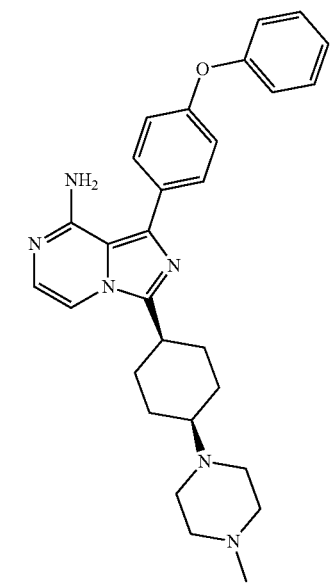 [SMILES: CN1CCN([C@H]2CC[C@@H](c3nc(-c4ccc(Oc5ccccc5)cc4)c4c(N)nccn43)CC2)CC1]

1-Bromo-8-chloro-3-((cis)-4-(4-methylpiperazin-1-yl)cyclohexyl)imidazo[1,5-a]pyrazine To a solution of 8-chloro-3-((cis)-4-(4-methylpiperazin-1-yl)cyclohexyl)imidazo [1,5-a] pyrazine (200 mg, 0.6 mmol), in DCM (10 mL) was added NBS (128 mg, 072 mmol) at 20° C. under N$_2$ atmosphere. Then the reaction was stirred under reflux for 3 hours. Detected by LC-MS and TLC, the starting material was consumed up. The reaction was quenched by NaHCO$_3$ solution (20 mL), extracted with DCM (20 mL×3), washed with brine (20 mL), dried over Na$_2$SO$_4$ and concentrated in vacuo to give the desired product as a yellow solid which was used in next step without further purification (240 mg, 98%, yield). LCMS: Calculated Exact Mass=411.08; Found [M+H]$^+$ (ESI)= 412.1.

1-Bromo-3-((cis)-4-(4-methylpiperazin-1-yl)cyclohexyl)imidazo[1,5-a]pyrazin-8-amine To a solution of 1-bromo-8-chloro-3-((cis)-4-(4-methylpiperazin-1-yl)cyclohexyl) imidazo[1,5-a]pyrazine (190 mg, 0.46 mmol) in 1,4-dioxane (10 mL) was added NH$_3$·H$_2$O (10 mL) in a sealed tube. Then the reaction was stirred at 120° C. for 48 hours. Detected by LC-MS and TLC, the starting material was nearly consumed up. It was extracted with EA (30 mL×3). The organic layer was washed with brine (40 mL), dried over Na$_2$SO$_4$, and concentrated in vacuo. The crude was purified by flash column chromatography (DCM:MeOH=100:1-10:1) to give the desired product as a yellow solid (160 mg, 80% yield).

3-((cis)-4-(4-Methylpiperazin-1-yl)cyclohexyl)-1-(4-phenoxyphenyl)imidazo[1,5-a]pyrazin-8-amine A suspension of 1-bromo-3-((cis)-4-(4-methylpiperazin-1-yl)cyclohexyl)imidazo [1,5-a]pyrazin-8-amine (160 mg, 0.4 mmol)) and 4-phenoxyphenylboronic acid (100 mg, 0.48 mmol), Na$_2$CO$_3$ (128 mg, 1.2 mmol) and Pd(dppf)Cl$_2$ (60 mg, 0.08 mmol) in THF (15 mL) and water (3 mL) was stirred at 80° C. under N$_2$ atmosphere for 3 hours. Detected by LC-MS and TLC, the starting material was consumed up. The reaction was concentrated in vacuo and purified by flash column chromatography eluting with (PE:EA=10:1-3:1) and Prep-HPLC to give the desired product as a white solid. (40 mg, 40% yield) LCMS: Calculated Exact Mass=482.28; Found [M+H]$^+$ (ESI)=483.3; $^1$H NMR (600 MHz, METHANOL-d$_4$) δ ppm: 7.76 (d, J=5.95 Hz, 1H), 7.69 (d, J=8.47 Hz, 2H), 7.42 (t, J=7.90 Hz, 2H), 7.20 (t, J=7.32 Hz, 1H), 7.15 (d, J=8.47 Hz, 2H), 7.11 (d, J=8.01 Hz, 2H), 6.97 (d, J=5.95 Hz, 1H), 3.31-3.60 (m, 9H), 3.21 (br. s., 1H), 2.90 (s, 3H), 2.17-2.29 (m, 4H), 1.88-2.06 (m, 4H).

Example 175

1-(4-(8-amino-3-((trans)-4-(4-methylpiperazin-1-yl)cyclohexyl)imidazo[1,5-a]pyrazin-1-yl)phenyl)-3-(5-(tert-butyl)isoxazol-3-yl)urea

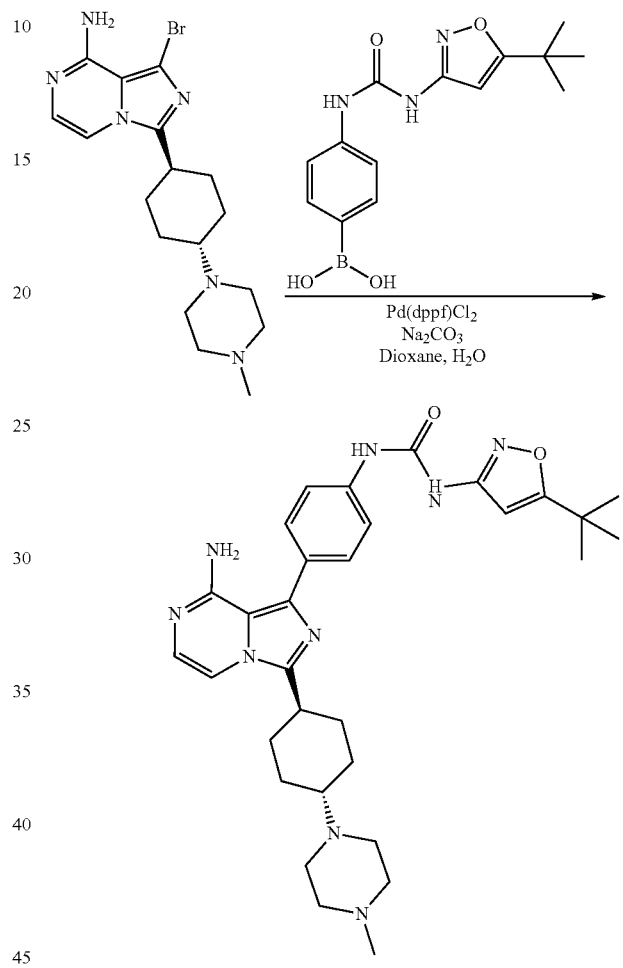

A mixture of 5-bromo-7-((trans)-4-(4-methylpiperazin-1-yl)cyclohexyl)-7H-pyrrolo [2,3-d]pyrimidin-4-amine (60 mg, 0.153 mmol), (4-(3-(5-(tert-butyl)isoxazol-3-yl)ureido)phenyl)boronic acid (70 mg, 0.23 mmol), Pd(dppf)Cl$_2$ (11 mg, 0.015 mmol) and Na$_2$CO$_3$ (49 mg, 0.459 mmol) in dioxane-H$_2$O (10:1, 22 mL) was heated to 80° C. The reaction mixture was stirred for 2 hours. TLC (MeOH: DCM=1:10) showed complete consumption of the starting material. The solvent was evaporated in vacuo. The residue was extracted with DCM (100 mL). The combined organic layer was washed with 1M NaOH (200 mL), dried over anhydrous Na$_2$SO$_4$ and concentrated in vacuo. The crude was purified by Prep-HPLC to give the product as a white solid (16 mg, 18% yield). LCMS: Calculated Exact Mass=574.3, Found [M+H]$^+$ (ESI)=575.3; $^1$H NMR (DMSO-d$_6$) δ ppm: 9.82 (s, 1H), 9.36 (s, 1H), 7.95 (s, 1H), 7.56-7.67 (m, 4H), 7.10-7.12 (m, 1H), 6.52 (s, 1H), 3.05-3.25 (m, 5H), 1.50-2.25 (m, 8H), 1.30 (s, 12H).

Example 176
7-((cis)-4-(4-methylpiperazin-1-yl)cyclohexyl)-5-(4-phenoxyphenyl)-5H-pyrrolo[3,2-d]pyrimidin-4-amine
and
Example 177
7-((trans)-4-(4-methylpiperazin-1-yl)cyclohexyl)-5-(4-phenoxyphenyl)-5H-pyrrolo[3,2-d]pyrimidin-4-amine
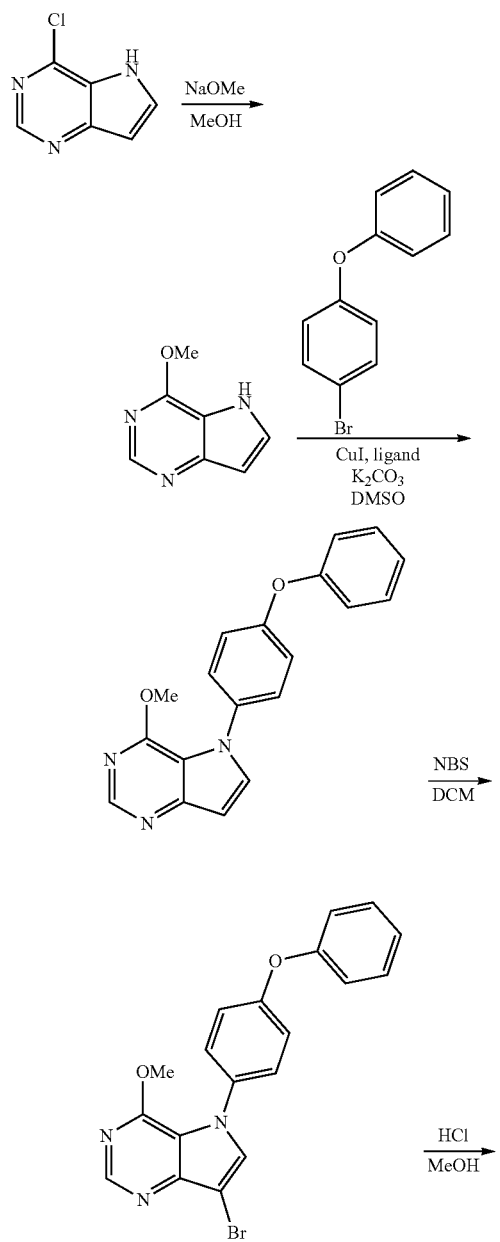
-continued
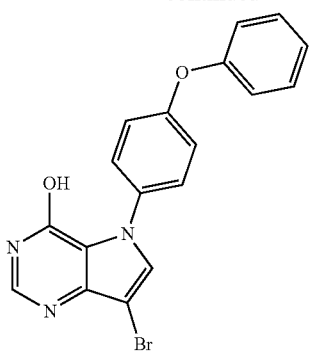
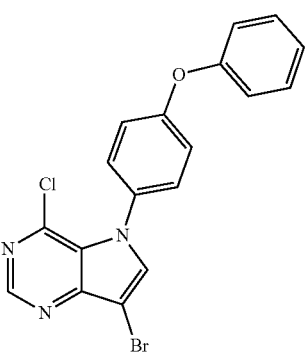
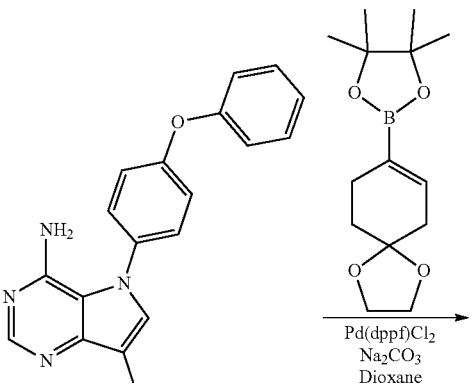
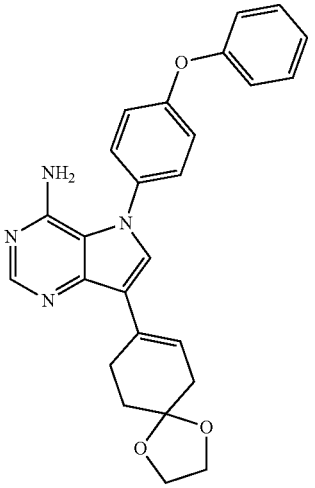

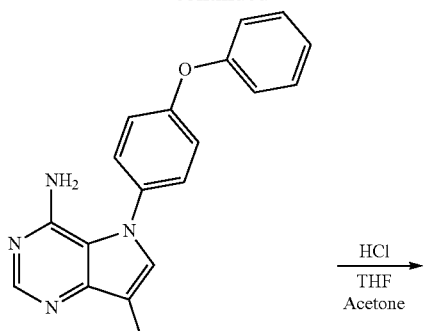

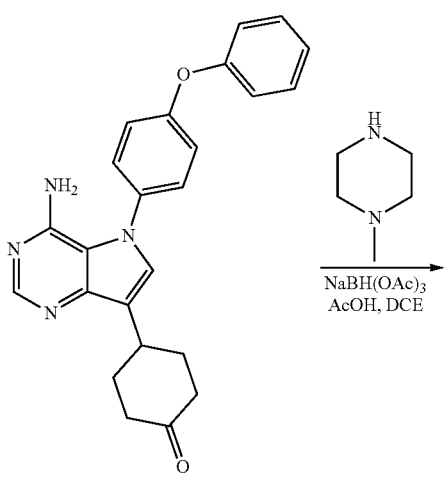

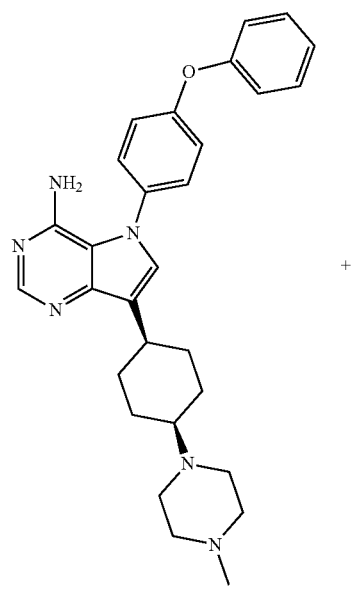

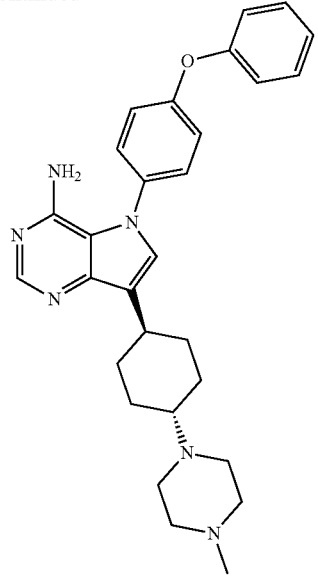

4-Methoxy-5-(4-phenoxyphenyl)-5H-pyrrolo[3,2-d]pyrimidine

To a mixture of 4-methoxy-5H-pyrrolo[3,2-d]pyrimidine (650 mg, 4.36 mmol), 1-bromo-4-phenoxybenzene (1.3 g, 5.22 mmol), CuI (1.66 g, 8.72 mmol), (1R,2R)—N1,N2-dimethylcyclohexane-1,2-diamine (1.24 g, 8.72 mmol), $K_2CO_3$ (1.8 g, 13.08 mmol) in DMSO (50 mL) was heated at 140° C. under Ar atmosphere for 3 hours. Cooled to room temperature and filtrated, the filtrate was quenched with water and extracted with EtOAc, dried and concentrated. The residue was purification via column chromatography (PE:EA=3:1) to obtain product (750 mg, 53% yield) LCMS: Calculated Exact Mass=317.1; Found [M+H]$^+$ (ESI)=318.0.

7-Bromo-4-methoxy-5-(4-phenoxyphenyl)-5H-pyrrolo[3,2-d]pyrimidine

To a mixture of 4-methoxy-5-(4-phenoxyphenyl)-5H-pyrrolo[3,2-d]pyrimidine (1 g, 3.2 mmol), in DCM (50 mL) was added NBS (670 mg, 3.8 mmol). The mixture was stirred at room temperature for 2 hours. Quenched with saturated NaHCO$_3$, extracted with DCM, dried and concentrated, the residue was purification via column chromatography (PE:EA=2:1) to obtain product (1 g, 79% yield) as a yellow solid. LCMS: Calculated Exact Mass=395.0; Found [M+H]$^+$ (ESI)= 395.9.

7-Bromo-5-(4-phenoxyphenyl)-5H-pyrrolo[3,2-d]pyrimidin-4-ol

To a mixture of 7-bromo-4-methoxy-5-(4-phenoxyphenyl)-5H-pyrrolo[3,2-d]pyrimidine (1 g, 2.5 mmol) in MeOH (20 mL) with 6 N HCl (20 mL) was refluxed overnight. Then cooled to room temperature and concentrated. The residue was neutralized with saturated NaHCO$_3$ and filtrated. The filtrated cake was dried to obtained product (850 mg 88% yield) as a light yellow solid.

LCMS: Calculated Exact Mass=381.0; Found [M+H]$^+$ (ESI)=382.2.

7-Bromo-4-chloro-5-(4-phenoxyphenyl)-5H-pyrrolo[3,2-d]pyrimidine

To a suspension of 7-bromo-5-(4-phenoxyphenyl)-5H-pyrrolo[3,2-d]pyrimidin-4-ol (850 mg, 2.2 mmol) in POCl$_3$ was stirred at 100° C. for 1.5 hours. Then cooled to room temperature and concentrated, the residue was quenched with saturated NaHCO$_3$, extracted with DCM, dried and concentrated to obtain the product (900 mg, 100% yield) as a light yellow solid. LCMS: Calculated Exact Mass=399.0; Found [M+H]$^+$ (ESI)=399.9.

7-Bromo-5-(4-phenoxyphenyl)-5H-pyrrolo[3,2-d]pyrimidin-4-amine

To a suspension of 7-bromo-4-chloro-5-(4-phenoxyphenyl)-5H-pyrrolo[3,2-d]pyrimidine (900 mg, 2.24 mmol) in 1,4 Dioxane (20 mL) was added NH$_3$·H$_2$O (20 mL), the mixture was stirred at 130° C. in sealed tube overnight. Then cooled to room temperature and concentrated. The suspension was filtrated to obtain the product (900 mg, 100% yield). LCMS: Calculated Exact Mass=380.0; Found [M+H]$^+$ (ESI)=380.8.

5-(4-Phenoxyphenyl)-7-(1,4-dioxaspiro[4.5]dec-7-en-8-yl)-5H-pyrrolo[3,2-d]pyrimidin-4-amine A mixture of 7-bromo-5-(4-phenoxyphenyl)-5H-pyrrolo[3,2-d]pyrimidin-4-amine (750 m g, 1.97 mmol), 4,4,5,5-tetramethyl-2-(1,4-dioxaspiro[4.5]dec-7-en-8-yl)-1,3,2-dioxaborolane (2.6 g, 9.84 mol), Pd(dppf)Cl$_2$ (288 mg, 0.39 mmol) and Na$_2$CO$_3$ (1.04 g, 9.84 mmol) in dioxane-H$_2$O (40 mL-4 mL) was heated at 100° C. under Ar atmosphere for 4 hours. After cooled to room temperature, the reaction mixture was concentrated and extracted with DCM. The organic layers were concentrated and purified by flash column chromatography (EtOAc, 100%) to afford the product (50 mg, 6% yield). LCMS: Calculated Exact Mass=440.2; Found [M+H]$^+$ (ESI)=440.9.

5-(4-Phenoxyphenyl)-7-(1,4-dioxaspiro[4.5]decan-8-yl)-5H-pyrrolo[3,2-d]pyrimidin-4-amine To a solution of 5-(4-phenoxyphenyl)-7-(1,4-dioxaspiro[4.5]dec-7-en-8-yl)-5H-pyrrolo[3,2-d]pyrimidin-4-amine (40 mg, 0.092 mmol) in EtOAc/MeOH (50 mL) was added Pd/C (20 mg, 10% in activity carbon). The mixture was stirred at room temperature under H$_2$ atmosphere overnight. Then filtrated and the filtrate was concentrated to obtain product (40 mg, 100% yield). LCMS: Calculated Exact Mass=442.2; Found [M+H]$^+$ (ESI)=442.8.

4-(4-Amino-5-(4-phenoxyphenyl)-5H-pyrrolo[3,2-d]pyrimidin-7-yl)cyclohexan-1-one To a mixture of 5-(4-phenoxyphenyl)-7-(1,4-dioxaspiro[4.5]decan-8-yl)-5H-pyrrolo[3,2-d]pyrimidin-4-amine (50 mg, 0.11 mmol) in acetone (5 mL) was added 6 N HCl in THF (2 mL). The mixture was stirred at 40° C. for 3 hours. Then cooled to room temperature, the mixture was neutralized with NaOH aqueous, extracted with DCM, dried and concentrated. The residue was purified by flash column chromatography (EtOAc, 100%) to afford the product (15 mg, 30% yield). LCMS: Calculated Exact Mass=398.17; Found [M+H]$^+$ (ESI)=398.9.

7-((cis)-4-(4-Methylpiperazin-1-yl)cyclohexyl)-5-(4-phenoxyphenyl)-5H-pyrrolo[3,2-d]pyrimidin-4-amine and

7-((trans)-4-(4-Methylpiperazin-1-yl)cyclohexyl)-5-(4-phenoxyphenyl)-5H-pyrrolo[3,2-d]pyrimidin-4-amine To a mixture of 4-(4-amino-5-(4-phenoxyphenyl)-5H-pyrrolo[3,2-d]pyrimidin-7-yl)cyclohexan-1-one (15 mg, 0.038 mmol), 1-methylpiperazine (19 mg, 0.19 mmol) in DCE (5 mL) was added AcOH (1 drop). The reaction was stirred at room temperature for 2 hours. NaBH(OAc)$_3$ (64 mg, 0.304 mmol) was added portion-wise. The reaction was stirred at room temperature overnight. The reaction was quenched with saturated NaHCO$_3$, extracted with DCM, dried and concentrated. The residue was purified via Prep-TLC (DCM:MeOH=10:1) to obtained product. 7-((trans)-4-(4-methylpiperazin-1-yl)cyclohexyl)-5-(4-phenoxyphenyl)-5H-pyrrolo[3,2-d]pyrimidin-4-amine (3 mg, 16% yield) LCMS: Calculated Exact Mass=482.3; Found [M+H]$^+$ (ESI)= 483.3; $^1$H NMR (CHLOROFORM-d) δ 8.40 (s, 1H), 7.41-7.44 (m, 2H), 7.35 (d, J=8.5 Hz, 2H), 7.19-7.25 (m, 1H), 7.11 (dd, J=7.9, 6.1 Hz, 5H), 4.90 (br. s., 2H), 3.03 (br. s., 9H), 2.53 (br. s., 3H), 2.30 (d, J=16.2 Hz, 4H), 1.60-1.71 (m, 6H); and 7-((cis)-4-(4-methylpiperazin-1-yl)cyclohexyl)-5-(4-phenoxyphenyl)-5H-pyrrolo[3,2-d]pyrimidin-4-amine (2 mg, 11% yield) LCMS: Calculated Exact Mass=482.3; Found [M+H]$^+$ (ESI)=483.3; $^1$H NMR (CHLOROFORM-d) δ 8.40 (s, 1H), 7.35-7.52 (m, 5H), 7.17-7.23 (m, 1H), 7.11 (t, J=9.3 Hz, 4H), 4.82-5.01 (m, 2H), 3.00 (br. s., 6H), 2.54 (br.s., 3H), 2.03 (br. s., 2H), 1.87 (br. s., 2H), 1.77 (d, J=10.7 Hz, 2H), 1.63 (d, J=7.6 Hz, 2H).

HCK Kinase Assay:

HCK kinase reaction (10 μL) containing 4 nM N-terminally GST-tagged HCK (75-526), purified from insect expression system, 5 μM Control AMC Substrate, 2 μM Src-Family Kinase R110 Substrate, and 50 μM ATP in kinase reaction buffer (40 mM Tris-HCl pH 7.5, 20 mM MgCl$_2$, 0.1 mg/mL BSA, 1 mM MnCl$_2$, 0.1 mM Sodium Vanadate), and test compound 1:3 serially-diluted starting at 1 μM were incubated at room temperature (22-25° C.) for 60 minutes in 384 well plate (Corning, Cat. No. 4514). The procedure of ProFluor Src-Family Kinase Assay (Promega, Cat. No. V1271) was then followed. To the reaction was added 5 μL Protease solution and the mixture was incubated for 60 minutes at room temperature (22-25° C.), followed by 5 μL Stabilizer solution. The fluorescence signal was read on an Envision multilabel plate reader (Perkin Elmer). The R110 was then read at an excitation wavelength of 485 nm and an emission wavelength of 530 nm. The AMC signal was read at an excitation wavelength of 355 nm and an emission wavelength of 460 nm.

| Description of HCK Inhibitory Activity | |
|---|---|
| HCK Inhibitory Activity | Descriptor |
| IC$_{50}$ < 50 nM | +++ |
| IC$_{50}$ between 50 and 250 nM | ++ |
| IC$_{50}$ between 250 and 10,000 nM | + |
| Not determined | N.D. |

TABLE of HCK Inhibitory Activity

| Example # | HCK Activity |
|---|---|
| 1 | +++ |
| 2 | ++ |
| 3 | +++ |
| 4 | + |
| 5 | + |
| 6 | +++ |
| 7 | +++ |
| 8 | ++ |
| 9 | +++ |
| 10 | +++ |
| 11 | ++ |
| 12 | + |
| 13 | +++ |
| 14 | +++ |
| 15 | +++ |
| 16 | ++ |
| 17 | +++ |
| 18 | + |
| 19 | +++ |
| 20 | +++ |
| 21 | +++ |
| 22 | +++ |
| 23 | +++ |
| 24 | +++ |
| 25 | ++ |
| 26 | +++ |
| 27 | +++ |
| 28 | ++ |
| 29 | ++ |
| 30 | ++ |
| 31 | +++ |
| 32 | ++ |
| 33 | +++ |
| 34 | +++ |
| 35 | +++ |
| 36 | ++ |
| 37 | +++ |
| 38 | +++ |
| 39 | +++ |
| 40 | +++ |
| 41 | +++ |
| 42 | ++ |
| 43 | +++ |
| 44 | +++ |
| 45 | + |
| 46 | +++ |
| 47 | ++ |
| 48 | +++ |
| 49 | +++ |
| 50 | ++ |
| 51 | +++ |
| 52 | +++ |
| 53 | ++ |
| 54 | +++ |
| 55 | +++ |
| 56 | +++ |
| 57 | +++ |
| 58 | ++ |
| 59 | +++ |
| 60 | +++ |
| 61 | +++ |
| 62 | +++ |
| 63 | + |
| 64 | N.D. |
| 65 | ++ |
| 66 | ++ |
| 67 | ++ |
| 68 | +++ |
| 69 | ++ |
| 70 | ++ |
| 71 | +++ |
| 72 | +++ |
| 73 | +++ |
| 74 | ++ |
| 75 | ++ |
| 76 | ++ |
| 77 | +++ |
| 78 | + |
| 79 | ++ |
| 80 | + |
| 81 | +++ |
| 82 | +++ |
| 83 | ++ |
| 84 | ++ |
| 85 | +++ |
| 86 | ++ |
| 87 | +++ |
| 88 | N.D. |
| 89 | +++ |
| 90 | +++ |
| 91 | ++ |
| 92 | ++ |
| 93 | ++ |
| 94 | +++ |
| 95 | + |
| 96 | +++ |
| 97 | +++ |
| 98 | +++ |
| 99 | +++ |
| 100 | ++ |
| 101 | ++ |
| 102 | +++ |
| 103 | +++ |
| 104 | +++ |
| 105 | +++ |
| 106 | +++ |
| 107 | +++ |
| 108 | +++ |
| 109 | +++ |
| 110 | +++ |
| 111 | ++ |
| 112 | +++ |
| 113 | +++ |
| 114 | +++ |
| 115 | +++ |
| 116 | +++ |
| 117 | ++ |
| 118 | ++ |
| 119 | +++ |
| 120 | +++ |
| 121 | +++ |
| 122 | +++ |
| 123 | +++ |
| 124 | ++ |
| 125 | +++ |
| 126 | +++ |
| 127 | +++ |
| 128 | ++ |
| 129 | +++ |
| 130 | ++ |
| 131 | ++ |
| 133 | +++ |
| 134 | +++ |
| 135 | ++ |
| 136 | ++ |
| 137 | ++ |
| 138 | +++ |
| 139 | ++ |
| 140 | ++ |
| 141 | +++ |
| 142 | +++ |
| 143 | ++ |
| 144 | +++ |
| 145 | +++ |
| 146 | +++ |
| 147 | +++ |
| 148 | ++ |
| 149 | +++ |
| 150 | +++ |
| 151 | +++ |
| 152 | +++ |
| 153 | +++ |

TABLE of HCK Inhibitory Activity -continued

| Example # | HCK Activity |
|---|---|
| 154 | +++ |
| 155 | +++ |
| 156 | +++ |
| 157 | +++ |
| 158 | ++ |
| 159 | +++ |
| 160 | ++ |
| 161 | +++ |
| 162 | +++ |
| 163 | +++ |
| 164 | ++ |
| 165 | +++ |
| 166 | + |
| 167 | + |
| 168 | +++ |
| 169 | +++ |
| 170 | ++ |
| 171 | +++ |
| 172 | +++ |
| 173 | +++ |
| 174 | + |
| 175 | +++ |
| 176 | + |
| 177 | +++ |

Assessment of In Vitro Metabolic Stability

Dog liver microsomes (0.5 mg/mL) were purchased from Corning. Stock solutions were prepared at 10 mM in DMSO for the test compound. Aliquots of the stock solutions were diluted to 0.5 mM with acetonitrile, and then further diluted upon the addition of liver microsomes/buffer to 1.5 µM. An aliquot of 30 µL of 1.5 µM solutions was mixed with 15 µL of 6 mM NADPH and the final concentration of NADPH was 2 mM, which had been pre-warmed to 37° C. Test compound and Ketanserin final concentrations were 1 µM. The plates were kept in a 37° C. water bath for the duration of the experiment. At each time point (0, 5, 15, 30, 45 minutes), 135 µL of acetonitrile was added into corresponding wells. After the final time point was quenched by acetonitrile, the assay plates were shaken (IKA, MTS 2/4) for 10 min (600 rpm/min) and then centrifuged at 5,594 g for 15 min (Thermo Multifuge×3R). Aliquots of the supernatant were taken, diluted 1:1 into distilled water, and analyzed by LC-MS/MS. The peak area response ratio to internal standard (PARR) of the compounds at 5, 15, 30, 45 minutes was compared to the PARR at time 0 to determine the percent of test compound remaining at each time point. Half-lives were calculated using Excel software, fitting to a single-phase exponential decay equation.

Assessment of In Vivo Pharmacokinetics

A total of 6 Male Non-naïve Beagle dog, weighing approximately 8.00-10.00 kg (Beijing Marshall Biotechnology Co. LTD), were dosed by intravenous injection (iv) or oral gavage (po) at 1 mg/kg or 3 mg/kg. The vehicles of IV and PO are 100% saline and 100% (0.5% MC in water), respectively. The IV dose was conducted via cephalic vein injection, PO via gavage administration. The animals were restrained manually, and approximately 0.5 mL blood/time point was collected from cephalic vein into pre-cooled $K_2EDTA$ tubes. Blood sample was put on wet ice and centrifuged at 4° C. (2000 g, 5 min) to obtain plasma within 15 minutes of sample collection. Plasma samples were analyzed by UPLC/MS-MS. PK parameters were estimated by non-compartmental model using WinNonlin6.4.

The following compounds were evaluated for their inhibitory activity towards HCK and for the circulating half-life ($t_{1/2}$) in dog LM. The compounds were synthesized as described above.

| Structure | Ex. No. | HCK $IC_{50}$ (nM) | Dog LM $t_{1/2}$ (min) | Dog BAV (% F) |
|---|---|---|---|---|
| 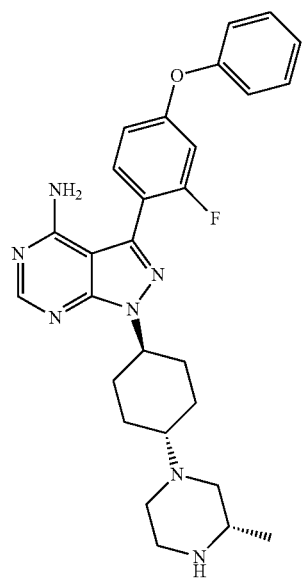 [SMILES: C[C@H]1CN([C@H]2CC[C@H](n3nc(-c4ccc(Oc5ccccc5)cc4F)c4c(N)ncnc43)CC2)CCN1] | 127 | 5.1 | 118 | 57 |

-continued
| Structure | Ex. No. | HCK IC$_{50}$ (nM) | Dog LM t$_{1/2}$ (min) | Dog BAV (% F) |
|---|---|---|---|---|
| 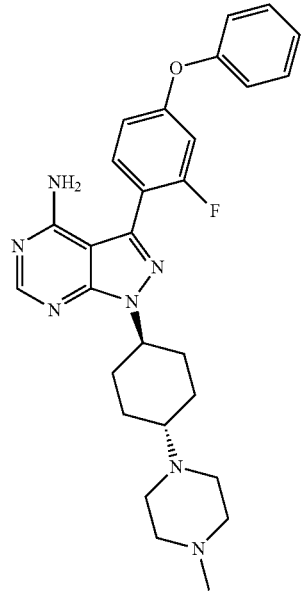 [SMILES: CN1CCN([C@H]2CC[C@H](n3nc(-c4ccc(Oc5ccccc5)cc4F)c4c(N)ncnc43)CC2)CC1] | 103 | 4.1 | 58 | 24 |
| 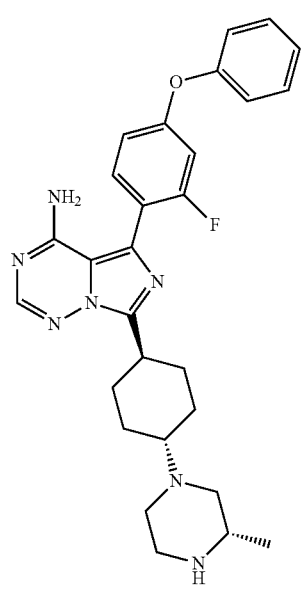 [SMILES: C[C@H]1CN([C@H]2CC[C@H](c3nc(-c4ccc(Oc5ccccc5)cc4F)c4c(N)ncnn43)CC2)CCN1] | 165 | 5.0 | 167 | N.D. |

-continued
| Structure | Ex. No. | HCK IC$_{50}$ (nM) | Dog LM t$_{1/2}$ (min) | Dog BAV (% F) |
|---|---|---|---|---|
| 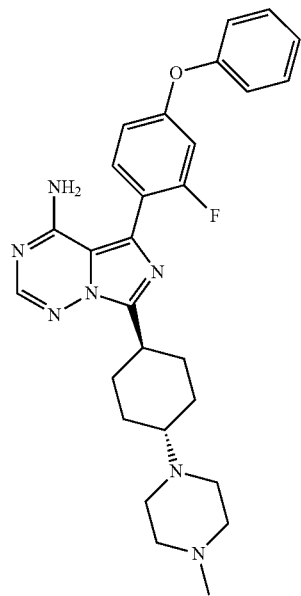 [SMILES: CN1CCN([C@H]2CC[C@H](c3nc(-c4ccc(Oc5ccccc5)cc4F)c4c(N)ncnn43)CC2)CC1] | 163 | 1.1 | 108 | 51 |
| 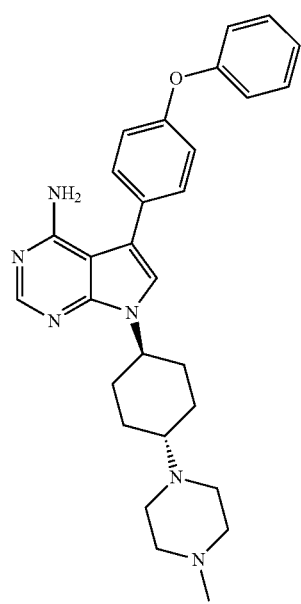 [SMILES: CN1CCN([C@H]2CC[C@H](n3cc(-c4ccc(Oc5ccccc5)cc4)c4c(N)ncnc43)CC2)CC1] | 1 | 3.3 | 11 | 0 |

-continued
| Structure | Ex. No. | HCK IC$_{50}$ (nM) | Dog LM t$_{1/2}$ (min) | Dog BAV (% F) |
|---|---|---|---|---|
| 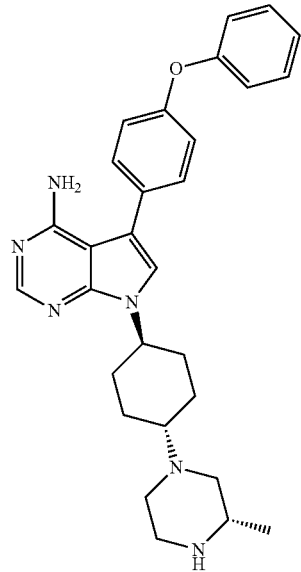 [SMILES: C[C@H]1CN([C@H]2CC[C@H](n3cc(-c4ccc(Oc5ccccc5)cc4)c4c(N)ncnc43)CC2)CCN1] | 19 | 17 | 84 | N.D. |
| 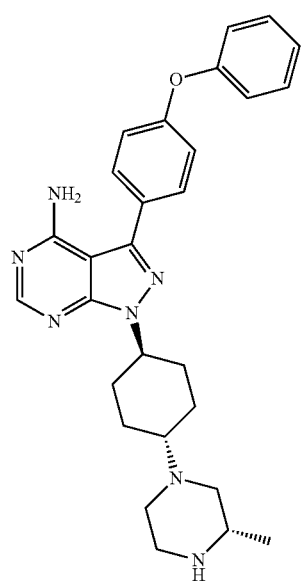 [SMILES: C[C@H]1CN([C@H]2CC[C@H](n3nc(-c4ccc(Oc5ccccc5)cc4)c4c(N)ncnc43)CC2)CCN1] | 21 | 43 | 128 | N.D. |

| Structure | Ex. No. | HCK IC$_{50}$ (nM) | Dog LM t$_{1/2}$ (min) | Dog BAV (% F) |
|---|---|---|---|---|
| 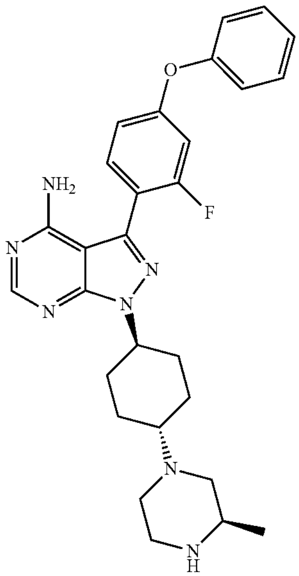 [SMILES: C[C@@H]1CN([C@H]2CC[C@H](n3nc(-c4ccc(Oc5ccccc5)cc4F)c4c(N)ncnc43)CC2)CCN1] | 17 | 16.5 | N.D. | N.D. |

As shown in the data table above, the compounds of examples 127, 103, 165, 163, 19, and 21 had higher t$_{1/2}$ than the compound of example 1. While the compound of example 1 had a half-life of 11 min, moving the piperazinyl-methyl group one position surprisingly increased the t$_{1/2}$ to 84 min in the compound of example 19. Replacing the pyrrole ring of example 19 with a pyrazole ring in the compound of example 21 further increased t$_{1/2}$ to 128 min. Alternatively, replacement of the pyrrole ring of the compound of example 1 with a pyrazole ring, and addition of an ortho fluorine substituent, in the compound of example 103 increased t$_{1/2}$ to 58 min. Moving the piperazinyl-methyl group of the compound of example 103 one position further increased the t$_{1/2}$ to 118 min in the compound of example 127. Replacing the pyrazole ring of the compound of example 127 with an imidazole led to the highest t$_{1/2}$ observed, 167 min for in the compound of example 165. Moving the piperazinyl-methyl group of the compound of example 165 back to the terminal piperazinyl nitrogen diminished t$_{1/2}$ slightly, to 108 min in the compound of example 163. The longer t$_{1/2}$ for examples 103, 127, and 163 was confirmed by the lower plasma clearance and higher bioavailability in vivo.

In addition, the compounds studied also showed surprising effects of substitution on potency. For example, the compounds of examples 127 and 21 differ only by a fluorine group, but the compound of example 127 surprisingly shows nearly an order of magnitude higher potency. As another example, the compounds of examples 127 and 17 differ only in the stereochemistry of the methyl group, but the compound of example 127 shows nearly three times greater potency.

We claim:

1. A compound of Formula (I):

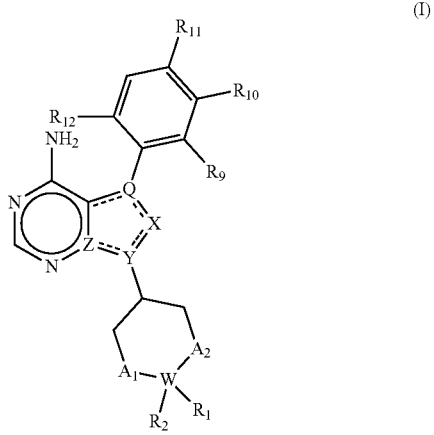

(I)

or a pharmaceutically acceptable salt thereof,
wherein
each Q, Y and Z are independently selected from N and C, and X is N or C—R$^a$;
provided that at least one of Q, X, Y and Z is N, and
each dashed bond is independently a single or double bond such that the bicycle they form is a heteroaryl;

$R_1$ is

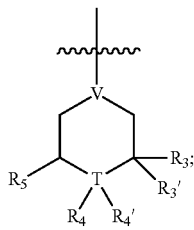

V is N or CH;
either T is N and $R_4'$ is absent, or T is C;
$R_3$ is selected from H, halo, CN, alkyl, alkoxy, hydroxy, acyloxy, amino, amido, cycloalkyl, heterocyclyl, carboxy, and alkoxycarbonyl;
$R_3'$ is H or alkyl, or
$R_3$ and $R_3'$ taken together with the carbon atom to which they are attached form a cycloalkyl;
$R_4$ is selected from H, halo, CN, alkyl, alkoxy, acyloxy, amino, and amido;
$R_4'$ is H or alkyl;
$R_5$ is H or alkyl;
either
  a) W is N, $R_2$ is absent, and $A_1$ and A2 are each $CH_2$; or
  b) W is C, $R_2$ is selected from H, halo, CN, alkyl, alkoxy, hydroxy, acyloxy, and amino, and $A_1$ and $A_2$ are each independently selected from $CH_2$ and O;
$R^a$ is selected from H, halo, CN and alkyl;
$R_9$ is selected from H, halo, alkyl, alkoxy, hydroxy, acyloxy, and amino;
$R_{10}$ is H or alkoxy;
$R_{11}$ is aryloxy, heteroaryloxy, arylalkyl, alkoxycarbonyl, ureido or —C(O)-aryl; and
$R_{12}$ is selected from H, halo, CN, alkyl, alkoxy, and acyloxy;
provided that either $R_3$ is alkyl or $R_9$ is halo.

2. The compound of claim 1, having the structure:

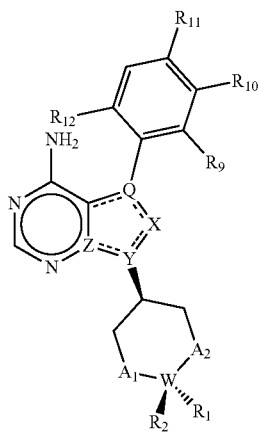

wherein $R_2$ is H.

3. The compound of claim 2, wherein
Q is C, X is N, Y is C and Z is N;
Q is C, X is C—$R^a$, $R^a$ is H, Y is N and Z is C; or
Q is C, X is N, Y is N and Z is C.

4. The compound of claim 3, wherein $A_1$ and $A_2$ are both $CH_2$.

5. The compound of claim 1, wherein
W is C,
$R_2$ is H,
V is N and
T is N.

6. The compound of claim 5, wherein $R_3$ is methyl.
7. The compound of claim 5, wherein $R_4$ is H or methyl.
8. The compound of claim 5, wherein $R_9$ is H or F.
9. The compound of claim 5, wherein $R_{12}$ is H or halo.
10. The compound of claim 1, wherein
$R_{11}$ is selected from

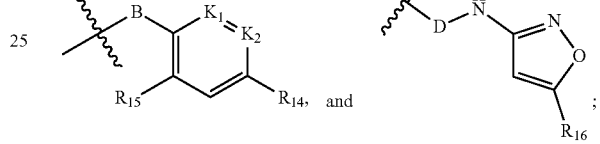

B is selected from —O—, $CH_2$, CHOH, NH, $N(C_{1-6}$ alkyl) and carbonyl;
$K_1$ and $K_2$ are independently selected from N and $CR_{13}$;
D is selected from —$CH_2$—C(O)—, —NH—C(O)—, $N(C_{1-6}$ alkyl)-C(O), and —$CH_2S(O)_2$—;
$R_{13}$ is selected from H, halo, CN, alkyl, alkoxy, hydroxy, acyloxy, amino, amido, and alkoxycarbonyl;
$R_{14}$ is selected from H, halo, CN, alkyl, alkoxy, hydroxy, acyloxy, amino, amido, and alkoxycarbonyl;
$R_{15}$ is selected from H, halo, CN, alkyl, alkoxy, hydroxy, acyloxy, amino, amido, and alkoxycarbonyl; and
$R_{16}$ is selected from H, halo, CN, alkyl, alkoxy, hydroxy, acyloxy, amino, amido, and alkoxycarbonyl.

11. The compound of claim 10, wherein $R_{11}$ is

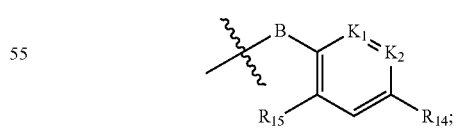

B is O;
$K_1$ and $K_2$ are each CH;
$R_{14}$ is H; and
$R_{15}$ is H.

12. The compound of claim 1, wherein $R_9$ is halo.
13. The compound of claim 1, wherein $R_9$ is F.

14. A compound selected from:

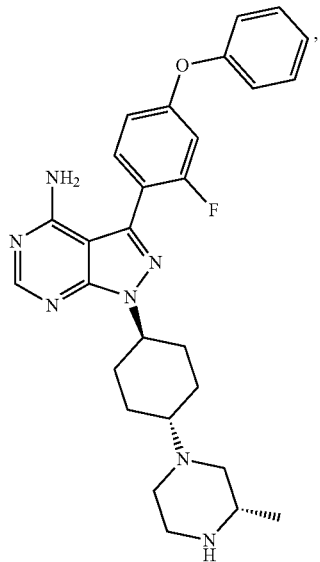

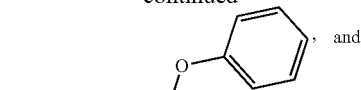

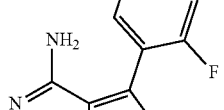

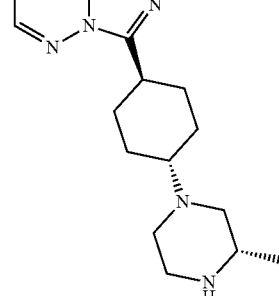

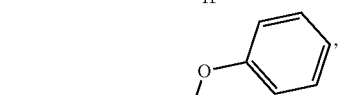

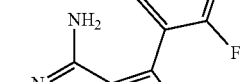
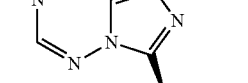
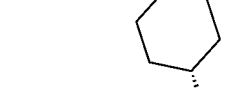

a pharmaceutically acceptable salt thereof.

15. A method of co-inhibiting HCK and BCL-2 in a cell, comprising contacting the cell with a compound of formula (I) according to claim 1 and a BCL-2 inhibitor.

16. A method of killing a cell having an FLT3-ITD mutation, comprising contacting the cell with a compound of formula (I) according to claim 1 and a BCL-2 inhibitor.

17. A method of treating acute myeloid leukemia, comprising conjointly administering to a subject a compound of formula (I) according to claim 1 and a BCL-2 inhibitor.

18. The method of claim 17, wherein the subject has FLT3-ITD+ acute myeloid leukemia.

19. The method of claim 17, wherein the BCL-2 inhibitor is ABT-199.

* * * * *

UNITED STATES PATENT AND TRADEMARK OFFICE
CERTIFICATE OF CORRECTION

PATENT NO. : 11,963,960 B2
APPLICATION NO. : 17/201827
DATED : April 23, 2024
INVENTOR(S) : Serrano-Wu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Twenty-ninth Day of April, 2025

Coke Morgan Stewart
*Acting Director of the United States Patent and Trademark Office*